US006455494B1

(12) United States Patent
Jefferies et al.

(10) Patent No.: US 6,455,494 B1
(45) Date of Patent: Sep. 24, 2002

(54) USE OF P97 AND IRON BINDING PROTEINS AS DIAGNOSTIC AND THERAPEUTIC AGENTS

(75) Inventors: Wilfred A. Jefferies, South Surrey; Patrick L. McGeer, Vancouver, both of (CA); Sylvia Rothenberger, Epalinges (CH); Michael R. Food, Vancouver (CA); Tatsuo Yamada, Tokyo (JP); Malcolm Kennard, Vancouver (CA)

(73) Assignee: University of British Columbia, Vancouver (CA)

( * ) Notice: Subject to any disclaimer, the term of this patent is extended or adjusted under 35 U.S.C. 154(b) by 0 days.

(21) Appl. No.: 09/285,040

(22) Filed: Apr. 1, 1999

Related U.S. Application Data

(60) Division of application No. 08/520,933, filed on Aug. 31, 1995, now Pat. No. 5,981,194, which is a continuation-in-part of application No. 08/367,224, filed on Mar. 30, 1999, now abandoned, which is a continuation-in-part of application No. 07/912,291, filed on Jul. 10, 1992, now abandoned.

(30) Foreign Application Priority Data

Jul. 9, 1993 (WO) .............................. PCT/CA93/00272

(51) Int. Cl.[7] .............................................. A61K 38/00
(52) U.S. Cl. ...................... 514/2; 530/350; 530/387.1; 435/7.1
(58) Field of Search .............................. 514/2; 530/350, 530/387.1; 435/7.1

(56) References Cited

U.S. PATENT DOCUMENTS

| | | | |
|---|---|---|---|
| 4,414,148 A | * 11/1983 | Jansen et al. ........... 260/112 B |
| 4,522,750 A | 6/1985 | Ades et al. ................. 530/397 |
| 4,801,575 A | 1/1989 | Pardridge ...................... 514/4 |
| 4,902,505 A | 2/1990 | Pardridge et al. ........... 424/85.7 |
| 5,034,223 A | * 7/1991 | Abrams et al. ............ 424/85.8 |
| 5,154,924 A | 10/1992 | Friden ..................... 424/179.1 |
| 5,182,107 A | 1/1993 | Friden ..................... 424/179.1 |
| 5,527,527 A | 6/1996 | Friden ..................... 424/178.1 |
| 5,672,683 A | 9/1997 | Friden et al. |

FOREIGN PATENT DOCUMENTS

| | | | |
|---|---|---|---|
| GB | 2188637 | 10/1987 |
| WO | WO 85/00812 | 2/1985 |
| WO | 94/01463 | * 1/1994 |

OTHER PUBLICATIONS

Mahoney, Proceed. Natl. Acad. Sci USA. 96(8): 4536–4539, 1999.*
Elliott, J L. Neurobiology of Disease, 6(5): 310–20, 1999.*
Grua, Science 278 : 1041–1042, 1997.*
Jain. Sci. Amer. 271 : 58–65, 1994.*
Curti. Cut. Rev. Oncol/Hematology 14:29–39, 1993.*
Hartwell. Science 278: 1064–1068, 1997.*
Neuwelt, EA, Neurosurgery, 20(6): 885–95, 1987.*
Crichton and Charloteaux–Wauters, M. Eur. J. Biochem., 164:485–506, 1987.
Richardson and Baker, Biochem. Biophys. Acta, 1053:1–12, 1990.
Richardson and Baker, Biochem. Biophys. Acta. 1091:294–302, 1991.
Richardson and Baker; Biochem. Biophys. Acta. 1093:20–28, 1991.
Brown et al. J. Immunol., 127:539, 1981.
Brown et al. Proc. Nat. Acad. Sci. U.S.A. 78:539, 1981.
Woodbury, et al., Int. J. Cancer, 27:145, 1981.
Sciot et al., Liver, 9:110, 1989.
Richardson and Baker, Biochem. Biophys. Acta. 1103:275–280, 1992.
Evans et al., J.A.M.A., 262,2551–2556, 1989.
McKhann et al., Neurology, 34:939–944, 1984.
Folstein et al., J. Psych. Res. 12:189–198, 1975.
Khachatunan, Arch. Neurol. 42:1097–1105, 1985.
Esiri, Alzheimer's Disease Current Research in Early Diagnosis, Becker and Giacobini (eds.), pp. 239–252, 1990.
Soininen et al., Alzheimer's Disease Current Research in Early Diagnosis, Becker and Giacobini (eds.), pp. 159–167, 1990.
Leedom and Miller, Alzeheimer's Disease Current Research in Early Diagnosis, Becker and Giacobini (eds.), pp. 297–313, 1990.
Bird, Prog. Neurobiol., 19:91–115, 1982.
Wilson, et al., Neurology, 32:1054–1057, 1982.
Yerby et al., Neurology, 35:1316–1320, 1985.
Luxenberg et al., Can. J. Neurol. Sci. 13:570–572, 1986.
Friedland et al., Ann. Int. Med. 109:298–311, 1988.
Parks and Becker, Alzheimer's Disease Current Research in Early Diagnosis, Becker and Giacobini (eds.), pp. 315–327, 1990.
Mena et al., Alzheimer's Disease Current Research in Early Diagnosis, Becker and Giacobini (eds.), pp. 339–355, 1990.
Jagust et al., Neurology, 38:909–912, 1988.
Prohovnik et al., Neurology, 38:931–937, 1988.
Waldemar et al., Aging Brain and Dementia: New Trends in Diagnosis and Therapy p. 405–416, Alan R. Liss, Inc., 1990.
Wolozin, Alzheimer's Disease Current Research in Early Diagnosis, Becker and Giacobini (eds.), pp.217–235, 1990.
Wolozin et al., Science 232:648–650, 1986.

(List continued on next page.)

Primary Examiner—Anthony C. Caputa
Assistant Examiner—Minh-Tam Davis
(74) Attorney, Agent, or Firm—Bereskin & Parr; Micheline Gravelle

(57) ABSTRACT

The invention related to a GPI-anchored p97 and a soluble form of p97 and derivatives thereof and methods for preparing the same. Methods of using p97 in modulating iron transport, in the delivery of therapeutic agents, and in the treatment of conditions involving disturbances in iron metabolism are described. The treatment and diagnosis of Alzheimer's Disease in view of the finding that p97 and transferrin receptor are markers for microglial cells associated with senile plaques are also described.

7 Claims, 64 Drawing Sheets

OTHER PUBLICATIONS

St. George–Hyslop et al., Science, 235:885–890, 1987.
Giacobini et al., Alzeheimer's Disease Current Research in Early Diagnosis, Becker and Giacobini (eds.), pp. 137–156, 1990.
Tamminga et al., Neurology, 37:161–165, 1987.
Volicer et al., Arch. Neurol., 42:127–129, 1985.
Gibson et al. Arch. Neurol., 42:489–492, 1985.
Cutler et al., Arch. Neurol., 43:153–154, 1986.
Elble, Alzeheimer's Disease Current Research in Early Diagnosis, Becker and Giacobini (eds.), Taylor & Francis (pub.), N.Y., pp. 19–30, 1990.
Bowen et al., Brain, 99:459–496, 1976.
Summers et al., N. Eng. J. Med. 315:1241–1245, 1986.
Etienne et al., Neurology, 31:1552–1554, 1981.
Tang et al., Current Research in Alzeheimer Therapy Becker and Giacobini (eds.), pp. 289–293, 1988.
Domino, Alzeheimer's Disease Current Research in Early Diagnosis, Becker and Giacobini (eds.), pp. 295–303, 1988.
Moss et al., Alzeheimer's Disease Current Research in Early Diagnosis, Becker and Giacobini (eds.), pp. 305–314, 1988.
Johns et al., Banbury Report, 15:435–449, 1983.
Brufani et al., Alzeheimer's Disease Current Research in Early Diagnosis, Becker and Giacobini (eds.), pp. 343–352, 1988.
Lin et al., Science, 249:677, 1990.
Ferguson and Williams, Ann. Rev. Biochem. 57:285–320, 1988.
Schellenberg et al., Science, 241;1507, 1988.
Huse et al., Science, 246:1275, 1989.
Ghosal and Saedler, 275:611, 1978.
Ikezawa and Taguchi, Methods in Enzymology, 71:731, 1981.
Glasky and Reading, Hydridoma, 8:377, 1989.
Gibson et al., Arch. Neurol., 42:489, 1985.
Volwerk et al., J. Cell. Biochem., 39:315, 1989.
Low et al., J. Immunol. Methods, 113:101, 1988.
Real et al., Cancer Research, 45:4401, 1985.
Woodbury et al., Proc. Natl. Acad. Sci. USA, 77:2183, 1980.
Baker et al., F.E.B.S. Letters, 298:215, 1992.
Richardson and Baker, J. Biol. Chem., 267:13972, 1992.
Brown et al., Nature, 296:171, 1982.
Liao et al., J. Cell. Biochem., 27:303, 1985.
Alemany et al., J. Cell. Sci. 104:1162, 1993.
Craven et al., Proc. Natl. Acad. Sci. USA, 84:3457, 1987.
Friden et al., Science, 259:373, 1993.
Low, M.G. Biochem. Biophys. Acta, 988:427, 1989.
Morgenthaler, *Biotech Brainstorming*, Barron's p. 8, Feb. 8, 1993.
Pardridge et al., J. Pharm. Expr. Thera. 253:884, 1990.
Pippard, M.J., *Clinical Use of Iron Chelation* p. 361 1989.
Selkoe, D.J., Scientific American, p. 68, 1991.
Schnabel, Science, 260:1993.
Trowbridge and Lopez, Proc. Natl. Acad. Sci. USA, 79:1175, 1982.
Trowbridge and Omary, Proc. Natl. Acad. Sci. USA, 78:3039, 1981.
Trowbridge et al., Methods in Enzymology, 147:265, 1987.
Iacopetta et al., Cell., 54:485, 1988.
Rothenberger et al., Cell., 49:423, 1987.
Rothenberger et al., Nucleic Acids Research, 18:1175, 1990.
Jefferies et al., Immunology, 54:333, 1985.
Jefferies et al., Nature, 312:163, 1984.
Dippold et al., Proc. Natl. Acad. Sci., 77:6114–6118, 1980.
Vieira and Messing, Gene, 19:259, 1982.
Bolivar et al., Gene, 2:95, 1977.
Bowen et al., Brain, 99:459, 1976.
Turnball et al., Biotechnology, 7:169, 1989.
Malik and Low, Biochem. J., 240:519, 1986.
Wolozin and Davies, Ann. Neurol. 22:521, 1987.
Kuhn et al., Iron and Transport Storage, CRC Press, Boca Raton, Ann Arbor and Boston, 1990, p. 149.
Doering et al J. Biol. Chem. 265:611–614, 1990.
Basset et al., Cancer Res. 46:1644–1647, 1986.
Sturrock et al., J. Biol. Chem. 265:3139–3145, 1990.
Thorstensen, K., J. Biol. Chem. 263:16837–16841, 1988.
Estin et al., Proc. Nat. Acad. Sci. U.S.A. 85:1052–1056, 1988.
Rose et al., Proc. Nat. Acad. Sci. U.S.A. 83:1261, 1986.
Baker et al., Trends Biochem. Sci. 12:350, 1987.
Dippold et al. Proc. Nat. Acad. Sci. U.S.A. 77:6114, 1980.
Kennard et al., Biotechnology and Bioengineering, 42:480–486, 1993.
Food et al., J. of Biol. Chem., 269:1–7, 1994.
Kennard and Piret, Biotech. Bioeng., 44:45–54, 1994.

* cited by examiner

FIG. 2A

```
GCGGACTTCC TCGGACCCGG ACCCAGCCCC AGCCCGGCCC CAGCCAGCCC CGACGGCGCC        60

ATG CGG GGT CCG AGC GGG GCT CTG TGG CTG CTC CTG GCT CTG CGC ACC         108
Met Arg Gly Pro Ser Gly Ala Leu Trp Leu Leu Leu Ala Leu Arg Thr
 1           5                  10                  15

GTG CTC GGA GGC ATG GAG GTG CGG TGG TGC GCC ACC TCG GAC CCA GAG         156
Val Leu Gly Gly Met Glu Val Arg Trp Cys Ala Thr Ser Asp Pro Glu
             1           5                  10

CAG CAC AAG TGC GGC AAC ATG AGC GAG GCC TTC CGG GAA GCG GGC ATC         204
Gln His Lys Cys Gly Asn Met Ser Glu Ala Phe Arg Glu Ala Gly Ile
        15                  20                  25

CAG CCC TCC CTC CTC TGC GTC CGG GGC ACC TCC GCC GAC CAC TGC GTC         252
Gln Pro Ser Leu Leu Cys Val Arg Gly Thr Ser Ala Asp His Cys Val
 30                  35                  40                  45

CAG CTC ATC GCG GCC CAG GAG GCT GAC GCC ATC ACT CTG GAT GGA GGA         300
Gln Leu Ile Ala Ala Gln Glu Ala Asp Ala Ile Thr Leu Asp Gly Gly
                 50                  55                  60

GCC ATC TAT GAG GCG GGA AAG GAG CAC GGC CTG AAG CCG GTG GTG GGC         348
Ala Ile Tyr Glu Ala Gly Lys Glu His Gly Leu Lys Pro Val Val Gly
             65                  70                  75

GAA GTG TAC GAT CAA GAG GTC GGT ACC TCC TAT TAC GCC GTG GCT GTG         396
Glu Val Tyr Asp Gln Glu Val Gly Thr Ser Tyr Tyr Ala Val Ala Val
         80                  85                  90

GTC AGG AGG AGC TCC CAT GTG ACC ATT GAC ACC CTG AAA GGC GTG AAG         444
Val Arg Arg Ser Ser His Val Thr Ile Asp Thr Leu Lys Gly Val Lys
         95                  100                 105

TCC TGC CAC ACG GGC ATC AAT CGC ACA GTG GGC TGG AAC GTG CCC GTG         492
Ser Cys His Thr Gly Ile Asn Arg Thr Val Gly Trp Asn Val Pro Val
110                 115                 120                 125
```

FIG. 2B

```
GGC TAC CTG GTG GAG AGC GGC CGC CTC TCG GTG ATG GGC TGC GAT GTA      540
Gly Tyr Leu Val Glu Ser Gly Arg Leu Ser Val Met Gly Cys Asp Val
                130                 135                 140

CTC AAA GCT GTC AGC GAC TAT TTT GGG GGC AGC TGC GTC CCG GGG GCA      588
Leu Lys Ala Val Ser Asp Tyr Phe Gly Gly Ser Cys Val Pro Gly Ala
                145                 150                 155

GGA GAG ACC AGT TAC TCT GAG TCC CTC TGT CGC CTC TGC AGG GGT GAC      636
Gly Glu Thr Ser Tyr Ser Glu Ser Leu Cys Arg Leu Cys Arg Gly Asp
                160                 165                 170

AGC TCT GGG GAA GGG GTG TGT GAC AAG AGC CCC CTG GAG AGA TAC TAC      684
Ser Ser Gly Glu Gly Val Cys Asp Lys Ser Pro Leu Glu Arg Tyr Tyr
    175                 180                 185

GAC TAC AGC GGG GCC TTC CGG TGC CTG GCG GAA GGG GCA GGG GAC GTG      732
Asp Tyr Ser Gly Ala Phe Arg Cys Leu Ala Glu Gly Ala Gly Asp Val
190                 195                 200                 205

GCT TTT GTG AAG CAC AGC ACG GTA CTG GAG AAC ACG GAT GGG AAG ACG      780
Ala Phe Val Lys His Ser Thr Val Leu Glu Asn Thr Asp Gly Lys Thr
                210                 215                 220

CTT CCC TCC TGG GGC CAG GCC CTG CTG TCA CAG GAC TTC GAG CTG CTG      828
Leu Pro Ser Trp Gly Gln Ala Leu Leu Ser Gln Asp Phe Glu Leu Leu
                225                 230                 235

TGC CGG GAT GGT AGC CGG GCC GAT GTC ACC GAG TGG AGG CAG TGC CAT      876
Cys Arg Asp Gly Ser Arg Ala Asp Val Thr Glu Trp Arg Gln Cys His
                240                 245                 250
```

FIG. 2C

```
CTG GCC CGG GTG CCT GCT CAC GCC GTG GTG GTC CGG GCC GAC ACA GAT        924
Leu Ala Arg Val Pro Ala His Ala Val Val Val Arg Ala Asp Thr Asp
    255             260             265

GGG GGC CTC ATC TTC CGG CTG CTC AAC GAA GGC CAG CGT CTG TTC AGC        972
Gly Gly Leu Ile Phe Arg Leu Leu Asn Glu Gly Gln Arg Leu Phe Ser
270             275             280             285

CAC GAG GGC AGC AGC TTC CAG ATG TTC AGC TCT GAG GCC TAT GGC CAG       1020
His Glu Gly Ser Ser Phe Gln Met Phe Ser Ser Glu Ala Tyr Gly Gln
            290             295             300

AAG GAT CTA CTC TTC AAA GAC TCT ACC TCG GAG CTT GTG CCC ATC GCC       1068
Lys Asp Leu Leu Phe Lys Asp Ser Thr Ser Glu Leu Val Pro Ile Ala
            305             310             315

ACA CAG ACC TAT GAG GCG TGG CTG GGC CAT GAG TAC CTG CAC GCC ATG       1116
Thr Gln Thr Tyr Glu Ala Trp Leu Gly His Glu Tyr Leu His Ala Met
        320             325             330

AAG GGT CTG CTC TGT GAC CCC AAC CGG CTG CCC CCC TAC CTG CGC TGG       1164
Lys Gly Leu Leu Cys Asp Pro Asn Arg Leu Pro Pro Tyr Leu Arg Trp
335             340             345

TGT GTG CTC TCC ACT CCC GAG ATC CAG AAG TGT GGA GAC ATG GCC GTG       1212
Cys Val Leu Ser Thr Pro Glu Ile Gln Lys Cys Gly Asp Met Ala Val
350             355             360             365

GCC TTC CGC CGG CAG CGC CTC AAG CCA GAG ATC CAG TGC GTG TCA GCC       1260
Ala Phe Arg Arg Gln Arg Leu Lys Pro Glu Ile Gln Cys Val Ser Ala
            370             375             380

AAG TCC CCC CAA CAC TGC ATG GAG CGG ATC CAG GCT GAG CAG GTC GAC       1308
Lys Ser Pro Gln His Cys Met Glu Arg Ile Gln Ala Glu Gln Val Asp
            385             390             395
```

FIG. 2D

```
GCT GTG ACC CTA AGT GGC GAG GAC ATT TAC ACG GCG GGG AAG AAG TAC      1356
Ala Val Thr Leu Ser Gly Glu Asp Ile Tyr Thr Ala Gly Lys Lys Tyr
        400                 405                 410

GGC CTG GTT CCC GCA GCC GGC GAG CAC TAT GCC CCG GAA GAC AGC AGC      1404
Gly Leu Val Pro Ala Ala Gly Glu His Tyr Ala Pro Glu Asp Ser Ser
        415                 420                 425

AAC TCG TAC TAC GTG GTG GCC GTG GTG AGA CGG GAC AGC TCC CAC GCC      1452
Asn Ser Tyr Tyr Val Val Ala Val Val Arg Arg Asp Ser Ser His Ala
430                 435                 440                 445

TTC ACC TTG GAT GAG CTT CGG GGC AAG CGC TCC TGC CAC GCC GGT TTC      1500
Phe Thr Leu Asp Glu Leu Arg Gly Lys Arg Ser Cys His Ala Gly Phe
                450                 455                 460

GGC AGC CCT GCA GGC TGG GAT GTC CCC GTG GGT GCC CTT ATT CAG AGA      1548
Gly Ser Pro Ala Gly Trp Asp Val Pro Val Gly Ala Leu Ile Gln Arg
                465                 470                 475

GGC TTC ATC CGG CCC AAG GAC TGT GAC GTC CTC ACA GCA GTG AGC GAG      1596
Gly Phe Ile Arg Pro Lys Asp Cys Asp Val Leu Thr Ala Val Ser Glu
            480                 485                 490

TTC TTC AAT GCC AGC TGC GTG CCC GTG AAC AAC CCC AAG AAC TAC CCC      1644
Phe Phe Asn Ala Ser Cys Val Pro Val Asn Asn Pro Lys Asn Tyr Pro
        495                 500                 505

TCC TCG CTG TGT GCA CTG TGC GTG GGG GAC GAG CAG GGC CGC AAC AAG      1692
Ser Ser Leu Cys Ala Leu Cys Val Gly Asp Glu Gln Gly Arg Asn Lys
510                 515                 520                 525

TGT GTG GGC AAC AGC CAG GAG CGG TAT TAC GGC TAC CGC GGC GCC TTC      1740
Cys Val Gly Asn Ser Gln Glu Arg Tyr Tyr Gly Tyr Arg Gly Ala Phe
                530                 535                 540
```

FIG. 2E

```
AGG TGC CTG GTG GAG AAT GCG GGT GAC GTT GCC TTC GTC AGG CAC ACA      1788
Arg Cys Leu Val Glu Asn Ala Gly Asp Val Ala Phe Val Arg His Thr
            545             550             555

ACC GTC TTT GAC AAC ACA AAC GGC CAC AAT TCC GAG CCC TGG GCT GCT      1836
Thr Val Phe Asp Asn Thr Asn Gly His Asn Ser Glu Pro Trp Ala Ala
            560             565             570

GAG CTC AGG TCA GAG GAC TAT GAA CTG CTG TGC CCC AAC GGG GCC CGA      1884
Glu Leu Arg Ser Glu Asp Tyr Glu Leu Leu Cys Pro Asn Gly Ala Arg
            575             580             585

GCC GAG GTG TCC CAG TTT GCA GCC TGC AAC CTG GCA CAG ATA CCA CCC      1932
Ala Glu Val Ser Gln Phe Ala Ala Cys Asn Leu Ala Gln Ile Pro Pro
590             595             600             605

CAC GCC GTG ATG GTC CGG CCC GAC ACC AAC ATC TTC ACC GTG TAT GGA      1980
His Ala Val Met Val Arg Pro Asp Thr Asn Ile Phe Thr Val Tyr Gly
            610             615             620

CTG CTG GAC AAG GCC CAG GAC CTG TTT GGA GAC GAC CAC AAT AAG AAC      2028
Leu Leu Asp Lys Ala Gln Asp Leu Phe Gly Asp Asp His Asn Lys Asn
            625             630             635

GGG TTC AAA ATG TTC GAC TCC TCC AAC TAT CAT GGC CAA GAC CTG CTT      2076
Gly Phe Lys Met Phe Asp Ser Ser Asn Tyr His Gly Gln Asp Leu Leu
            640             645             650

TTC AAG GAT GCC ACC GTC CGG GCG GTG CCT GTC GGA GAG AAA ACC ACC      2124
Phe Lys Asp Ala Thr Val Arg Ala Val Pro Val Gly Glu Lys Thr Thr
            655             660             665

TAC CGC GGC TGG CTG GGG CTG GAC TAC GTG GCG GCG CTG GAA GGG ATG      2172
Tyr Arg Gly Trp Leu Gly Leu Asp Tyr Val Ala Ala Leu Glu Gly Met
670             675             680             685
```

FIG. 2F

```
TCG TCT CAG CAG TGC TCG GGC GCA GCG GCC CCG GCG CCC GGG GCG CCC      2220
Ser Ser Gln Gln Cys Ser Gly Ala Ala Ala Pro Ala Pro Gly Ala Pro
            690                     695                 700

CTG CTC CCG CTG CTG CTG CCC GCC CTC GCC GCC CGC CTG CTC CCG CCC      2268
Leu Leu Pro Leu Leu Leu Pro Ala Leu Ala Ala Arg Leu Leu Pro Pro
            705                 710                 715

GCC CTC TGAGCCCGGC CGCCCCGCCC CAGAGCTCCG ATGCCCGCCC GGGGAGTTTC       2324
Ala Leu

CGCGGCGGCC TCTCGCGCTG CGGAATCCAG AAGGAAGCTC GCGA                      2368
```

FIG. 22A
FIG. 22C
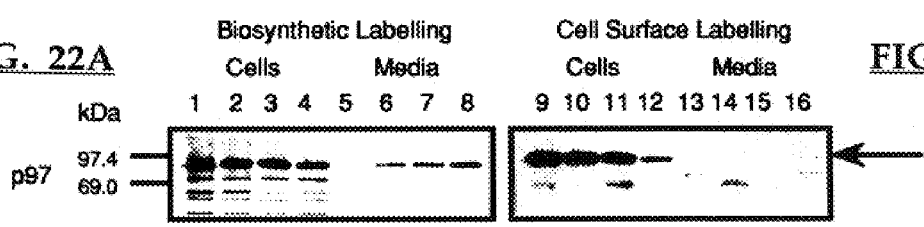
FIG. 22B
FIG. 22D
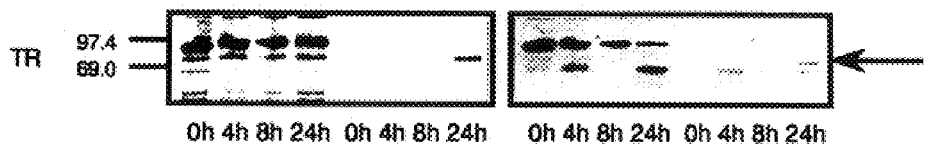

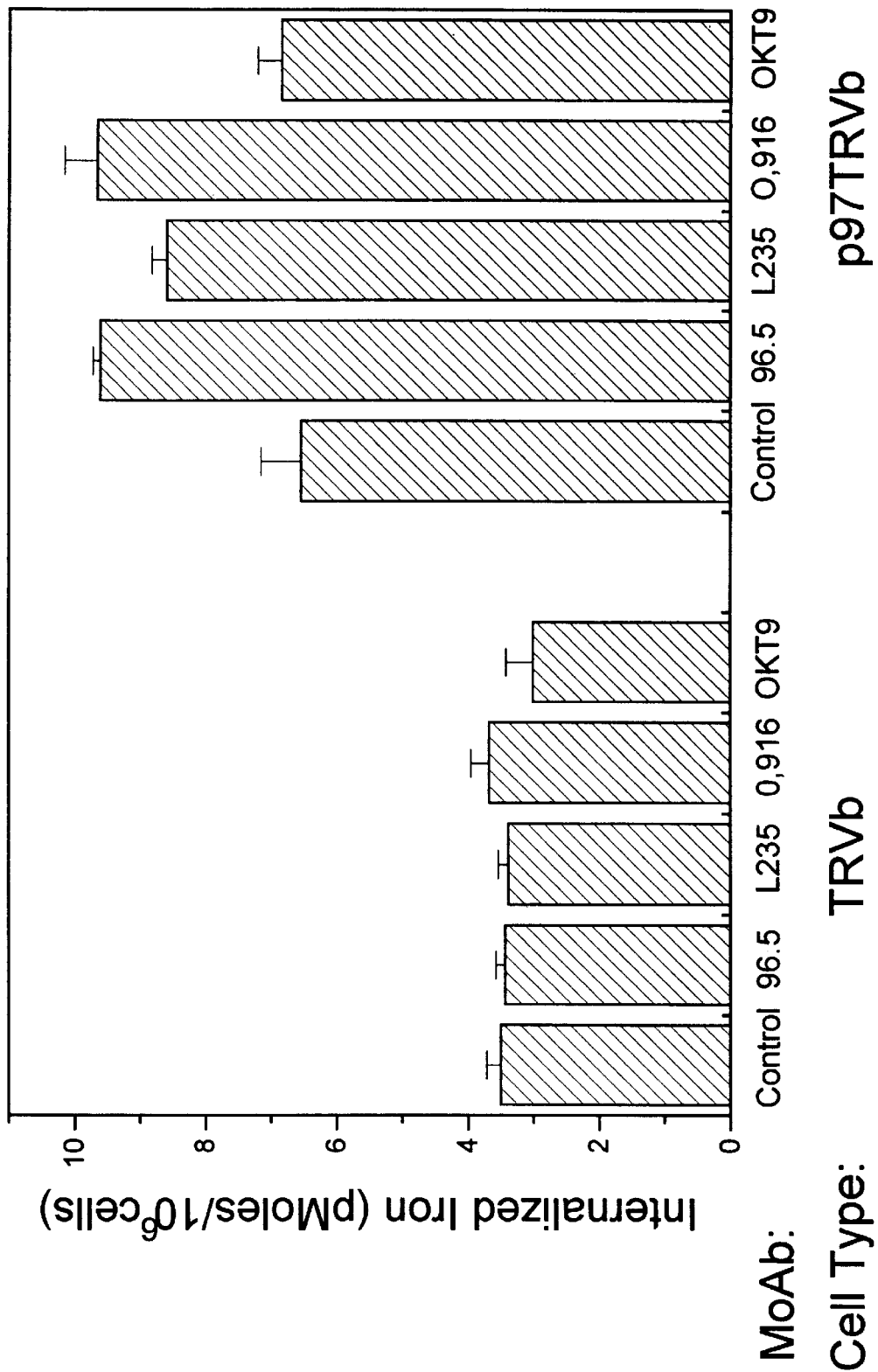

USE OF P97 AND IRON BINDING PROTEINS AS DIAGNOSTIC AND THERAPEUTIC AGENTS

This application is a divisional of application Ser. No. 08/520,933 filed on Aug. 31, 1995, now patented, U.S. Pat. No. 5,981,194, which is a continuation-in-part of U.S. Ser. No. 08/367,224, filed Mar. 30, 1999 now abandoned, (national phase entry of International Application No. PCT/CA93/00272), which is a continuation-in-part of U.S. Ser. No. 07/912,291, filed Jul. 10, 1992, abandoned which are incorporated herein by reference in their entirety.

FIELD OF THE INVENTION

TECHNICAL FIELD

The present invention relates to GPI-anchored p97, a secreted form of p97 and derivatives thereof; methods of using p97 in modulating iron transport, in the delivery of drugs, and in the treatment of conditions involving disturbances in iron metabolism; and methods of treating and diagnosing Alzheimer's Disease.

BACKGROUND OF THE INVENTION

Iron is a fundamental component required by all cells for growth and normal physiological processes (Crichton, R. R. and Charloteaux-Wauters, M. Eur. J. Biochem. 164:485–506 and Ponka, P. et al, Iron Transport and Storage, CRC Press, Boca Raton, Ann Arbor and Boston, 1990). Rapidly proliferating cells have a higher iron requirement than quiescent cells. In humans this iron requirement is thought to be provided by the binding of iron to the major serum iron-transporting protein, transferrin. Transferrin bound to iron can bind as a complex to the transferrin receptor expressed on the plasma membrane (Ponka, P. et al, Iron Transport and Storage, CRC Press, Boca Raton, Ann Arbor and Boston, 1990). After binding, the iron/transferrin/transferrin receptor complex remains membrane bound and is concentrated and then endocytosed via endocytotic vesicles. The endosomes become acidified and the iron is released from the complex within the cell and the apotransferrin remains bound to the receptor and is recycled to the surface where it is released to participate in the uptake of further iron into the cell (Kuhn L. C. et al., in Iron Transport and Storage, CRC Press, Boca Raton, Ann Arbor and Boston, 1990, p. 149).

Disruption of blood circulation deprives cells of oxygen and iron and may result in cell death. Deposition of iron from cell death, for example in ischemic injury may result in the generation of highly reactive and toxic superoxide or hydroxyl free radicals which can result in further tissue damage. Accordingly, the abundance of iron and its availability can greatly alter survival of damaged tissues. Rapidly proliferating cells, such as malignant cells, have an increased requirement for iron and must possess efficient mechanisms to obtain iron. Limiting the ability of malignant cells to acquire iron may provide a method of killing tumor cells or of modulating their uncontrolled cell growth.

Fe is rarely found in the blood plasma in the free state since it is highly toxic (Lauffer, R. B. (1992). Iron and Human Disease (Boca Ranton, Fla.: CRC Press)) and Tf serves mainly to mop up free Fe and to shuttle Fe, in a soluble non-toxic form, among the organs of the body. The established mechanism by which cells acquire Fe from Tf involves Tf binding to the transferrin receptor (TR) and Fe being internalized by the mechanism of receptor mediated endocytosis(RME) (Aisen, P. (1989). Iron carriers and iron proteins. In Iron carriers and iron proteins. T. M. Loehr, ed. (New York: VCH), pp. 353–372.; Thorstensen, K. and Romslo, I. Biochem. J., 271, 1–10, 1990). Since normal levels of serum Tf are high and about 99% of Fe in the plasma is bound to Tf (May, P. M. et al, (1980). Biological significance of low molecular weight iron(III) complexes. In Metal ions in biological systems. H. Sigel, ed. (New York: Marcel Dekker Inc.), pp. 29–76), Fe uptake is believed to be regulated by the level of TR expression (Thorstensen, K. and Romslo, I. Biochem. J., 271, 1–10, 1990; Young, S. P. and Aisen, P. Hepatology, 1, 114–119, 1981; Brissot, P. et al., J.Clin.Invest., 76, 1463–1470, 1985). Any free Fe generally circulates as low molecular weight complexes such as citrate (Grootveld, M. et al.,J. Biol. Chem., 264, 4417–4422, 1989) and certain amino acids or in association with other serum proteins such as albumin (May, P. M. et al, (1980). Biological significance of low molecular weight iron(III) complexes. In Metal ions in biological systems. H. Sigel, ed. (New York: Marcel Dekker Inc.), pp. 29–76). High levels of free Fe are usually only found in the plasma from dying cells or during iron overload disorders such as haemochromatosis (Smith, L., West. J. Med., 153, 296–308, 1990), thalassaemia (Modell, B. and Berdoukas, V. (1984). The clinical approach to thalessemia (New York: Grune and Stratton).) and atransferrinanemia (Kaplan, J. et al,J. Biol. Chem., 266, 2997–3004, 1991).

Based on studies where cells were grown in serum free, hence Tf-free, media and in cases of iron overload disorders it has become evident that some cells are able to obtain Fe independent of Tf and the RME pathway.

Although cellular iron uptake has been shown to be mediated mainly by the transferrin receptor (Doering, T. L. et al, J. Biol. Chem. 265:611–614, (1990), a non-transferrin-mediated pathway has been implicated for iron incorporation into cells, including leukemic cells (Basset, P. et al, Cancer Res. 46:1644–1647, 1986), HeLa cells (Sturrock, A. et al, J. Biol. Chem. 265:3139–3145, 1990), hepatocytes (Thorstensen, K., J. Biol. Chem. 263:16837–16841, 1988) and melanoma cells (Richardson, D. R. and Baker, E., Biochem. Biophys. Acta. 1053:1–12, 1990; Richardson, D. R. and Baker, E., Biochem. Biophys. Acta. 1091:294–302, 1991a and; Richardson, D. R. and Baker, E., Biochem. Biophys. Acta. 1093:20–28, 1991a).

p97, also known as melanotransferrin, a human melanoma-associated antigen, was one of the first cell surface markers associated with human skin cancer (Hellstrom, K. E. and Hellstrom, I. (1982) in Melanoma Antigens and Antibodies, Ed. Reisfield, R. and Ferrone, S., Plenum Press, New York, pp187–341). p97 is a monomeric membrane-associated protein with a molecular mass of 97,000 daltons (Brown, J. P. et al. J. Immunol. 127:539, 1981) and has been suggested as a melanoma specific marker (Estin, C. D. et al., Proc. Nat. Acad. Sci. U.S.A. 85:1052–1056, 1988). As well as being associated with the cell surface of melanomas and some other tumors and cell lines (Brown, J. P. et al., Proc. Nat. Acad. Sci. U.S.A. 78:539, 1981), p97 has also been found in certain fetal tissue (Woodbury, R. G. et al., Int. J. Cancer 27:145, 1981) and, more recently on endothelial cells of the human liver (Sciot, R., et al., Liver 9:110, 1989).

The primary structure of p97, deduced from its mRNA sequence indicates that it belongs to a group of closely related iron binding proteins found in vertebrates (Rose, T. M. et al., Proc. Nat. Acad. Sci. U.S.A. 83:1261, 1986). This family includes serum transferrin, lactoferrin and avian egg white ovotransferrin. Human p97 and lactoferrin share 40% sequence homology (Baker, E. N. et al., Trends Biochem.

Sci. 12:350, 1987), however, in contrast to the other molecules of the transferrin family, p97 is the only one which is directly associated with the cell membrane. The deduced sequence of p97 has, in addition to a transferrin-like domain, a hydrophobic segment at its C terminal which was thought to allow the molecule to be inserted into the plasma membrane (Rose, T. M. et al., Proc. Nat. Acad. Sci. USA 77:6114, 1980).

Detergent-solubilized p97 has been reported to bind iron (Doering, T. L. et al., J. Biol. Chem. 265:611–614, 1990). However, the role of p97 in iron transport is far from clear. Iron binding to p97 at the plasma membrane has not been demonstrated and, despite numerous studies, no evidence of a role for p97 in iron mediated transport has been obtained to date. Recent studies have concluded that p97 does not play a role in iron transport (Richardson, D. R. and Baker, E. Biochem. Biophys. Acta. 1103:275–280, 1992; Richardson, D. R. and Baker, E. Biochem. Biophys. Acta. 1093:20–28, 1991 and; Richardson, D. R. and Baker, E. Biochem. Biophys. Acta. 1091:294–302, 1991). The physiological role of p97 in normal and malignant cells has not been determined.

Alzheimer's Disease has become a significant health care problem due to increases in number and longevity of the elderly. In the near future, it is predicted that a significant proportion of the elderly population may be affected. The incidence of Alzheimer's Disease increases sharply from 1% at age 65, to over 20% at age 80. After age 85, nearly half of the population in the United States meets the diagnostic criteria for Alzheimer's Disease (Evans et al, J.A.M.A. 262:2551–2556, 1989).

There are two alternative "criteria" which are utilized to clinically diagnose Alzheimer's Disease: the DSM-IIIR criteria and the NINCDS-ADRDA criteria (which is an acronym for National Institute of Neurological and Communicative Disorders and Stroke (NINCDS) and the Alzheimer's Disease and Related Disorders Association (ADRDA); see McKhann et al., Neurology 34:939–944, 1984). Briefly, the criteria for diagnosis of Alzheimer's Disease under DSM-IIIR include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgement, abstract thought, and other higher cortical functions, and changes in personality and behaviour." (DSM-IIR, 1987).

In contrast, the NINCDS-ADRDA criteria sets forth three categories of Alzheimer's Disease, including "probable," "possible," and "definite" Alzheimer's Disease. Clinical diagnosis of "possible" Alzheimer's Disease may be made on the basis of a dementia syndrome, in the absence of other neurologic, psychiatric or systemic disorders sufficient to cause dementia. Criteria for the clinical diagnosis of "probable" Alzheimer's Disease include (a) dementia established by clinical examination and documented by a test such as the Mini-Mental test (Foldstein et al., J. Psych. Res. 12:189–198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia. The criteria for definite diagnosis of Alzheimer's Disease include histopathologic evidence obtained from a biopsy, or after autopsy. Since confirmation of definite Alzheimer's Disease requires histological examination from a brain biopsy specimen (which is often difficult to obtain), it is rarely used for early diagnosis of Alzheimer's Disease.

Neuropathologic diagnosis of Alzheimer's Disease is typically based upon the numbers of plaques and tangles in the neurocortex (frontal, temporal, and parietal lobes), hippocampus and amygdala (Khachaturian, Arch. Neurol. 42:1097–1105; Esiri, "Anatomical Criteria for the Biopsy diagnosis of Alzheimer's Disease," Alzheimer's Disease, Current Research in Early Diagnosis, Becker and Giacobini (eds.), pp. 239–252, 1990). A diagnosis of Alzheimer's Disease based upon neuropathologic criteria alone, however, is often difficult because there are a significant number of plaques and tangles in the neurocortex, hippocampus, and amygdala of normal elderly people. In addition, the density of neocortical plaques and tangles has only a rough correlation with the degree of dementia.

Some researchers have suggested the use of quantitative electroencephalographic analysis (EEG) to diagnose Alzheimer's Disease. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159–167, 1990) in order to arrive at diagnosis of Alzheimer's Disease. This method, however, produces results which are difficult to interpret without control data (such as a routine EEG) from the very same patient prior to onset of Alzheimer's Disease.

Other researchers have attempted to diagnose Alzheimer's Disease by quantifying the degree of neural atrophy, since such atrophy is generally accepted as a consequence of Alzheimer's Disease. Examples of these methods include computed tomographic scanning (CT), and magnetic resonance imaging (MRI) (Leedom and Miller, "CT, MRI, and NMR Spectroscopy in Alzheimer's Disease," Alzheimer's Disease, Current Research in Early Diagnosis, Becker and Giacobini (eds.), pp. 297– 313, 1990). Although these methods show promise, they cannot yet be utilized to reliably differentiate Alzheimer's patients from normal elderly people (Bird, Prog. Neurobiol. 19:91–115, 1982; Wilson et al., Neurology 32:1054–1057, 1982; Yerby et al., Neurology 35:1316–1320, 1985; Luxenberg et al., J. Neurol. Sci. 13:570–572, 1986; and Friedland et al., Ann. Int. Med. 109:298–311, 1988).

Other researchers have noticed that patients with Alzheimer's Disease often exhibit decreased cerebral blood flow or metabolism in the posterior temporoparietal cerebral cortex. These researchers have therefore attempted to measure decreased blood flow or metabolism by positron emission tomography (PET) (Parks and Becker, "Positron Emission Tomography and Neuropsychological Studies in Dementia," Alzheimer's Disease's, Current Research in Early Diagnosis, Becker and Giacobini (eds.), pp. 315–327, 1990), single photon emission computed tomography (SPECT) (Mena et al., "SPECT Studies in Alzheimer's Type Dementia Patients," Alzheimer's Disease, Current Research in Early Diagnosis, Becker and Giacobini (eds.), pp. 339–355, 1990), and xenon inhalation methods (Jagust et al., Neurology 38:909–912; Prohovnik et al., Neurology 38:931–937; and Waldemar et al., Senile Dementias: II International Symposium, pp. 399407, 1988). These methods, however, are apparently insensitive to damage in structures such as the hippocampus and amygdala, which are believed to be the sites of damage in the earliest stages of Alzheimer's Disease's. Therefore, patients may exhibit significant memory loss, and yet exhibit no abnormalities in cerebral blood flow or metabolism.

Various researchers have also attempted to immunologically diagnose Alzheimer's Disease (Wolozin, "Immunochemical Approaches to the Diagnosis of Alzheimer's Disease," Alzheimer's Disease, Current Research in Early Diagnosis, Becker and Giacobini (eds.), pp. 217–235, 1990). Wolozin and coworkers (Wolozin et al., Science 232:648–650, 1986) produced a monoclonal antibody "Alz50," that reacts with a 68-kDa protein "A68," which is expressed in the plaques and neuron tangles of patients with Alzheimer's Disease. Using the antibody Alz50 and Western blot analysis, A68 was detected in the cerebral spinal fluid (CSF) of some Alzheimer's patients and not in the CSF of normal elderly patients (Wolozin and Davies, Ann. Neurol. 22:521–526, 1987). This method, however, is not presently suitable as a definitive method for diagnosing Alzheimer's Disease because detectable levels of A68 could not be found in all patients with "probable" Alzheimer's Disease (as defined above).

Some researchers have attempted to identify genetic markers for Alzheimer's Disease. While genetic abnormality in a few families has been traced to chromosome 21 (St. George-Hyslop et al., Science 235:885–890, 1987), such markers on chromosome 21 have not been found in other families with early and late onset of Alzheimer's Disease (Schellenberg et al., Science 241:1507–1510, 1988).

Others have attempted to identify neurochemical markers of Alzheimer's Disease. Neurochemical markers which have been associated with Alzheimer's Disease include reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137–156, 1990), reduced somatostatin (Tamminga et al., Neurology 37:161–165, 1987), a negative relation between serotonin and 5-hydroxyindoleacetic acid (Volicer et al., Arch Neurol. 42:127–129, 1985), greater probenecid-induced rise in homovanyllic acid (Gibson et al., Arch. Neurol. 42:489–492, 1985) and reduced neuron-specific enolase (Cutler et al., Arch. Neurol. 43:153–154, 1986). None of these markers, however, is believed to be sensitive or specific enough to provide an early diagnosis of Alzheimer's Disease (see Elby, "Early Diagnosis of Alzheimer's Disease," Alzheimer's Disease: Current Research in Early Diagnosis, Becker and Giacobini (eds.), Taylor & Francis (pub.), N.Y., pp. 19–30, 1990).

Alzheimer's Disease has been difficult to not only diagnose, but to treat. The discovery that levels of acetylcholinestease are markedly reduced in the cortex and hippocampus of patients with Alzheimer's Disease (Bowen et al., Brain 99:459–496, 1976) has resulted in the development of a number of pharmaceutical compounds which restore or replace cholinergic function. Examples of such compounds include tacrine (THA) (Summers et al., N. Eng. J. Med. 315:1241–1245); oral administration of choline and lecithin (Etienne et al. Neurology 31:1552–1554, 1981); huperzine A and B (Tank et al., "Studies on the Nootropic Effects of Huperzine A and B: Two Selective AChE Inhibitors," Current Research in Alzheimer's Therapy, Giacobini and Becker (eds.), pp. 289–393, 1988); galanthamine (Domino, "Galanthamine: Another Look at an Old Cholinesterase Inhibitor," Current Research in Alzheimer's Therapy, Giacobini and Becker (eds.), pp. 295–303, 1988); methanesulfonyl fluoride (Moss et al., "Methanesulfonyl Fluoride: A CNS Selective Cholinesterase Inhibitor," Current Research in Alzheimer's Therapy, Giacobini and Becker (eds.), pp. 305–314, 1988); physostigmine, an irreversible inhibitor of acetylcholinesterase Johns et al., Banbury Report 15:435–449, 1983); and physostigmine derivatives (Brufani et al., "From Physostigmine to Physostigmine Derivatives as New Inhibitors of Cholinesterase," Current Research in Alzheimer's Therapy, Giacobini and Becker (eds.), pp. 343–352, 1988). In general, however, these compounds have met with only limited success.

Given the increasing number of individuals with Alzheimer's Disease, it is critical that new methods for monitoring and treating the disease be discovered. The present invention provides methods for monitoring Alzheimer's Disease, as well as methods and compositions for treating Alzheimer's Disease. These methods and compositions overcome disadvantages of prior methods and compositions, and further provide other related advantages.

SUMMARY OF THE INVENTION

The present inventors have surprisingly found that p97 is a GPI-anchored protein. The GPI-anchored protein may be reacted with an enzyme that cleaves at the GPI-anchor to provide a cleaved GPI-anchored p97 protein. The cleaved p97 can be prepared using a novel semi-continuous process. Other cleaved GPI-anchored proteins can also be prepared using the novel semi-continuous process.

The present inventors have also unexpectedly found a soluble form of p97. This soluble form is hydrophilic and is present exclusively in the aqueous phase after Triton-X-114 phase separation; it does not contain ethanolamine, and it has a slower rate of transport than GPI-anchored p97. The soluble form of p97 may be present in biological fluids such as cerebrospinal fluid (CSF), blood, or urine. The present inventors have also shown that p97 is involved in iron transport. GPI-anchored p97 expressed on the cell surface has been shown to bind iron and bound iron is released after phospholipase treatment. Significantly, the present inventors have demonstrated a transferrin independent p97-mediated iron uptake pathway. The presence of p97 was found to double iron uptake into CHO cells.

p97 and transferrin were also found to be expressed in brain capillary endothelial cells in normal controls and pathological brains. Most of the p97 molecule is intracellular and its expression is coincidental with the transferrin receptor. EM also indicates that p97 crosses the blood brain barrier. p97 has also been shown to bind to a soluble form of transferrin receptor. Results of affinity chromatography experiments suggest that there is a receptor which co-recognizes p97 and the transferrin receptor.

These findings suggest that p97 may be used to modulate iron uptake in cells. Iron uptake in cells could be modulated by varying the concentration of p97, inhibiting p97 binding to iron or to the transferrin receptor, or inhibiting binding to the receptor which co-recognizes p97 and the transferrin receptor. Accordingly, p97, and stimulants, agonists or antagonists of p97 may be useful in the treatment of conditions where there is a disturbance in iron metabolism. For example, such substances may be useful in the treatment of conditions such as haemochromatosis, neurodegenerative diseases, ischemic tissue damage, including ischemic stroke or trauma, heart disease, and tumors, in particular skin cancer.

The finding of a role for p97 in iron uptake and iron transport, and in particular the finding that p97 can cross the blood brain barrier, suggests that p97 can be used to transport substances such as therapeutic agents across the blood brain, blood eye or blood placenta barrier.

The present inventors have significantly shown that Alzheimer's patients have elevated levels of p97 in their serum and cerebrospinal fluid and that p97 levels increase with duration of the disease. The levels of p97 in patient samples may thus be used to diagnose and to monitor the progression of the disease and the efficacy of therapeutic treatments for Alzheimer's Disease.

The present inventors have also significantly found that reactive microgial cells associated with senile plaques in Alzheimer's Disease express p97 and transferrin receptor. Therefore, p97 and transferrin receptor can be used in the diagnosis of Alzheimer's Disease. The finding that microgial cells which deposit the amyloid protein have a high level of proteins which operate in procurement of iron also suggests methods of treatment of Alzheimer's disease based on depletion of iron from these cells using substances such as p97, transferrin, and iron chelators, for example, lactoferrin, ferritin, ovotransferrin.

Broadly stated the present invention relates to a GPI-anchored form of p97 and derivatives thereof. The invention also contemplates methods of preparing p97 and derivatives thereof.

Within one embodiment of the present invention methods are provided for preparing a cleaved form of the GPI-anchored p97, comprising incubating a cell which expresses p97 on its surface with an enzyme that cleaves glycosyl-phosphatidylinositol (GPI) anchors to produce the cleaved form of the GPI-anchored p97, and isolating the cleaved form. Within the context of the present invention, phospholipase cleaved p97 or cleaved p97 refers to p97 which has been cleaved from its glycosyl-phosphatidylinositol (GPI) anchor.

Preferably, a semi-continuous process for preparing cleaved GPI-anchored proteins such as cleaved GPI-anchored p97 is utilized. The semi-continuous process comprises (a) providing a cell capable of expressing a GPI-anchored protein on its surface; (b) growing the cell under conditions suitable for the expression of the GPI-anchored protein on the cell surface; (c) incubating the cell with an enzyme which is capable of cleaving the GPI anchor to form a cleaved protein; (d) recovering the cleaved protein; and (e) repeating steps (b) to (d) until a desired amount of cleaved protein is obtained. Preferably, the cell is genetically engineered to express the GPI-anchored protein.

Within another aspect of the present invention, isolated soluble p97 is provided. The soluble form of p97 is hydrophilic; present exclusively in the aqueous phase after Triton-X-114 phase separation; it does not contain ethanolamine, and it has a slower rate of transport than GPI-anchored p97. The soluble p97 can be isolated based on its hydrophilic property.

Within yet another aspect of the present invention an isolated DNA sequence is provided which encodes truncated p97. Within various embodiments of the invention, the sequence which encodes truncated p97 consists essentially of the sequence which encodes the C-terminal domain of p97, or the sequence which encodes the N-terminal domain of p97. Also provided are recombinant expression vectors for expressing such sequences, as well as the host cells which contain these expression vectors.

Within one embodiment of the invention, the p97 is labelled, the label being selected from the group consisting of fluorescent molecules, enzymes, luminescent molecules, radionuclides, substances having therapeutic activity, and toxins.

The invention also contemplates methods of modulating iron metabolism using p97. In particular, the present invention relates to a method for treating conditions involving disturbances in iron metabolism comprising administering an iron modulating amount of p97, or a stimulant, agonist or antagonist of p97. Conditions involving disturbances in iron metabolism which may be treated using the method of the invention include haemochromatosis, neurodegenerative diseases, ischemic tissue damage, including ischemic stroke or trauma, heart disease, and tumors, in particular skin cancer.

A substance which is a stimulant, agonist or antagonist of p97 may be identified by determining the effect of the substance on the binding activity of p97 and iron, or p97 and the transferrin receptor, or the effect of the substance on the expression of p97 in cells capable of expressing p97 including cells genetically engineered to express p97 on there surface.

The invention therefore in one aspect relates to a method of identifying stimulants, agonists or antagonists of p97 comprising reacting a substance suspected of being a stimulant, agonist or antagonist of p97 with p97 and iron under conditions such that p97 is capable of binding to the iron; measuring the amount of p97 bound to iron; and determining the effect of the substance by comparing the amount of p97 bound to iron with an amount determined for a control. The invention also relates to a method of identifying stimulants, agonists or antagonists of p97 comprising reacting a substance suspected of being a stimulant, agonist or antagonist of p97 with p97 and transferrin receptor under conditions such that p97 is capable of binding to the transferrin receptor; measuring the amount of p97 bound to transferrin receptor; and determining the effect of the substance by comparing the amount of p97 bound to transferrin receptor with an amount determined for a control.

The invention also relates to a method of identifying stimulants, agonists or antagonists of p97 comprising reacting a substance suspected of being a stimulant, agonist or antagonist of p97 with a cell which expresses p97, measuring the amount of p97 expressed by the cell, and determining the effect of the substance by comparing the amount of expression of p97 with an amount determined for a control.

The invention further relates to a method for identifying a stimulant, agonist or antagonist of p97-mediated iron uptake comprising: incubating a cell expressing p97 on its surface and a substance suspected of being a stimulant, agonist or antagonist of p97 in the presence of iron and in the absence of transferrin, measuring the amount of iron uptake into the cell and identifying a stimulant, agonist or antagonist of p97-mediated iron uptake by comparing the amount of iron uptake in the cell with the amount of iron uptake in a cell from a control incubation in the absence of the substance.

In an embodiment, the cell is incubated in the presence of labelled iron and the amount of iron uptake in the cell is determined by measuring the amount of labelled iron in the cell. The label may be, for example, radioactive or fluorescent.

The invention also relates to a composition for delivering an agent across the blood brain barrier comprising p97 or a substance which is capable of specifically binding to p97, in association with the agent and a pharmaceutically acceptable carrier or diluent. The p97 or substance, preferably antibody to p97 may be conjugated to the agent or a p97 fusion protein may be used in the composition. The agent may be a substance having therapeutic activity such as a growth factor or lymphokine. The invention also relates to a method of delivering an agent across the blood brain barrier comprising administering the agent in association with p97 or antibody to p97. The composition of the invention may also be used for delivering an agent across the blood eye or blood placenta barrier.

Within one aspect of the present invention, a composition for the preservation of organs intended for transplantation is provided comprising p97 or a derivative thereof in a pharmaceutically acceptable organ preservation solution. The invention also contemplates a method for preserving an organ intended for transplantation using the composition.

The present invention also provides methods for diagnosing and monitoring Alzheimer's Disease, as well as compositions and methods suitable for treating Alzheimer's Disease. Within one aspect of the present invention, methods are provided for monitoring Alzheimer's Disease, comprising detecting the presence of soluble p97 in a patient. Within various embodiments, the p97 may be detected in various bodily fluids, including for example, urine, blood, serum and cerebral spinal fluid. Various methods may be utilized to detect p97, including, for example, radioimmunoassays, competitive assays, and enzyme linked immunosorbant assays (ELISA) such as the sandwich assay. Within other aspects of the present invention, methods are provided for monitoring Alzheimer's Disease comprising detecting the presence of transferrin receptors, and/or detecting the presence of p97, on microglial cells associated with amyloid plaques in a patient.

The invention also provides a method for diagnosing or monitoring Alzheimer's Disease in a patient, comprising determining the concentration of p97 in a sample from the patient and comparing the determined concentration to the level of p97 in other samples from the patient, control subjects and/or Alzheimer's Disease patients. The concentration of p97 may be determined by a radioimmunoassay, immunofluorescent assay, competitive assay, or enzyme linked immunosorbant assay. In an embodiment, the sample is a serum sample or a cerebrospinal fluid sample. The sample may be from a patient being monitored to assess the efficacy of a therapeutic treatment, such as the administration of a pharmaceutical composition, for Alzheimer's Disease.

The invention also contemplates a bispecific antibody capable of binding to a microglial cell which expresses p97 and/or transferrin receptor and to a label preferably a detectable substance, or a substance having toxic or therapeutic activity. The bispecific antibody may be prepared by forming a hybrid hybridoma from a fusion between a first cell line which produces a first monoclonal antibody which is capable of binding to a microglial cell which expresses p97 and/or transferrin receptor and a second cell line which produces a second monoclonal antibody which is capable of binding to the label.

The invention further contemplates a tetrameric immunological complex of a first monoclonal antibody which is capable of binding to a microglial cell which expresses p97 and/or transferrin receptor and a second monoclonal antibody which is capable of binding to a label preferably a detectable substance or a substance having toxic or therapeutic activity wherein the first and second antibody are from a first animal species, conjugated to form a cyclic tetramer with two monoclonal antibodies of a second animal species directed against the Fc-fragment of the antibodies of the first animal species.

The tetrameric immunological complex may be formed by reacting a first monoclonal antibody which is capable of binding to a microglial cell which expresses p97 and/or transferrin receptor and a second monoclonal antibody which is capable of binding to a label preferably a detectable substance or a substance having toxic or therapeutic activity wherein the first and second antibody are from a first animal species, with an about equimolar amount of antibodies of a second animal species which are directed against the Fc-fragments of the antibodies of the first animal species and isolating the tetrameric complex formed.

The bispecific antibodies and tetrameric antibody complexes of the invention when coupled with a detectable substance may be used to identify microglial cells associated with Alzheimer's Disease.

The present invention also relates to a method of treating Alzheimer's Disease in a patient comprising depleting iron in the brain, preferably the microglial cells of the patient. In a preferred method of the invention, the treatment comprises administering p97, transferrin, transferrin receptor, or substances which are capable of reacting with p97 or transferrin receptor, preferably antibodies to p97 and transferrin or iron chelators. Exemplary iron chelators are lactoferrin, ferritin, and ovotransferrin.

Within another aspect of the present invention, a method for treating Alzheimer's Disease is provided comprising the step of administering to a patient labelled p97 or a substance which is capable of binding to p97 conjugated to a label. In one embodiment a labelled antibody to p97, or a bispecfic antibody complex or tetrameric antibody complex specific for a label and p97, and which are conjugated to the label, may be administered. The label may be a toxin selected from the group consisting of ricin, abrin, diptheria toxin, cholera toxin, gelonin, pokeweed antiviral protein, tritin, Shigella toxin, and Pseudomonas exotoxin A.

Within another aspect of the present invention a method for treating Alzheimer's Disease is also provided comprising the step of administering to a patient a transferrin receptor blocking agent. Examples of transferrin receptor blocking agents include a transferrin receptor blocking antibody, p97 and transferrin. An antibody to the transferrin receptor conjugated to a label as described herein or a bispecfic antibody complex or a tetrameric antibody complex specific for the transferrin receptor and the label, and which is conjugated to the label, may also be used to treat Alzheimer's Disease.

Within another aspect of the present invention, methods are provided for treating Alzheimer's Disease comprising administering an antibody which blocks the binding of p97 to iron. Within one embodiment, the antibody is a human antibody.

The invention also contemplates a method of purifying microglial cells associated with Alzheimer's Disease beta amyloid plaques comprising reacting a sample suspected of containing microglial cells associated with Alzheimer's Disease beta amyloid plaques with a substance which is capable of specifically binding p97 or transferrin receptor under conditions such that the microglial cells bind to the substance; and isolating the microglial cells bound to the substance. The isolated cells may be transformed to produce a cell line. The cell line may be used to test for substances which affect the microglial cells associated with Alzheimer's Disease beta amyloid plaques. Accordingly, substances may be identified which are effective in the treatment of Alzheimer's Disease.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

FIGS. 2A–F (SEQ ID NO:1) depicts the nucleic acid sequence of p97.

FIG. 22 is a series of autoradiograms showing soluble and membrane bound p97 and transferrin receptor.

FIG. 42 is a graph showing the effect of pre-treating TRVb and p97TRVb cells with mABs against p97 on Fe uptake.

DETAILED DESCRIPTION OF THE INVENTION

Figure 1:
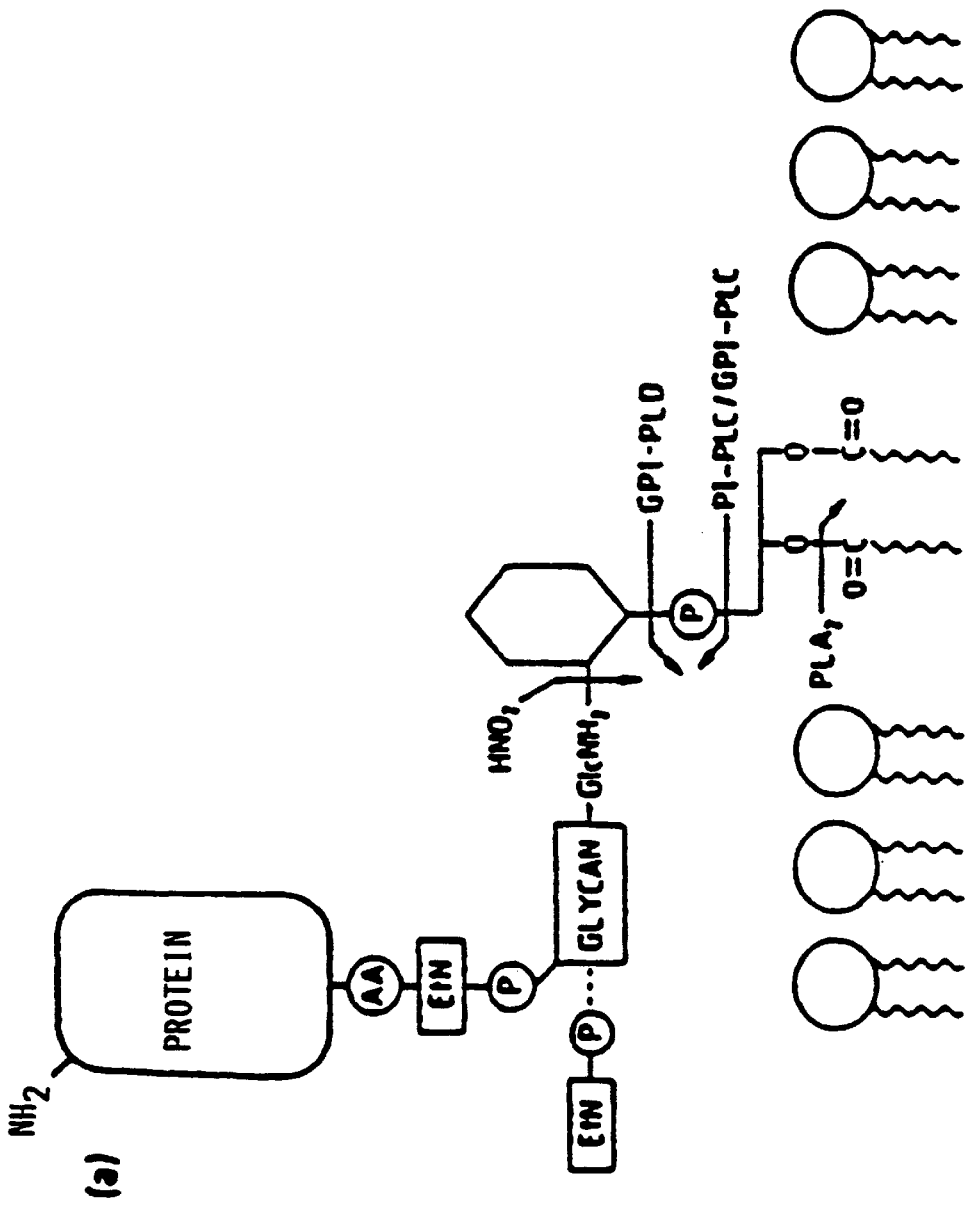
FIG. 1 depicts the structure of a GPI anchor.

As hereinbefore mentioned the present inventors have surprisingly found that membrane-bound p-97 is a GPI-anchored protein. Accordingly, the present invention provides a GPI-anchored p-97 which is associated with the plasma membrane. The GPI-anchored p-97 is characterised in that it is sensitive to enzymes known to cleave GPI-anchors, and therefore a cleaved form of p97 can be removed from the membrane using enzymes such as bacterial PI-PLC. The present invention therefore also provides a method for isolating a phospholipase cleaved form of p-97 from the cell surface by cleavage with an enzyme which is capable of cleaving a GPI-anchor, preferably PI-PLC. The presence of the GPI anchor may be shown by sensitivity to PI-PLC, insensitivity to pronase, partitioning behaviour in the detergent phase of Triton X-114 and metabolic labelling with [$^3$H] ethanolamine.

The present inventors have also surprisingly found a soluble form of p-97. The soluble form of p-97 is present exclusively in the aqueous phase after Triton-X114 phase separation and does not contain a GPI-anchor or ethanolamine. Cell surface biotinylation of membrane bound p-97 confirmed that GPI-anchored p-97 is not shed in soluble form into the medium and that p-97 exists in two different forms, a membrane-bound form and a soluble form. The surprisng discovery of a soluble form of p-97 suggests a role for soluble p-97 in binding iron in solution and then mediating its uptake via a receptor system, similar to the transferrin receptor system.

The biological activity of the membrane-bound, soluble and phopholipase cleaved forms of p97 and derivatives thereof, may be readily established by one of ordinary skill in the art by, for example, iron binding assays. For example, the biological activity of soluble p97 may be determined by titrating aliquots of iron (ferric nitrilotriacetate or "FeNTA") into solutions containing 1.2 mg/ml iron-free p97 in 0.025 M Tris-HCl, 0.01 M NaHCO$_3$, 0.1 M NaCl, pH 7.8. Iron binding to soluble p97 may be determined by an increase in adsorbance (measured at 420 nm). Within another embodiment, the biological activity of p97 which is anchored to a cell membrane may also be determined (see Brown et al., Nature 296:171–173, 1982). Briefly, within one embodiment melanoma cells (e.g., SK-MEL-28) are washed three times with 25 ml of phosphite-buffered saline (PBS), pH 7.2, and incubated at 37° for 1 hr. with 10 μl PBS containing 2 mM NaHCO$_3$, 1 mM sodium citrate and 10$^7$ c.p.m. of either $^{59}$FeCl$_3$ or $^{55}$FeCl$_3$. Cells are washed and then lysed in 40 ml of 20 mM Tris-HCl buffer, pH 8.0, containing 100 mM NaCl, 1 mM EDTA and 0.5% Nonidet-P40, supplemented with 1 mM phenylmethylsulphonyl fluoride, followed by centrifugation at 300,000 g at 4° C. for one hour. An anti-p97 antibody (e.g., L235 or 96.5 as described below) is added to the lysate at a concentration of about 5 μg/ml, which is then passed through a 0.2 ml column of protein-A-Sepharose CL-4B at 4° C. The column is then washed, and eluted with 2 ml of 100 mM citrate buffer (pH 5), containing 0.5% Nonidet P40. Retention of $^{59}$Fe or $^{55}$Fe in the column indicates binding of the p97 to iron.

Preparation of P97

As noted above, within one aspect of the present invention methods are provided for preparing a cleaved form of p97 comprising the step of incubating a cell which expresses p97 on its surface with an enzyme that cleaves phospholipid anchors. Briefly, prior to the present invention, it was unknown that the p97 protein is anchored to the cell surface by a glycosyl-phosphatidylinositol (GPI) anchor (see FIG. 1). Various enzymes display a specificity toward GPI linkages, and thus may be utilized within the context of the present invention to cleave the GPI anchor. Representative examples include bacterial phosphatidyl inositol-phospholipase Cs (PI-PLCs) (see Ikezawa et al., Methods Enzymol. 71:731–741, 1981; Taguchi et al., Arch. Biochem.

Biophys. 186:196–201, 1978; Low, Methods Enzymol. 71:741–746, 1981), eukaryotic GPI-PLCs (see Ferguson et al., J. Biol. Chem. 260:4963–68, 1985; Bulow et al., FEBS Lett. 187:105–110, 1985), and eukaryotic phospholipase Ds (GPI-PLD$_2$ or "PLD") (see Malik et al., Biochem. J. 240:519–527, 1986) (see generally, Ferguson and Williams, "Cell-Surface Anchoring of Proteins via Glycosyl-Phosphatidylinositol Structures," Ann. Rev. Biochem. 57:285–320,1988).

A particularly preferred GPI enzyme is phospholipase C (PI-PLC) which may be obtained either from bacterial sources (see Low, "Phospholipase Purification and Quantification" The Practical Approach Series: Cumulative Methods Index, Rickwood and Hames, eds. IRC Press, Oxford, N.Y., N.Y., 1991; Kupe et al., Eur. J. Biochem. 185:151–155, 1989; Volwerk et al., J. Cell. Biochem. 39:315–325, 1989) or from recombinant sources (Koke et al., Protein Expression and Purification 2:51–58, 1991; and Henner et al., Nuc. Acids Res. 16:10383, 1986).

p97 may be cleaved from the surface of a variety of cells including, for example, SK-MEL-28 cells (American Type Culture Collection No. HTB 72) (see also Real et al., PNAS USA 85:3965–3969, 1988; and Real et al., Can. Res. 45:44014411, 1985), as well as cells which have been infected or transfected with a vector which expresses p97 (see below). If desired, the cleaved (solubilized) p97 may then be purified utilizing techniques which are also described in more detail below, including affinity chromatography.

The soluble form of p97 may be prepared by culturing cells which contain the soluble p97 through the log phase of the cell's growth and collecting the supernatant. Preferably, the supernatant is collected prior to the time the cells reach confluency. Soluble p97 may then be purified as described below, in order to yield isolated soluble p97. Methods for purifying the soluble p97 can be selected based on the hydrophilic property of the soluble p97. For example, the soluble p97 may be readily obtained by Triton X-114 Phase Separation.

Within another aspect of the present invention, p97 or derivatives thereof may be recombinantly produced. Within one embodiment, DNA which codes for p97 may be obtained by polymerase chain reaction (PCR) amplification of the p97 sequence (see generally, U.S. Pat. Nos. 4,683,202, 4,683,195 and 4,800,159; see also PCR Technology: Principles and Applications for DNA Amplification, Erlich (ed.), Stockton Press, 1989). Briefly, double-stranded DNA from cells which express p97 (e.g., SK-MEL-28 cells) is denatured by heating in the presence of heat stable Taq polymerase, sequence specific DNA primers such as 5' GCGGACTTCCTCGG 3' (SEQUENCE ID NO: 4) and 5' TCGCGAGCTTCCT 3' (SEQUENCE ID NO: 5), ATP, CTP, GTP and TIP. Double-stranded DNA is produced when synthesis is complete. This cycle may be repeated many times, resulting in a factorial amplification of p97 DNA. The amplified p97 DNA may then be readily inserted into an expression vector as described below.

Alternatively, DNA which codes for p97 may be isolated using the cloning techniques described by Brown et al. in UK Patent Application No. GB 2188 637. Clones which contain sequences encoding p97 cDNA have been deposited with the American Type Culture Collection (ATCC) under deposit numbers CRL 8985 (PMTp97b) and CRL 9304 (pSVp97a).

Within the context of the present invention, p97 and derivatives thereof may include various structural forms of the primary protein which retain biological activity. For example, a p97 protein may be in the form of acidic or basic salts, or in neutral form. In addition, individual amino acid residues may be modified by oxidation or reduction. Furthermore, various substitutions, deletions, or additions may be made to the amino acid or DNA nucleic acid sequences, the net effect of which is to retain biological activity of p97. Due to code degeneracy, for example, there may be considerable variation in nucleotide sequences encoding the same amino acid sequence.

Other derivatives of p97 within the scope of this invention include conjugates of p97 along with other molecules such as proteins or polypeptides. This may be accomplished, for example, by the synthesis of N-terminal or C-terminal fusion proteins to facilitate purification or identification of p97 (see U.S. Pat. No. 4,851,341, see also, Hopp et al., Bio/Technology 6:1204, 1988.) Thus, fusion proteins may be prepared by fusing through recombinant techniques the N-terminal or C-terminal of p97 or other portions thereof, and the sequence of a selected protein with a desired biological function. The resultant fusion proteins contain p97 or a portion thereof fused to the selected protein. Examples of proteins which may be selected to prepare fusion proteins include lymphokines such as gamma interferon, tumor necrosis factor, IL-1, IL-2,IL-3, Il-4, IL-5, IL-6, IL-7, IL-8, IL-9, IL-10, IL-11, GM-CSF, CSF-1 and G-CSF. Particularly preferred molecules include nerve growth factor and the Fc portion of immunoglobulin molecules.

Sequences which encode the above-described molecules may generally be otained from a variety of sources, including for example, depositories which contain plasmids encoding sequences including the American Type Culture Collection (ATCC, Rockville Md.), and the British Biotechnology Limited (Cowley, Oxford England). Examples of such plasmids include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon,) ATCC Nos. 31902 and 39517 (which contains sequences encoding beta interferon), ATCC No. 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC Nos. 57592 (which contains sequences encoding Interleukin-4). ATCC Nos. 59394 and 59395 (which contain sequences encoding Interleukin-5), and ATCC No. 67153 (which contains sequences encoding Interleukin-6.

Within a particularly preferred embodiment of the invention, P97 is cloned into an expression vector as a fusion gene with the constant region of human immunoglobulin γ1. Briefly, the expression vectors pNUTΔGH and pVL1393 are prepared for cloning by digestion with SmaI followed by dephosphorylation by calf intestinal alkaline phosphatase. The linear product is isolated after agarose gel electrophoresis. The p97 genes are then generated by polymerase chain reaction using the cloned p97 cDNA as a template. In particular, the fusion p97 is synthesized from WJ47, the 5' PCR primer encompassing coordinates 36 to 60 (coordinates based on cDNA map) and additionally containing a SnaBI restriction site. The sequence of WJ47 is 5'-GCG C TA CGT ACT CGA GGC CCC AGC CAG CCC CGA CGG CGC C-3' (Seq ID:10). The 3' primer for the fusion p97, WJ46, encompasses coordinates 2172 to 2193 and additionally contains a BclI restriction site. The sequence of WJ46 is 5'-CGC GTA CGT ATG ATC ACC CGA GCA CTG CTG AGA CGA C-3' (Seq ID:9). The resulting p97 amplified product lacks the hydrophobic domain of p97. Following amplification this product is digested with SnaBI and BclI.

The constant region of human γ1 gene is then prepared from pUCB7Ig monomer. Briefly, the $C_H$ gene is isolated by digestion with XbaI which cuts at the 3' end of the gene followed by treatment with *E. coli* DNA polymerase I in the presence of all four dNTPs in order to create a blunt end. The plasmid is then digested with BclI which cuts at the 5' end of the gene. The fragment containing the heavy chain gene is isolated after electrophoresis in an agarose gel.

The fusion p97 amplified fragment is inserted into each prepared vector along with the heavy chain fragment. Orientation of the resulting plasmids is determined by PCR with one priming oligo which anneals to vector sequence and the other priming oligo which anneals to the insert sequence. Alternatively, appropriate restriction digests can be performed to verify the orientation. The sequence of the fusion p97/immunoglobulin constant region gene can be verified by DNA sequencing.

Within one embodiment of the present invention, truncated derivatives of p97 are provided. For example, site-directed mutagenesis may be performed with oligo WJ31 5'CTCAGAGGGCCGCTGCGCCC-3'(SEQ ID NO:6) in order to delete the C-terminal hydrophobic domain beyond nucleotide 2219 (see FIG. 2), or with oligo WJ32 5' CCA GCG CAG CTAGCGGGGGCAG3' (SEQ ID NO:7) in order to introduce an Nhe I site and a STOP codon in the region of nucleotides 1146–1166, and thereby also constructing a truncated form of p97 comprising only the N-terminal domain. Similarly, mutagenesis may also be performed on p97 such that only the C-terminal domain is expressed. Within one embodiment, Xho sites are inserted by mutagenesis with oligo WJ 5' ACA CCAGCGCAGCTC-GAGGGGCAGCCG 3' (SEQ ID NO:8) into both the N-terminal and C-terminal domains, allowing subsequent deletion of the N-terminal domain. Various other restriction enzymes may also be utilized within the context of the present invention in order to construct deletion or truncation derivatives of p97, including for example, Eco RI.

Mutations in nucleotide sequences constructed for expression of derivatives of p97 must preserve the reading frame phase of the coding sequences. Furthermore, the mutations will preferably not create complementary regions that could hybridize to produce secondary mRNA structures, such as loops or hairpins, which would adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, as noted above oligonucleotide-directed site-specific mutagenesis procedures may be employed to provide an altered gene having particular codons altered according to the substitution, deletion, or insertion required. Deletion or truncation derivatives of p97 may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (Molecular cloning A Laboratory Manual, 2d Ed., Cold Spring Harbor Laboratory Press, 1989).

Within a particularly preferred embodiment of the invention p97 is cloned into an expression vector as a truncated gene. Briefly, the expression vectors pNUTΔGH and pVL1393 are prepared for cloning by digestion with SMAI followed by dephosphorylation by calf intestinal alkaline phosphatase. The linear product of the vector is isolated after agarose gel electrophoresis. The p97 gene is then generated by polymerase chain reaction (PCR) using the cloned p97 cDNA as a template. The truncated p97 is synthesized from WJ47, the 5' PCR primer encompassing coordinates 36 to 60 (coordinates based on cDNA map) and additionally containing a SnaBI restriction site. The sequence of WJ47 is 5'-GCG CTA CGT ACT CGA GGC CCC AGC CAG CCC CGA CGG CGC C-3' (Seq ID:10). The 3' primer, WJ48, encompasses coordinates 2172 to 2193 and additionally contains both a TGA termination codon and a SnaBI restriction site. The DNA sequence of WJ48 is 5'-CGC G TACGT ATG ATC ATC AGC CCG AGC ACT GCT GAG ACG AC-3' (Seq ID:11). Following amplification the truncated p97 product is digested with SnaBI and inserted into pNUTΔGH and pVL1393 by a T4 DNA ligase reaction. Orientations of the resulting plasmids may be determined by PCR using one priming oligo which anneals to the vector sequence and the other priming oligo which anneals to the insert sequence. Alternatively, appropriate restriction digests can be performed to verify the orientation. Expression of the amplified sequence results in the production of a p97 protein lacking the hydrophobic domain.

As noted above, the present invention provides recombinant expression vectors which include either synthetic, or cDNA-derived DNA fragments encoding p97 or derivatives thereof, which are operably linked to suitable transcriptional or translational regulatory elements. Suitable regulatory elements may be derived from a variety of sources, including bacterial, fungal, viral, mammalian, or insect genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector.

DNA sequences encoding p97 may be expressed by a wide variety of prokaryotic and eukaryotic host cells, including bacterial, mammalian, yeast or other fungi, viral, plant, or insect cells. Methods for transforming or transfecting such cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Bacterial host cells suitable for carrying out the present invention include *E. coli, B. subtilis, Salmonella typhimurium,* and various species within the genus' Pseudomonas, Streptomyces, and Staphylococcus, as well as many other bacterial species well known to one of ordinary skill in the art. Representative examples of bacterial host cells include DH5α (Stratagene, Lajolla, Calif.), JM109 ATCC No. 53323, HB101 ATCC No. 33694, and MN294.

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.).

Yeast and fungi host cells suitable for carrying out the present invention include, among others *Saccharomyces cerevisiae,* the genera Pichia or Kluyveromyces and various species of the genus Aspergillus. Suitable expression vectors for yeast and fungi include, among others, $YC_p50$ (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter, as well as other transcriptional and translational control sequences. Common promoters include SV40, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., supra).

Given the teachings provided herein, promoters, terminators, and methods for introducing expression vectors of an appropriate type into plant, avian, and insect cells may also be readily accomplished. For example, within one embodiment, p97 or derivatives thereof may be expressed from plant cells (see Sinkar et al., J. Biosci (Bangalore) 11:47–58, 1987, which reviews the use of *Agrobacterium rhizogenes* vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Within a particularly preferred embodiment of the invention, p97 is expressed from baculoviruses, (see Example 2 below) (see also Luckow and Summers, Bio/Technology 6:47, 1988; Atkinson et al., Petic. Sci 28:215–224, 1990). Use of baculoviruses such as AcMNPV is particularly preferred due to the expression of GPI-cleaved forms of p97 from the host insect cells.

p97 may be prepared by culturing the host/vector systems described above, in order to express the recombinant p97. Recombinantly produced p97 may be further purified as described in more detail below.

Alternatively, p97 may be expressed in non-human transgenic animals such as mice, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866). Briefly, an expression unit, including a DNA sequence to be expressed together with appropriately positioned expression control sequences, is introduced into pronuclei of fertilized eggs. Introduction of DNA is commonly done by microinjection. Integration of the injected DNA is detected by blot analysis of DNA from tissue samples, typically samples of tail tissue. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene. Animals which develop tissue-specific expression of p97 (e.g., in the brain) may be utilized as disease models for Alzheimer's Disease. Alternatively, yeast artificial chromosomes (YACs) may be utilized to introduce DNA into embryo-derived stem cells by fusion with yeast spheroblasts carrying the YAC (see Capecchi, Nature 362:255–258, 1993; Jakobovits et al., Nature 362:255–258, 1993). Utilizing such methods, animals may be developed which express p97 in tissue (e.g. the brain). and which are therefore useful as a disease model for Alzheimer's Disease. Animals which do not produce p97 may be developed in order to study the function of p97.

Continuous Process for Producing GPI-Anchored Proteins

The present invention provides a semi-continuous process to recover heterologous proteins at increased concentrations and purities. Proteins attached to mammalian cell membranes by GPI anchors can be selectively released into the supernatant by enzymes displaying a specificity toward GPI linkages which are discussed in detail above. The present inventors have determined that this process may be repeated and used to recover increased amounts of protein. Cells may be repeatedly harvested by separating cell growth and protein expression from the enzyme treatment. The method of the invention may be carried out with a culture of cells expressing a GPI-anchored protein, preferably a cell line genetically engineered to produce the GPI anchored protein to be prepared. GPI anchored proteins which may be produced using the method of the invention include hydrolytic enzymes for example Alkaline phosphatase, 5'-Nucleotidase, Acetylcholinesterase (AChE), Trehalase, Alkaline phosphodiesterase I, gp63 proteinase, Dipeptidase, p76 proteinase, Aminopeptidase P, Lipoprotein lipase; Mammalian antigens for example, Thy-1, Thy-3, RT-6, Qa, Ly-6, MEM-43, Carcinoembryonic antigen (CEA), NCA, Blast-1, MRC OX-45, CD14, Mo3, CD48; protozoal antigens for example Ssp-4, 90 kDa glycoprotein, Variant surface glycoprotein (VSG) Procyclin, surface antigens, 195 kDa antigen, Transferring receptor, P30; Cell-cell interaction proteins for example, LFA-3, Heparan sulfate proteoglycan, Neural cell adhesion molecule, Contact site A, PH-20, F11; and Decay accelerating factor (DAF), 130 kDa hepatoma glycoprotein, 34 kDa growth factor, scrapie prion protein, GP-2, CD16 (Fcγ receptor III), Oligodendrocyte-myelin protein, Antigen 117, 125 kDa glycoprotein C8 binding protein, Folate binding protein, Sgp-1, Sgp-2, 26 kDa glycoprotein 150 kDa glycoprotein, 82 and 68 kDa proteins, surface antigens, I-Antigenic glycoprotein GP-3, preferably p97.

In a preferred embodiment of the invention CHO cells genetically engineered to express the GPI-anchored p97 were grown in culture. The GPI-anchored protein may be harvested by a brief incubation with an enzyme capable of cleaving the GPI anchor, such enzymes are kown in the art (Ferguson, M. J., Ann. Rev. Bichem. 57:285–320, 1988) and representative examples are described above. Preferably PI-PLC or GPI-PLC are used in the method of the invention. The cleaved soluble protein may be recovered from the medium and the cells returned to growth medium for further expression of the protein. Cycles of growth and harvest may be repeated until sufficient quantities of the protein are obtained.

In a preferred embodiment, CHO cells may be grown in spinner cultures on porous microcarriers such as Cultispher-GH porous microcarriers, solid microcarriers such as Cytodex-1, or spheroids.

Purification of P97 p97 and derivatives thereof, as well as soluble p97, may be readily purified given the teaching provided herein. Briefly, p97 may be purified either from supernatants containing solubilized p97, or from cultured host/vector systems as described above. A variety of purification steps, used either alone or in combination may be utilized to purify p97. For example, supernatants obtained by solubilizing p97, or from host/vector cultures as described above, may be readily concentrated using commercially available protein concentration filters, for example, an Amicon or Millipore Pellicon ultrafiltration unit, or by "salting out" the protein followed by dialysis. In addition to concentration, supernatants (or concentrates) may be applied to an affinity purification matrix such as an anti-p97 antibody which is bound to a suitable support. Alternatively, an anion exchange resin may be employed, for example, a matrix or substrate having pendant diethylaminoethyl (DEAE) groups. Representative matrices include acrylamide, agarose, dextran, cellulose or other types commonly employed in protein purification. Similarly, cation exchangers may be employed which utilize various insoluble matrices such as sulfopropyl or carboxymethyl groups.

Finally, one or more reversed-phase high performance liquid chromatography (RP-HPLC) steps employing hydrophobic RP-HPLC media, e.g, silica gel having pendant methyl or other alipathic groups, can be employed to further purify a glucagon receptor composition.

Within the context of the present invention, "isolated" or "purified," as used to define the purity of p97, means that the protein is substantially free of other proteins of natural or endogenous origin, and contains less than about 1% by mass of protein contaminants due to the residual of production processes. p97 may be considered "isolated" if it is detectable as a single protein band upon SDS-PAGE, followed by staining with Coomasie Blue.

Preparation of Antibodies

Antibodies which are reactive against p97 are well known in the art. Representative examples include L235 (ATCC No. HB 8466; see Real et al., Cancer Res. 45:4401 4411, 1985), 4.1, 8.2, 96.5 and 118.1 (see Brown et al., J. Imm. 127(2):539–546, 1981; and Brown et al., PNAS USA 78(1): 539–543, 1981) and 33B6E4.

Alternatively, p97 or derivatives thereof, soluble p97, or cells which contain p97 on their surface (including cells transfected with p97 DNA) may be utilized to prepare antibodies. Within the context of the present invention, antibodies are understood to include monoclonal antibodies, polyclonal antibodies, antibody fragments (e.g., Fab, and F(ab')$_2$ and recombinantly produced binding partners. Antibodies are understood to be reactive against p97 if it binds with a $K_a$ of greater than or equal to $10^{-7}$ M. As will be appreciated by one of ordinary skill in the art, antibodies may be developed which not only bind to a ligand such as p97, but which also block the biological activity of the ligand (e.g, by blocking the binding of iron or transferrin receptor to p97).

Polyclonal antibodies may be readily generated by one of ordinary skill in the art from a variety of warm-blooded animals such as horses, cows, various fowl, rabbits, mice, or rats. Briefly, p97 is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to p97. Particularly preferred polyclonal antisera will give a signal on one of these assays that is at least three times greater than background. Once the titer of the animal has reached a plateau in terms of its reactivity to p97, larger quantities of antisera may be readily obtained either by weekly bleedings, or by exsanguinating the animal.

Monoclonal antibodies may also be readily generated using conventional techniques (see U.S. Pat. No. RE 32,011, U.S. Pat. Nos. 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Briefly, within one embodiment a subject animal such as a rat or mouse is injected with p97. The p97 may be admixed with an adjuvant such as Freund's complete or incomplete adjuvant in order to increase the resultant immune response. Between one and three weeks after the initial immunization the animal may be reimmunized with another booster immunization, and tested for reactivity to p97 using assays described above. Once the animal has plateaued in its reactivity to p97, it is sacrificed, and organs which contain large numbers of B cells such as the spleen and lymph nodes are harvested.

Cells which are obtained from the immunized animal may be immortalized by transfection with a virus such as the Epstein bar virus (EBV) (see Glasky and Reading, Hybridoma 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells may be placed into culture plates containing a suitable medium, such as RPMI 1640, or DMEM (Dulbecco's Modified Eagles Medium) URH Biosciences, Lenexa, Kans.), as well as additional ingredients, such as Fetal Bovine Serum (FBS, ie., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against p97. A wide variety of assays may be utilized to determine the presence of antibodies which are reactive against p97, including for example Countercurrent Immuno-Electrophoresis, Radioimmunoassays, Radioimmunoprecipitations, Enzyme-Linked Immuno-Sorbent Assays (ELISA), Dot Blot assays, Inhibition or Competition Assays, and sandwich assays (see U.S. Pat. Nos. 4,376,110 and 4,186,530; see also Antibodies: A Laboratory Manual, Harlow and Lane (eds.), Cold Spring Harbor Laboratory Press, 1988). Following several clonal dilutions and reassays, a hybridoma producing antibodies reactive against p97 may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al. supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Labelling of P97 p97, soluble p97, cleaved p97, and GPI-anchored p97, and derivatives thereof, soluble p97, and antibodies which are described above may be labelled with a variety of molecules, including for example, fluorescent molecules, toxins, substances having therapeutic activity i.e. therapeutic agents, luminescent molecules, enzymes, and radionuclides. Representative examples of fluorescent molecules include fluorescien, phycoerythrin, rodamine, Texas red and luciferase. Representative examples of toxins include ricin, abrin diptheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I131, Re-186, Re-188, Au-198, Au-199, Pb-203, At-211, Pb-212 and Bi-212. Examples of suitable enzymes include horseradish peroxidase, biotin, alkaline phosphatase, β-galactosidase, or acetylcholinesterase; and an example of a luminescent material includes luminol. In addition, the p97 or antibodies described above may also be labelled or conjugated to one partner of a ligand binding pair. Representative examples include avidin-biotin, and riboflavin-riboflavin binding protein.

Methods for conjugating or labelling the p97 or antibodies discussed above with the representative labels set forth above may be readily accomplished by one of ordinary skill in the art (see Trichothecene Antibody Conjugate, U.S. Pat. No. 4,744,981,; Antibody Conjugate, U.S. Pat. No. 5,106,951; Fluorogenic Materials and Labelling Techniques, U.S. Pat. No. 4,018,884; Metal Radionuclide Labelled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, Methods In Enzymology, Vol. 34, Affinity Techniques, Enzyme Purification: Part B, Jakoby and Wichek (eds.), Academic Press, New York, p. 30, 1974; see also Wilchek and Bayer, "The Avidin-Biotin Complex in Bioanalytical Applications," AnaL Biochem. 171:1–32, 1988).

In some embodiments of the present invention, transferrin, transferrin receptor or antibodies to transferrin receptor are labelled using the techniques generally known in the art and briefly mentioned above.

P-97 Mediated Iron Transport

A. Treatment of Conditions Involving Disturbances of Iron Metabolism

The present inventors have identified at the molecular level the components of an alternative pathway to the RME of transferrin (Tf) and the transferrin receptor (TR) for Fe uptake and have clearly identified p97 as being the Fe binding protein mediating this pathway. The present inventors have convincingly shown that p97 is able to bind and internalize Fe into cells from Fe-citrate but not from Fe-Tf. p97 is, therefore, identified as the first membrane-bound protein that internalizes Fe in the absence of Tf and the TR. This pathway is able to internalize Fe at a rate equivalent to Fe uptake from Tf via the RME pathway. As described in Example 16 herein, the presence of p97 on transformed cells of the CHO cell line, TRVb, which expresses a defective hamster transferrin, resulted in over a doubling of the measured internalized Fe uptake. This effect was clearly due to increased internalization of Fe and not the presence of pronase resistant p97 on the cell surface, since Fe bound to this pronase resistant p97 was less than 10% of difference in internalized Fe after 4 hours incubation. Furthermore, the internalized Fe was very sensitive to temperature with a ten-fold reduction in internalized Fe at 4oC, whereas the membrane-bound Fe did not change, although it took longer at 4oC to reach the saturated level of bound Fe at 37oC. This together with the fact that the internalization of Fe was saturatable at an Fe concentration of 2.5 $\mu$M indicates an energy dependent carrier mediated process rather than passive diffusion or simple fluid phase pinocytosis. The fact that PI-PLC treatment of the cells prior to Fe uptake experiments resulted in over a 50% reduction in internalized Fe by p97 transfected cells and the fact that MoAbs against p97 caused modulation of the Fe uptake confirmed the role of p97 in Fe uptake. The binding of Fe to p97 and the internalization of Fe is consistent with a GPI-anchored protein being involved in the binding and internalization of a ligand.

As blood plasma usually contains very little free Fe, the p97 Fe uptake route may not function in the normal recirculation of Fe within the body. It may, however, play a role during Fe overload conditions acting as an Fe scavenger to reduce toxic levels of Fe. This pathway does not appear to be tightly regulated since in iron overload disorders it is the cells with apparently elevated levels of p97 that are most likely to be damaged due to excessive Fe uptake (Sciot, R. et al.,Liver, 9, 110–119, 1989; Grace, N. D. and Powell, L. W.Gastroenterology, 67, 1257–1259, 1974). In the body, p97 may be used to scavenge free Fe and to reduce the toxic effect of Fe released during normal cell death. p97 may also function to pump iron into cells for use in the production of nitric oxide which affects nerve transmission and which may result in cell death.

As hereinbefore mentioned, the present invention provides a method for treating conditions involving disturbances of iron metabolism by modulating p-97 mediated transport and iron uptake. p-97, agonists, antagonists and stimulants of p-97 including antibodies to p-97 and antisense to p97, may be used to modulate p97 mediated transport and iron uptake. Antibodies to p97 and their preparation have been described above. Other substances which affect p97 i.e. agonists, antagonists and stimulants of p-97 may be identified by determining the affect of the substance on the binding activity of p97 with iron or the transferrin receptor, or the affect of the substance on the expression of p97 in cells, including cells genetically engineered to express p97 such as p97aWTBc3, p97aWTBc7, and SEK-MEL-28.

The invention therefore relates to a method of identifying stimulants, agonists or antagonists of p97 comprising reacting a substance suspected of being a stimulant, agonist or antagonist of p97 with p97 and iron under conditions such that p97 is capable of binding to the iron; measuring the amount of p97 bound to iron, and determining the effect of the substance by comparing the amount of p97 bound to iron with an amount determined for a control. The method of the invention may use the iron binding assays which are described above. The p97 which may be used in the method of the invention may be the GPI-anchored p97, soluble p97, cleaved p97 or derivatives thereof, preferably recombinant p97. In the method of the invention the amount of p97 bound to iron may be determined by measuring the amount of p97 bound to iron, unbound p97 or unbound iron. p97 bound to iron may be isolated by conventional isolation techniques, for example, salting out, chromatography, electrophoresis, gel filtration, fractionation, absorption, polyacrylamide gel electrophoresis, agglutination, or combinations thereof. To facilitate the measurement of p97 bound to iron or of unbound p97, antibody against p97 may be utilized.

The invention also relates to a method of identifying stimulants, agonists or antagonists of p97 comprising reacting a substance suspected of being a stimulant, agonist or antagonist of p97 with p97 and transferrin receptor under conditions such that p97 is capable of binding to the transferrin receptor; measuring the amount of p97 bound to transferrin receptor; and determining the effect of the substance by comparing the amount of p97 bound to transferrin receptor with an amount determined for a control. The p97 which may be used in this method includes the GPI-anchored p97, soluble p97, or cleaved p97 or derivatives thereof, preferably recombinant p97. In the method of the invention the amount of p97 bound to transferrin receptor may be determined by measuring the amount of p97 bound to transferrin receptor, unbound p97 or unbound transferrin receptor. p97 bound to transferrin receptor may be isolated by conventional isolation techniques, for example, salting out, chromatography, electrophoresis, gel filtration, fractionation, absorption, polyacrylamide gel electrophoresis, agglutination, or combinations thereof. To facilitate the measurement of p97 bound to transferrin receptor or of unbound p97, or unbound transferrin receptor antibody against p97 or transferrin receptor which are described above may be utilized.

The invention also relates to a method of identifying stimulants, agonists or antagonists of p97 comprising reacting a substance suspected of being a stimulant, agonist or antagonist of p97 with a cell which expresses p97, measuring the amount of p97 expressed by the cell, and determining the effect of the substance by comparing the amount of p97 expression with an amount determined for a control. The p97 which may be used in this method includes the GPI-anchored p97, soluble p97, cleaved p97 or derivatives thereof, preferably recombinant p97. Cells expressing p97 which may be used in the method of the invention are p97aWTBc3, p97aWTBc7, and SK-MEL-28. The amount of p97 expressed on the cell may be determined by using methods known in the art, preferably labelled antibodies to p97 may be used to measure p97 expression.

In an embodiment, the invention also relates to a method for identifying a stimulant, agonist or antagonist of p97-mediated iron uptake comprising: incubating a cell expressing p97 on its surface and a substance suspected of being a stimulant, agonist or antagonist of p97 in the presence of iron and in the absence of transferrin, measuring the amount of iron uptake into the cell and identifying a stimulant, agonist or antagonist of p97-mediated iron uptake by comparing the amount of iron uptake in the cell with the amount of iron uptake in a cell from a control incubation in the absence of the substance.

The present inventors have described p97-mediated iron uptake in the Examples herein. Iron uptake refers to the internalization of iron into the cell across the cell plasma membrane.

It will be appreciated that a wide range of cells may be employed in the method of the invention. Cells may be selected which express endogenous p-97. Alternatively a cell lacking in p-97 expression may be selected and transfected with an expression vector encoding p-97. In an embodiment, a cell may be selected which is lacking in the transferrin receptor and lacking in p-97 expression, such as the CHO cell line TRVb. Transfection of such cells with p-97 as described herein provides cells in which p-97-mediated iron uptake may be studied in the complete absence of the transferrin/transferrin receptor pathway of iron uptake. However, cells having the transferrin receptor may also be used in the method of the invention as the incubation is preferably carried out in the absence of transferrin, which is required for the transferrin/transferrin receptor pathway.

In the method, the iron may be present as a salt, such as iron citrate and in an embodiment of the method, the cell is incubated in the presence of labelled iron, such as radioactively labelled iron, for example 59Fe. Iron may also be labelled by conjugating iron to a label, preferably a detectable label. Examples of detectable labels are provided herein.

Iron uptake may be determined by measuring the amount of iron uptake into the cell. Iron in the cell may be measured, for example, by quantitating the amount of labelled iron in the cell. Iron which is bound to p-97 on the cell surface may be removed, for example, by treatment with pronase or PI-PLC.

In order to distinguish p97-mediated iron uptake from iron uptake by the transferrin/transferrin receptor pathway, the cell is preferably incubated in the absence of transferrin. However, other suitable controls may be employed to distinguish p97-mediated iron uptake from iron uptake by the transferrin/transferrin receptor pathway based on the characteristics of the p97-mediated iron transport described herein. For example, control cells may be treated with PI-PLC prior to incubation with iron and the decrease in uptake resulting from the removal of GPI anchored p-97 from the cell surface may be determined.

It is anticipated that p97 may play a role in the binding and uptake of other metals such as zinc or aluminum and thus may play a role in modulating or regulating Alzheimer's disease proteins or metaloproteins such as zinc dependent metaloproteins.

Stimulants, agonists or antagonists of p97-mediated iron uptake may be identified by the effect which they have on the amount of iron uptake into the cell.

In an embodiment of the method of the invention stimulants, agonists or antagonists of p97-mediated iron uptake from iron citrate may be identified in the complete absence of transferrin and the transferrin receptor using the CHO cell line TRVb, transfected with human p97.

Conditions which involve disturbances in iron metabolism which may be treated using the methods of the invention and using stimulants, agonists and antagonists of p97-mediated iron uptake, are for example, those involving excessive iron absorption from the diet, defects in iron uptake into cells, excessive iron uptake into cells or those requiring regular treatment by blood transfusion (e.g. dyserythropoietic anaemias, in particular thalassaemia disorders. Examples of conditions are haemochromatosis, neurodegenerative diseases (e.g. Alzheimer's Disease, Huntington's Disease and Parkinson's Disease), ischemic tissue damage, heart disease and tumors, inflammation and infections (see Pippard, J. Clinical Use of Iron Chelation, in Iron in Immunity, Cancer and Inflammation ed. M. de Sousa and J. H. Brock, 1989,John Wiley & Sons, which is incorporated herein by reference).

Haemochromatosis is a human iron absorptive disease which involves the absorption and deposition of an excessive amount of iron which results in tissue damage (Smith, L. H., Western J. Med. 153:296–308, 1990). It is unlikely that the defect, which may be carried by as many as one in 20 individuals is a structural defect in the p97 molecule because the p97 molecule is encoded on chromosome 3 in humans while the haemochromatosis gene is linked to the ferritin and HLA A genes on chromosome 6 (Zappone, E. et al.,Hum. Genet. 86(6):557–61, 1991). However, the defect operates in trans and the defect may effect p97 expression. The present invention provides a method for the diagnosis of haemochromatosis by assaying for increased expression of p97 by affected cells and for increased levels of soluble p97 in bodily fluids. The present invention also provides p97, or antagonists or agonists of p97 as a treatment for haemochromatosis. The efficacy of treatment may be tested in animal models for haemochromatosis, such as the hypo-transferrinemic rodent model described in Craven, C. M. et al Proc. Nat. Acad. Sci. USA 84:3457–3461, 1987.

The present invention provides p-97 or antagonists or agonists of p97 and p97-mediated iron uptake as a treatment for traumatic and ischemic tissue damage, such as that resulting from heart conditions and stroke. Deposition of iron resulting from cell death may result in the generation of highly reactive and toxic superoxide or hydroxyl free radicals which facilitate further tissue damage. Thus the availabilty and abundance of iron can greatly alter the survival of damaged tissues. The efficacy of p-97 or antagonists or agonists of p97 as a treatment for traumatic and ischemic tissue damage may be tested in experiments with perfused organs, such as heart and lung, which upon transplantation suffer reperfusion injury from iron mediated generation of hydroxyl free radicals. Compounds of the invention may also be tested in animal models of heart and stroke disease, such as the Levine model (Levine, S., Amer. J. Pathol. 36:1–17, 1960) or the carbon monoxide hypoxia-oligemia model described in MacMillan V. Brain Research 151:353–368, 1978.

Rapidly proliferating malignant cells have an increased requirement for iron and must have efficient mechanisms for iron transport. An antibody-ricin conjugate prepared from a monoclonal antibody specific for transferrin receptor has been used to inhibit protein synthesis and cause cell death in a human leukemic cell line (Trowbridge, I. S. and Domingo, D. L., Cancer Surveys 1:543–556. Antibodies to transferrin receptor have also been used as pharmacological anti-tumor agents to directly block cell proliferation (Trowbridge, I. S and Lopez, F. Proc. Nat. Acad. Sci. USA 79:1175–1179, 1982). However, anti-transferrin receptor antibodies do not significantly inhibit the growth of melanoma cells (Trowbridge, I. S. et al, Methods in Enzymol. 14:265–279.

Since p97 is found expressed at high levels on tumour cells, especially melanoma cells, these rapidly proliferating cells may be using p97 as a primary pathway to increase the Fe uptake. Although, under physiological circumstances where almost all Fe is bound to serum Tf, it is not clear how these cells are able to obtain the excess Fe. However, it is known that metastasing tumour cells secrete various enzymes that act to lyse neighbouring normal cells and that p97 may be used to scavenge the released Fe.

The present invention has demonstrated that p-97, a melanoma associated antigen plays a role in the transport and cellular internalisation of iron. The present invention therefore provides a method of inhibiting protein synthesis and tumor growth and of killing tumor cells expressing p-97, such as melanoma cells, by interfering with p-97 mediated uptake of iron, for example by providing antagonists of p-97 mediated iron uptake. It is also contemplated to specifically target and kill tumor cells expressing p-97 using monoclonal antibodies specific to p-97, such as L235. Antibodies to p-97 may also be conjugated to a label, preferably a toxin, most preferably a cytotoxic agent. Agents cytotoxic to tumor cells which may be conjugated to antibodies are well known in the art and include conventional cytotoxic drugs such as daunomycin or adriamycin and various toxins of plant or bacterial origin such as ricin, abrin or diphtheria toxin (Trowbridge, I. S. and Domingo, D. L., Cancer Surveys 1:543–556).

The present invention demonstrates that the melanoma associated p-97 is involved in the transport and internalisation of iron and provides a treatment for melanoma by modulating iron transport with p-97 antagonists, antibodies directed against p97 and with other compounds effective in the removal of iron, such as iron chelators. Iron chelators are known in the art which attach ligands to iron and include lactoferrin, ferritin, porphyrin and ovotransferrin.

Within another aspect of the present invention, methods and compositions suitable for treating melanomas are provided. Briefly, as noted above, p97 was originally discovered as a cell surface marker associated with human skin cancer. Within one aspect of the present invention, a method is provided for treating skin cancer comprising administering a toxin conjugated to soluble p97. Various toxins may be conjugated to soluble p97 as described above, including, for example, bacterial exotoxins and plant toxins. Particularly preferred toxins include ricin, abrin, diphtheria toxin, cholera toxin, gelonin, pokeweed antiviral protein, tritin, Shigella toxin, and Pseudomonas exotoxin A.

Alternatively, skin cancer may also be treated or diagnosed by administering a radiolabeled soluble p97 to a patient. Briefly, the soluble p97 may be either radiolabeled directly, or conjugated to a radiolabel. Preferred radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, 20 Pb-212 and Bi-212.

B. Preservation of Organs

Transplantation of organs is a definitive treatment for patients with end stage liver, kidney, heart and pancreas disease. However, there are a number of problems associated with the ex vivo storage of cadaveric organs and thus the viability of organ transplants. One such problem is damage to the organ resulting from iron. Accordingly, p97 may be used in organ preservation solutions to control iron levels and thus improve organ preservation.

The present invention therefore relates to a composition for the preservation of an organ intended for transplantation comprising p97 or a derivative thereof in a pharmaceutically acceptable organ preservation solution. The terms "preservation", or "preserving" used herein include but are not limited to perfusion, flushing and storage of an organ intended for transplantation.

The pharmaceutically acceptable organ preservation solution used in the composition of the invention may be any commonly used preservation solution. The ingredients of exemplary commonly used preservation solutions are set forth in U.S. Pat. No. 4,920,004; Collins et al., Lancet 2:1219, 1969; Sacks, S. A., Lancet 1:1024, 1973; Siegel, N. J. et al., Am. J. Physiol. 245:F530, 1983: Stromski, M. E. et al, Am. J. Physiol. 250:F834, 1986; Sumpio, B. E. et al., Am. J. Physiol. 247:R1047; Stromski, M. E. et al., Am J. Physiol, 250:F834, 1986); Belzer et al., Transpl. Proc. 16:161, 1984; U.S. Pat. Nos. 4,920,004; 4,798,824 and 4,873,230; U.S. Pat. Nos. 4,879,283; and 4,879,283 (the University of Wisconsin solution or UW solution).

The present invention also contemplates a method for preserving an organ intended for transplantation using the composition described above. Generally, an organ may be flushed during harvesting and after its removal from the donor with a composition of the invention. The organ is then stored in a composition of the invention under hypothermic conditions. In the alternative, after initial flushing, the organ may be connected to a pump wherein a cold perfusate of the composition of the invention is continuously circulated through the organ. Prior to transplantation the organ may be flushed again with the composition.

The preservation method and composition of the invention may be used to preserve any organ intended for transplantation, preferably an intraabdominal organ such as the liver, pancreas and kidney.

C. Drug Delivery Compositions and Methods

A major obstacle to testing drugs for use in the treatment of Alzheimer's disease and other neurological conditions is the lack of an efficient non-invasive means to deliver drugs or chemotherapeutic agents across the blood brain barrier and other blood barriers, such as the blood eye and blood placenta barriers. Drug and solute transport into the brain from blood is restricted by the limited permeability of the brain capillary endothelial wall due to the endothelial tight junctions and the lack of aqueous pores in the endothelial cells (Pardridge, W. M. et al., J. Pharmacol. & Expt. Therapeut. 253:884–891, 1990). The present invention provides a mechanism for delivering blood-borne agents into the brain across the blood brain barrier. The inventors have demonstrated that p-97 is expressed on the surface of the brain capillary endothelial cells in a pattern similar to that of transferrin receptor. The present inventors have importantly demonstrated that p97 binds to the transferrin receptor. p97 on the endothelial cells appears to be involved in the transport of iron across the blood brain barrier, possibly via an interaction with the transferrin receptor.

The invention contemplates a composition for delivering agents into the brain from the blood via a p-97 mediated uptake mechanism. The delivery composition may contain p97 conjugated to the agent; a p97 fusion protein comprising p97 or a portion thereof fused to the agent; or a substance capable of binding to p97, e.g. anti-p-97 antibody, conjugated to the agent, and a pharmaceutically acceptable carrier or diluent.

p97 which may be used in the delivery compositions of the invention include soluble p97, cleaved p97, and derivatives and portions thereof. Antibodies to p97 which may be used in the delivery composition have been described above. Representative examples of p97 fusion proteins include a p97-nerve growth factor fusion protein, a p97-Ig fusion protein, or an anti-p97 antibody-nerve growth factor or Ig fusion protein. p97, antibodies to p-97 and stimulants, agonists or antagonists of p97 may also be used directly as therapeutic agents as described herein.

Agents which may be used in the delivery composition of the invention are those known for the treatment of neurological conditions or suspected of having activity against neurological conditions. Accordingly, neurological conditions which may be treated using the delivery compositions of the invention include those conditions susceptible to therapeutics delivered into the brain and include, for example tumors of the brain, neurodegenerative diseases (Alzheimer's disease, Parkinson's disease, Huntington's disease), demyelinating diseases (e.g. multiple sclerosis), amyotrophic lateral sclerosis, bacterial and viral infections, and deficiency diseases (e.g. Wernicke's Disease and nutritional polyneuropathy).

Suitable cytotoxic therapeutic agents for the treatment of tumors are discussed elsewhere in the application.

Possible therapeutic agents which can be used in the compositions of the invention for the treatment of Alzheimer's disease include iron sequestering compounds, such as iron chelators, and anti-inflammatory drugs. Proteins such as growth factors, including nerve growth factor, brain-derived neurotrophic factor, and lymphokines including gamma interferon, tumor necrosis factor, the interleukins, GM-CSF, CSF-1, and G-CSF are also contemplated as therapeutic agents for use in the delivery compositions of the invention. Cholinergic neurons of the basal forebrain, which degenerate in Alzheimer's disease, are known to depend on nerve growth factor for their survival. Nerve growth factor has also been shown to rescue degenerating cholinergic neurons in the forebrain (Hefti, F. J. Neurosci 6:2155, 1986).

The delivery compositions may be prepared using techniques known in the art. For example, antibodies and therapeutic agents which are proteins may be conjugated by methods known in the art, such as the introduction of a sulfhydryl group on the antibody and the introduction of a cross-linker containing a reactive thiol group on to the protein agent through carboxyl groups (Wawizynczak, E. J. and Thorpe, P. E. in Immunoconjugates: Antibody Conjugates in Radioimaging and Therapy of Cancer, C. W. Vogel (Ed.) Oxford Univeristy Press, 1987, pp. 28–55.; and Blair, A. H. and T. I. Ghose, J. Immunol. Methods 59:129,1983). A p97 fusion protein comprising p97 or a portion thereof fused to the agent may be prepared using the methods described above.

The delivery compositions of the invention may be tested for their ability to cross the blood brain barrier and provide the desired pharmacological effect using in vitro and in vivo models of the blood brain barrier. Examples of in vitro models include bovine capillary endothelial cell lines, which in culture form an endothelial monolayer with high resistance to drug and solute transport (Pardridge, W. M. et al., J. Pharmacol. & Expt. Therapeut. 253:884–891, 1990). Examples of in vivo models of the blood brain barrier include intraocular transplants of septal tissue in rats. The grafted tissue develops the endothelial and astrocytic mechanism characteristic of the blood brain barrier.

The invention also contemplates a method for delivering a selected agent across the blood brain barrier comprising administering a delivery composition of the invention containing the agent. Any route of administration which dilutes the composition into the blood stream could be used. Preferably, the composition is administered peripherally, most preferably intravenously or by cardiac catheter. Dosages to be administered will depend on individual needs, on the desired effect and on the chosen route of administration.

Delivery compositions may also be administered encapsulated in or attached to viral envelopes or vesicles. Vesicles are micellular particles which are usually spherical and which are frequently lipid. Liposomes are vesicles formed from a bilayered membrane. Suitable vesicles include unilamellar vesicles and multilamellar lipid vesicles or liposomes, which may be made from a wide range of lipid or phospholipid compounds, such as phosphatidylcholine, phosphatidic acid, phosphatidylserine, phosphatidylethanolamine, sphingomyelin, glycolipids, gangliosides etc. using known techniques, such as those described in U.S. Pat. No. 4,394,448. Such vesicles or liposomes may be used to administer compounds intracellularly and to deliver compounds across the blood brain barrier. Controlled release of the therapeutic agent may also be achieved by using encapsulation (U.S. Pat. No. 5,186,941).

It is contemplated that p97 may be incorporated into vesicles, viral envelopes or cells for transport across the blood brain barrier. It is also contemplated that p97 and the delivery compositions of the invention may be delivered across the blood eye and blood placenta barrier.Delivery across the blood placenta barrier is expected to have useful applications in gene therapy for providing recombinant DNA molecules to the foetus. In gene therapy, a functional gene may be introduced into a foetus in need to correct a genetic defect. The transfer of a recombinant DNA molecule into a mammalian foetus may be used, for example in gene therapy to correct an inherited or acquired disorder through the synthesis of missing or defective gene products in vivo. The recombinant DNA molecule may be incorporated into the above-noted vesicles, liposomes or viral envelopes. It is also contemplated that p97 and the delivery compositions of the invention may be useful for delivering therapeutic agents and pharmaceuticals, e.g. antibiotics across the blood placenta barrier.

It is also contemplated that bacterial proteins which cross the blood brain barrier may be used as delivery vehicles, such as bacterial proteins from Listeria. Listeria is an example of a bacteria which can cross the blood brain barrier and such bacteria have been shown to bind p97, providing further support for the role of p97 in transport across the blood brain barrier.

Monitoring Alzhemier's Disease

The present invention provides methods for monitoring and diagnosing Alzheimer's Disease in a patient, as well as compositions and methods suitable for treating Alzheimer's Disease. These compositions and methods are based on the finding by the present inventors that p97 and transferrin receptor can be found on microglial cells associated with amyloid plaques in an Alzheimer's Disease patient and on the discovery that a soluble form of p97 may be detected in the cerebrospinal fluid of an Alzheimer's disease patient.

For the purpose of monitoring or diagnosing Alzheimer's Disease, the presence of p97 may be detected from a variety of sources in the body, including tissues, cells and fluids.

Within one embodiment of the invention, methods are provided for monitoring Alzheimer's Disease comprising the step of detecting the presence of either p97 or transferrin receptors on microglial cells associated with amyloid plaques in a patient. Briefly, samples may be obtained from a patient either by biopsy (e.g, computed tomographic (CT)-guided stereotactic biopsy, see Alesch et al., Acta Neurochir. (Wien) Suppl. 53: 33–36, 1991; Lazareff Acta Neurochir. (Wien) 113(1–2):82–83, 1992; Marks et al., N.Z. Med. J. 105(929):85–86, 1992; Yeo et al., Singapore Med. J. 32(5):307311, 1992), or upon autopsy, and prepared for staining according to standard histopathological procedures (see, for example, Example 8 below).

Microglial cells which are associated with amyloid plaques may be readily identified given the disclosure provided herein (see also, Basic Histopathology, Wheator ed. Churchill Livingstone, New York; Color Atlas of Histology, Gartner ed., Williams and Wilkins, Baltimore, Md.; Histology, Ross ed., Harper and Row, San Francisco, Calif.; Elbe, "Early Diagnosis of Alzheimer's Disease," Alzheimer's Disease: Current Research in Early Diagnosis, supra; Beyruther et al., "Mechanisms of amyloid deposition in Alzheimer's disease," Ann. N.Y. Acad Sci 640:129–139, 1991; Kawai et al., "Subcellular localization of amyloid precursor protein in senile plaques of Alzheimer's disease," Am. J. Pathol. 140(4):947–958, 1992).

Figure 19A:
FIG. 19A is a photograph of a section of an Alzheimer's Disease brain, stained with anti-p97 and anti-β, amyloid antibodies.
Figure 19B:
FIG. 19B is a photograph of a section of an Alzheimer's Disease brain, stained with anti-p97 antibodies.
Figure 19C:
FIG. 19C is a photograph of a section of negative control brain, stained with anti-p97 antibodies.

Particularly preferred methods for identifying microglial cells which are associated with amyloid plaques are described in more detail below in Example 8. Briefly, as shown in FIG. 19A, microglial cells (MC) which are stained with an anti-p97 antibody are directly associated with amyloid plaques (P). Blood vessels are identified as "BV". Staining of microglial cells with antitransferrin receptor antibodies in place of anti-p97 antibodies produces results similar to that seen in FIG. 19A. Although normal microglial cells may have, for example, as many as 300–400 transferrin receptors on the cell surface, microglial cells from an Alzheimer's Disease patient usually have 5,000 or greater transferrin receptors on the cell surface. The increased numbers of transferrin receptors or p97 on microglial cells of an Alzheimer's Disease patient thus allows visualization of the microglial cell upon staining, whereas, microglial cells from a normal patient will not be stained (see FIG.

19C). Therefore, it should be understood within the context of the present invention that the presence of p97 or transferrin receptors is detected, if the microglial cells may be visualized by staining with anti-p97 or anti-transferrin receptor antibodies.

Samples which have been obtained as described above may be readily stained with either anti-p97 antibodies, or anti-transferrin receptor antibodies. Anti-p97 antibodies such as L235 are described in more detail above. Anti-transferrin receptor antibodies may similarly either be prepared utilizing techniques similar to those described above, or obtained from commercial sources. Representative anti-transferrin receptor antibodies include OKT 9 (ATCC No. CRL 8021), SE9C11 (ATCC No. HB 21), L5.1 (ATCC No. HB 84), R17 217.1.3 (ATCC No. TTB 219), and R17 208.2 (ATCC No. TIB 220) (Cell Immunol. 83:14–25, 1984; J. Cell. Physiol. 112:403–410, 1982; and Blood 59:671–678, 1982). Finally, anti-β amyloid plaque antibodies may also be readily obtained utilizing techniques similar to those described above (see also, Allsop et al., Proc Natl. Acad. Sci USA 85:2790–2794, 1988; Arai et al., Proc Natl. Acad. Sci USA 87:2249–2253, 1990; Benowitz et al., Exp. Neurol. 106:237–250, 1989; Cole et al., Neurobiol. Aging 12:85–91, 1991; Cras et al., Am. J. Patol. 137:241–246, 1990; Currie et al., Neuropathol. Exp. Neurol. 48:328, 1989; Ghiso et al, Biochem. Biophys. Res. Commun. 163:430–437, 1989; Ishii et al., Neuropathol. Appl. Neurobiol. 15:135–147, 1989; Joachim et al., Am. J. Pathol. 138:373–384, 1991; Kametani et al., Biomed. Res. 10:179–183, 1989; and Palmert, Biochem. Biophys, Res. Commun. 156:432–437,1988).

Within another aspect of the present invention, methods are provided for monitoring Alzheimer's Disease, comprising the step of detecting the presence of soluble p97 in a patient. The presence of p97 may be determined from a variety of bodily fluids, including for example, urine, cerebral spinal fluid (CSF) and blood. Briefly, within one embodiment, a sample of fluid is removed from a patient and assayed for the presence of soluble p97. A variety of assays may be utilized, including for example Countercurrent Immuno-Electrophoresis (CIEP), Radioimmunoassays, Radioimmunoprecipita-tions, and Enzyme-Linked Immuno-Sorbent Assays (ELISA), Dot Blot assays, Inhibition or Competition assays and sandwich assays (see U.S. Pat. Nos. 4,376,110 and 4,486,530; see also Antibodies: A Laboratory Manual, supra).

Within one embodiment, 100 μl of an anti-p97 antibody such as L235 is incubated in a 96 well plate overnight at 37° C. The next day the plate is rinsed and then incubated with 200 μl of 5% PBS/BSA for 30 minutes at 37° C. The plate is then washed, and 100 μl of patient fluid serially diluted in 1% PBS/BSA (along with appropriate positive and negative controls) is placed in the wells of the plate. The plate is incubated for 1 hour at 37° C., and then washed three times with 1% PBS/BSA One hundred microliters of another anti-p97 antibody such as 96.5 diluted in 1% PBS/BSA is then incubated at 37° C. in the wells for 30 minutes, followed by three washes with 1% PBS/BSA. One hundred microliters of horse radish peroxidase goat anti-mouse IgG diluted in 1% PBS/BSA is then incubated in the well for 30 minutes, followed by three washes with 1% PBS/BSA. One hundred microliters per well of O-Phenylenediomine (OPD) substrate solution (1 mg/ml OPD (00–2003, Zymed), 0.001% $H_2O_2$, in 0.1 M citrate buffer pH 4.5) is added to each well. Plates may be read on a Titertek Multiscan Plate reader (Flow Laboratories) at 450 nm after 15 minutes. Presence of soluble p97 in the bodily fluid is indicated by the presence and degree of color, as compared to negative controls.

The present invention also relates to a method for diagnosing or monitoring Alzheimer's Disease in a patient, comprising determining the concentration of p97 in a sample from the patient and comparing the determined concentration to the level of p97 in other samples from the patient, control subjects and/or Alzheimer's Disease patients. The concentration of p97 in the sample may be determined using a variety of methods such as radioimmunoassay, immunofluorescent assay, competitive assay, or enzyme linked immunosorbant assay.

In a preferred embodiment an assay based on a rapid immunofluorescent technique, "Particle concentration fluorescence immunoassay" (PCFIA) introduced in 1984 (Jolley et al. 1984, J. Immunol. Meth., 67, 21–35) may be used to determine levels of p97 in the sample. This method employs capture antibodies (Ab) bound to sub-micron polystyrene beads. This "activated" solid phase acts as a specific absorbent for the protein of interest. A fluorescent labeled second Ab, also specific for the protein, is then incubated with the solid capture phase to form a complex whose fluorescent signal was proportional to the original protein concentration. The reactions may be carried out in specially designed 96 well plates (Catalog 22-400-1; Idexx Laboratories Inc., Wesbrook, Me.). Each well contains a 0.22 μm cellulose acetate membrane that allows the wells to be drained under vacuum to concentrate the fluorescent complex in the base of each well. The plates may be washed and each well read for fluorescence at varying wavelengths using a Pandex Fluorescence Concentration Analyzer (FCA; Idexx).

Activated beads for use in the assay may be prepared using anti-p97 antibodies to coat carboxy polystyrene particles (0.77 μm, 0.25% v/v; Idexx). Suitable anti-p97 antibodies include the anti-p97 mouse monoclonal Ab, Hyb C (33B6E4; Dr. Shuen-Kuei Liao, McMaster University, Hamilton, OREG.), or 9B6 (Dr. Wilf Jefferies, Biotechnology Laboratory, UBC, BC), or anti-p97 rabbit antisera (Dr. Wilf Jefferies, Biotechnology Laboratory, UBC, BC).

The fluorescently labelled second antibody may be prepared using the anti-p97 mouse monoclonal antibody, L235 (ATCC-HB8446 L235 (H-19)) or anti-p97 rabbit antisera (Dr. Wilf Jefferies, Biotechnology Laboratory, UBC, BC), fluoresceinated with fluorescein isothiocyanate (FITC).

A p97 standard may be prepared from p97, for example, p97 purified from the supernatant of phosphatidylinositol phospholipase C (PI-PLC) treated Chinese hamster ovary (CHO) cells, transfected with human p97), by immunoaffinity chromatography.

Preferably samples for use in the method are obtained from bodily fluids, such as blood, lymph, bile, sputum or cerebrospinal fluid. Cell samples are also contemplated, such as blood cells, preferably monocytes. In particular, it is anticipated that activated macrophages expressing p97 may be assayed. In a particularly preferred embodiment blood serum samples are used. Serum samples may be obtained from a patient's blood using known techniques. Samples may be stored and frozen prior to use and may be used neat and/or diluted, for example in 50% v/v fetal calf serum (FCA) in Pandex buffer (DNEM containing 0.1% NaH3 and 1.0% w/v BSA).

Figure 44:
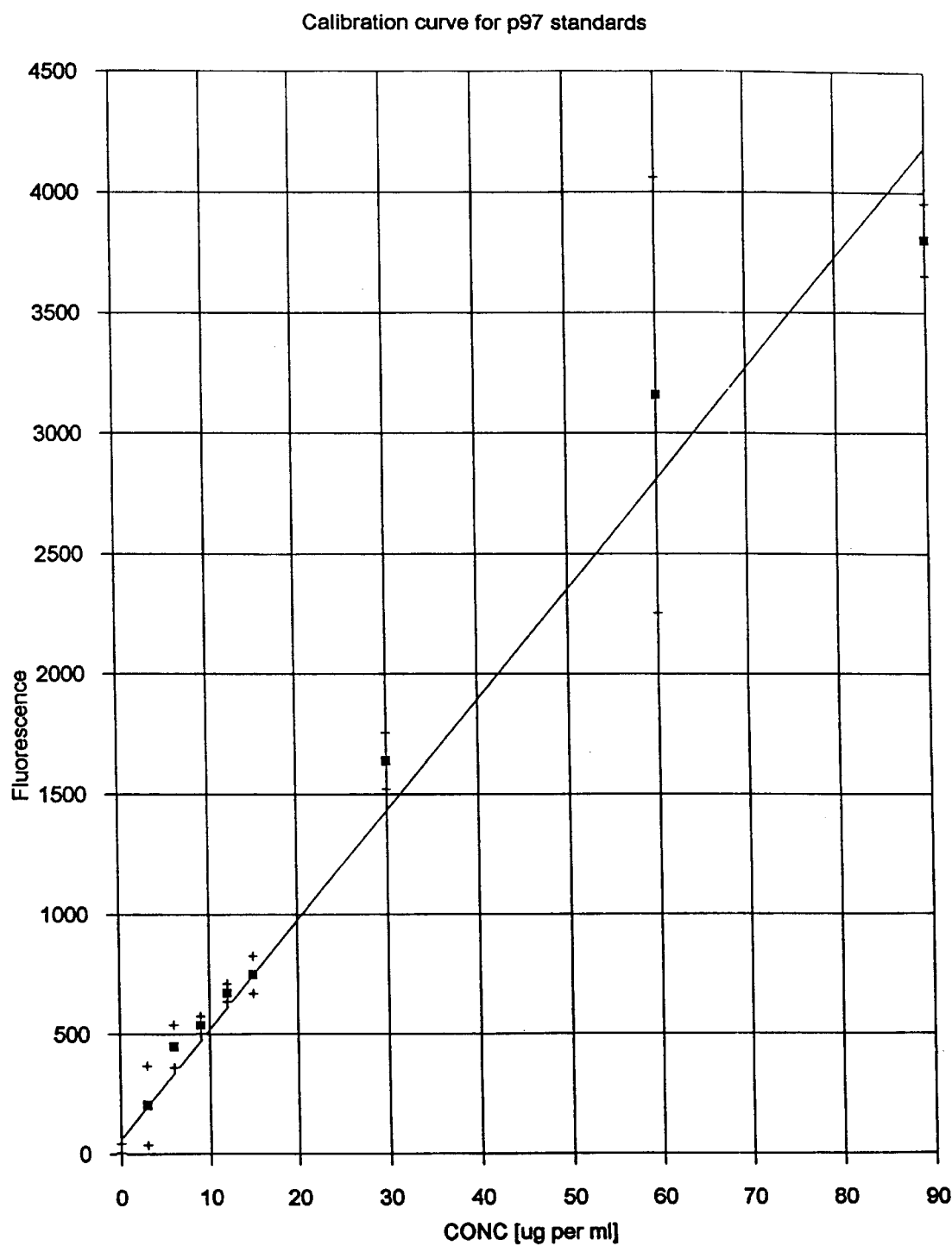
FIG. 44 is a graph showing a calibration curve for p97 standards.

In a particularly preferred embodiment, the blood serum p97 assay may be carried out in the special 96 well plates (22-401-1; Idexx) and the fluorescence read in the FCA (Idexx). 60μL of the blood serum sample at the appropriate dilution in the 50% FCA solution may be added to a well on the 96 well plate. p97 standards may be used for calibration curve preparation. A sample calibration curve preparation is shown in Table 4 and a calibration curve is shown in FIG. 44.

To diagnose Alzheimer's Disease, the concentration of p97 in the patient sample may be compared to levels of p97 from control subjects. Levels of p97 in the serum of control subjects are shown in Tables 5 and 6 and in FIGS. 45 and 46. Elevated levels of p97 in the sample compared to controls may be used to diagnose Alzheimer's Disease. The present inventors have found that levels of p97 in the serum of Alzheimer's Disease patients are elevated at least two to three times over levels in the serum of control subjects. High levels of p97 may also be used as an early prognosis for the disease. Diagnosis may also be made by a finding of increased levels of p97 compared to previous readings from the same patient.

Figure 46:
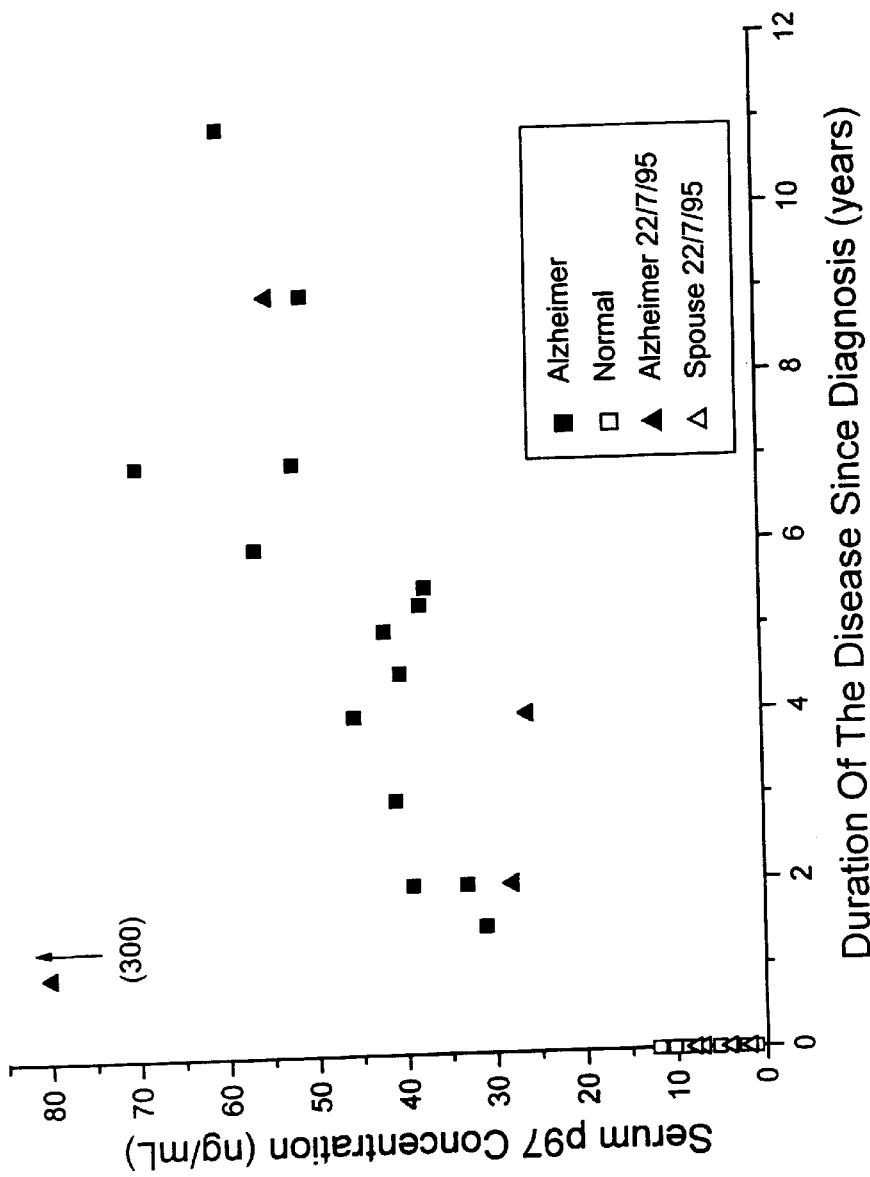
FIG. 46 is a graph showing a comparison between serum p97 levels for Alzheimer's disease patients and control subjects based on duration of disease.

To monitor Alzheimer's Disease, the concentration of p97 in the patient sample may be compared to levels of p97 from control subjects, from other Alzheimer's Disease patients or from previous readings from the same patient. FIG. 46 shows that p97 levels in serum increase with increasing duration of the disease. Thus, the method of the invention may be used to monitor the progression of disease in a patient and to assess the stage and severity of the disease.

In an embodiment of the method, the sample is from a patient being monitored to assess the efficacy of a therapeutic treatment for Alzheimer's Disease. Samples may be taken prior to, during and/or after treatment and efficacy of the treatment determined by the affect of the treatment on the concentration of p97 in the samples. An effective treatment will be expected to be a treatment which results in lower levels of p97 in the samples compared to a control.

It is contemplated that the method may be used to monitor the efficacy of any type of treatment for Alzheimer's Disease, in particular the use of pharmaceutical compositions suspected of having efficacy in the treatment of Alzheimer's Disease. Examples of pharmaceuticals which may have some efficacy in the treatment of Alzheimer's Disease include substances which restore or replace cholinergic function, such as tacrine, choline, lecithin, huperzine A and B, galanthamine, methanesulfonyl fluoride, physostigmine and deprenyl.

The invention also contemplates a bispecific antibody capable of binding to a microglial cell which deposits the amyloid protein and which expresses p97 and/or transferrin receptor, and to a label preferably a detectable substance such as a fluorescent molecule, luminescent molecule, enzyme, and radionuclide, representative examples of which are set out herein.

Bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). In general, a hybrid hybridoma is formed by fusing a first cell line which produces a first monoclonal antibody which is capable of binding to a microglial cell expressing p97 and/or transferrin receptor and a second cell line which produces a second monoclonal antibody which is capable of binding to a label preferably a detectable substance. The first monoclonal antibody may be specific for p97 or transferrin receptor. The bispecific antibodies may also be constructed by chemical means using procedures such as those described by Staerz et al., (1985, Nature, 314:628) and Perez et al., (1985 Nature 316:354).

Bispecific chimeric monoclonal antibodies containing a variable region of an antibody for example, murine antibody, specific for p97 and/or transferrin receptor, a variable region of an antibody which is capable of binding to a label preferably a detectable susstance and the constant regions of human immunoglobin such as human IgG1, IgG2, IgG3 and IgG4 antibody may also be constructed as described above.

The invention further contemplates a tetrameric immunological complex of a first monoclonal antibody which is capable of binding to a microglial cell expressing p97 and/or transferrin receptor and a second monoclonal antibody which is capable of binding to a label preferably a detectable substance wherein the first and second antibody are from a first animal species, conjugated to form a cyclic tetramer with two monoclonal antibodies of a second animal species directed against the Fc-fragment of the antibodies of the first animal species.

A tetrameric immunological complex may be prepared by preparing a first monoclonal antibody which is capable of binding to a microglial cell expressing p97 and/or transferrin receptor and a second monoclonal antibody which is capable of binding to a label preferably a detectable substance. The first and second antibody are from a first animal species. The first and second antibody are reacted with an about equimolar amount of antibodies of a second animal species which are directed against the Fc-fragments of the antibodies of the first animal species or the Fab fragments of such antibodies. The tetrameric complex formed is then isolated. (See U.S. Pat. No. 4,868,109 to Lansdorp for a description of methods for preparing tetrameric antibody complexes). The first monoclonal antibody may be specific for p97 or transferrin receptor.

The label should be capable of provoking the production of antibodies in order to prepare the bispecific antibody and tetrameric antibody complexes of the invention. Examples of detectable substances which are capable of provoking production of antibodies are enzymes, such as horseradish peroxidase, alkaline phosphatase, glucose oxidase and galactosidase. Examples of toxins which are capable of provoking the products of antibodies are radionucleotides, diptheria toxin and ricin or attenuated derivatives thereof as described. It is also contemplated that cytotoxic cells such as macrophages, neutrophils, eosinophils, NK cells, LAK cells, and large granular lymphocytes may be used as a label. It will be appreciated that the antibody may be directed against the Fc receptor on cytotoxic cells.

Bispecific antibodies and tetrameric antibody complexes of the invention coupled to the label preferably a detectable substance, may be used to identify micorglial cells associated with Alzheimer's Disease.

The present invention also contemplates that the above-noted methods for diagnosing and monitoring Alzheimer's Disease can be used in combination with other diagnostic methods. Beta amyloid protein is internalised into cells as a conjugate with elastase. More particularly beta amyloid binding elastase may be used in combination with the methods of the present invention to target diseased microglial cells.

The invention further provides a method for purifying microglial cells associated with Alzheimer's Disease beta amyloid plaques to provide a purified population of diseased cells which may be used to test for substances which may be effective in the treatment of Alzheimer's Disease. The cell population may be purified using techniques known in the art. Prefrably, the cell population is purified using a substance which is capable of specifically binding p97 or transferrin receptor. In one embodiment, the cell population is purified by affinity chromatography employing immobilised anti-p97 antibodies to selectively bind microglial cells, which have been demonstrated to express high levels of surface associated p97. The purified cell population may be transformed, to produce a cell line of Alzheimer's disease microglial cells. Macrophages may be succesfully immortalised using methods known in the art, for example using SV-40 virus (Kreuzburg-Duffy, U. and MacDonald, C., Immunol. 72:368–372, 1991). Accordingly, the invention contemplates the preparation of macrophage cell lines exhibiting the elevated levels of p-97, characteristic of the diseased brain in Alzheimer's disease. This cell line will be particularly useful for further characterisation of the disease state and to provide an in vitro system for testing for substances which may have therapeutic utility in the treatment of the disease. Themethod may also be used to purge bone marrow cells of microglial cells associated with Alzheimer's Disease beta amyloid plaques.

It will be appreciated that the presence of p97 on the microglial cells associated with Alzheimer's Disease indicates that p97 may also be a useful marker for activated macrophages or monocytes. Accordingly, p97 may be a general indicator of disease and in particular inflammation. Thus, the above described methods and compositions for monitoring and diagnosing Alzheimer's disease may be applied to the monitoring and diagnosis of disease states and in particular inflammatory conditions such as rheumatoid arthritis, pulmonary vasculitis, allergic encephalomyelitis, allograft rejection, chemical tissue injury. (See Pippard M. J. supra).

It will also be appreciated that p97 may also be useful in purging bone marrow of p97 positive bone marrow cells i.e. diseased cells. Thus, the methods described above for microglial cells associated with Alzheimer's Disease may be used to purge bone marrow cells.

Treatment of Alzheimer's Diease

As noted above, the present invention provides methods and compositions suitable for treating Alzheimer's Disease. Microglial cells have been implicated as a causative agent of Alzheimer's Disease (Schnabel, J., Science 260:1719–1720, 1993). The finding by the present inventors that microglial cells which deposit the amyloid protein have a high level of proteins i.e. p97 and transferrin receptor, which operate in procurement of iron suggests that Alzheimer's Disease may be treated by depleting iron from the microglial cells. Iron may be depleted from the microglial cells using p97, transferrin, transferrin receptor, antibodies to p97 or transferrin receptor and iron chelators such a alctoferrin, ferritin, desferrithiocin, and ovotransferrin. (See Pippard, M. J., supra).

Accordingly, within another embodiment of the present invention, a method is provided for treating Alzheimer's Disease comprising administering to a patient a transferrin receptor blocking agent. Transferrin receptor blocking agents may be readily identified by one of ordinary skill in the art given the disclosure provided herein, and including, for example, transferrin and transferrin receptor blocking antibodies. Transferrin receptor blocking antibodies may be readily prepared utilizing methods described above for making antibodies (e.g., by immunizing mice with the transferrin receptor or transferrin receptor bearing cells), and by assaying for the blocking of transferrin-transferrin receptor binding (e.g., for example, by competition assays).

Within another embodiment of the present invention, a method is provided for treating Alzheimer's Disease comprising administering to a patient an antibody which blocks the binding of p97 to iron. Antibodies which block the binding of p97 to iron may be readily prepared as described above (e.g., by immunizing mice with p97), and by assaying for antibodies which competitively inhibit the binding of p97 to iron.

Within one embodiment of the present invention, a method is provided for treating Alzheimer's Disease, comprising the step of administering to a patient labelled p97 or transferrin receptor. The transferrin receptor or p97 is preferably labelled with a toxin as described above, in order to destroy microglial cells which are associated with amyloid plaques in a patient. Representative examples of suitable toxins include ricin, abrin, diptheria toxin, cholera toxin, gelonin, pokeweed antiviral protein, tritin, Shigella toxin, and Pseudomonas exotoxin A.

As discussed above, the present inventors have identified p97 and transferrin receptor as specific markers for microglial cells associated with beta-amyloid damaged neurons in the brain of Alzheimer's disease patients. Accordingly, the microglial cells which are associated with amyloid plaques may be targeted using substances which are capable of binding to p97 or transferrin receptor. Therefore the invention provides a method for treating Alzheimer's Disease comprising administering a substance which is capable of binding to p97 or transferrin receptor conjugated to a label, preferably a substance have therapeutic activity or a toxin as described above. The substance may be anti-p97 antibody or anti-transferrin receptor antibody, representative examples of which are described above.

The invention also contemplates a bispecific antibody capable of binding to a microglial cell which deposits the amyloid protein which expresses p97 and/or transferrin receptor, and to a label preferably, a substance having toxic or therapeutic activity. Examples of toxic substances and substances having therapeutic activity in Alzheimer's Disease are set out herein. It should be noted that the toxic substance may also be a cytotoxic cell as described above. The bispecific antibody should be capable of crosslinking the microglial cell and toxic substance. Where the label is a cytotoxic cell, the crosslinking of the microglial cell and the cytotoxic cell will facilitate lysis of the microglial cell.

The bispecific antibody may be prepared as described in detail above. Generally, a hybrid hybridoma is formed from a fusion between a first cell line which produces a first monoclonal antibody which is capable of binding to a microglial cell which expresses p97 and/or transferrin receptor and a second cell line which produces a second monoclonal antibody which is capable of binding to a label preferably a substance having toxic or therapeutic activity.

The invention further contemplates a tetrameric immunological complex of a first monoclonal antibody which is capable of binding to a microglial cell expressing p97 and/or transferrin receptor and a second monoclonal antibody which is capable of binding to a label preferably, a substance having toxic or therapeutic activity wherein the first and second antibody are from a first animal species, conjugated to form a cyclic tetramer with two monoclonal antibodies of a second animal species directed against the Fc-fragment of the antibodies of the first animal species.

The tetrameric immunological complex may be formed as described above. Generally, a first monoclonal antibody which is capable of binding to a microglial cell expressing p97 and/or transferrin receptor is reacted with and a second monoclonal antibody which is capable of binding to a label preferably a substance having toxic or therapeutic activity wherein the first and second antibody are from a first animal species, with an about equimolar amount of antibodies of a second animal species which are directed against the Fc-fragments of the antibodies of the first animal species and isolating the tetrameric complex formed.

The bispecific antibodies and tetrameric immunological complexes of the invention directed against a substance having toxic or therapeutic activity coupled with the substance having toxic or therapeutic activity may be used to treat Alzheimer's Disease. Accordingly the invention provides a composition comprising bispecific antibodies or tetrameric immunological complexes in a pharmaceutically acceptable carrier wherein the bispecific antibodies or tetrameric immunological complexes are capable of binding to a substance having toxic or therapeutic activity and to a micorglial cell expressing p97 and/or transferrin receptor.

The invention also provides a method for treating Alzheimer's Disease comprising administering to a patient in need of such treatment a therapeutically effective amount of bispecific antibodies or tetrameric immunological complexes which are specific to a substance having toxic or therapeutic activity and to microglial cells expressing p97 and/or transferrin receptor, and which are coupled to the substance and, monitoring the progress of the disease state, and, if desired, repeating the administration.

Within yet another aspect of the present invention, viral vectors may be utilized to treat Alzheimer's Disease. Briefly, within one embodiment of the invention, viral vectors may be utilized to direct the expression of antisense p97 RNA in order to prohibit expression of p97. Viral vectors suitable for use in the present invention are well known in the art including recombinant vaccinia viral vectors (U.S. Pat. Nos. 4,603,112 and 4,769,330), recombinant pox virus vectors (PCT Publication No. WO 89/01973), and preferably, retroviral vectors ("Recombinant Retroviruses with Arnphotropic and Ecotropic Host Ranges," PCT Publication No. WO 90/02806; "Retroviral Packaging Cell Lines and Processes of Using Same," PCT Publication No. WO 89/07150; and "Antisense RNA for Treatment of Retroviral Disease States," PCT Publication No. WO 87/03451).

Therapeutic compositions of the present invention (including for example, labelled p97, labelled anti-p97 antibody, p97 fusion proteins, p97 conjugated to an agent, bispecific antibodies, tetrameric antibody complexes, transferrin receptor blocking agents, and antibodies which block the binding of p97 to iron) may be administered to a patient for treatment in a manner appropriate to the indication. Typically, therapeutic compositions described above will be administered in the form of a pharmaceutical composition comprising purified protein in conjunction with physiologically acceptable carriers, excipients or diluents. Such carriers will be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. The amount and frequency of administration will depend, of course, on such factors as the nature and severity of the indication being treated, the desired response, the condition of the patient, and so forth. Typically, the compositions may be administered by bolus injection, continuous infusion, sustained release from implants, or other suitable technique. Preferably, however, the pharmaceutical compositions are delivered directly into the cerebrospinal fluid.

The present invention also relates to a method of treating Alzheimer's disease by bone marrow transplant. Bone marrow transplants are performed in patients whose immune and blood forming-systems have been devastated by leukemia, cancer, chemotherapy, radiation therapy and the like. Stem cell transplants can also treat metabolic disorders of macrophages, such as osteopetrosis and severe Gaucher's disease (Goldie, D. W. Scintific American, December 1991, p. 86–93. Based on the present finding that microglial cells associated with beta amyloid plaques in Alzheimer's Disease brain have very high levels of expression of p97, the present invention provides a method of treating Alzheimer's Disease by bone marrow transplant to repopulate the patient with genetically altered macrophages. Microglial cells are macrophages which have populated the brain. For example, it is contemplated that a patient's own myeloid stem cells may be genetically altered to produce macrophages expressing chemotherapeutic agents in the brain after autologous transplant. Stem cells may be transformed prior to transplant to express a chemotherapeutic agent under the control of a macrophage specific promoter. Antagonists of p97 and other compounds which would deprive the cells of iron are examples of suitable chemotherapeutic agents. Suitable chemotherapeutic agents may also be selected from cytotoxic anti-tumor drugs, discussed above, and drugs which inhibit inflammation and growth. Anti-inflammatory drugs are known in the art and have been implicated in the treatment of Alzheimer's disease (Schnabel, J. Science 260:1719–1720, 1993). Examples of anti-inflammatory drugs include non-steroidal anti-inflammatory compounds such as indomethacin and aspririn-like compounds.

Monitoring and Tratment of Conditions Involving Activated Pericytes

An examination of the photographs of the sections of Alzheimer's disease brains stained with anti-p97 antibody appeared to show the presence of darkly stained pericytes associated with the capillary endothelial cells, suggesting that these pericytes are positive for p-97. Thus p-97 may be a marker for pericytes associated with the brain capillary endothelial cells and may also be a specific marker for activated pericytes and for pericytes in Alzheimer's disease brains. Interestingly, swelling of pericytes connected to brain endothelial cells has previously been associated with Alzheimer's disease.

Pericytes are multipotent cells closely associated with microvessel endothelial cells and are considered to be phagocytic in the central nervous system. Pericytes form close connections with endothelial cells and are thought to play a role in the regulation of epithelial cells and in capillary growth, for example in wound healing and in the vascularization of tumors. In the brain, pericytes are particularly associated with the blood brain barrier and may form a secondary line of defence by phagocytising materials which cross the blood brain barrier (Sims, D. E., Can. J. Cardiol. 7:431–443, 1991). Pericytes concentrate tound endothelial cell junctions and exhibit a contractile response to inflammation. Pericytes are more numerous on brain capillary endothelial cells in Alzheimer's patients, resulting in a drastic alteration in the morphology of cerebral microvessels (Sims, D. E., Can. J. Cardiol. 7:431–443, 1991).

The present invention indicates that p97 may be a marker for pericytes, activated pericytes, tumor vascularization and Alzheimer's diseased brain and can therefore be used to monitor and diagnose conditions involving activated pericytes as described herein. It is also contemplated that the compositions of the present invention utilising p-97 described herein, preferably compositions comprising substances capable of binding to p97 conjugated to a toxin or a substance having therapeutic activity, will be useful in the treatment of conditions involving activated pericytes, such as Alzheimer's disease, diabetes, tumors with active vascularisation, inflammatory conditions and neurological disorders.

The following examples are offered by way of illustration, and not by way of limitation.

EXAMPLES

Example 1
Transfection of Cells with P97 cDNA

The Chinese Hamster Ovary ("CHO") cell lines WTB (Wild-Type) and TRVB (Transferrin Receptor Minus) (see McGraw et al., J. Cell. Biol. 105(1):207–214, 1987) were plated on 60 mm culture dishes. Hams F12 medium supplemented with 10% FBS, 20 mM HEPES, 100 U/ml penicillin, 100 µg streptomycin, and 2 mM L-glutamine was used to maintain the cell lines prior to the procedure. More particularly, the TRVb-1 line, which does not express the hamster TR but expresses the transfected human TR, was maintained in the same media with the addition of 100 µg/ml G418 sulfate (Gibco). The cells were incubated at 37° C. in a humidified 5% $CO_2$ environment until they were 80% to 85% confluent.

Figure 3:
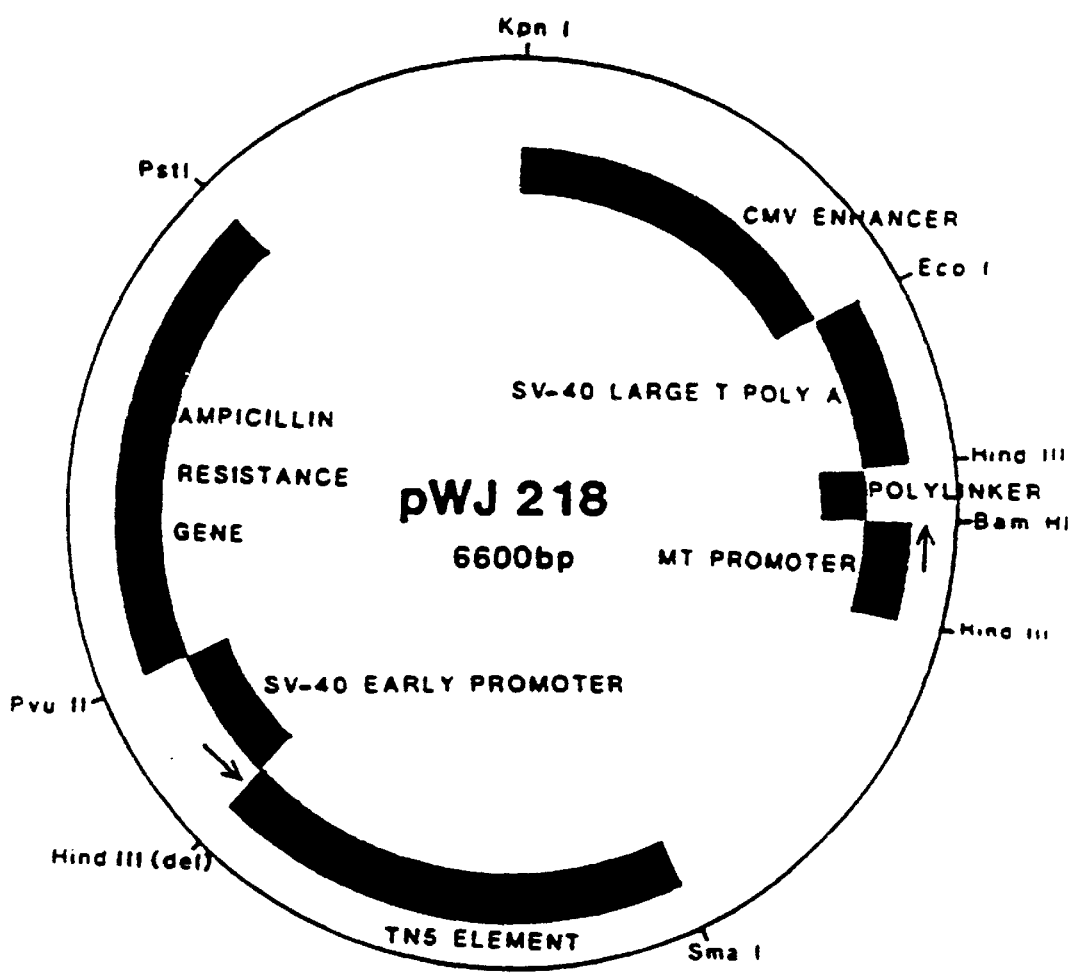
FIG. 3 schematically depicts pWJ218.

Mixed DNA (27 µg pSV2p97a (ATCC No. CRL 9304) in 3 µl, 0.5 µg pWJ218 (see FIG. 3) in 0.5 µl, and 46.5 µl sterile distilled water) was combined with 50 µl of Lipofectin™ Reagent (Life Technologies Inc./Bethesda Research Laboratories, Gaithersburg Md.) according to the manufacturers' instructions. The cells were then washed twice with 3 ml of serum-free Hams F12 medium, resuspended in 3.0 ml of medium and gently swirled in tissue culture dishes. More particularly, the plasmids pSV2 p97a, a human p97 expression vector containing the entire coding region of p97 cDNA driven by the SV40 early promoter (ATCC NO. 9304), and pWJ218 containing the G1418 resistance gene were cotransfected into the cell lines by the LipoFectin™ method (Gibco, New York) following the procedure recommended by the manufacturer. The cells were then incubated for 36 hours at 37° C. in a humidified, 5% $CO_2$ environment.

An equal volume of Hams F12 medium containing 20% Fetal Bovine Serum (FBS) and 1600 µg/ml G418 (Geneticin/Gibco) was added to the tissue culture dishes. The cells were washed and the media (Hams F12 with all supplements including 10% FBS and 800 µg/ml G418) changed daily for a week. Utilizing the anti-p97 antibody L235 (more particularly, L235 is an $IgG$ monoclonal antibody secreted by the hybridoma cell line ATCC No. HB 8446) cell populations expressing p97 were analyzed by flow cytometry ("FACS"). Positive cell populations were then further sorted for cells which expressed higher levels of p97.

More particularly, the cells were counted ($10^6$ cells/tube) and washed twice in fluorescence activated cell sorting ("FACS") buffer, which consisted of DMEM containing 0.5% (wt.vol) bovine serum albumin, 20 mM HEPES, and 20 mM $NaN_3$. The cells were incubated with the various monoclonal antibodies for 45 min at 4° C., then washed and labelled with the appropriate fluoresceinated secondary antibody for 45 min at 4° C. The cells were then washed and fixed in 1.5% (vol/vol) p-formaldehyde in PBS. A Becton-Dickinson FACScan flow cytometer was used to measure 5000 events per sample. The fluorescence intensities were normalized with respect to unstained control samples. The following primary antibodies were used in immunohistochemistry studies: anti-human MTf(L235, 1:1,000 dilution, mouse monoclonal, $IgG_1$, ATCC (HB104); anti-human Tf(A-061, 1:1,000 dilution, rabbit polyclonal, DAKO); and anti-human TR (OKT9, 1:1,000 dilution, mouse monoclonal, $IgG_1$, ATCC CRL 8021). Tissue culture supernatants or Protein G column (Pharmacia) purified preparations were used as a source of antibody in the experiments. Positive cell populations were then further sorted for cells which expressed higher levels of p97.

Positive cells were then sub-cloned by limiting dilution. The resultant cell lines were once again analyzed by FACS to ensure high expression of p97. Two clones which stably expressed high levels of p97 were isolated: p97aWTBc3 and p97aWTBc7.

Example 2
Expression of P97 on the Surface of Cells Transfected with p97 cDNA A. Preparation of Plasmid D5-9(+)

The expression vector pVL1393 (see, Luckow, "Cloning and Expression of Heterologous Genes in Insect Cells with Baculovirus Vectors", Cloning Techniques and Applications, pp. 122–123) was digested with SmaI, followed by digestion with Calf Intestinal Phosphatase ("CIP") to prevent self-ligation.

Human p97 cDNA from plasmid pSV2p97a was amplified, and a miniprep of plasmid DNA prepared. Plasmid DNA was then digested with HindIII and NruI, and a 233 bp fragment isolated from a 1% agarose gel in TAE. The 3' overhang created by the HindIII digest was filled in, and the fragment was purified.

Figure 4:
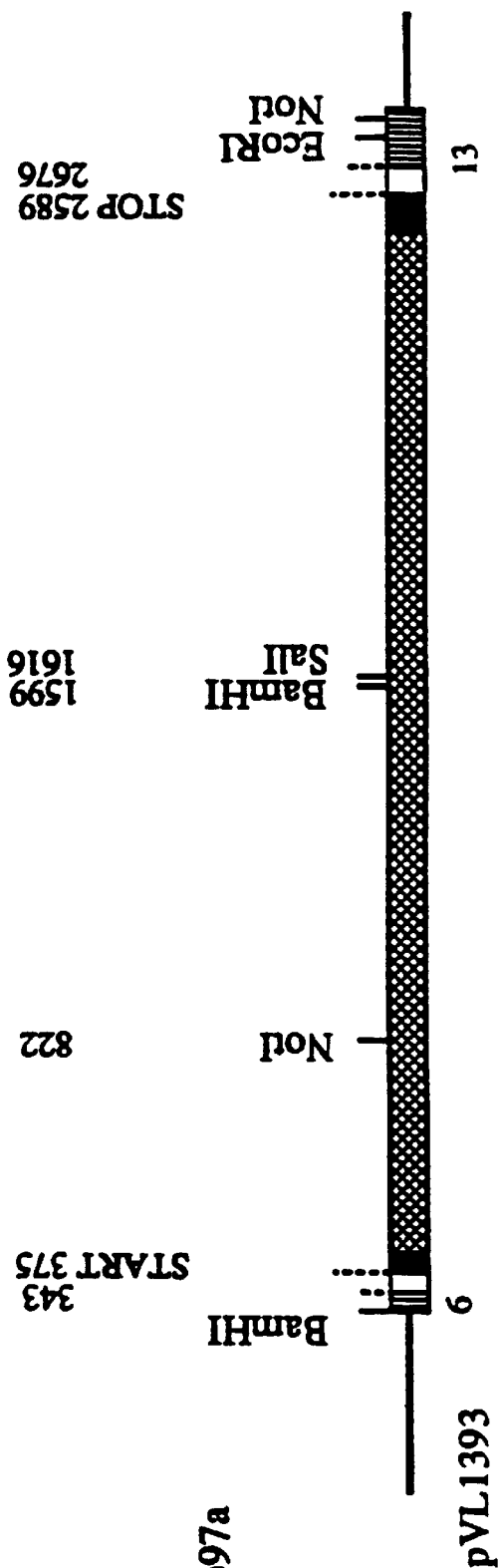
FIG. 4 schematically depicts plasmid D5-9(+).

The HindIII-NruI p97 fragment and the pVL1393/SmaI CIP linearized vector were ligated, and used to transform competent DH5n cells (Hanahan, D., DNA Cloning Vol 1, A Practical Approach Series, Glover, ed., Chapter 6, pp. 10–135, IRL press, 1985). Positive clones were picked, and plasmid DNA was produced from minipreps of each clone. A particularly preferred plasmid, D5-9(+), is schematically depicted in FIG. 4.

B. Transfection of Sf9 Cells

Spodoptera frugiperda or "Sf9" cells (ATCC No. CRL 1711) were transfected with a mixture of wild type AcMNPV genomic DNA and D5-9(+) plasmid DNA described above, essentially according to the method of Summers and Smith (A Manual of Methods for Baculovirus Vectors and Insect Cell Culture Procedures, Texas Agricultural Experiment Station, Bulletin No. 1555, 1988 (1988; Section 4.4.1 Transfection of Sf9 Cells—Method I), in order to incorporate the human p97 gene into the AcMNPV genome.

Human p97 recombinant viruses were purified using a plaque assay described by Summers and Smith, supra. Three rounds of plaque assays were done in order to isolate the recombinant viruses carrying the p97 gene. These included: Round 1: $10^{-5}$, dilutions of transfection mix; Round 2: $10^{-1}$, $10^{-2}$, dilutions of plaques picked in round 1; and Round 3: $10^{-3}$, $10^{-4}$, dilutions of plaques picked in round 1.

C. Results

SK-MEL-28 cells (which are known to express p97 and, for greater clarity, are a human melanoma cell line, ATCC HTB72), uninfected Sf9 cells, wild type AcMNPV infected Sf9 cells, and p97 recombinant virus infected Sf9 (p97 B-1-1 and p97 B-2-1) were analyzed by Fluorescence Activated Cell Sorting (FACS) to detect the expression of p97 on the cell surface. Hybridoma supernatant from anti-p97 antibody L235 was used as the first antibody and goat anti-mouse (GAM) IgG-FITC antibodies were used as the second antibody. Controls were treated with No Fluorescent Antibody ("NFA"), and PI-PLC (which cleaves the GPI anchor, releasing p97 from the cell surface).

As can be seen from Table I below, SK-MEL-28 cells and the p97 recombinant virus infected Sf9 cells (p97 B-1-1 and p97 B-2-1) were positive for p97 expression while the uninfected Sf9 cells and the wild type virus infected Sf9 cells were not. In addition, when the samples were preincubated at 37° C. for 60 minutes with PI-PLC and then labelled with first and second antibodies, the amount of p97 on the surface of SK-MEL-28 cells, and on the surface of the p97 recombinant virus infected Sf9 cells was reduced drastically. This result suggests that p97 expressed on the surface of Sf9 cells is attached by a lipid anchor as it is in SK-MEL-28 cells.

Example 3
Release of P97 by Bacterial PI-PLC in Transfected Cell Lines
A. Effect of PI-PLC on Cells PI-PLC was prepared by first transfecting a culture of Bacillus subitlis (BG2320) with the PI-PLC gene from Bacillus thuringiensis. PI-PLC was then purified from the supernatants of transfected cells essentially according to the procedure described by Low et al. in J. Immunol. Methods 113:101–111, 1988.

More particularly, *B. Subtilis* (BG2320) transfected with the gene for PI-PLC from B. thuringiensis (Henner et al., Nucleic Acids Research 16:10383, 1988) was cultured using a procedure adapted from that previously used to grow B. thuringiensis (Low et al., J. Immunol. Methods 113:101–111, 1988). The growth medium containing 10 g/L Polypeptone, 10 g/L yeast extract, 5 g/L NaCl, 0.4 g/L $Na_2HPO_4$ and 15 µg/ml chloramphenicol (pH adjusted to 7.0 with NaOH) was inoculated with 1.5–3% (v/v) of overnight preculture (initial). $D_{0.600}=0.1$). Cells were cultured in Erlenmeyer flasks and shaken at 150 rmp, 37° C. for 6 to 12 hours. Cells were removed by centrifugation and the supernatant filtered through a 0.2 µm membrane (VacuCap, Gelman Sciences, Mich.). The supernatant was concentrated 20-fold using an ultrafiltration cell (Model 8400, Amicon Corp. MA) and a 10,000 MW YM10 ultrafilter (Amicon, MA). The concentrated enzyme solution was then washed two times with 5 volumes of PBS in the ultrafiltration cell. The enzyme solution was assayed and stored in 1 ml aliquots at −20° C. When the enzyme was required, the frozen PI-PLC was rapidly thawed and diluted in PBS to the specified concentrations. All enzyme samples used in this study came from the same 2L batch fermentation.

SK-MEL-28 (ATCC No. HTB 72) cells and p97aWTBc3 cells (prepared as described above) were grown up, counted, placed into tubes ($10^6$ cells/tube), and washed two times with FACS buffer (DMEM containing 0.5% (wt/vol) bovine serum albumin, 20 mM HEPES, and 20 mM $NaN_3$). The cells were then incubated for 1 hour at 37° C. with purified phosphatidylinositol-specific phospholipase C (PI-PLC) at a concentration of 1.7 U/$10^6$ cells in FACS buffer. The cells were washed, and stained with anti-p97 antibody L235 at 4° C. for 45 min. The cells were washed again in FACS buffer and then incubated with fluoresceinated goat anti-mouse IgG at 4° C. for 45 min. The cells were then washed and fixed in 1.5% (vol/vol) p-formaldehyde in PBS.

Figure 5:
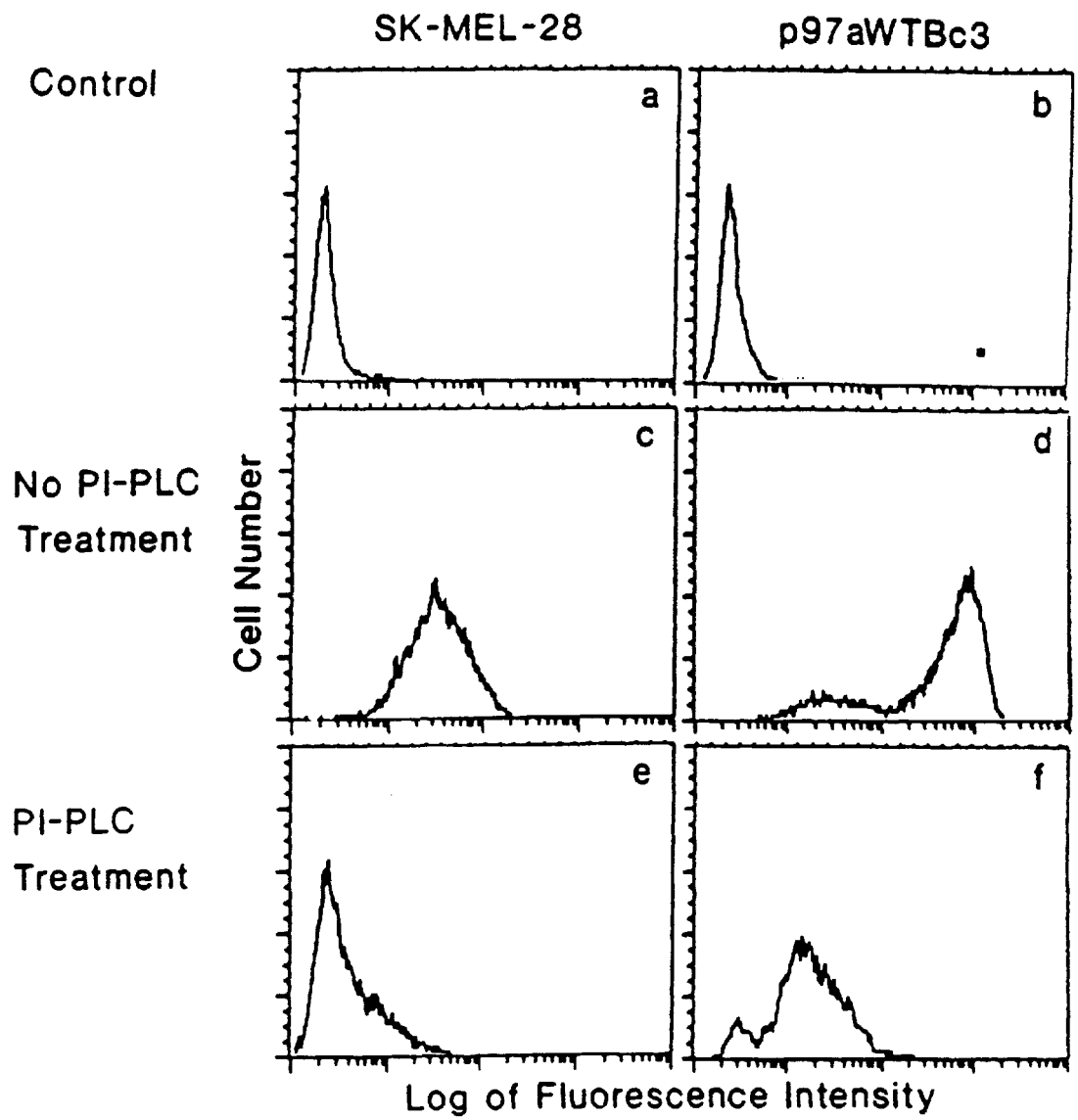
FIG. 5 is a series of graphs which show the release of p97 by PI-PLC treatment as measured by flow cytometry.

A Becton-Dickinson FACScan flow cytometer was used to measure 5000 events per sample. More particularly, data from individual experiments were compared to unstained negative controls and values expressed as percentages of untreated positive controls. The results are set forth in FIG. 5. Briefly, as shown in FIGS. 5(c) and (d), a significantly higher fluorescent intensity resulted for both SK-MEL-28 cells and p97aWTBc3 cells which were not treated with PI-PLC as compared to those that were (FIGS. 5e and f).

Control cells which were not stained with anti-p97 antibodies (FIGS. 5a and 5b), showed only background fluorescence. Therefore, the treatment of the SK-MEL-28 and p97a WTBc3 cell with bacterial PI-PLC resulted in a decrease in p97 expression at the cell surface.

B. Pronase Treatment of Cells

In order to determine whether the bacterial PI-PLC contained a non-specific protease, Pronase was used to treat cells which were then stained for either p97 or the transferrin receptor. Briefly, cells were treated as described above, except that cells were incubated with 1 mg/ml of Pronase (a Type XIV Protease from Streptomyces griseus (Sigma Chemical Co.)) for 1 hour in FACS buffer at 37° C., rather than with PI-PLC.

Also included in this study were EL-4 cells which express the Thy-1 and transferrin receptor proteins on its cell surface. For greater clarity, EL-4 cells are mouse lymphoma cells (ATCC TIB 39). Thy-1 is known to be GPI-anchored to the cell surface.

Results are presented in Table 2 below for SK-MEL-28, EL-4, p97aWTBc3 and p97aWTBc7 cells. For these experiments, p97 was labelled with monoclonal antibody L235 and the transferrin receptor was labelled with monoclonal OKT9. Thy-1 was labelled with the T24/37.1 MAb (obtained from Dr. R. Hyman, The Salk Institute, San Diego, Calif.) while the mouse transferrin receptor was labelled with the monoclonal antibody λE1/9.9.3 (obtained from Dr. F. Takei, the University of British Columbia, Canada). Appropriate fluoresceinated secondary antibodies were used according to the type of primary antibody. The results were converted from logarithimic to linear scale using the formula: linear mean fluorescence=$10^{(log\ mean\ fluorescence/256\ channels)}$. Fluorescence intensities were normalized with respect to unstained control samples and values expressed as percentages (±s.d.) of untreated stained control samples.

As shown in Table 2 below, both the p97 protein on SK-MEL-28 cells and the Thy-1 protein on EL4 cells were sensitive to the effects of PI-PLC, but not to the effects of Pronase. In contrast, the transferrin receptors on both SK-MEL-28 cells and EL-4 cells were sensitive to Pronase, but not PI-PLC.

This data also shows that the amount of p97 expression on SK-MEL-28 cells was decreased to 10% of initial levels by treatment with bacterial PI-PLC. In contrast, the expression of the human transferrin receptor (TR) on SK-MEL-28 cells was not changed at all by bacterial PI-PLC treatment.

Example 4
Affinity Purification of p97
A. Preparation of the Affinity Matrix p97 was affinity purified essentially as described below. Briefly, 2 ml of mixed beads (Protein A Sepharose CL-4B, Pharmacia #17-0963-03) were removed from the vial and washed three times in 5 ml of 0.1 M borate (pH 8.2). The beads were then resuspended in 6 ml of borate (pH 8.2) containing 2.5 mg of Rabbit Anti-Mouse IgG (Jackson Immunorearch, #315-005-003), and incubated for 60 minutes at 4° C. with shaking. The beads were then centrifuged at 1800 rpm for 3 minutes, followed by three cycles of washing with 5 ml 0.1 M borate (pH 8.2).

L35 hybridoma supernatant (mouse anti-human p97 IgG) was added to the beads and incubated for 60 minutes at 4° C. with shaking. The beads were then centrifuged as described above and washed three times in 5 ml 0.1 M borate (pH 8.2), followed by washing three times in 5. ml 0.2 M triethanolamine (pH 8.2). The beads were then resuspended in 20 ml Dimethyl Pimelidate HCl in 0.2 M triethanolamine, and thereafter centrifuged (500×g) for 1 minute. The cells were resuspended in 20 ml of 20 mM ethanolamine (pH 8.2), and incubated for 5 minutes at 22° C. The beads were then washed three times with 5 ml 0.1 M borate (pH 8.2), and stored at 4° C. in 5 ml of 0.1 M borate containing 20 mM azide.

B. Purification of p97 on the Affinity Column p97aTRV6c3 cells were grown to 75–95% confluence in Hams medium supplemented with LBS, HEPES, L-Glu, FEMS, and 800µg G418. 100ml of the medium was concentrated with an Amicon Centriprep 30 and purified using affinity chromatography as described below. An affinity column for the purification of p97 was prepared essentially as described in J. Biol. Chem. 257:10766–10769, 1982. Briefly, beads (prepared as described above) were washed with 0.1 M borate buffer (10 ml), and utilized to prepare the affinity column. The column was then preeluted with 2 ml of elution buffer 0.05 diethylamine, pH 11.5, containing 0.5% sodium deoxycholate and a sample of tissue culture media from cells were then passed through the column. The column was then washed successively with 5 ml of buffer B (0.2% NP-40, 150 mM NaCl, 2 mM EDTA, 10 mM Tris-HCl pH 7.5), 5 ml of buffer C (0.2% NP-40, 0.5 M NaCl, 2 mM EDTA, 10 mM Tris-HCl pH 7.5) and 5 ml of buffer D (10 mM Tris-HCl pH 7.5). Five milliliters of elution buffer was then added, and 1 ml aliquots were collected. One hundred microliters of 0.5 M $NaH_2PO_4$ was added to each of the aliquots in order to bring the sample to neutrality.

Figure 34:
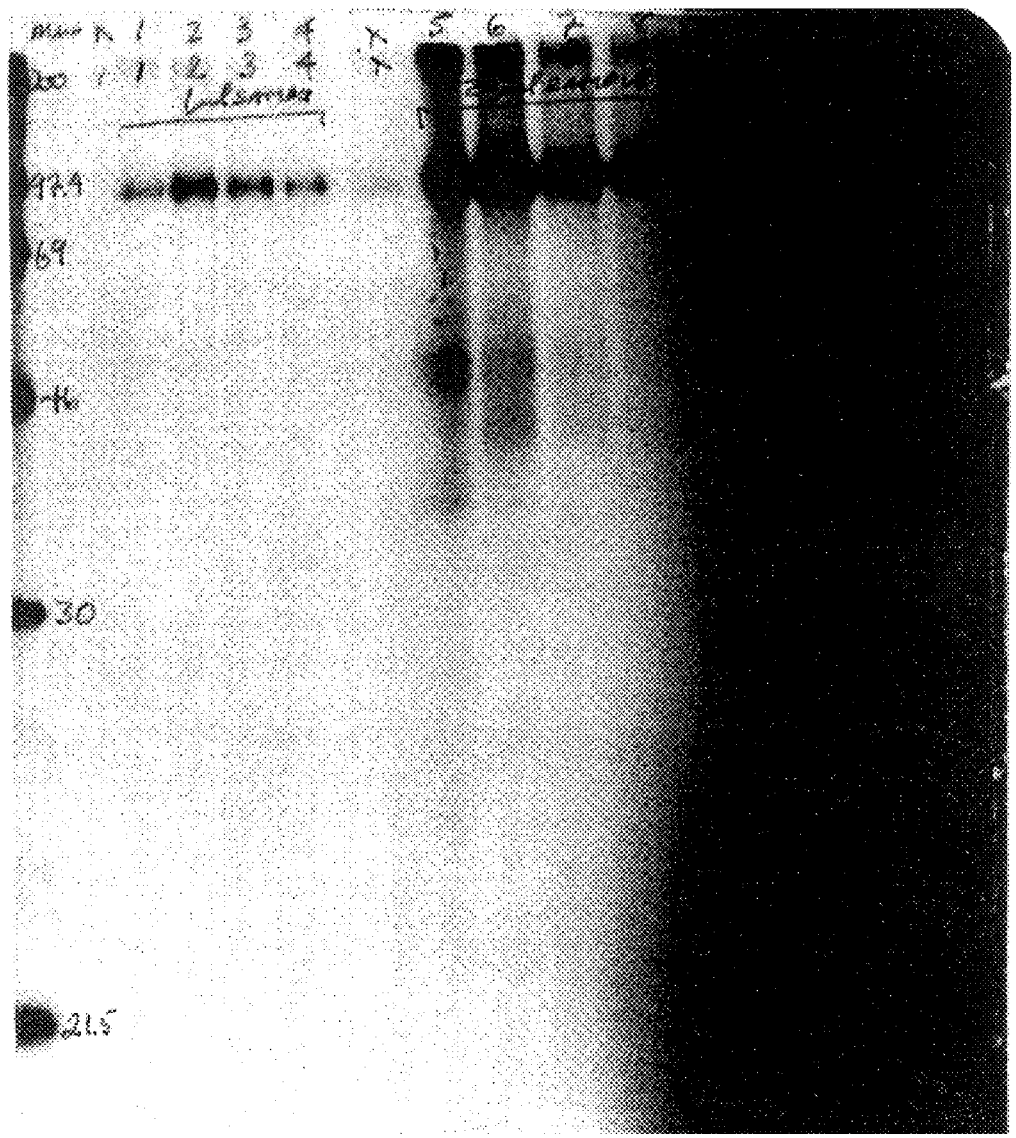
FIG. 34 is an autoradiogram showing the purification of p97 by affinity chromatography.

Purity was tested by PAGE (with Coomassie blue, silver staining, or autoradiography), and spectrophotometry. FIG. 34 shows the purification of p-97.

Example 5

Cell Surface Biotinylation, PI-PLC Treatment, and Immunoprecipitation

Figure 6:
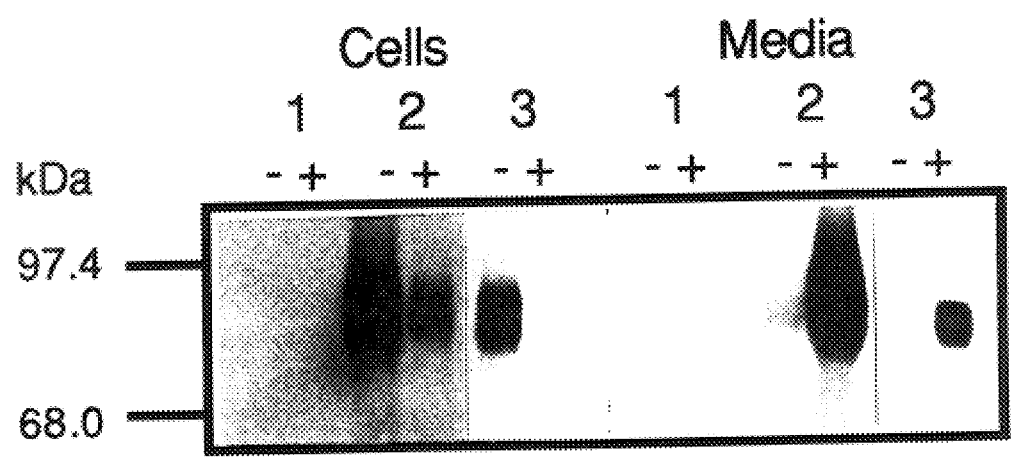
FIG. 6 is two Western Blots which show the effect of bacterial PI-PLC on p97 expressed at the surface of SK-MEL-28 cells and a cell line transfected with the human p97 cDNA.

The effect of bacterial PI-PLC and the specificity of monoclonal antibody L235 was further characterized in FIG. 6 where surface proteins from either WTB (lane 1), p97aWTBc7 (lane 2) or SK-MEL-28 cells (lane 3) were labelled with Biotin, followed by immunoprecipitation of p97 and analysis by SDS-PAGE under reducing conditions.

Briefly, surface proteins of $3.0 \times 10^6$ SK-MEL-28 cells were labelled with 0.2 mg Biotinamidocaproate N-Hydroxysuccinimide Ester (Biotin, Sigma) essentially as described by von Boxberg et al. (Eur. J. Biochem. 190:249–256, 1990). The cells were washed several times in DMEM, and divided into two samples that were incubated for 60 min at 6° C. in the presence or absence of PI-PLC (1.7 U/$10^6$ cells) respectively. Both the cell supernatant and the cell pellet were subsequently processed. The cells were washed once more and lysed in 50 mM Tris-HCl pH 7.4, 150 mM NaCl, 2 mM EDTA, 0.5% NP-40, 1 mM phenylmethylsulfonylfluoride (PMSF) and 100 µg/ml lysine to block the excess of free Biotin. The same buffer was added to the supernatant. The samples were centrifuged at 12,000 g for 10 min at 4° C. to remove the cell nuclei and cell debris. The samples were precleared for 2 h with washed protein A-agarose.

The p97 was immunoprecipitated with antibody L235 followed by protein A-agarose precoated with rabbit anti-mouse IgG (Jackson ImmunoResearch). After immunoprecipitation, the beads were washed 6 times in 50 mM Tris-HCl pH 6.5, 150 mM NaCl, 2 mM EDTA, and 0.5% NP-40. The proteins were eluted from the beads in sodium dodecyl sulfate (SDS) polyacrylamide gel electrophoresis (PAGE) loading buffer and separated on an 8% SDS-PAGE gel under reducing conditions. The proteins were transferred onto Immobilon membranes (Millipore) by electroblotting, and detected using peroxidase-conjugated streptavidin (Jackson ImmunoResearch) and the chemiluminescence ECL Western blotting detection system (Amersham) using the conditions recommended by the manufacturer.

As shown in FIG. 6, a single protein of 95–97,000 daltons molecular mass was immunoprecipitated in both lane 2 (p97aWTBc7) and in smaller quantities in lane 3 (SK-MEL-28), but not from lane 1 (WTB). PI-PLC treatment of the cells resulted in a decreased amount of protein due to a large loss of protein from the cell surface (compare FIG. 6A, lanes 2 (+) and (−)), which was subsequently recovered in the cell supernatant (FIG. 6B). Under the conditions used in this experiment, no difference in the molecular mass between the plasma membrane associated form and the released form could be detected.

Example 6

Biosynthetic Labelling with [$^3$H]-ETHANOLAMINE

In order to determine whether the decrease in expression of p97 observed after bacterial PI-PLC treatment was an indirect effect due to the association of p97 with another PI-PLC sensitive protein at the cell surface, SK-MEL-28 cells were biosynthetically labelled with [$^3$H] ethanolamine, which is known to be a component of the phospholipid moiety of GPI-anchored proteins.

Briefly, SK-MEL-28 cell line monolayers were biosynthetically labelled for 24 hours with [$^3$H] ethan-1-ol-2-amine hydrochloride (20 µCi/ml, 30.4 Ci/mmol, Amersham) in DMEM containing 5% dialyzed FBS, 20 mM HEPES, 100 U/ml penicillin, 100 µg/ml streptomycin, 2 mM L-glutamine, and $5.0 \times 10^{-5}$ M 2-mercaptoethanol. The cells were washed in PBS and lysed in 20 mM Tris-HCl pH 7.2, 150 mM NaCl, 2 mM EDTA and 0.5% NP-40 with 20 µg/ml PMSF. The lysates and cell supernatants were then cleared by centrifugation, in particular at 100,000 g for 1 hour, prior to the immunoprecipitation. The primary antibodies used were the L235 for p97 and the OKT9 for the human TR. Protein A-agarose (BioRad) coated with rabbit anti-mouse IgG antibody (Jackson ImmunoResearch) was added to the samples and incubated for 8 hours at 4° C. The resulting complex was washed in 50 mM Tris HCl pH 6.5, 150 mM NaCl, 2mM EDTA, and 0.5% NP-40 and resuspended into SDS-PAGE loading buffer. The samples were run under reducing conditions on a 10–15% gradient SDS-PAGE gel. After fixation the gel was treated with Amplify™ (Amersham), dried, and autoradiographed.

Figure 7:
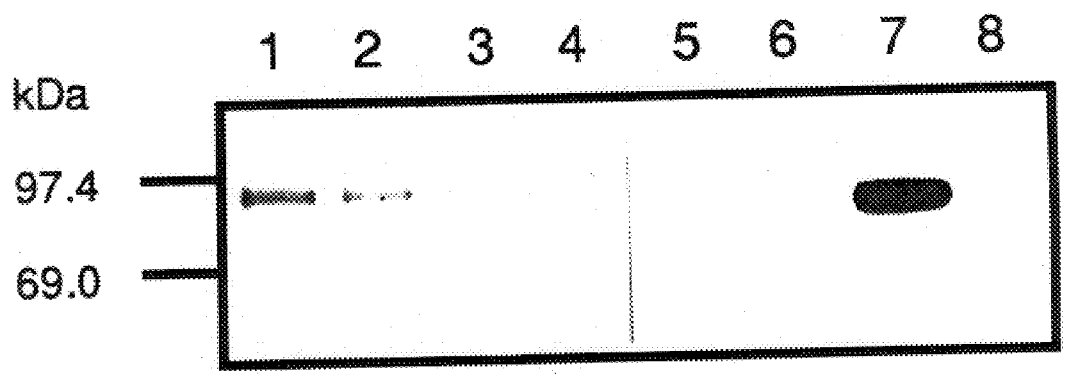
FIG. 7 is a Western Blot which indicates the results of labelling p97 with [$^3$H]-ethanolamine.

As shown in FIG. 7, in Lanes 1 and 2 p97 was immunoprecipitated with the anti-p97 antibody L235, and is visible due to labelling by [$^3$H]-ethanolamine. In contrast, the human transferrin receptor was immunoprecipitated with the anti-transferrin receptor antibody OKT9 in lanes 3 and 4, but is not visible because it was not labelled by the [$^3$H]-ethanolamine.

Figure 8:
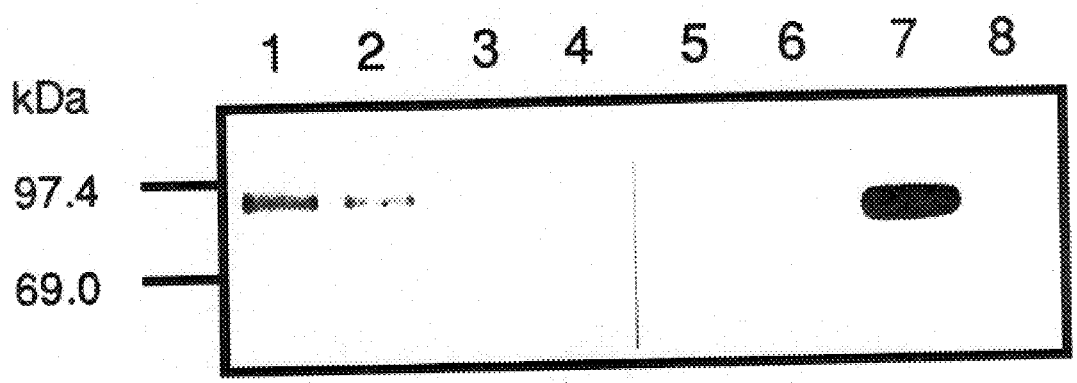
FIG. 8 is a Western Blot which indicates the results of labelling p97 with [$^3$H]-ethanolamine.

WTB cells (Lanes 1,2) and p97aWTBc3 cells (Lanes 3,4) were biosynthetically labelled with [$^3$H]-ethanolamine following the procedures described above. Proteins were then precipitated by the anti-p97 antibody L235 (Lanes 1 and 3), and the anti-transferrin receptor antibody (Lanes 2 and 4). As is shown in FIG. 8, only protein (p97) from the p97aWTBc3 cell line precipitated and was labelled with [$^3$H]-ethanolamine.

Example 7

Phase Separation of p97 in Triton X-114

The technique of phase separation in Triton X-114 can be used to assess the amphipathic or hydrophilic character of a protein and is especially useful to identify GPI-anchored proteins. This technique is based on the ability of the detergent Triton X-114 to partition into two phases: a detergent rich phase and a detergent poor phase. Amphipathic proteins which possess a hydrophobic membrane anchor, such as a GPI anchor, partition into the detergent rich phase, whereas hydrophillic proteins partition into the aqueous phase.

In order to investigate p97 partitioning in Triton X-114, the cell surface proteins of 8.0×10⁶ SK-MEL-28 cells were labelled with 0.4 mg Biotin (Sigma) as described above, following the methods described in von Borberg, Y. et al., (Eur. J. Biochem., supra). The cells were washed several times in DMEM, divided into two samples that were incubated for 60 min at 6° C., in the presence or absence of PI-PLC (1.7 U/10⁶ cells) respectively. Both the cell supernatant and the cell pellet were subsequently processed. The cells were washed once more and lysed in a buffer containing 10 mM Tris-HCl pH 7.4, 150 mM NaCl, 1% Triton X-114, 1 mM PMSF and 100 $\mu$g/ml lysine to block Biotin. Triton X-114 (Sigma) was precondensated as described by Bordier (J. Biol. Chem. 256:1604–1607, 1981). The same buffer was added to the supernatant. The samples were centrifuged at 12,000 g for 10 min at 4° C. to remove the cell nuclei and cell debris. The phase separation was obtained by incubation at 30° C. followed by a centrifugation at 3000 g for 3 min at room temperature. The samples were re-extracted 3 times in order to improve the separation and the corresponding phases were pooled.

The samples were precleared for 2 hours with washed protein A-agarose and subsequently divided into two halves for immunoprecipitation of p97 and the transferrin receptor using L235 and OKT9 monoclonal antibodies, respectively, followed by protein A-agarose precoated with rabbit anti-mouse IgG (Jackson ImmunoResearch). After immunoprecipitation, the samples were washed 6 times in 50 mM Tris-HCl pH 6.5, 150 mM NaCl, 2 mM EDTA, and 0.5% NP-40. The proteins were eluted from beads in SDS-PAGE loading buffer and separated on an 8% SDS-PAGE gel under reducing conditions. The proteins were transferred onto Immobilon membranes (Millipore) by electroblotting, and detected using peroxidase-conjugated streptavidin (Jackson ImmunoResearch) and the chemiluminescence ECL Western blotting detection system (Amersham) using the conditions recommended by the manufacturers.

Figure 9:
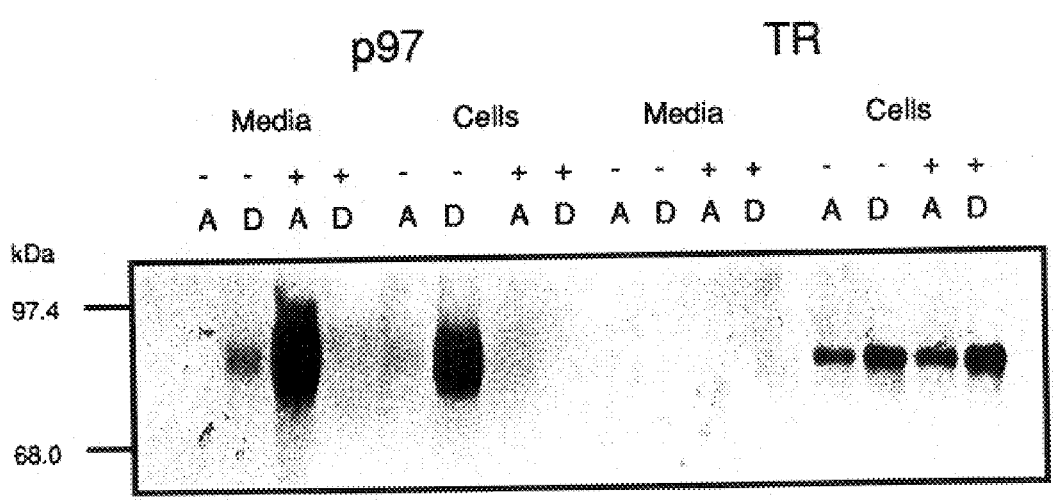
FIG. 9 is a Western Blot which indicates the results of a phase separation of p97 and TR in Triton X-114 solution.

FIG. 9 depicts results from cells which were washed in DMEM and incubated in the presence (+) or absence (−) of PI-PLC (1.7 U/10⁶ cells) for 60 min at 6° C. Proteins from the cell pellet (P) or the cell supernatant (S) were separated in Triton X-114 solution, and p97 and TR were immunoprecipitated from both the aqueous phase (A) or the detergent phase (D). FIG. 9 shows that all p97 molecules expressed at the surface of untreated human melanoma SK-MEL-28 cells partition into the detergent-rich phase. No p97 was detected in the supernatants of untreated cells. Treatment with bacterial PI-PLC led to the partitioning of p97 into the aqueous phase of the cell supernatant sample, indicating that the protein was cleaved from the plasma membrane and released as a hydrophilic form. No p97 could be detected in the bacterial PI-PLC treated cell pellet, indicating that most molecules were bacterial PI-PLC sensitive and that p97 is not simultaneously expressed in a transmembrane and GPI-anchored form at the cell surface. In contrast to p97, the TR, which is inserted in the membrane through a hydrophobic peptide segment, is not affected by bacterial PI-PLC. The amphiphilic structure causes the protein to partition in both phases after separation.

Figure 10:
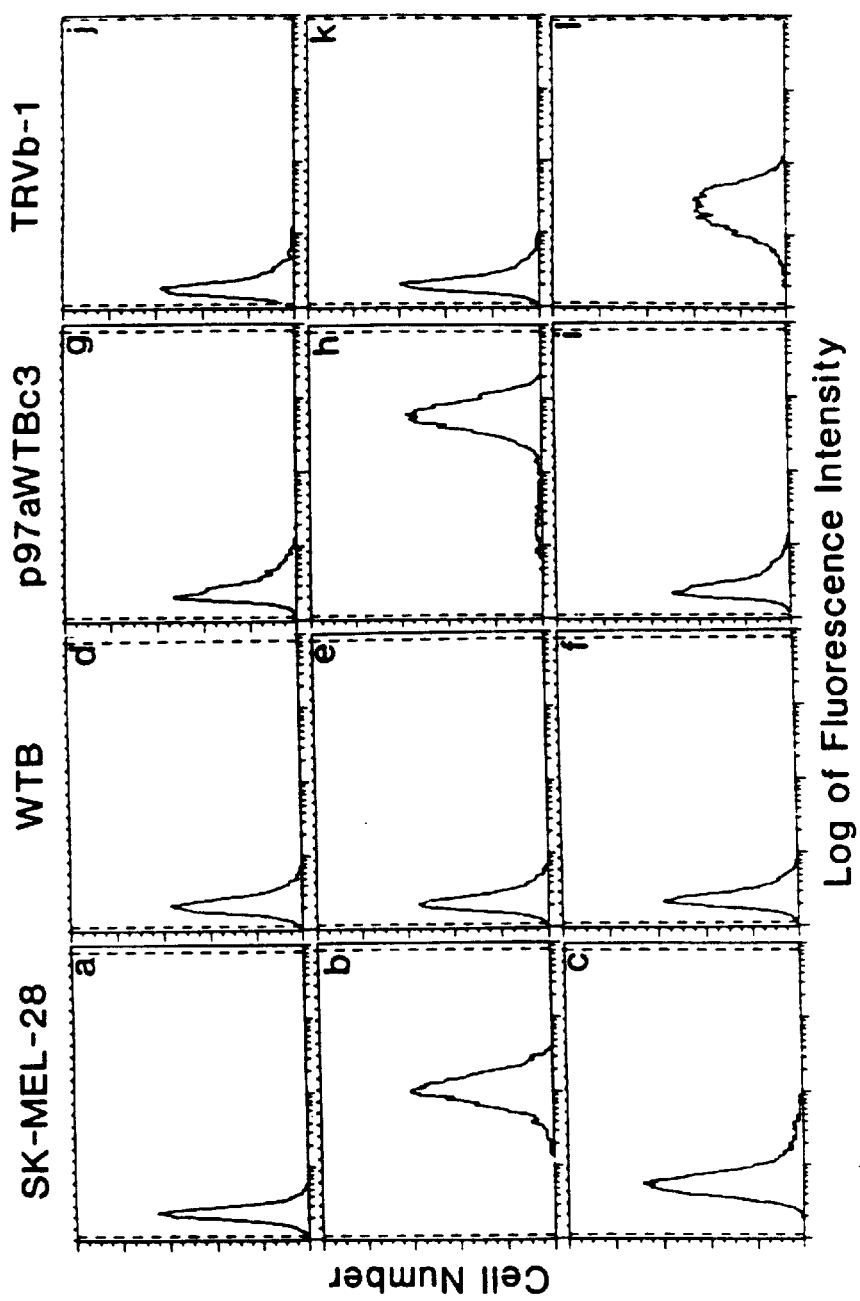
FIG. 10 is a series of graphs which represent FACS analysis of SK-MEL-28, WTB p97aWTBc 3 and TRVb-1 cell lines stained with no primary antibody (control), L235, and OKT9.

Example 8
Specificity of the Anti-P97 Antibody L235, and the Anti-transferrin Receptor Antibody OKT9
A. Cell Surface Expression The reactivities of the anti-p97 antibody L235 and OKT9 were confirmed. More particularly, the cell surface expression of human p97 and human TR were tested by staining the SK-MEL-28 cells with the L235 and OKT9 MAb and analyzing by FACS as outlined in Example 1. The human p97 molecule was shown to be expressed at a greater level than human TR. The expression of p97 by the p97aWTBc3 cell line (See Example 1 re preparation of p97aWTBc3) was found to be considerably higher than the SK-MEL-28 cell line (FIG. 10). The specificity of the L235 MAb to p97 was confirmed by the lack of reactivity to the parental (untransfected) CHO cell line WTB. At the same time the specificity of the OKT9 MAb for the human TR was demonstrated. The reactivity which is evident in the SK-MEL-28 line is absent in the WTB and p97aWTBc3 lines but is present in the TRVb-1 line.

B. Biosynthetic Labelling

The fates of p97 and TR after biosynthetic labeling of SK-MEL-28, WTB and p97aWTBc3 cells were also examined. SK-MEL-28, WTB and the p97 transfected p97aWTBc3 cells were cultured on petri dishes until reaching 80–90% confluence. The cells were then treated in minimal medium lacking methionine for 1 hour prior to labeling. Biosynthetic labeling of cells was done during 15 minutes with 2 ml of 150 uCi/ml of [³⁵S]-methionine per petri dish. Cells were then chased with normal medium containing an excess of cold methionine for various times. A separate petri dish was used for each time point. The cells were lysed in 20 mM Tris-HCl pH 7.2, 150 mM NaCl, 2 mM EDTA, and 1% NP-40 with 20 ug/ml PMSF. The lysates and cell supernatants were then cleared by centrifugation prior to immunoprecipitation. The primary antibodies used were L235 and OKT9 as described above. Immunoprecipitation and SDS-PAGE analysis were carried out as described in Kvist et al. (1982, Cell 29,61–69).

Figure 11:
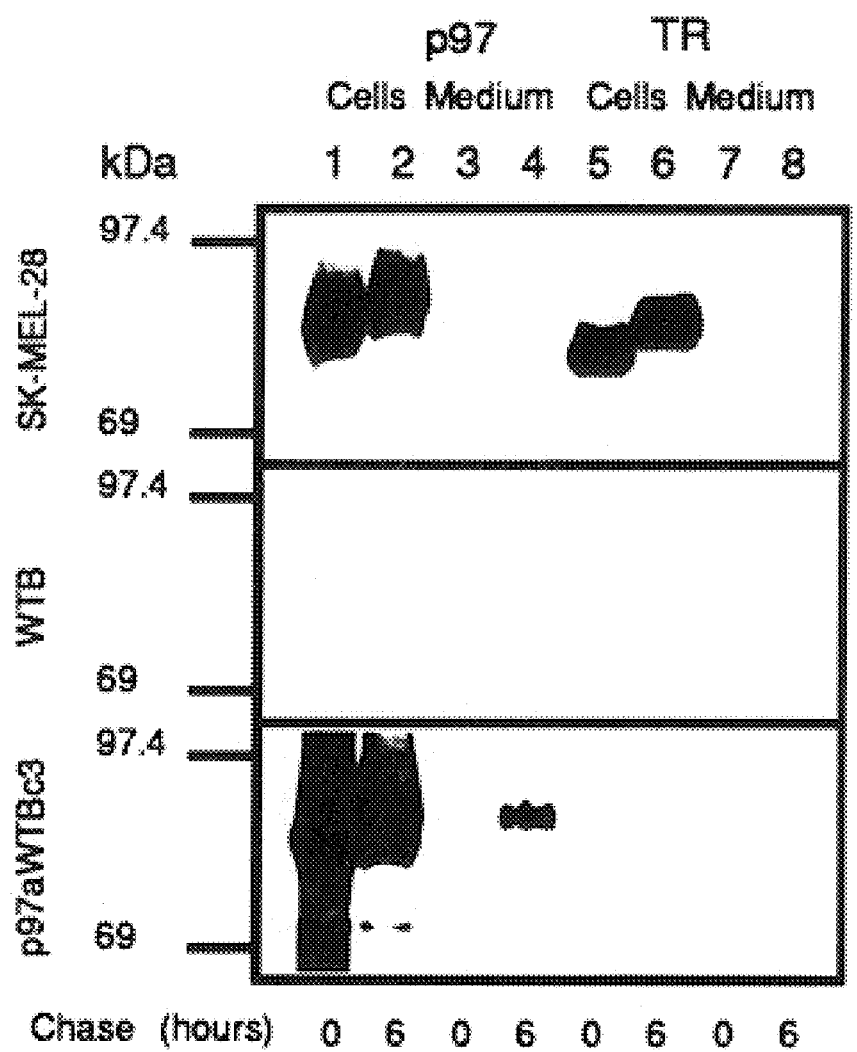
FIG. 11 is a series of autoradiograms which shows the effect of biosynthetic labelling on SK-MEL-28, WTB, and p97aWTBc 3 cells.

The L235 MAb recognized a protein with a mw of 93 kDa (FIG. 11, lane 1) that is processed to a higher mw of 95 kDa after 6 h of chase (FIG. 11, lanes 1, 2). This protein was not seen in WTB cells (FIG. 11, lanes 1, 2). A considerably greater amount of this protein is present in the p97 transfected CHO cells, p97aWTBc3 (FIG. 11, lanes 1, 2) identifying this protein as p97. In addition, a secreted form of p97 is present in the cell supernatant after 6 h of chase (FIG. 11, lane 4). The OKT9 MAb recognizes a protein with similar molecular weight in SK-MEL-28 cells corresponding to the reduced form of the human TR (FIG. 11, lanes 5, 6). The human TR is not seen in the cell supernatant (FIG. 11, lanes 7, 8). It is clear that the L235 and OKT9 MAb do not cross react with hamster p97 and TR in the CHO line WTB.

This data separately and collectively confirm the specificity of the L235 antibody for p97. They also confirm that p97 and TR are synthesized and transported to the cell surface. A form of p97 was also identified in the medium.

Example 9
Biosynthesis and Transport of P97
A. [³⁵S]-Methionine Pulse-Chase Experiments In order to investigate the biosynthesis and transport of p97 in melanoma cells, pulse-chase experiments were performed. Briefly, SK-MEL-28 cells were metabolically labeled with 150 $\mu$Ci/ml of [³⁵S]-methionine for 15 minutes, washed and subsequently chased with normal medium containing an excess of cold methionine at various timepoints. At each time point the supernatants from the Ocell cultures were collected in a separate petri dish, and the cells were lysed in nonionic detergent (20 mM Tris-HC1 pH 7.2, 50 mM NaCl, 2 mM EDTA and 1% NP-40 with 20 $\mu$g/ml PM:F). The lysates and cell supernatants were then cleared by centrifugation (100,000 for 1 h) prior to the immune precipitation. The primary antibodies used were L235 which recognizes p97 and OKT9 which recognizes the human transferrin receptor. The p97 molecule and, as a control, the TR, were immunoprecipitated from both the cell lysate (FIG. 12, lanes 1–7) and from the tissue culture supernatant (FIG. 12, lanes 8–14) and analyzed by SDS-PAGE.

Figure 12:
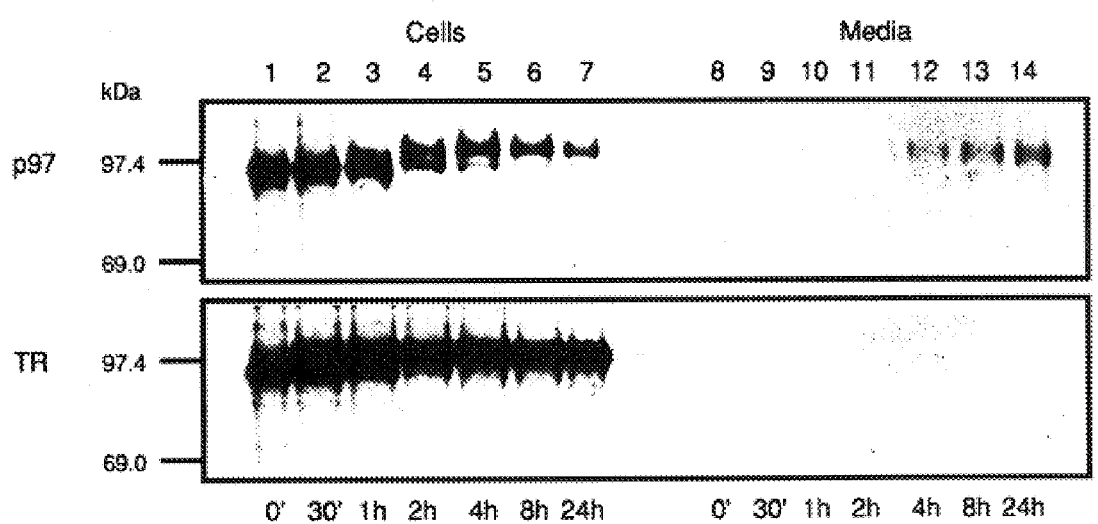
FIG. 12 is an autoradiogram which shows the results of an [$^{35}$S]-Methionine pulse-chase experiment.

As shown in FIG. 12, the p97 molecule is processed to a higher molecular weight form during the chase (FIG. 12, lanes 1–7). The processing of p97 is up to four times slower than the processing of the TR (FIG. 12, lanes 1–7). In addition, p97 is secreted into the medium (FIG. 12, lanes 8–14), whereas no TR is found in the medium. The appearance of the secreted form can be detected after only 1 hour of chase on an overexposed gel, indicating a transport rate of the secreted form that is comparable to the membrane associated form.

B. Endo H Digestion During [$^{35}$S]-Methionine Pulse-Chase

The transport of glycoproteins can be assessed by the modification of their glycans during successive exposure to Golgi specific enzymes becoming resistant to Endoglycosidase H (Endo H) digestion. Briefly, SK-MEL-28 cells were labeled for 15 min with [$^{35}$S]-methionine, and chased with an excess of unlabeled methionine for the time indicated at the bottom of FIG. 13, lysed, and subjected to immunoprecipitation with L235 MAb (p97) and OKT9 MAb (TR) as described above. Precipitates were digested with 5 mM of Endo H (Boehringer Mannheim) for 20 h at 37° C., and analysed as described above. The autoradiograms were developed after 3 days exposure of the gel.

Figure 13:
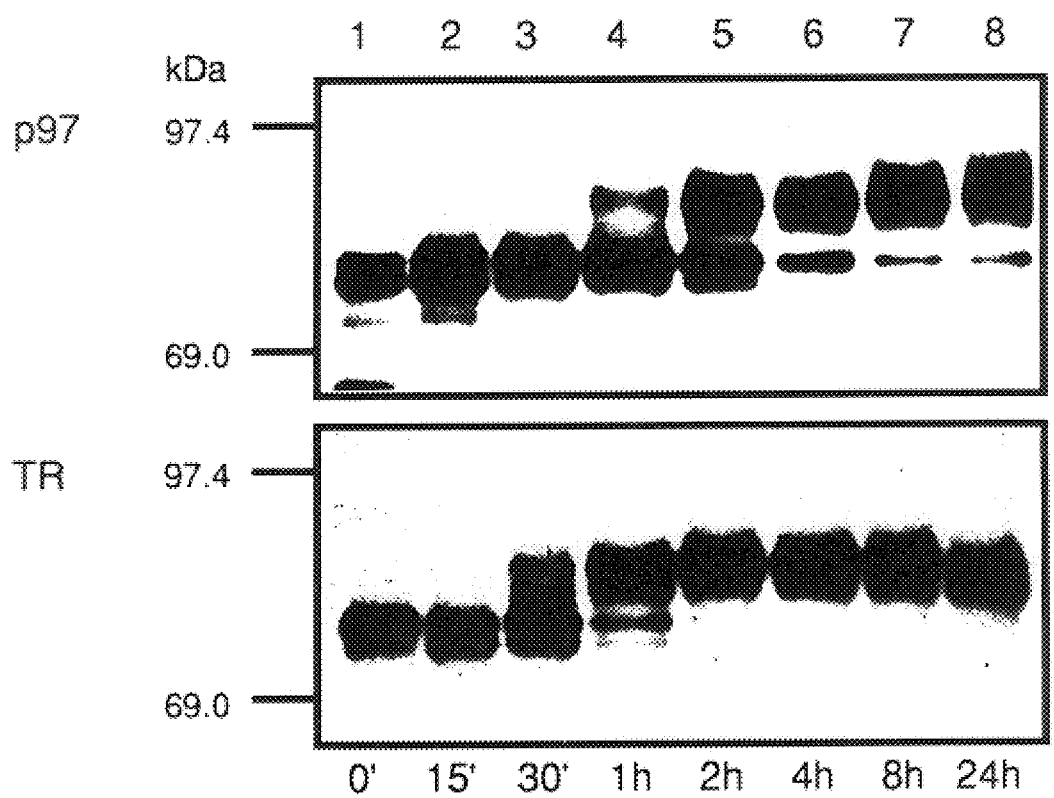
FIG. 13 is an autoradiogram which shows acquisition of Endo H digestion resistance during transport of p97 and TR in SK-MEL-28 cells.
Figure 35:
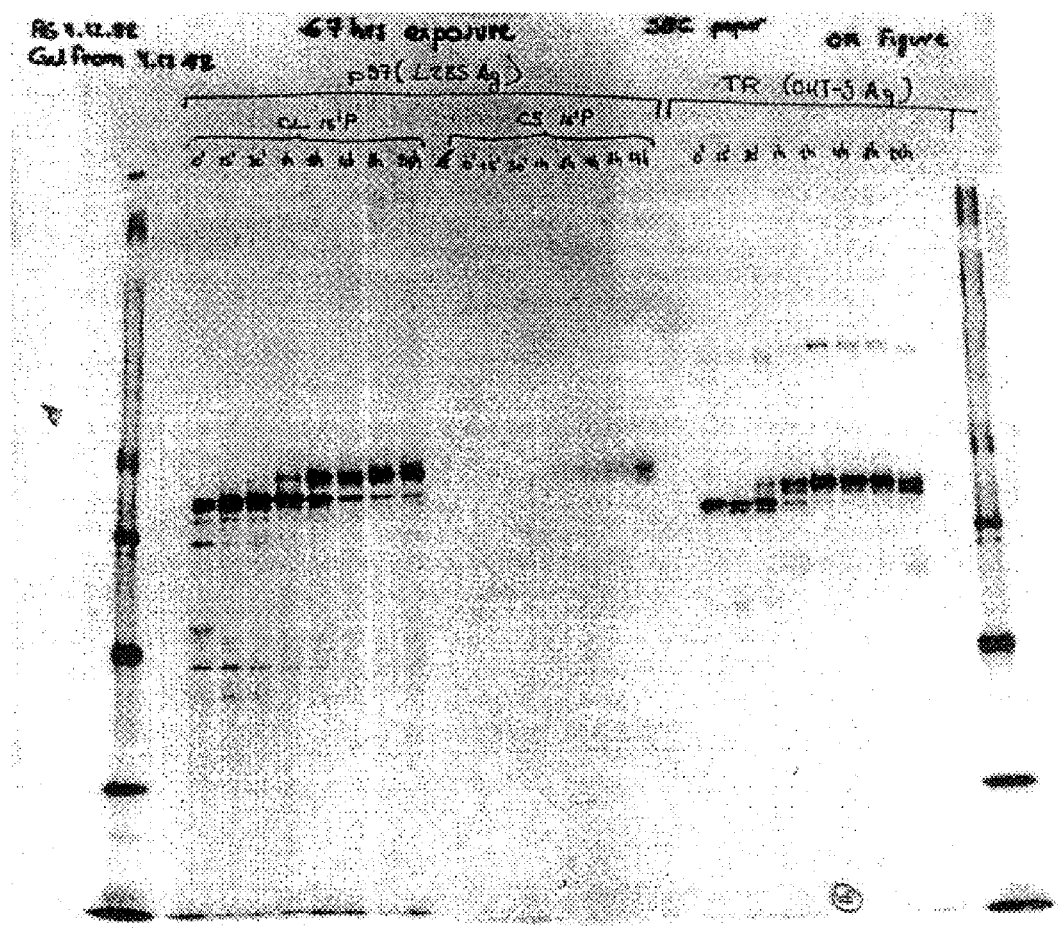
FIG. 35 is an autoradiogram showing that p97 is resistant to Endo-H digestion.

As shown in FIG. 13, most of the p97 molecules are Endo H resistant after 4 hour chase (FIG. 13, lane 6), in comparison, only 1 hour chase is necessary for the TR to become resistant to Endo H digestion (FIG. 13, lane 4). It therefore appears that the transport rate of both the secreted and GPI-anchored forms of p97 is much slower than the transport rate of TR. This difference may indicate that p97 needs more time in order to achieve a conformation or a structure allowing transport through the Golgi and to the cell surface. Also, the secreted form of p97 is resistant to Endo H digestion, indicating that the soluble form uses the normal secretory pathway for transport to the cell surface. Briefly, SK-MEL-28 cells were pulse labelled for 15 minutes with 200 μCi/ml $^{35}$S-methionine and chased in medium with excess cold methionine for 0 minutes, 30 minutes, 1, 2, 4, 8 or 24 hours. Proteins were immunoprecipitated using L235 and OKT-9 antibodies, using protein A sepharose precoated with rabbit anti-mouse IgG. Prior to pulse-chase labelling, cells were pre-treated with minimum medium without methionine. Radioactive cell lysates and cell supernatants were precleared with normal rabbit serum before immunoprecipitation. The results are shown in FIG. 35. The upper band corresponds to the soluble form and is resistant to Endo H digestion.

Figure 14:
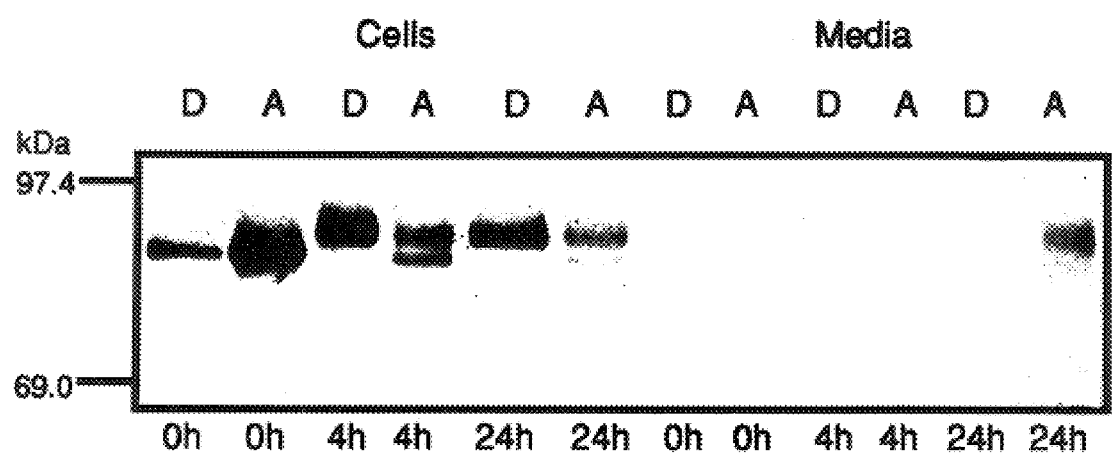
FIG. 14 is an autoradiogram which shows that in Triton X-114 the secreted form of p97 partitions in the aqueous phase.

C. Triton X-114 Phase Separation of [$^{35}$S]-Methionine Labeled SK-MEL-28 Cells The secreted form of p97 was analyzed by Triton X-114 phase separation on the cell supernatant (FIG. 14). Briefly, SK-MEL-28 cells were labeled for 30 min with [$^{35}$S]-methionine and chased with an excess of cold methionine for the time indicated on the top of FIG. 14. The aqueous (A) and detergent (D) phases from the medium were analysed after Triton X-114 phase separation, immunoprecipitated with L235 MAb (p97) and run on SDS-PAGE as described above. The autoradiogram was developed after 4 days exposure to the gel.

Figure 15:
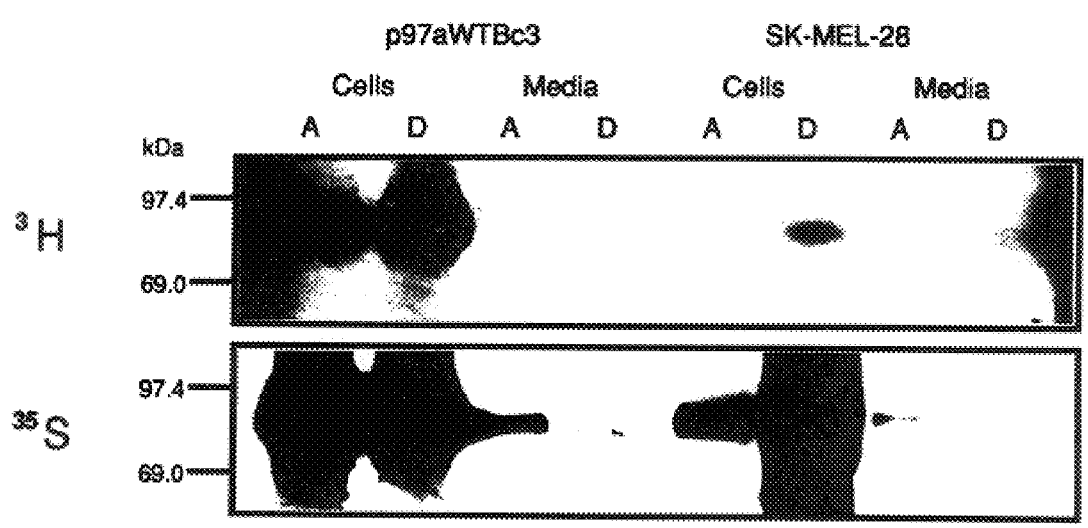
FIG. 15 is an autoradiogram which shows the results of biosynthetically labelling p97 with [$^3$H]-ethanolamine followed by Triton X-114 separation.

As shown in FIG. 14, p97 secreted in the cell medium after a 4 hour-pulse and a 24 hour-chase partitioned in the aqueous phase, demonstrating that this form has no hydrophobic tail. In addition, after 24 hours labeling with [$^{3}$H]-ethanolamine, and 30 days exposure, ethanolamine labeled p97 could not be detected in medium from p97 transfected p97aWTBc3 cells (FIG. 15, lanes 3 and 4) and SK-MEL-28 cells (FIG. 15, lanes 7 and 8). It is clear that there is [$^{3}$H]-ethanolamine labeled p97 (FIG. 15, lanes 1, 2 and 6) associated with the detergent lysates of the p97aWTBc3 and SK-MEL-28 cells, but the secreted form of p97 is not labeled. In a similar experiment with [$^{35}$S]-methionine labeling, the secreted form is clearly evident in a 3-day exposure of a 15 minute labeling (FIG. 12).

Figure 16:
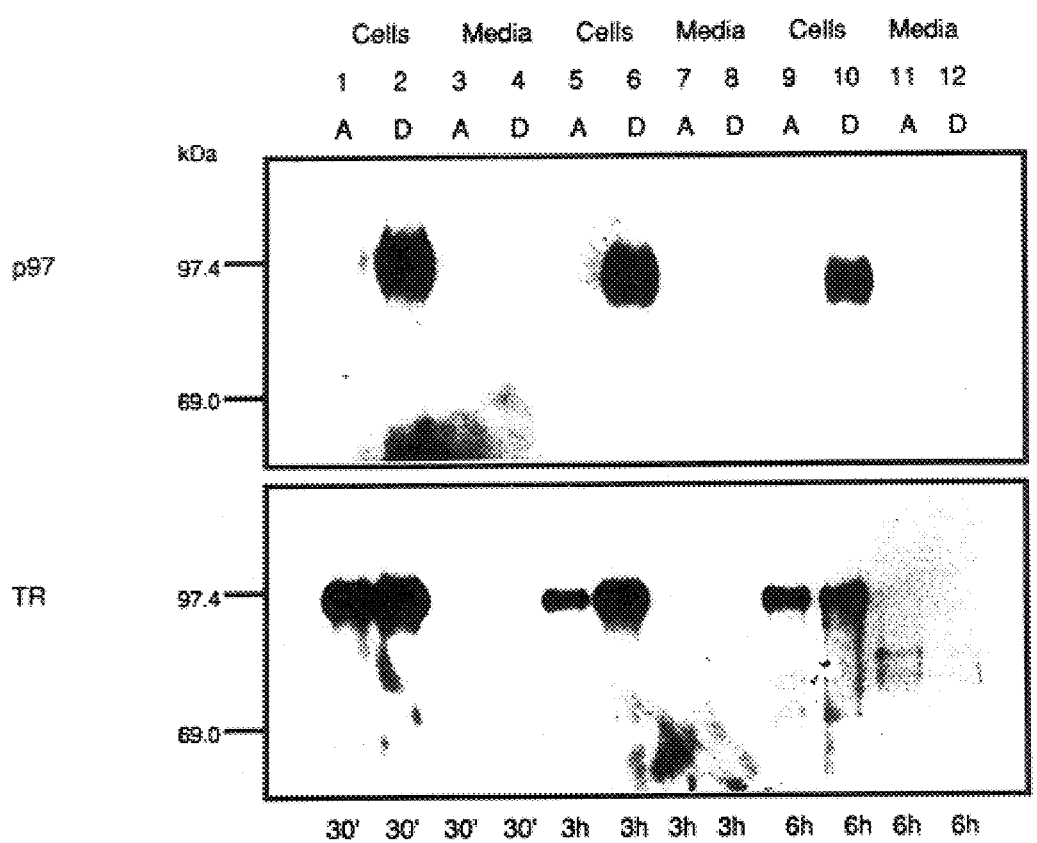
FIG. 16 is an autoradiogram which shows that membrane associated TR and p97 molecules expressed on cell surface are not released.

In order to determine whether the secreted form of p97 originates from either the release of cell surface GPI-anchored p97 or from a synthesized soluble form that is secreted into the medium, the fate of cell surface biotinylated p97 was followed (FIG. 16). Cell surface biotinylated p97 and TR were chased in normal medium, and analyzed by SDS-PAGE after immunoprecipitation, electroblotting, and detection by peroxidase conjugated streptavidin and the chemiluminescence ECL Western blotting detection system. The aqueous and detergent phase of Triton X-114 from cell lysate and medium were then analyzed.

As shown in FIG. 16, no p97 is accumulated in the medium after 6 hour chase (FIG. 16, lanes 11 and 12). p97, like TR, was always associated with cells (FIG. 16, lanes 1, 2, 5, 6, 9 and 10) and always partitioned in the detergent phase indicative of a hydrophobic protein (FIG. 16, lanes 2, 6, and 10). It therefore appears that two forms of p97 are synthesized, one is membrane bound by GPI-anchor and remains on the cell surface, and a second form is secreted into the medium.

Example 10

Localization of P97 in Brain Sections by Indirect Immunoperoxidase

A. Expression of the Transferrin Receptor and p97 in Healthy and Alzheimer's Disease Brain Tissues Thirty brains were examined, including 7 Alzheimer's disease (AD) (aged 67–81), 5 Parkinson's disease (PD) (aged 69–76) (3 of them had AD changes), 3 progressive supranuclear palsy (PSP) (60–66), 3 Huntington's chorea (HD) (aged 49–63), 2 multiple sclerosis (MS) (aged 56–66), 4 amyotrophic lateral sclerosis (ALS) (aged 48–81) and 7 non-neurological controls (aged 54–82). Brains in all cases were obtained 2–32 hours after death. Briefly, small blocks were dissected from various brain regions of non-neurological cases, angular, entorhinal cortices and hippocampus of AD, angular entorhinal cortices, hippocampus and substantia nigra in PD, precentral cortex, basal ganglia of PSP, striatum of HD, cerebral white matter having plaques of MS and precentral gyrus and spinal cord of ALS. These blocks were fixed for two days in phosphate-buffered 4% paraformaldehyde. They were then transferred to a maintenance solution of 15% sucrose in 0.1M phosphate buffer, pH 7.4, and kept in the cold until used. Sections were cut on a freezing microtome at 30 mm thickness and stained by single or double immunohistochemical procedures (McGeer et al., 1992) using primary antibodies. The antibodies and their dilutions were: anti-human p97, 1:1000 (murine monoclonal L235, American Type Cell Culture HB 8446; R-17, 1:10,000 (rabbit polyclonal against BAP, generously provided by Dr. Ishii); anti-HLA-DR antibody, 1:1,000; anti-human transferrin receptor antibody OKT9, American Type Cell Culture CRL 8021). For greater clarity, the specificities of the L235 monoclonal antibody and the OKT9 MAb monoclonal antibody for p97 and TR respectively were confirmed as set forth herein.

B. Expression of p97 and TR in Healthy and AD Brain Tissues

Figure 17:
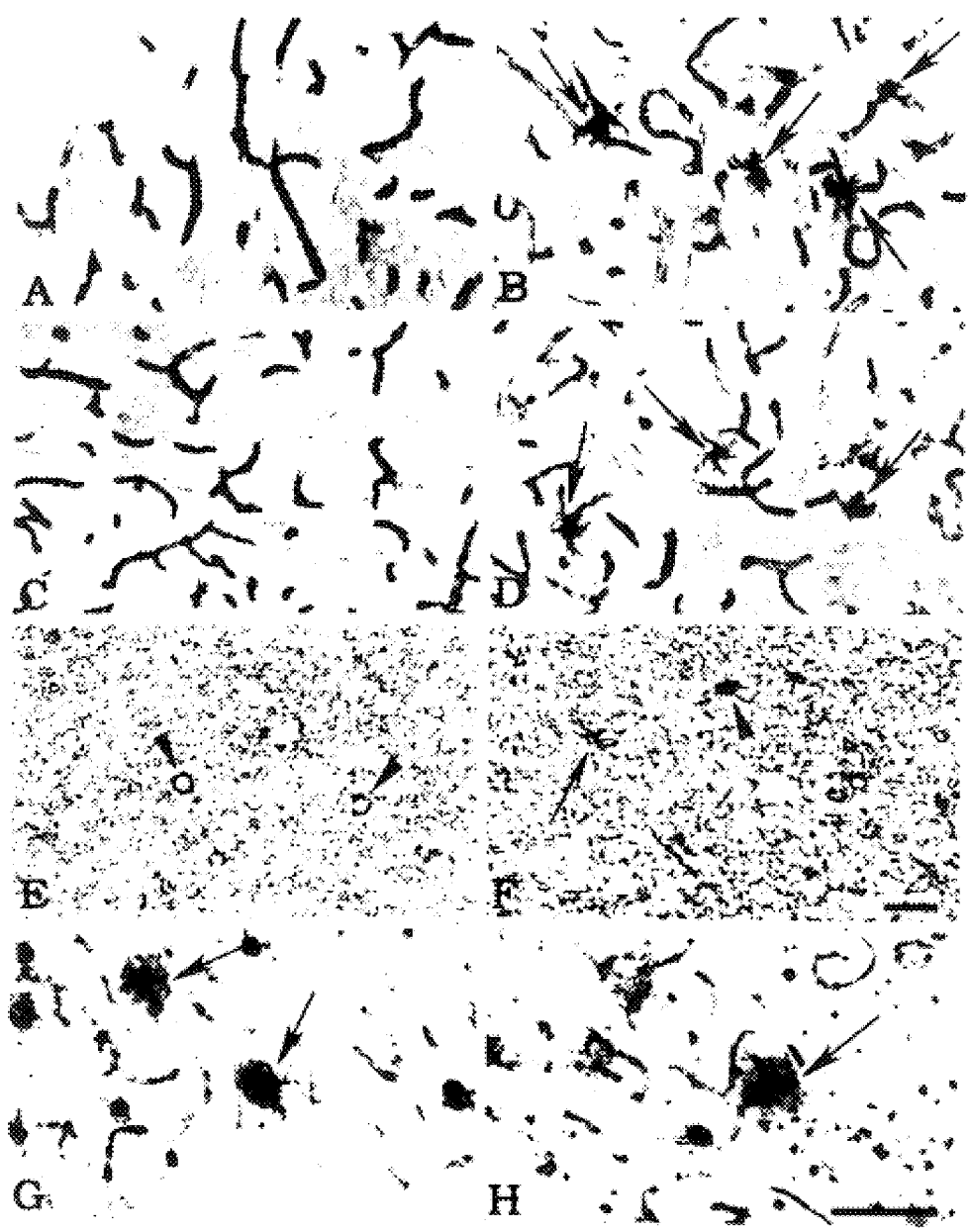
FIG. 17 is a series of photographs of sections of human brain tissue showing immunohistochemical staining for p97, transferrin and transferrin receptor.

Immunohistology methods were used to establish the distribution of p97 and TR in healthy human brain. The staining of control human brain tissue with the L235 (FIG. 17a), A-061 (FIG. 17b), and OKT9 MAb (FIG. 17c) is shown. In control human brain tissue (cortex), capillary endothelium were strongly stained by L235 (FIG. 17a) and OKT9 (FIG. 17c). In contrast the pattern of staining which was obtained with the anti-transferrin MAb is completely different and is not localised to these structures (FIG. 17e).

The limited staining with A-061 MAb is localised to small round oligodendrocytes as previously proposed (Connor et al., 1990). These data establish the coincident expression of TR and p97 on capillary endothelium in normal brain which form the blood/brain barrier and the Tf is not found in association with TR or p97. These results are suggestive of a close association between the functions of p97 and TR.

The identical pattern of expression of both TR and p97 was further investigated in neuropathological brain tissue. A comparison of normal and AD brain tissues stained for MTf and TR again demonstrated the coincident expression of p97 and TR.

FIG. 17A shows that normal angular cortical gray matter stained with anti-p97 MAb. Only capillary endothelium is positive. FIG. 17B indicates that angular cortical gray matter stained with anti-p97 MAb and, in addition, some microglia are positively stained (arrows). FIG. 17C shows a section nearby to section 17A stained with anti-transferrin receptor MAb. As in FIG. 17A, only capillary endothelium is positive. FIG. 17D shows a nearby section to B, stained with anti-transferrin receptor MAb. As in B, capillaries and some microglia (arrows) are positive. FIG. 17E shows normal angular cortex stained with anti-transferrin polyclonal antibody. The sparse cytoplasm of a few cells resembling oligodendroytes (arrows) are positive. FIG. 17F shows angular cortex from Alzheimer's Disease brain stained with anti-transferrin polyclonal antibody. Sparse cells resembling oligodendroytes (arrows) and rare cells resembling microglia (arrow) are positive.

The binding of the OKT9 antibody to capillary endothelial cells in Alzheimer's Disease brains is identical to that seen in control brains but, in addition, a subset of microglial cells is also stained. By contrast, the anti-transferrin MAb failed to stain capillaries, and stained only occasional oligodendrocytes and microglia in the white matter (FIG. 17F). Staining of sections of AD and normal tissue from the same region of the brain cortex, with the L235 MAb revealed that the distribution of p97 is identical to that of the TR (FIG. 17c, 17d). Both microglial cells and endothelial cells are labelled. In experiments on other pathologically affected brain tissue from cases of PD, PSP, HD, MS or ALS, no microglial labelling was seen with either the L235 or OKT9 MAb. In control experiments in which the primary antibody was omitted, no labelling of cells or any other structures was seen in AD or control brain tissue. These data support the unique and identical distributions of p97 and TR in AD tissue.

Upon viewing of the brain sections noted above, it was evident that the labelling of Alzheimer's Disease brain sections with anti-p97 antibody revealed an identical distribution to that of the transferrin receptor specific antibodies. In fact, both microglial cells and endothelial cells were labelled. In controls using secondary antibodies alone, however, no labelling of any cells or structures were seen in healthy or Alzheimer's Disease brain.

Figure 18:
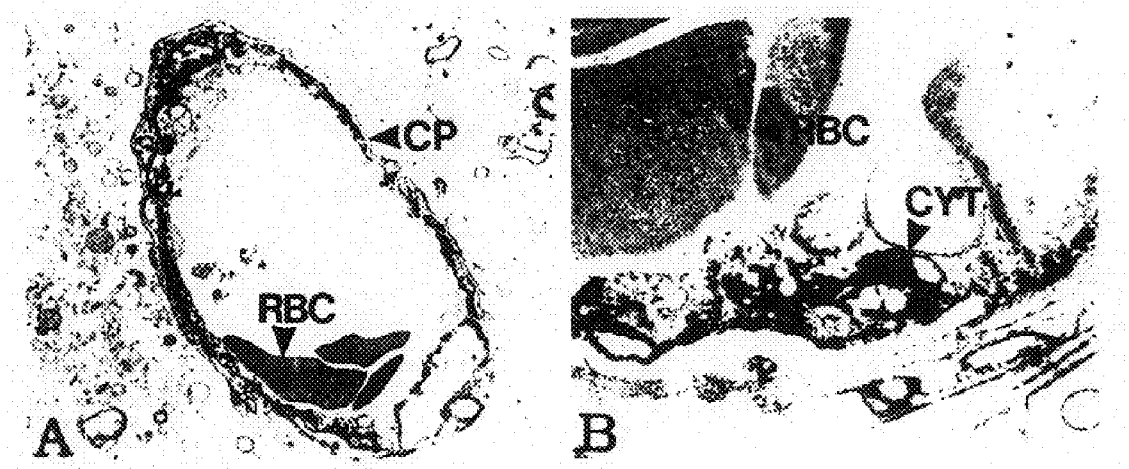
FIG. 18 is electron micrographs showing sections of human brain labelled with L235 antibody.

Electron microscopy was used to define the structures expressing p97 in capillaries. Brain tissue was prepared for electron microcopy as described in Example 10D. The DAB reaction products in sections stained with anti-p97 antibodies were found in the cytoplasm and attached to the membrane of endothelial cells (FIG. 18). These results showing the presence of p97 on the surface of capillary cells and within the cytoplasm of capillary cells indicate a role for p97 in transport through brain endothelium. In FIG. 18 capillary cells are labelled CP, red blood cells are labelled RBC and cytoplasm is labelled CYT.

In summary, the expression of p97 and transferrin receptors by microglial cells of Alzheimer's Disease brain section appeared to be specific to this neurological disorder. No microglial labelling was observed in brain sections from PD, PSP, HD, MS, or ALS.

C. Expression of the p97 Antigen is Confined to Microglial Cells
Associated with Amyloid Plagues In order to examine the frequency and distribution of microglial cells which express the p97 or transferrin receptor molecules, double labelling experiments were undertaken with antibodies which react with β-amyloid protein ("BAP") or HLA-DR molecules. FIG. 19I shows the double labelling of Beta Amyloid Protein (BAP) and HLA-DR. The BAP labelling appears as diffuse plaques. Microglial cells throughout the tissue are clearly labelled by the HLA-DR reactive antibody, including those cells not associated with amyloid plaques.

In double labelling studies with BAP reactive antibodies and p97 reactive antibodies a different labelling pattern appears. The p97 reactive antibody selectively identifies the subset of microglial cells associated with the senile plaque (FIG. 19H). This appears to be consistent throughout the AD tissues studied to date. Furthermore, it appears that the microglial cells which express p97 are associated with blood vessels. The reason for this is unclear. Double labelling experiments using antibodies against BAP and the transferrin receptor reveals a similar pattern to that seen with the p97 reactive antibody.

In summary, microglial cells staining with anti-p97 or transferrin receptor were only detected in the cortices and hippocampus of AD cases or in PD plus AD cases. Compared with HLA-DR staining, which chiefly reacts with all microglia, anti-p97 antibody revealed smaller numbers of reactive microglia which were associated only with BAP. The processes of these microglia were frequently attached to capillaries.

D. Distribution of the p97 Molecule on/in Alzheimer's Brain Endothelial and Microglial Cells at the Electron Microscope Level In order to establish the cellular structures which express the p97 molecule in AD brain, the distribution of the p97 molecule was determined by electron microscopy.

For electron microscopy, blocks of entorhinal cortex from two cases of AD were fixed in 1% glutaraldehyde/4% paraformaldehyde in 0.1M phosphate buffer, pH 7.4, for 24 hours at 4° C., followed by immersion in 15% sucrose in 0.1M phosphate buffer, pH 7.4, for several days at the same temperature. Sections were cut by vibratome at 50 mm thickness and incubated with anti-P97 (L235, 1:1,000) for 5 days at 4° C. They were then treated with the appropriate Vectastain and ABC second antibody systems. After the diaminobenzidine (DAB) reaction, the sections were osmified, dehydrated and embedded in Epon. Ultra-thin sections were cut and examined with a Phillips EM201 electron microscope, without counterstaining.

Figure 19D:
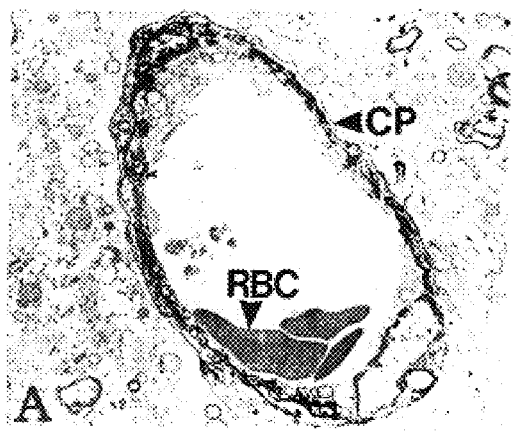
FIG. 19D is a photograph of a section of endothelia from an Alzheimer's Disease brain, stained with anti-p97 antibodies.
Figure 19E:
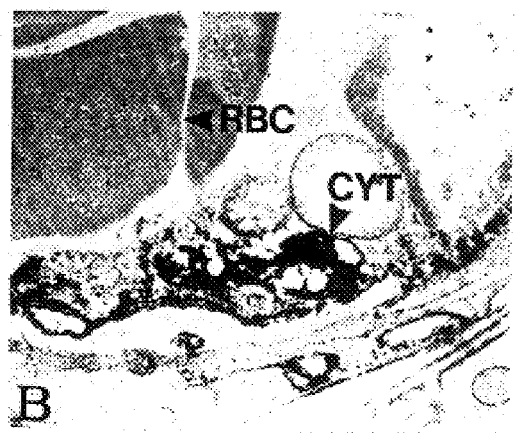
FIG. 19E is an enlargement of FIG. 19D.
Figure 19F:
FIG. 19F is a photograph of a section of a microglial cell stained with anti-p97 antibodies.
Figure 19G:
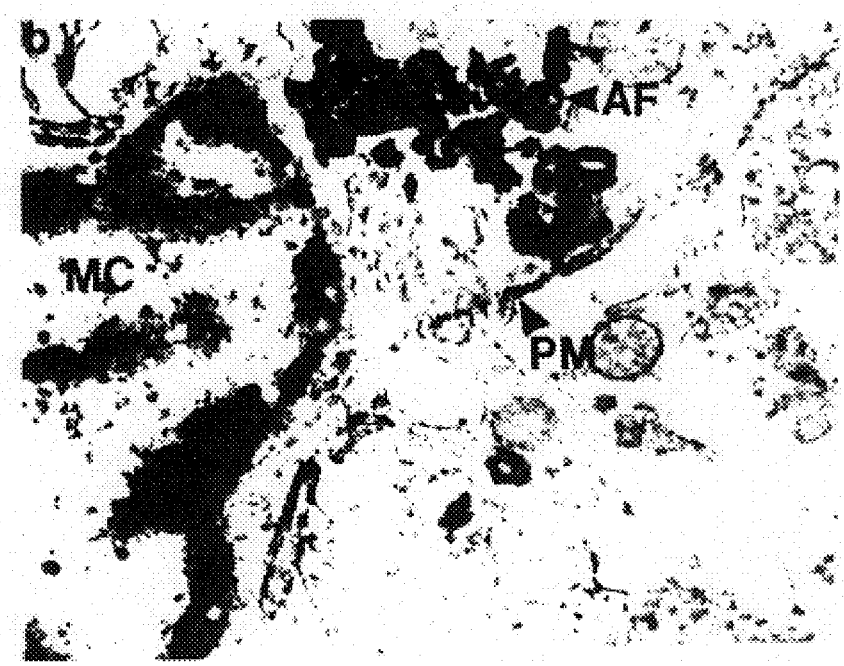
FIG. 19G is an enlargement of FIG. 19F.
Figures 19H, 19I:
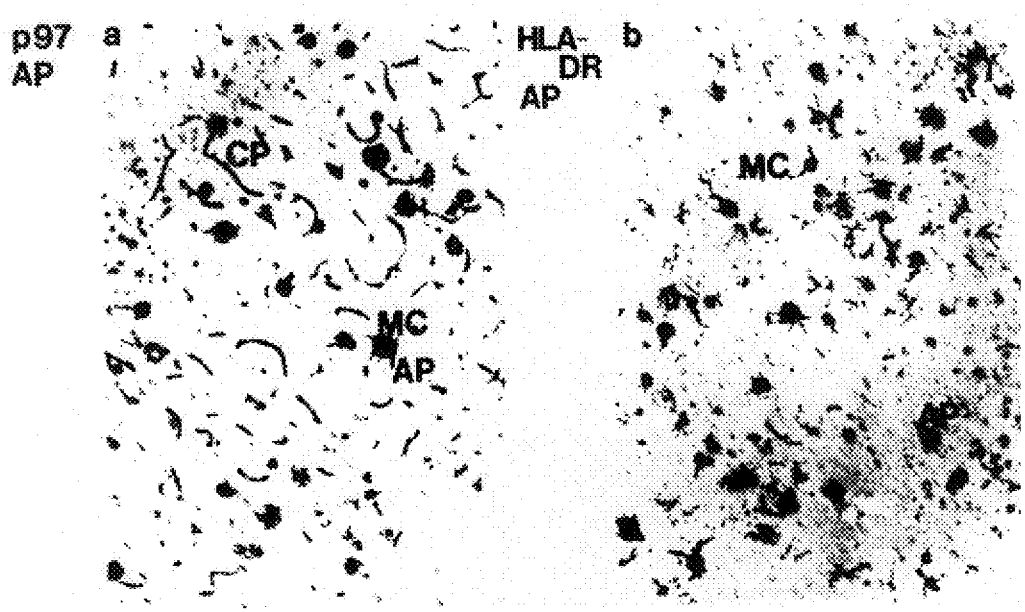
FIG. 19H is a photograph of a section of an Alzheimer's Disease brain, stained with anti-p97 and anti-β-amyloid antibodies.
FIG. 19I is a photograph of an adjacent section of the Alzheimer's Disease brain shown in FIG. 19H, stained with anti-HLA-DR and anti-β-amyloid antibodies.
Figure 19J:
FIG. 19J is a photograph of an Alzheimer's Disease brain section stained with anti-p97 antibodies.
Figure 19K:
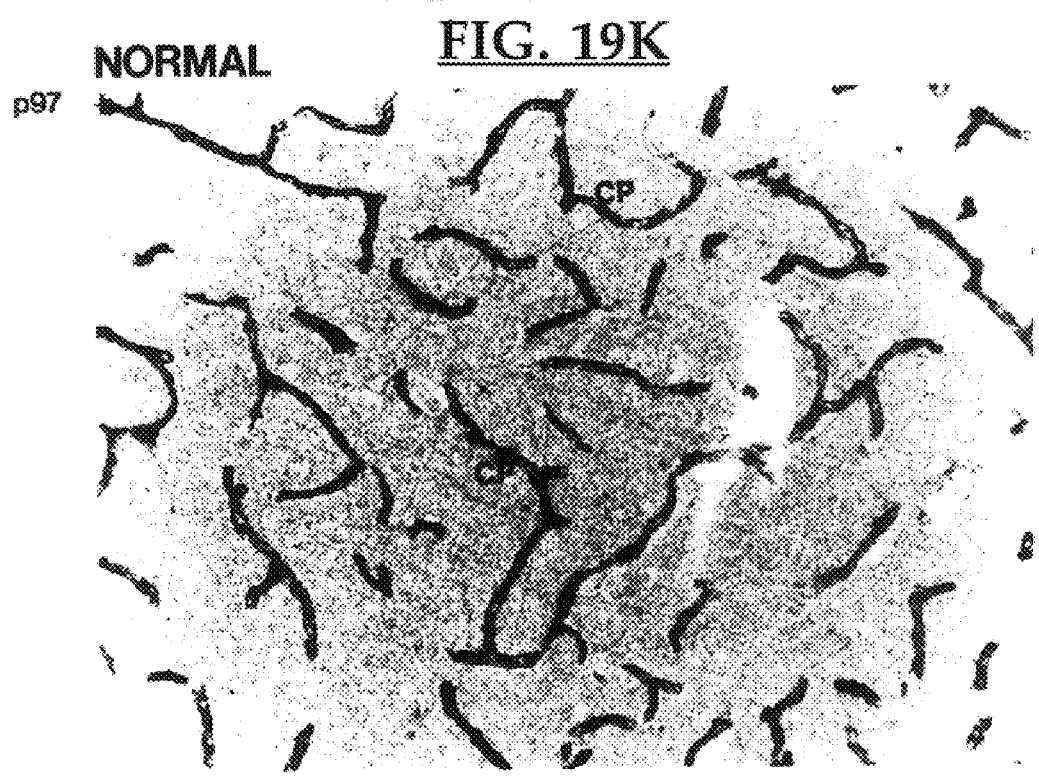
FIG. 19K is a photograph of an Alzheimer's Disease brain section stained with anti-p97 antibodies.

Electron-microscopically, DAB reactive products were seen in the membrane and cytoplasmic structures of endothelial cells labelled with anti p97 antibody (FIGS. 19D and 19E). In microglial cells, which are producing amyloid fibers, the reactivity of the antibody is limited to the cell membrane (FIGS. 19F and 19G). Thus it appears that the majority of the p97 molecule is expressed at the plasma membrane in both cell types. In addition, the p97 also appears to be expressed inside endothelial cells. This is consistent with the p97 molecule being made by microglial cells and being transported through endothelial cells.

E. PI-PLC Treatment of Alzheimer's Disease Brain Sections

Figure 19N:
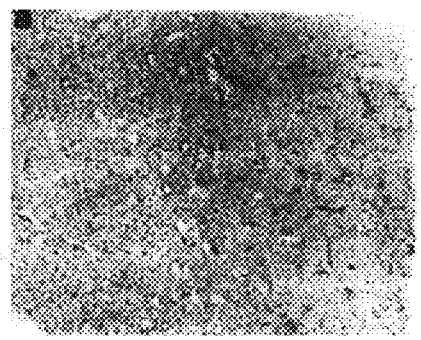
FIG. 19N is a photograph of an Alzheimer's Disease brain section stained with anti-p97 adsorbed, anti-p97 antibodies (ie., non-reactive with p97).
Figure 19L:
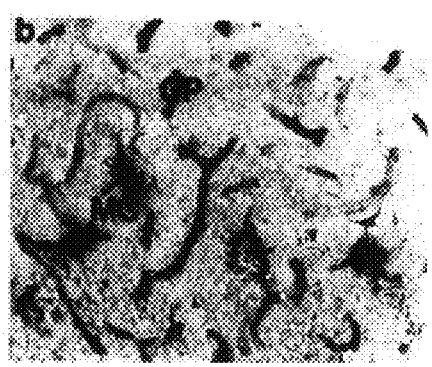
FIG. 19L is a photograph of an Alzheimer's Disease brain section stained with anti-p97 antibodies, and no PI-PLC treatment.
Figure 19M:
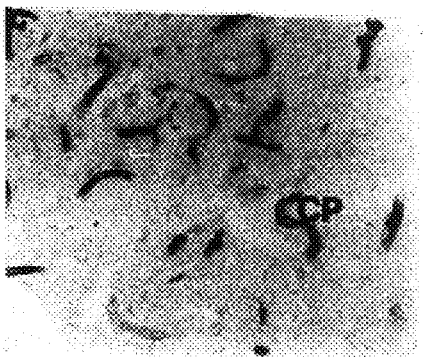
FIG. 19M is a photograph of an Alzheimer's Disease brain section treated with PI-PLC prior to staining with anti-p97 antibodies.

As shown in FIGS. 19L (no PI-PLC treatment) and 19M (PI-PLC treatment), PI-PLC treatment prevents visualization of microglial cells in tissue sections stained with anti-p97 antibodies. As an additional control, anti-p97 antibodies were absorbed with p97, and used to stain Alzheimer's Disease brain sections. As shown in FIG. 19N, no staining of microglial cells or blood vessels is evident.

Example 11
Detection of P97 in Alzheiemers's Disease Brain (Membrane and Cytoplasmic Fractions) by Western Blots A Western blot analysis was carried out under non-reducing conditions in order to demonstrate the identity of the L235 antigen recognized in the tissue sections of Alzheimer's Disease brain and p97 containing cell lines (SK-MEL-28, p97aWTBce).

Briefly, SK-MEL-28, WTB and p97aWTBc3 cell cultures were grown up, washed and thereafter lysed in nonionic detergent 20 mM Tris-HCl pH 7.2, 150 mM NaCl, 2 mM EDTA, 1% NP-40, and 20 µg/ml PMSF. Membrane fractions and cytoplasmic fractions isolated from Alzheimer's Disease brains were homogenized and then precleared by centrifugation at 4° C. at 10,000×g for 10 minutes. The membrane and cytoplasmic fractions were then separated by a high-speed centrifugation at 4° C. at 100,000×g for 60 minutes. The cell cytoplasmic and membrane samples were then analyzed by western blotting. Briefly, the proteins were separated on a 5–10% SDS-PAGE gel under non-reducing conditions, and then transferred onto Immobilon membranes (Millipore) by electroblotting. After incubation for 1 hour in blocking buffer (2% BSA, 0.05% Tween-20, 2.5×10$^{-4}$ M thimerosal in PBS), the membranes were washed 3 times in washing buffer (0.1% BSA, 0.05% Tween-20, 2.5×10$^{-4}$ M thimerosal in PBS), and then incubated for 1 hour with L235 tissue culture supernatant as a first antibody. After further washing of the membranes, they were incubated for 1 hour with the secondary antibody, a 1:10,000 dilution of donkey anti-mouse IgG conjugated with horseradish peroxidase (Jackson ImmunoResearch, 1:10,000 dilution). The specificity of the secondary antibody was determined after incubation with L235 as a first antibody or without a first antibody. After washing the proteins were detected by the chemiluminescence utilizing the ECL Western blotting detection system (Amersham).

Figure 20:
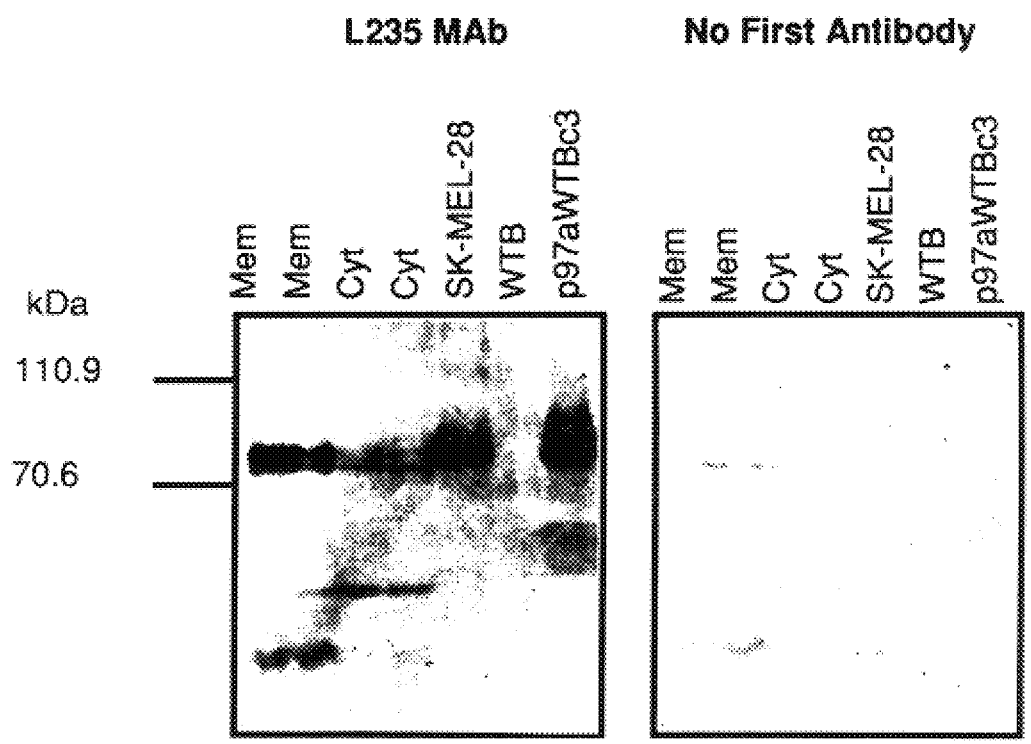
FIG. 20 shows two Western Blots of Alzheimer's Disease brain membrane and cytoplasmic samples, and SK-MEL-28, WTB and p97aWTBc3 cells stained with either L235 antibody or, no first antibody control.

Results are shown in FIG. 20. A specific band with the same molecular weight as p97 in SK-MEL-28 and p97aWTBc3 cells can be detected in the membrane and cytoplasmic fraction from Alzheimer's Disease brain tissues. These results indicate that the same molecule is recognized by the L235 monoclonal antibody in brain tissue and on the cell lines, and the molecule is p97.

Example 12
Detection of P97 in Cerebrospinal Fluid of Ad Patients

Samples of cerebrospinal fluid CSF (1–2ml) were obtained from eight AD patients and normal patients by spinal tap. Samples were concentrated by freeze drying at 135° C. Samples were analysed using the BioRad minigel system as follows. Protein were separated on an SDS-PAGE gel (10% SDS running gel and 5% SDS stacking gel) under non-reducing conditions. Samples were boiled for 5 minutes at 95° C. prior to loading in 20 µl of loading buffer (2M Tris-HCl, pH 8.8 containing sucrose and EDTA). Gels were removed and transferred to Immobilon membranes (Millipore) by electroblotting and dried overnight.

Figure 21:
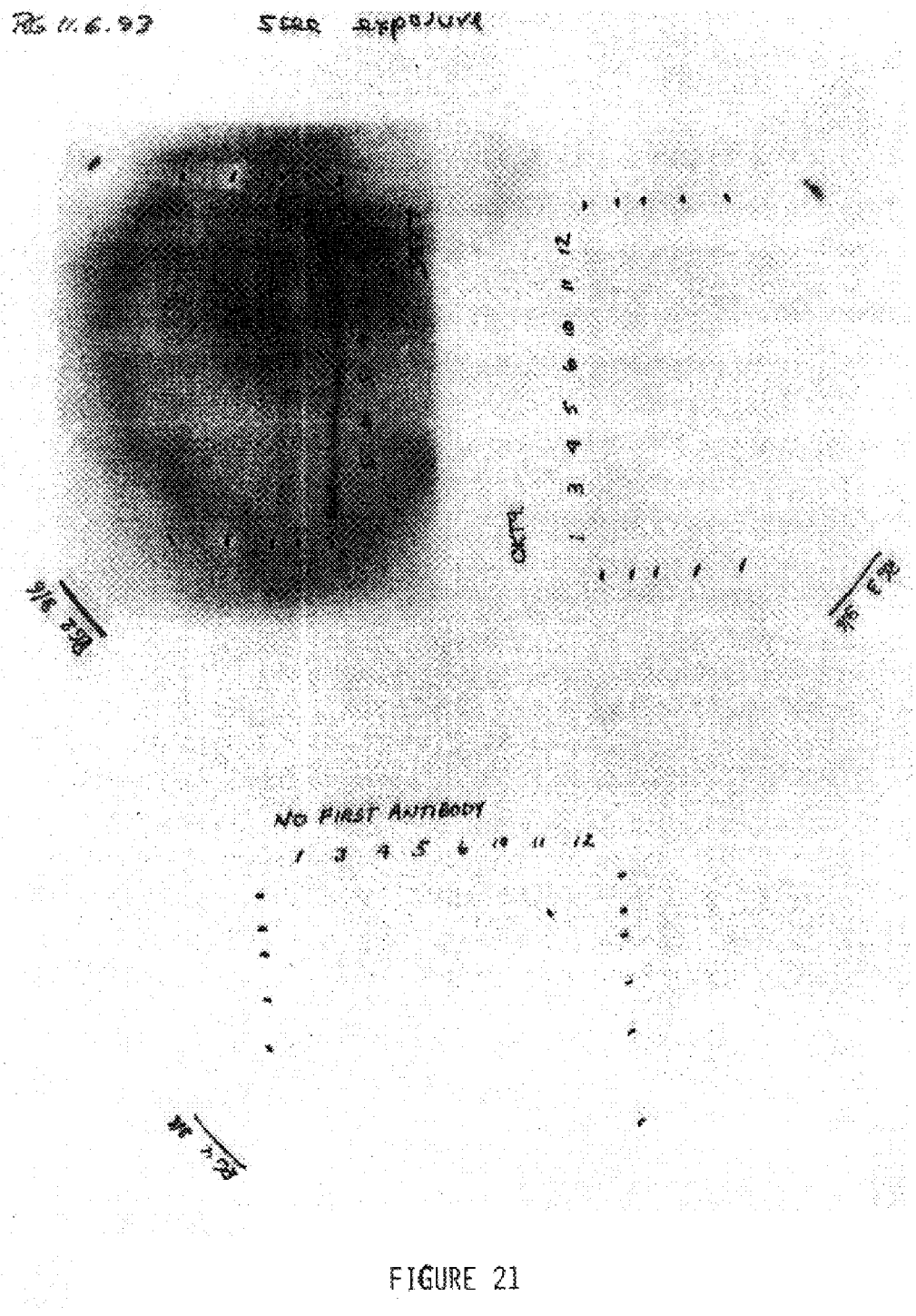
FIG. 21 is a series of autoradiograms showing the detection of p97 in cerebrospinal fluid of Alzheimer's Disease patients.

Western Blotting was carried out generally as described heretofore. More particularly, membranes were wet in methanol, incubated for 1 hour with western blocking buffer and incubated with 100 µl of L235 or OKT9 as a first antibody in 20 ml washing buffer for 1 hour at room temperature. Membranes were washed 3 times in washing buffer and incubated with secondary antibody: donkey anti-mouse IgG/HRPO (1:5000) or goat anti-mouse Ig/biotin (1:10,000) for 1 hour at room temperature. Membranes were washed 3 times in washing buffer and further in PBS, and incubated in streptavidin-horseradish peroxidase (1:5,000) for 30 minutes. After washing, the proteins were detected by chemiluminescence utilizing the ECL Western blotting detection system (Amersham). The results are shown in FIG. 21. Bands corresponding to p-97 can be seen in FIG. 21A showing the L235 filter. p-97 was not detected in the no first antibody control FIG. 21C. Bands corresponding to p-97 were found exclusively in the L235 filter, showing the presence of p-97 in the CSF of Alzheimer's disease patients. Results form the control subjects showed no band corresponding to p-97. FIG. 21B shows no band in the OKT9 filter. These results indicate that the presence of p-97 in the CSF may be a useful diagnostic for Alzheimer's disease patients.

Example 13
Identification of Soluable Forms of P97/Transferrin Receptor

SK-MEL-28 cells were pulsed with 200 µCi/ml of [$^{35}$S] methionine and washed twice with ice-cold biotinylation buffer. Cell surface antigens were biotinylated with NHS-LC-Biotin (100 µg/ml) sulfosuccinimidyl 6-(biotin amido) hexanoate (Pierce). 2 ml of ice cold biotinylation solution was used for 5 minutes. The cells were washed three times in normal medium with an excess of cold methionine and chased for 0, 1, 4, 8, or 24 hours. After chase, the supernatant was collected and the cells were lysed in solubilization buffer with PMSF and Lys (0.1 mg/ml). The cell supernatant and lysate were immunoprecipitated with L235 or OKT-9 as previously described and run under non-reducing conditions on a Bio-Rad mini-gel (10% SDS-PAGE). The protein was blotted on nitrocellulose membrane and the membrane was exposed to autoradiographic film for detection of radioactive proteins. Biotinylated proteins were detected by Western blots following the methodology previously described herein.

The results are shown in FIG. 22. FIG. 22A shows that p-97 labelled with [$^{35}$S]-methionine was detected in the supernatant (CS) and in the cell lysate (CL). Soluble p-97 was detected in the supernatant from 4–24 hours chase. Surprisingly, TR labelled with [$^{35}$S]-methionine was also detected in the supernatant (CS) and in the cell lysate (CL). The presence of labelled TR in the supernatant at 6–24 hours of chase suggests that there is a soluble form of TR. The results confirmed that the soluble form of p-97 does not originate from the membrane bound p-97, but must derive from another source. FIG. 22C shows that the soluble p-97 detected in the supernatant was not biotinylated and thus did not correspond to membrane-bound p-97 which had been released from the cell surface. FIG. 22D shows the biotinylation labelling of TR. These results indicate the presence of soluble forms of both p-97 and the transferrin receptor.

Example 14
Semi-continous Process to Produce P-97 from CHO Cells

A. Cell Line

The CHO cell line, WTB (obtained from Dr. Maxfield, New York University), was cotransfected with the p97 expression vector, pSV2p97a, and the G418 resistance vector, pWJ218 as described in Example 1. CHO cells were also adapted to suspension growth in serum free media, CHO-S-SFM (Gibco). Cells were cultured in either 75 cm2 T-flasks (Gibco) or 250 and 500 mL spinner flasks (Bellco). All cell lines were incubated at 37C in a 5% CO2 humidified atmosphere. When necessary, adherent lines were released by treatment with versene (saline solution of 2 mg/mL EDTA). Cell density and viability were determined using a hemocytometer and trypan blue exclusion.

B. Monoclonal Antibodies Against p97

Two mouse hybridoma cell lines that produced monoclonal antibodies against p97 were grown in 500 mL spinner flasks. Hybridoma 33B6E4 (a gift from Dr. Shuen-Kuei Liao, Biotherapeutic, Franklin) was grown in DMEM supplemented with 10% FCS, 1% mercaptoethanol, 2 mM L-glutamine, and 0.8 mg/mL geneticin. L235 (ATCC HB8446 L235 (M19)) was grown in RPMI supplemented with non-essential amino acids, 10% FCS, 1% mercaptoethanol, 2 mM L-glutamine, 2 mM Lproline, and 0.1 mg/mL penicillin/streptomycin. These hybridomas initially required a feeder layer of irradiated mouse embryonic fibroblast cells (ATCC X-56). L-235 cells were later selected to grow without the aid of a feeder layer and in the serum free media, HYBRIDOMA-SFM (Gibco).

Both cell lines were grown until their viability fell to below 50%. The cells were removed by centrifugation and the supernatant filtered through a 0.2 $\mu$m membrane (VacuCap, Gelman Sciences, Mich.). The monoclonal antibodies were then purified using a protein G affinity column (MAbTrap G, Pharmacia LKB Biotechnology Inc, N.J.), and later concentrated to 1–2 mg/mL using 10,000 MW ultrafilter (Centricon-10, Amicon Division, MA).

C. Flow Cytometry

Cell surface expression of p97 was monitored using immunofluorescence labelling and a non-sorting flow cytometer analyzer (FACScan, Becton Dickinson) as described in Example 1. Cells were labelled with primary antibody (33B6E4) at 4° C. for 45 min. Cells were washed again in FACS buffer and incubated with the fluoresceinated secondary antibody (Goat anti-mouse IgG-FITC conjugate, Gibco) at 4° C. for 45 min. Cells were then washed in PBS and fixed in 1.5% (v/v) p-formaldehyde in PBS.

The FACScan flow cytometer measured 5000 events per sample. Data from individual experiments were compared to unstained controls and values expressed either as mean fluorescence per cell or in the case of PI-PLC treated cells, as percentages of untreated controls. By comparing the mean flourescence/cell to p97 released by PI-PLC a linear relationship was found between mean fluorescence/cell and mean p97/cell.

D. Measurement of p97 Recovered in the PI-PLC Solution

The concentration of p97 released by PI-PLC was determined using a Pandex fluorescent concentration analyzer (Idexx Ltd, Portland, ON). This is a rapid immunofluorescence technique, described in Jolley, M. J. Immunol. Methods 67:21–35, 1984, using carboxylpolystyrene capture particles (0.8 $\mu$m, 0.25% v/v, Idexx) coated with anti-p97 IgG (ATCC-HB8446 L235 (M-19)). This "activated" solid phase acts as a specific adsorbent for p97. A second anti-p97 IgG (33B6E4) was labelled with fluorescin isothiocyanate (Sigma Chemical Co.). Samples were assayed according to Jervis and Kilbum (Biotechnol. Prog. 7:28–32, 1991).

E. p97 Standard p97 was purified from the supernatant of PI-PLC treated CHO cells by immunoaffinity chromatography. About 109 cells were treated with 1.0 mL of 0.1 U PI-PLC/mL in PBS and incubated for one hour at 37° C. The cells were removed by centrifugation and the supernatant filtered through a 0.2 $\mu$m membrane (Acrodisc 25, Gelman Sciences, Mich.). The filtrate was applied to a column (1×10 cm) of 33B6E4 Mab immobilized on Affi-Gel 10 (Bio-Rad, CA) that had been previously washed and regenerated in PBS, pH 7.2. The bound p97 was eluted with 0.1 M citric acid, pH 3.0, followed by neutralization with 1 M Tris-HCl, pH 9.0. The purified p97 was further concentrated using a 30,000 MW ultrafiltration membrane (Centricon-30, Amicon Division, MA) then dialysed in PBS and sterile filtered. The p97 sample was shown to be pure according to SDS-PAGE. PhastGel 12.5% homogeneous polyaclamide gel was run on the PhastSystemTM (Pharmacia LKB Biotechnology) and silver stained. The concentration of p97 was determined using the p97 extinction coefficient at 280 nm of $\epsilon 1\%=12.0$ cm$^{-1}$.

F. Production of PI-PLC

*B. subtilis* (BG2320) transfected with the gene for PI-PLC from *B. thuringiensis* was cultured using a procedure adapted from that described by Low, M. G. et al, J. Immunol. Methods113:101–111, 1988) prevously used to grow *B. thuringiensis*. The growth medium containing 10 g/L Polypeptone, 10 g/L yeast extract,5 g/L NaCl, 0.4 g/L Na2HPO4 and 15 $\mu$g/mL chloramphenicol (pH adjusted to 7.0 with NaOH) was inoculated with 1.5–3% (v/v) of overnight preculture (initial O.D.600=0.1). Cells were cultured in Erlenmeyer flasks and shaken at 150 rpm, 37° C. for 6 to 12 h. Cells were removed by centrifugation and the supernatant filtered through a 0.2 $\mu$m membrane (VacuCap, Gelman Sciences, Mich.). The supernatant was concentrated 20-fold using an ultrafiltration cell (Model 8400, Amicon Corp., MA) and a 10,000 MW YM10 ultrafilter (Amicon, MA). The concentrated enzyme solution was then washed two times with 5 volumes of PBS in the ultrafiltration cell. The enzyme solution was assayed and stored in 1 mL aliquots at −20° C. When the enzyme was required, the frozen PI-PLC was rapidly thawed and diluted in PBS to the specified concentrations. All enzyme samples used in this study came from the same 2L batch fermentation.

G. PI-PLC Assay

One unit of PI-PLC is defined as the enzyme activity that hydrolyses 1 $\mu$mol phosphatidyinositol per min at pH 7.5 and 37° C. Phosphatidylinositol dissolved in detergent containing buffer was incubated with the PI-PLC sample. The diglyceride released was subsequently hydrolysed to free fatty acids and glycerol by the addition of lipase. The glycerol concentration was then determined enzymatically (Assay no. 5646, Boehringer Mannheim Biochemica).

H. PI-PLC Treatment and Protein Harvesting

Approximately 25 mL of 1–2×10$^6$ suspension cells/mL were centrifuged at 1300 rpm for 5 min and washed two times with 5 mL of PBS. The cells were then resuspended in 0.5 mL of PI-PLC in PBS (10 mU/mL) and incubated at 37C for 30 min with periodic agitation. Cells were again centrifuged and the supernatant recovered. The supernatant was further centrifuged at 10,000 rpm for 20 min, filtered through a 0.2 $\mu$m membrane (Acrodisc 25, Gelman Sciences, Mich.) and stored at −20° C. prior to assaying for p97. A sample was concentrated 5-fold using a 3,000 MW ultrafiltration membrane (Centricon-3) for SDSPAGE analysis.

The enzyme treated cells were then washed two times with 15 mL PBS and once with 15 mL of CH0-S-SFM media. A sample of the cells were prepared for FACScan analysis and the rest resuspended in fresh CHO-S-SFM media at approximately 0.5–1.0×10⁶ cells/mL. The cells were then cultivated for a specified period before the protein harvest was repeated. Cell density, viability and glucose concentration of the media were determined prior to each protein harvest.

I. Expression of P97

Figure 23:
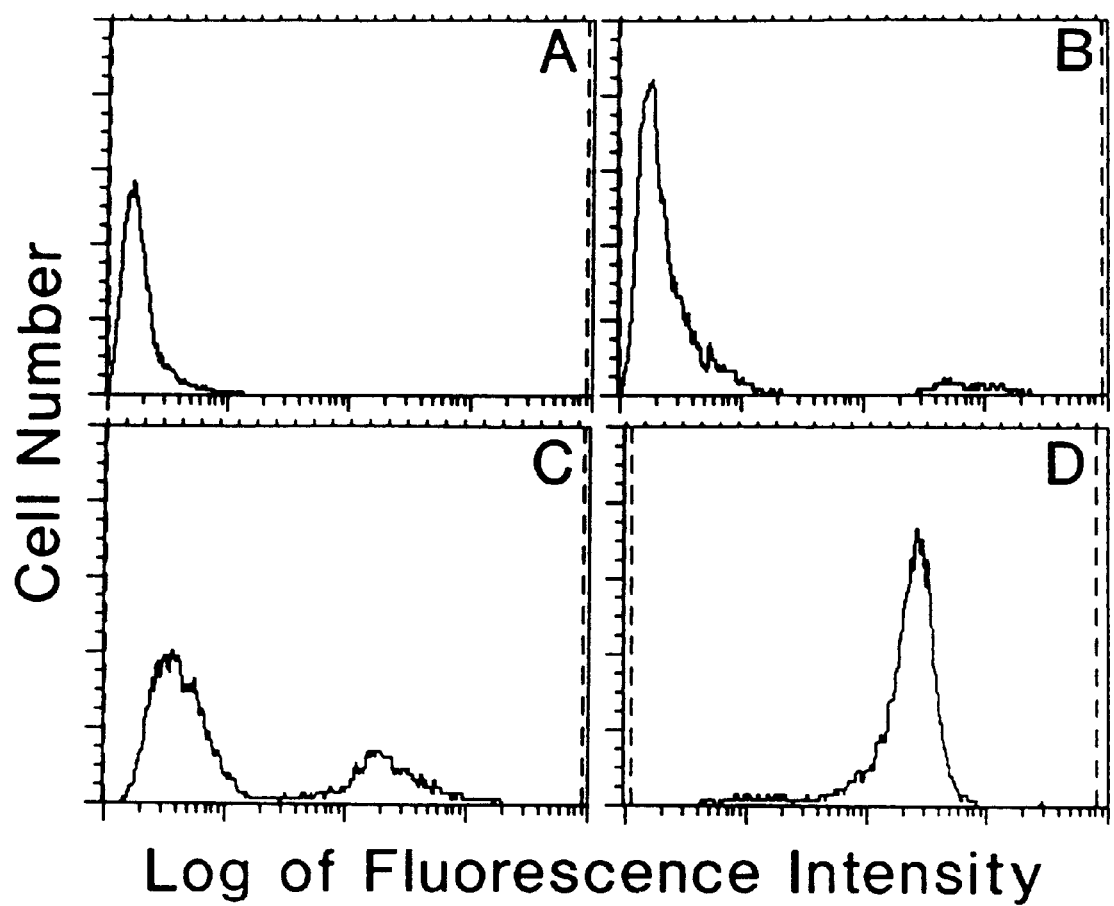
FIG. 23 shows fluorescent labelling of CHO cells labelled with L235 and secondary fluorescinated antibody.
Figure 24:
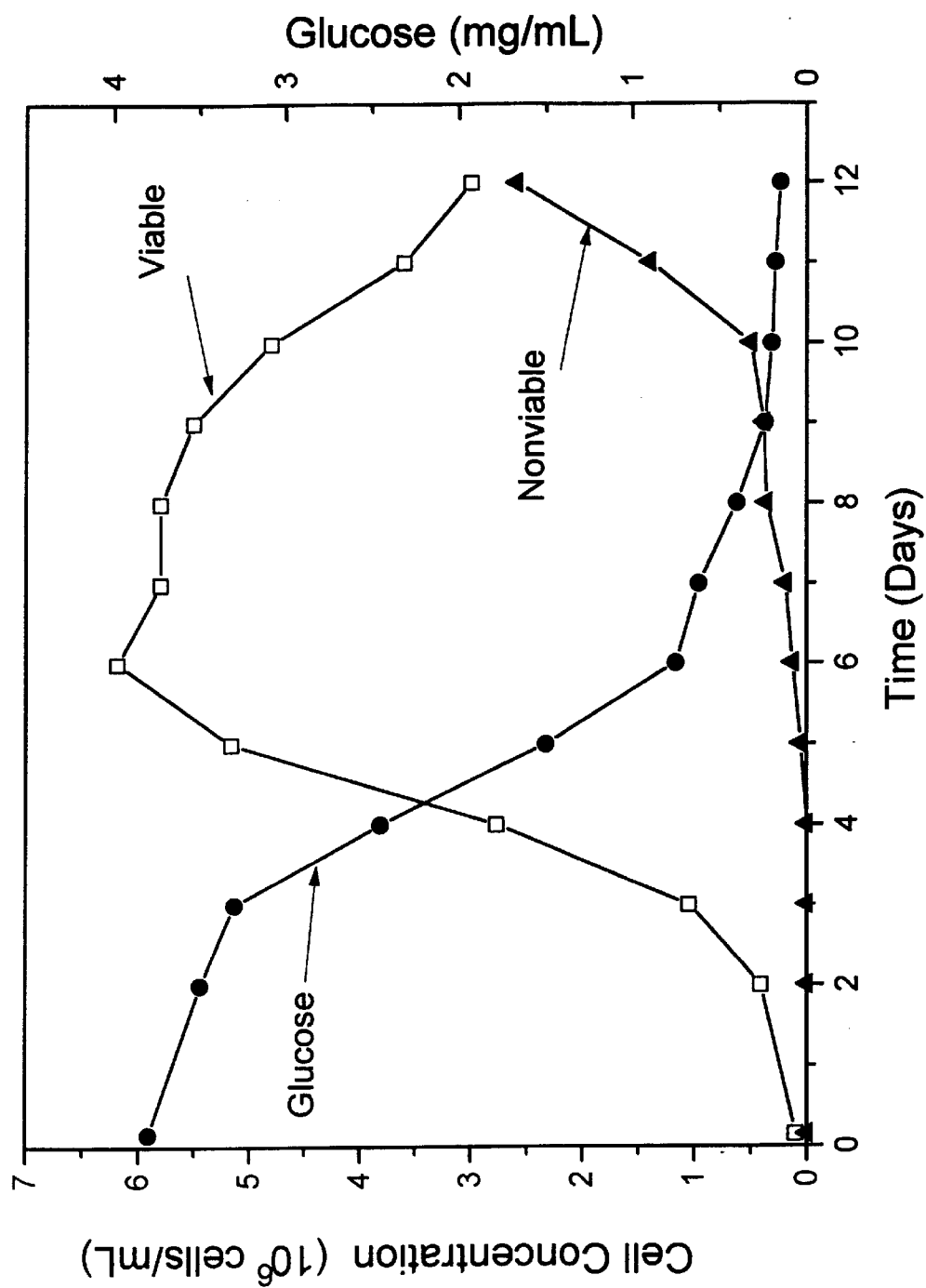
FIG. 24 is a graph of batch growth of CHO cells showing cell concentration and glucose consumption as a function of time.
Figure 25:
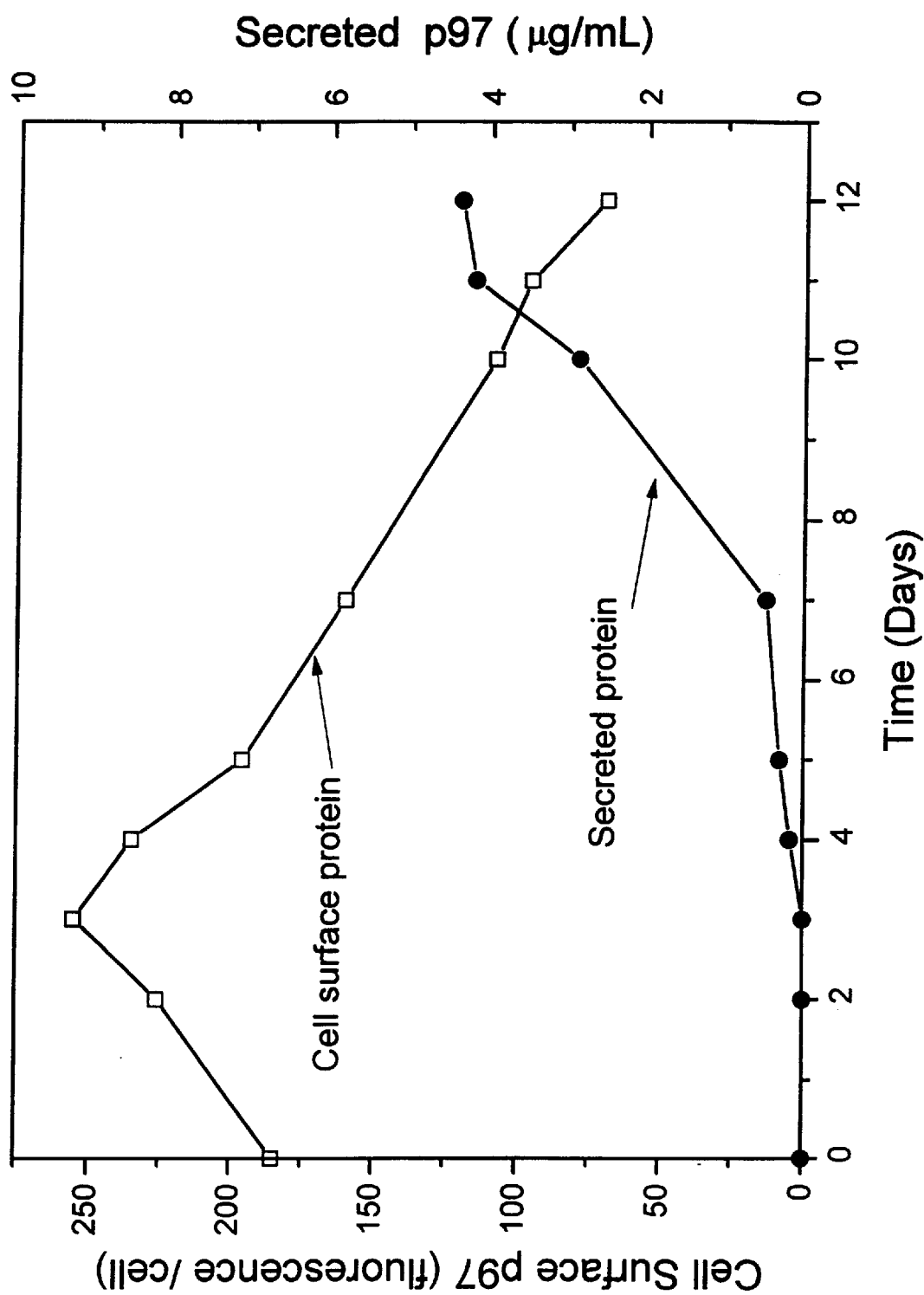
FIG. 25 is a graph showing batch CHO cell protein expression as a function of time

CHO cells transfected with p97 cDNA and selected in geneticin were analyzed for p97 expression using flow cytometry. Approximately 2% of the bulk population expressed p97 (FIG. 23). In FIG. 23 graph A shows log scale fluorescence profiles of untransfected cell line Wm, B shows bulks transfected cells, C shows sorted cells and D shows subcloned cells. These cells expressing p97 were enriched ten-fold using fluorescence activated cell sorting. The sorted population (about 20% expressing cells) was further subcloned using limiting dilution and the highest p97 expressing clones isolated (FIG. 23). Suspension CHO clones expressing p97 were grown in 75 cm2 T-flasks and 500 mL spinner flasks using serum-free medium. The growth profile for cells cultured in a 500 mL spinner flask is shown in FIG. 24. The cells reached a peak concentration of over 6×10⁶ viable cells/mL in 6 days from an inoculum level of 1.5×10⁵ cells/mL with a mean doubling time of 26 hours. Viability fell sharply after 9 days when glucose levels had fallen to about 0.2 mg/mL. The cell surface expression of p97 per cell was monitored by flow cytometry analysis using FITC conjugated antibodies against p97 (FIG. 25). Cell surface expression of p97 varied with the phase of cell growth. Maximal cell surface expression occurred after 3 days of growth at a cell density of 1×10⁶ cells/mL, after which there was a steady decline in cell specific expression. This decline could be partially explained by the reduction in average cell surface area as the culture viability decreases or cell death may release p97. The average cell diameter fell from 15 $\mu$m during exponential growth to 13 $\mu$m during the stationary phase with a corresponding reduction in viability from 99% to 90%.

A small amount of soluble, secreted p97 was detected in the supernatant at the end of the exponential phase of cell growth. When using the controlled release method of protein harvesting, secreted p97 would be discarded with the spent medium, and thus not recovered. However, this loss of p97 could be minimized if cells were harvested before the stationary phase of cell growth. This soluble p97 may result from the release of membrane bound protein, which could account for the reduction in average fluorescence per cell, or from the release of a soluble form of p97 that was not previously glipiated.

J. PI-PLC Treatment

Figure 26:
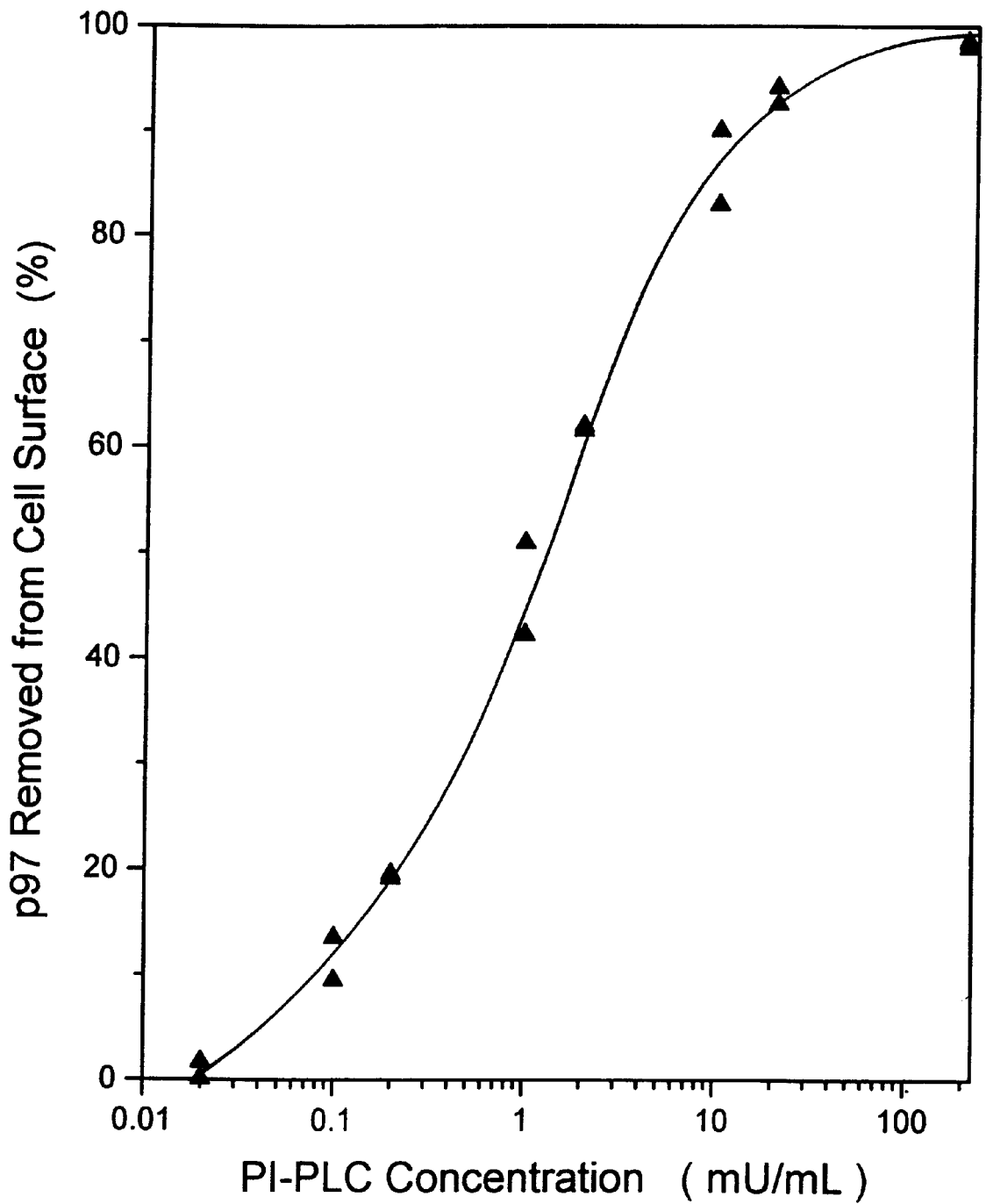
FIG. 26 is a graph showing removal of p97 from the cell surface as a function of PI-PLC concentration.

Cell surface p97 was monitored by flow cytometry and the solubilized protein released by PI-PLC treatment was assayed by an immunoabsorption assay. The effect of the enzyme concentration on the percentage of protein removal for a 30 min incubation period is shown in FIG. 26. Cells (108 cells/mL) were treated with varying concentrations of enzyme in PBS. An enzyme concentration of 10 mU/ml was found to be sufficient for the removal of at least 90% of glipiated p97 from the cell surface. This is equivalent to a recovery of approximately 4 to 5×107 $\mu$g of p97 per viable cell. It was also observed that cells remained viable after the enzyme treatment. Cell viability remained above 95% for incubation times of up to one hour, after which viability decreased. The PI-PLC concentration of 10 mU/mL is equivalent to approximately 0.02 $\mu$g/ml3 and, therefore, contributes a very low level of contaminating protein to p97 that has been harvested at over 1–40 $\mu$g/mL concentrations (see below).

The purity of the recovered p97 was estimated to be 30% based on Bio-Rad determination of total protein concentration using albumin as a standard. The contaminating proteins include other glipiated proteins removed from the cell surface by the action of PI-PLC.

K. Protein Re-expression

Figure 27:
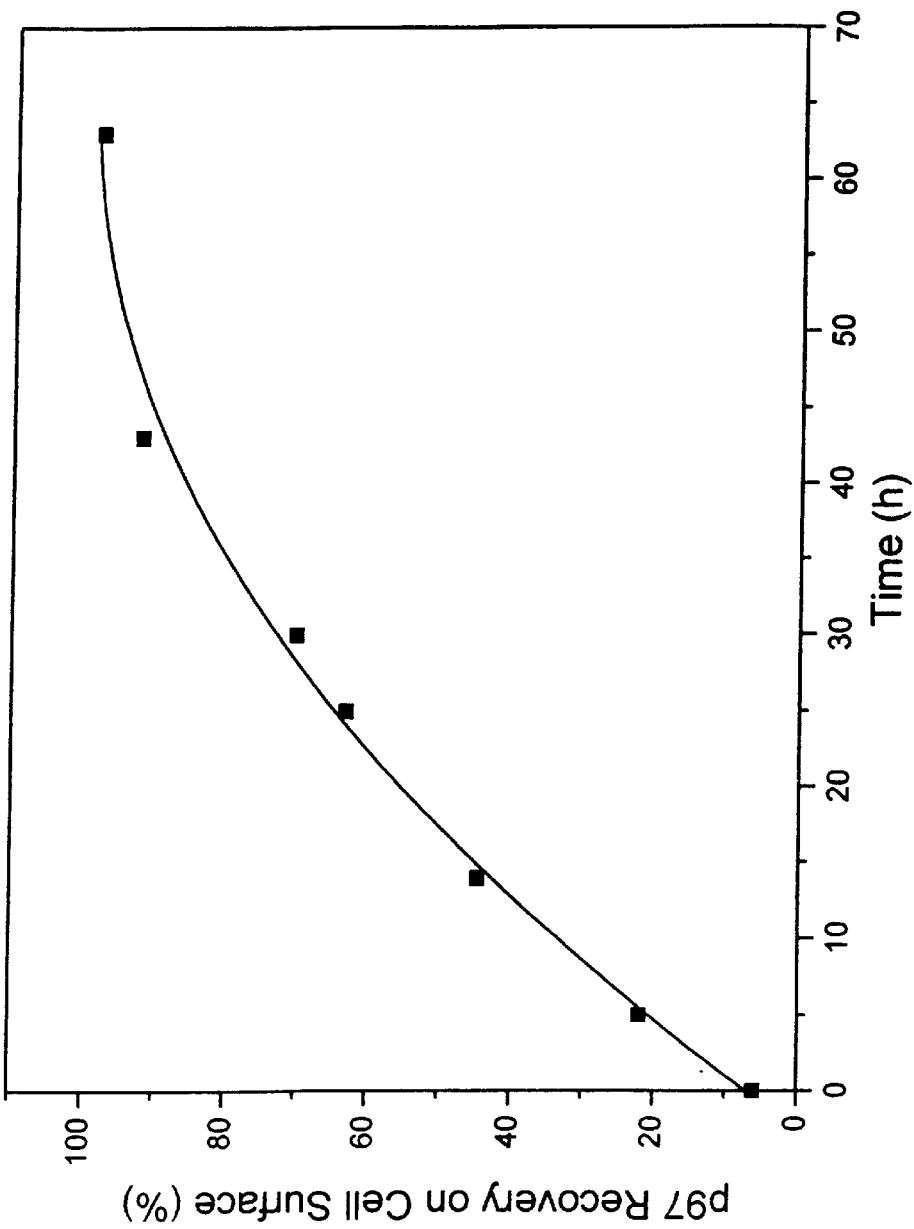
FIG. 27 is a graph showing recovery of p97 expression after PI-PLC treatment.

In order to develop a semi-continuous method of harvesting p97, the recovery of PI-PLC treated cells and re-expression of p 97 was investigated. Enzyme treated cells were washed two times in PBS and resuspended in fresh medium. After treatment with PI-PLC, suspension as well as adherent clones had doubling times identical to untreated cells. Surface re-expression of p97 was monitored using flow cytometry and the cells recovered 95% of their protein expression within 2 days (FIG. 27).

L. Cyclic Harvesting of p97

Having established that a 30 min incubation period with 10 mU/mL of PI-PLC in PBS was sufficient to remove at least 90% of the glipiated p97 from transfected CHO cells (FIG. 26) and that cells retained their viability and were able to recover their p97 expression after enzyme treatment, it was next determined if the level of protein expression and cell viability would be adversely affected by repeated harvesting.

Figure 28:
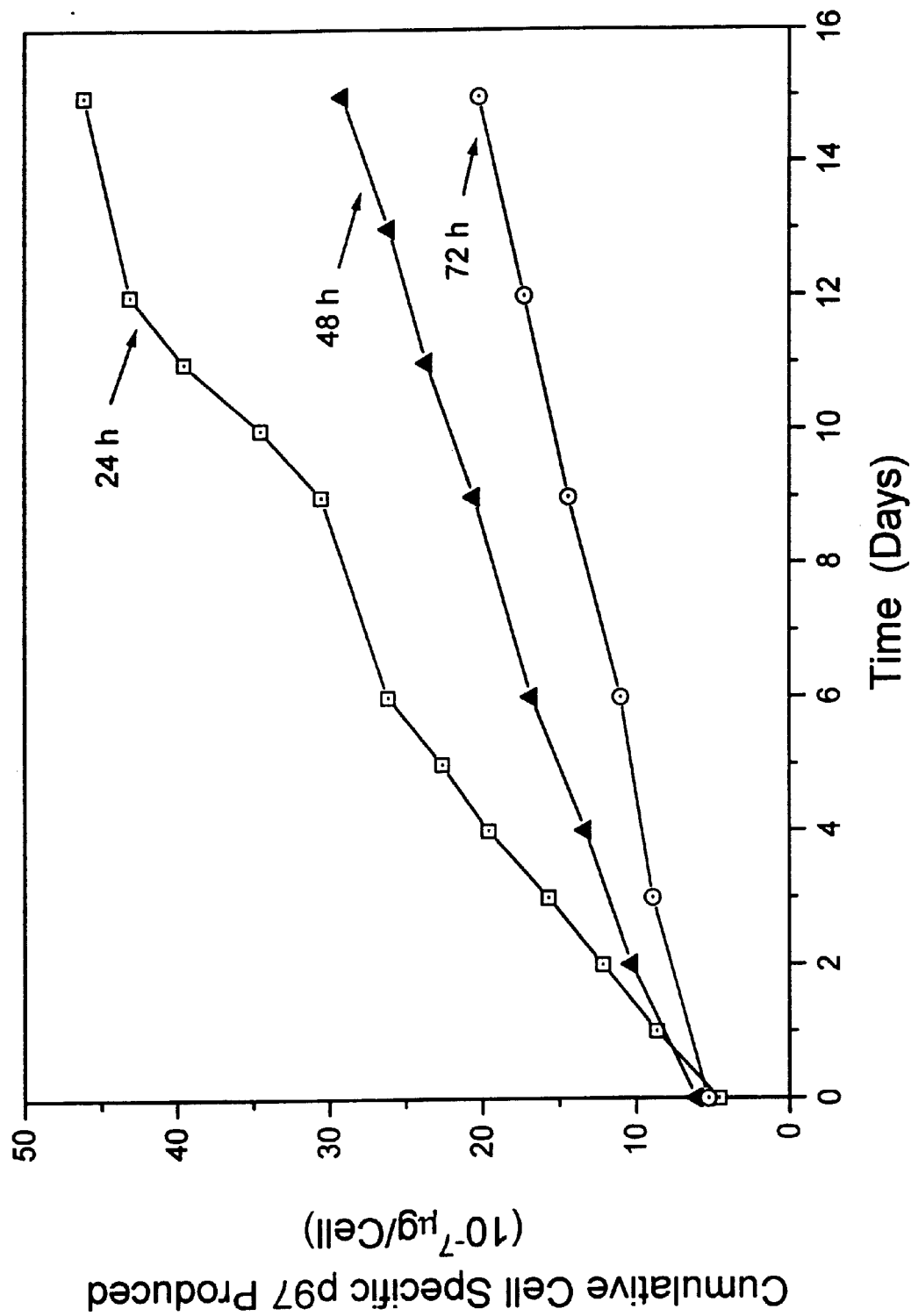
FIG. 28 is a graph showing cumulative cell specific protein release by PI-PLC as a function of harvest cycle.
Figure 29:
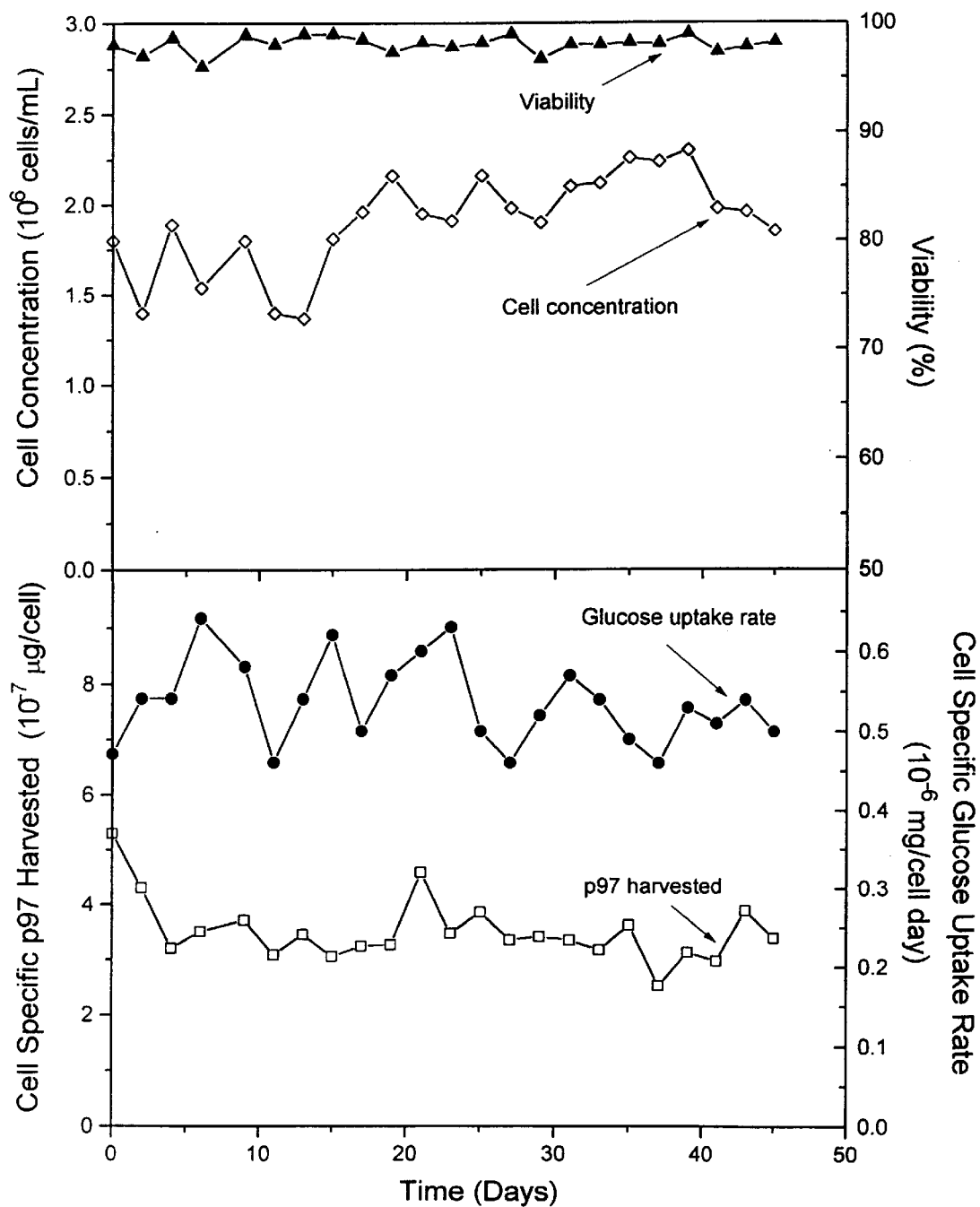
FIG. 29 is a graph showing cell viability, cell density, cell specific p97 harvested and, cell specific glucose uptake rate assayed at the end of each 48 hour harvest cycle.

Cells were grown in suspension up to 1–2×10⁶ cells/mL and then centrifuged and washed with PBS. Approximately 0.5×10⁸ cells were treated with 1 mL of PI-PLC in PBS (10 mU/mL). After 30 min incubation, cells were again centrifuged and washed twice in PBS before resuspension in fresh medium at a concentration of 1×10⁶ cells/mL. The cells were subjected to further enzyme treatment at 24, 48 or 72 h intervals. FIG. 28 shows the cumulative protein production per cell for all cycle times. The 24 h cycle produced the maximum amount of protein. However, based on medium utilization the 48 h cycle showed a greater yield of p97 (0.33 mg p97/g glucose consumed). Cell viability, cell density, cell specific p97 production and cell specific glucose consumption were monitored for each harvest cycle and were shown to be relatively stable for the duration of the experiments (FIG. 29).

Figure 30:
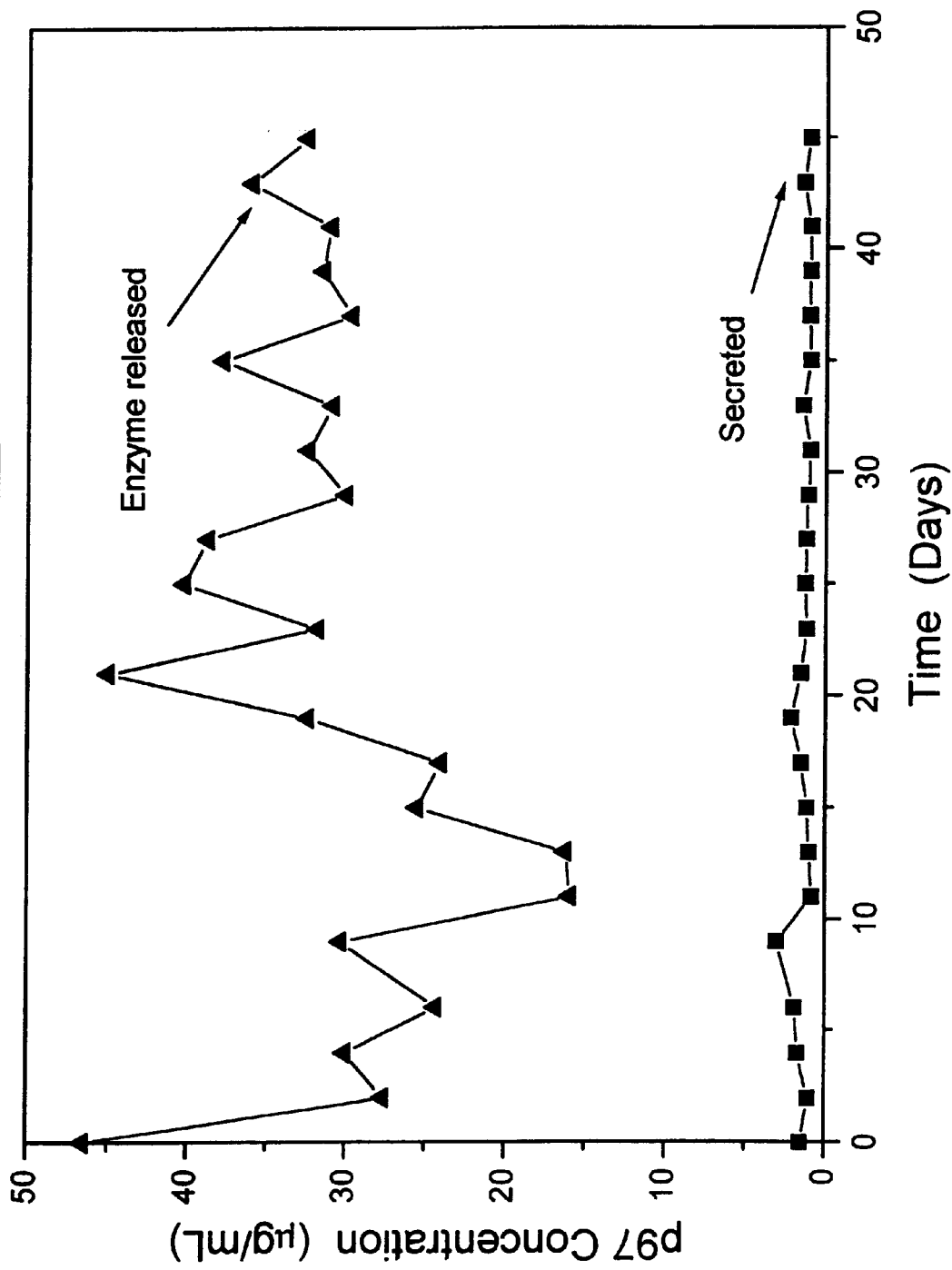
FIG. 30 is a graph showing p97 recovery in PI-PLC solution for 48 hour harvest cycle.

The concentration of p97 recovered after each 48 h harvest cycle is shown in FIG. 30. Over a 44 day period with over 20 enzyme treatments the production of p97 remained around 30 $\mu$g/ml. There appeared to be no drop in productivity over the duration of the experiment. It is also shown in FIG. 30 that the suspension CHO cells secreted a steady level of 1 to 2 $\mu$g/ml of p97 into the growth medium. This may be considered a loss from a production point of view since the secreted p97 is discarded with the spent medium. However, it was observed that the level of basal secretion depends on the transfected CHO cell clone selected. For example another clone did not secrete detectable levels of p97 and could be used for production purposes.

Figure 31:
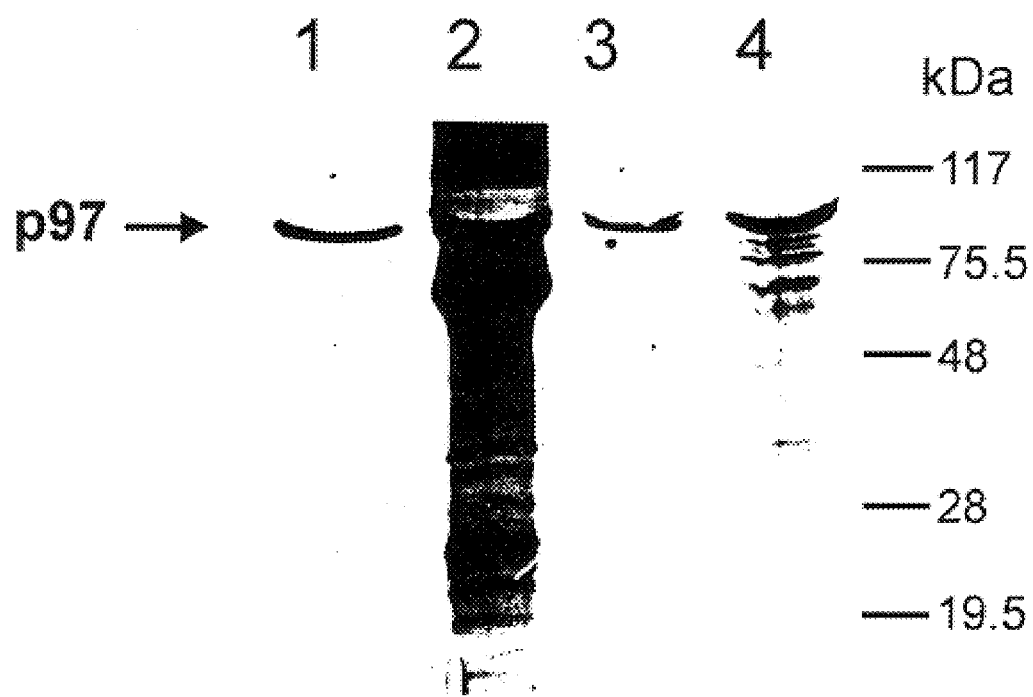
FIG. 31 is a photograph of an SDS-polyacrylamide gel showing p97 harvested with PI-PLC and p97 released directly into the medium.

The effectiveness of the various methods for the recovery of p97 are compared in Table 3. Direct addition of PI-PLC to adherent CHO cells growing with 10% serum resulted in the recovery of 1.2 $\mu$g/mL of p97 in medium containing a contaminating protein level of approximately 5.4 mg/mL. This represents a purity of 0.02% based on the total protein. When suspension cells growing in serum-free medium were treated with enzyme the results were substantially improved. Approximately 3 $\mu$g/ml of p97 was recovered in a media containing 380 $\mu$g/mL of protein, representing a purity of about 1%. The advantage of the cyclic harvest method was demonstrated by the finding that p97 was not only recovered at higher concentrations (30 $\mu$g/mL) but with a thousand-fold increase in purity to 30%. The silver stained SDS-PAGE gel shown in FIG. 31 compares p97 harvested into PI-PLC/PBS solution (Lanes 3 and 4) with p97 released directly into CHO-S-SFM serum free growth medium (Lane 2).

Example 15

Cell Surface P97 Binds Iron

The following cell lines were cultured as described herein: TRVb (no TR), TRVb-1 (human TR transfected), p97aTRVbc3 (human p-97 transfected) and p97aTRVbl5 (human p-97 and TR transfected). The cells were washed and counted. Approximately 6–10×10$^6$ cells were incubated with 1 µl $^{55}$[Fe] in FeCl salt for 0, 2, 6, 10 or 14 hours. 200 µl of cells and medium were removed at each time point and centifuged at maximum speed for 2 minutes at 4° C. and the pelleted cells and supernatant separated into scintillation vials. $^{55}$[Fe] levels in vials for all time points were measured in a scintillation counter.

Figure 32:
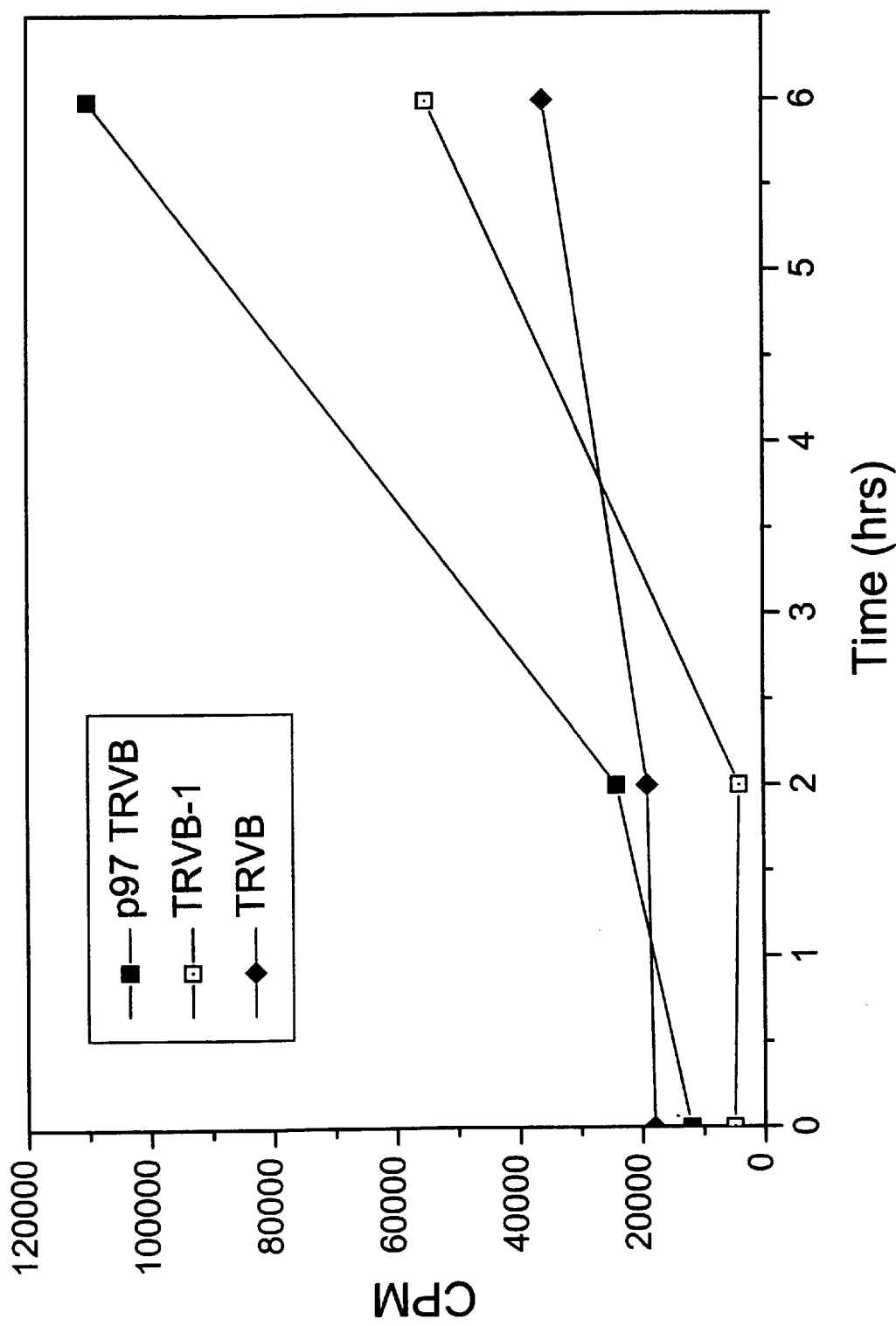
FIG. 32 is a graph showing the counts per minute of [$^{55}$Fe] associated with the TRVB, TRVB-1 and p97TRVB cell lines.
Figure 33A:
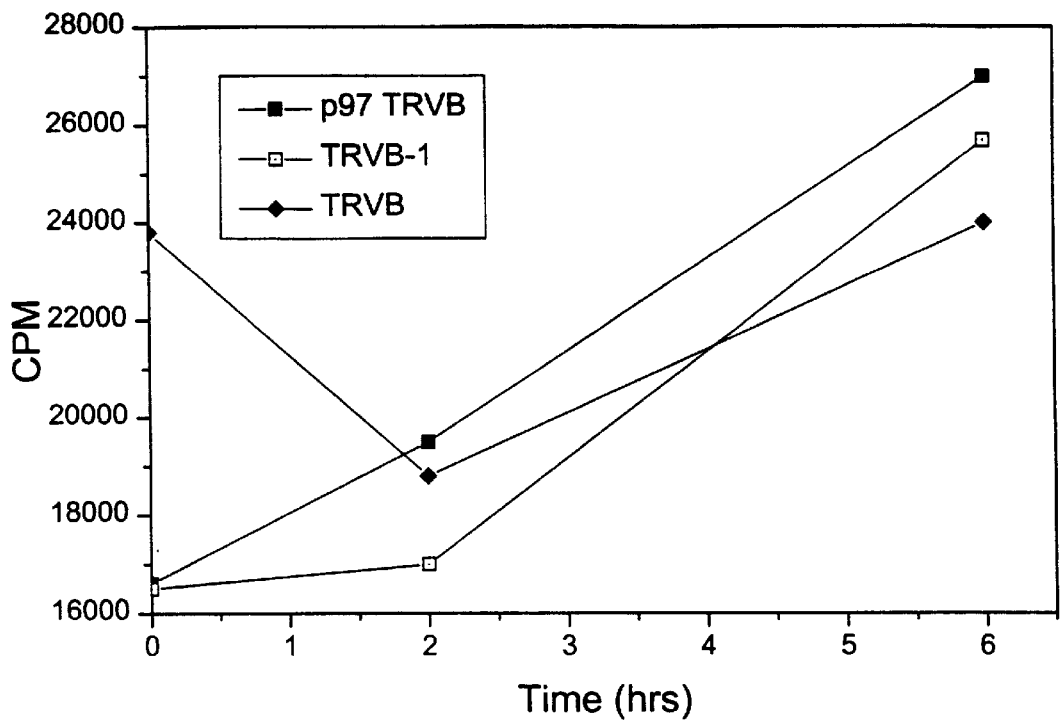
FIG. 33 is two graphs showing the counts per minute of [$^{55}$Fe] associated with the TRVB, TRVB-1 and p97TRVB cell lines before (A) and after (B) PI-PLC treatment.
Figure 33B:
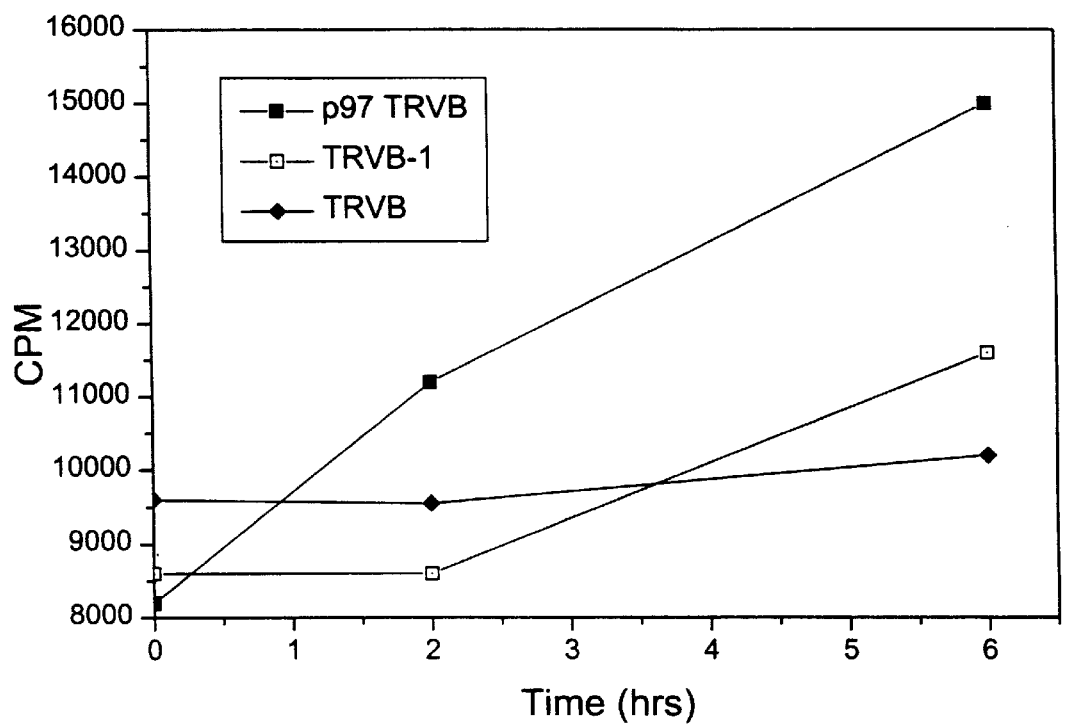

The experiments were repeated with the additional step of PI-PLC treatment (for 1 hour at 37° C.) of the cells and medium removed at each time point noted above. Following PI-PLC treatment the cells and medium were separated by centifugation prior to scintillation counting as described above. The results are shown in FIGS. 32 and 33. FIGS. 32 and 33A shows that TRVB cell line containing p-97 had the highest counts over 6 hours, indicating that labelled iron is bound to p-97. After PI-PLC treatment the counts associated with the p-97 containing cell line decreased (FIG. 33B), confirming that the cell surface, GPI-anchored p-97 binds iron.

Example 16

Iron Uptake Mediated by p97

A. Expression of p97 and TR in Transformed Cell Lines

The uptake of Fe from Fe-citrate complexes was investigated in the complete absence of Tf and the TR. The cell line used was the mutant CHO cell line TRVb that has defective or no TR (McGraw, T. E. et al. J. Cell Biol., 105, 207–214, 1987). These cells were transfected with human p97 in order to determine the affect of p97 on Fe uptake. Any difference in Fe uptake would be due to the presence of p97. We also tested the cell line TRVb-1, which was derived from TRVb and transfected with the human TR (McGraw et al., 1987). These cells were also transfected with human p97 in order to carry out a comparable set of experiments and to observe the effect of the presence of the human TR.

The CHO cell line, TRVb, which expressed no TR, was obtained from Dr. F. Maxfield (New York University, N.Y.) (McGraw, T. E. et al. J. Cell Biol., 105, 207–214, 1987) and co-transfected with the human p97 expression vector pSV2p97a and the geneticin (G418) resistance vector as described in Example 1. The p97 vector, which contained the entire coding region of p97 cDNA driven by the SV40 early promoter, was obtained from Dr. G. Plowman (Bristol-Myers Squibb, Seattle). Transfected cells were selected with 800 µg/ml G418 (Life Technologies, Inc.) and were analyzed and sorted by fluorescence activated flow cytometry (FACS) and finally subcloned by limiting dilution and subsequently called p97TRVb. The CHO cell line TRVb-1, transfected with the human TR (150,000 surface receptors/cell) was obtained from Dr. F Maxfield (McGraw, T. E. et al. J. Cell Biol., 105, 207–214, 1987). This clone was transfected with the p97 in the expression vector pNUT obtained from Dr.R. Palmiter (Howard Hughes Medical Institute, University of Washington, W.A.). Cells were selected with 500 µM methotrexate (Sigma, St. Louis, Mo.), sorted by FACS, subcloned by limiting dilution and called p97TRVb-1. All four cell lines were maintained in Ham's F12 medium (Gibco, Burlington, ON), supplemented with 10% fetal calf serum (Gibco), 20 mM Hepes, 100 units/mL penicillin, 100 µg/mL streptomycin and 2 mM L-glutamine (Gibco) at 37oC in a 5% CO2 humidified atmosphere.

In preparation for the Fe uptake experiments the cells were subcultured from confluent 75 cm2 T-flasks using 1 mM EDTA (Gibco) in PBS and transferred after pelletization and resuspension to 3.4 cm2 petri dishes at approximately 1×105 cells/cm2 in 1.5 mL of media. After 48 h the cells were checked for confluence and only totally confluent plates were subsequently used for the Fe uptake assay. Sample plates were examined to determine the cell density using a haemocytometer and trypan blue exclusion.

The expression of p97 and human TR for the cell lines were compared in a pulse-chase experiment. Cells were incubated in MEM medium without methionine for 1 h. The methionine depleted cells were then labelled with MEM containing 250 µCi/mL of (35S) methionine for 30 min and chased with normal MEM containing an excess of cold methionine. Labelled cells were lysed and immunoprecipitated with MoAbs against p97 and the human TR, as described herein. SDS-PAGE analysis was finally carried out as generally described in Kvist, S. et al., (Cell, 21, 61–69, 1982).

Figure 36:
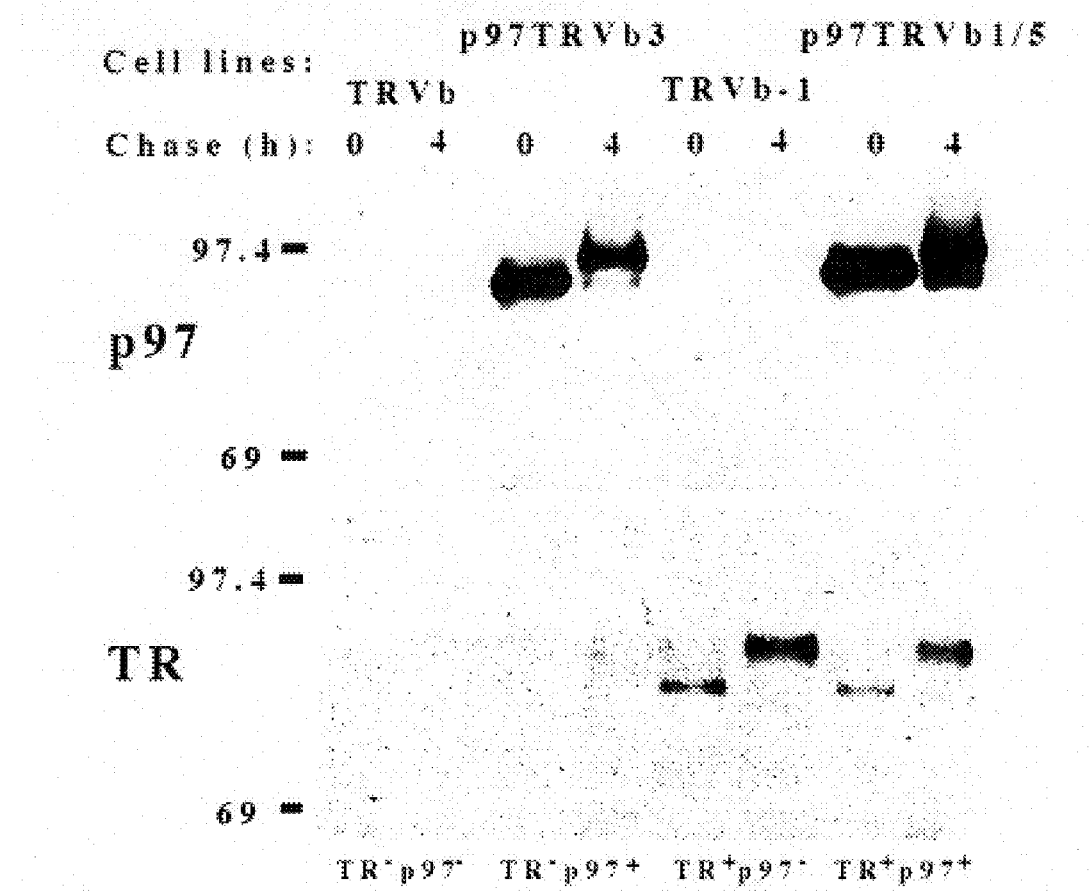
FIG. 36 is an autoradiogram showing expression and transport of p97 and the human transferrin receptor for TRVb, p97TRVb, TRVb-1 and p97TRVB-1 cells.

Results of the pulse chase experiments are shown in FIG. 36. Similar levels of p97 were expressed by the p97TRVb and p97TRVb-1 cell lines and similar levels of the human TR were expressed by the TRVb-1 and p97TRVb-1 cell lines. In addition, the higher molecular weight processing of p97 and TR after the 4 h chase indicates that these proteins are transported out of the ER at the same rate for each cell line.

The cell surface expression of TR and p97 was monitored by surface staining of EDTA released cells with fluorescent MoAbs against the TR and p97 over a 10 day period. Over the first four days of exponential growth, the expression of TR for p97TRVb-1 was 80 to 90% that for TRVb-1, by the fifth day of growth the TR expression for both cell lines had become identical. TR levels peaked after 3 days, eventually falling and levelling off to one half of the maximum expression by the fifth day. This slight reduction in TR expression during exponential growth for p97TRVb-1 cells may imply that the presence of p97 can affect TR expression. The expression of p97 for p97TRVb and p97TRVb-1 was also similar and the maximum expression occurred after four days during exponential growth. The expression then fell steadily to less than half of the maximum expression by ten days.

Based on the measurement of the concentration of p97 in the PI-PLC solution used to treat approximately 108 cells, it was possible to determine the number of molecules of p97 per cell. Approximately 108 cells were removed from T-flask cultures using 1 mM EDTA, counted, and resuspended in 1 mL of 300 mU/mL of PI-PLC in PBS and incubated for 1 h (Kennard, M. L. et al., Biotech. Bioeng., 42, 480–486, 1993). This removes over 98% of p97 from the cell surface as determined by FACS (Kennard, M. L. et al., Biotech. Bioeng., 42, 480–486, 1993) and fluorescence concentration analysis. The PI-PLC solution was recovered and the concentration of p97 determined by a rapid immunofluorescent assay (Kennard, M. L. et al., Biotech. Bioeng., 42, 480–486, 1993) using fluorescence concentration analysis. Based on the total cell number and total p97 removed, the number of molecules per cell could then be determined. At confluence the expression of p97 was calculated to be about 1.2+0.35×106 molecules of p97/cell for p97TRVb and 1.0+0.42×106 molecules of p97/cell for p97TRVb-1.

This study showed that the TR and p97 levels vary considerably with cell growth and emphasize the importance of having identical cell culture conditions when carrying out the Fe uptake experiments.

B. Batch Growth of Transformed Cell Lines

The growth of all four transformed cell lines were compared in a ten day batch study to determine if the various transformations had any affect on cell growth such as providing a proliferation advantage, which could, therefore, affect the Fe uptake. All four cell lines were seeded at ~1–2×10$^4$ cells/cm$^2$ in 10 mL of medium in 9 cm diameter petri dishes. Over a period of 14 days, parallel cultures were examined at daily intervals to determine cell density, glucose consumption and viability. p97 and TR expression were also monitored using a cellular immunofluorescent assay based on fluorescence concentration analysis (IDEXX, Westbrook, Me.).

The cell density of all four cell lines increased from approximately 1.25×10$^4$ cells/cm$^2$ to between 2 and 2.5× 10$^5$ cells/cm$^2$ after five days when complete confluence was reached. Overall there was little difference between growth of all cell lines. They had similar doubling times of 24+2 h, although the maximum cell density was highest for TRVb and TRVb-1 at ~2.5×10$^5$ cells/cm$^2$ versus ~2.0×10$^5$ cells/cm$^2$ for p97TRVb and p97TRVb-1. All cell lines remained over 98% viable for up to six days and had virtually identical glucose uptake rates with the glucose concentration falling from 1.7 mg/mL to around 0.95 mg/mL over the six days (ie. equivalent to ~50 $\mu$g glucose/10$^6$ cells/day at confluence). Overall the batch growth curves for all cell lines were similar and virtually identical to the batch growth curve of another p97 transfected CHO cell line (CHO-WTBp97) that was used in a previous study (Kennard, M. L. and Piret, J. M. Biotech. Bioeng, 44, 45–54, 1994). This is also in agreement with another study that showed there was no difference between the growth of TRVb and the wild type CHO-WTB cells (Chan, R. Y. Y. et al., Exp. Cell Res., 202, 326–336, 1992). It therefore, appears that the presence or absence of TR and p97 does not affect the growth of these CHO cells.

C. Iron Uptake from Fe-citrate

The role of p97 in Fe uptake from Fe-citrate was investigated with established techniques used to examine Fe uptake from small molecular weight Fe complexes (Richardson, D. R. and Baker, E. Biochim. Biophys. Acta, 1093, 20–28, 1991). Prior to the Fe uptake experiments, it was an essential prerequisite in these studies to ensure that the incubation media was free of Tf. Sussman et al. (Sussman, H. H. et al., (1985). Proteins of iron storage and transport. G. Spik, J. Montreuil, R. R. Crichton, and J. Mazurier, eds. (Amsterdam: Elsevier Science Publishers), pp. 143–153.) have shown that bovine Tf is able to bind Fe and donate it to CHO cells via the TR. To ensure complete depletion of bovine Tf from the cells (Richardson, D. R. and Baker, E. Biochim. Biophys. Acta, 1093, 20–28, 1991), three separate 30–45 min incubation periods at 37oC in MEM (Gibco) were used to wash the confluent plates. After this washing procedure, the medium was replaced with 1 mL of MEM containing 59Fe-citrate (molar ratio of Fe:citrate= 1:100 and Fe concentration of 2.5 $\mu$M), 1% NEAA, 20 mM Hepes (pH 7.4) and 5 mg/mL BSA. It should be noted that a 1:100 molar ratio of 59Fe (Dupont, NEN products, Boston, Mass.) to citrate was used to prevent hydrolytic polymerisation of Fe, which occurs at pH 7.4 (Spiro, T. G. et al. j. Am. Chem. Soc., 89, 5555–5559, 1967; Spiro, T. G. et al., J. Am. Chem. Soc., 89, 5559–5562, 1967). This labelling solution was then incubated with the cells for up to 4 h at 37oC or 4oC. At the end of the incubation period the plates were placed on ice, the medium decanted and the cells washed four times with ice cold balanced salt solution (BSS). The amount of 59Fe internalized was measured by incubation with the general protease, pronase (Boehringer Mannheim, Laval, Quebec) at 1 mg/mL in BSS, for 30 min at 4oC. The cells were then removed from the plate in the pronase solution using a Teflon spatula, transferred to ice cold microcentrifuge tubes and centrifuged at 14,000 rpm for 1 min in an Eppendorf microcentrifuge to separate internalized radioactivity in the pellet from formerly membrane-bound radioactivity in the supernatant. The radioactivity of the cell pellet and supernatant were measured separately in a gamma scintillation counter and the Fe uptake in all experiments expressed as pMoles Fe/10$^6$ cells. In some experiments, Fe uptake was investigated at a range of 59Fe-citrate concentrations (0.01–10 $\mu$M) to investigate saturatability of Fe uptake process.

Figure 37A:
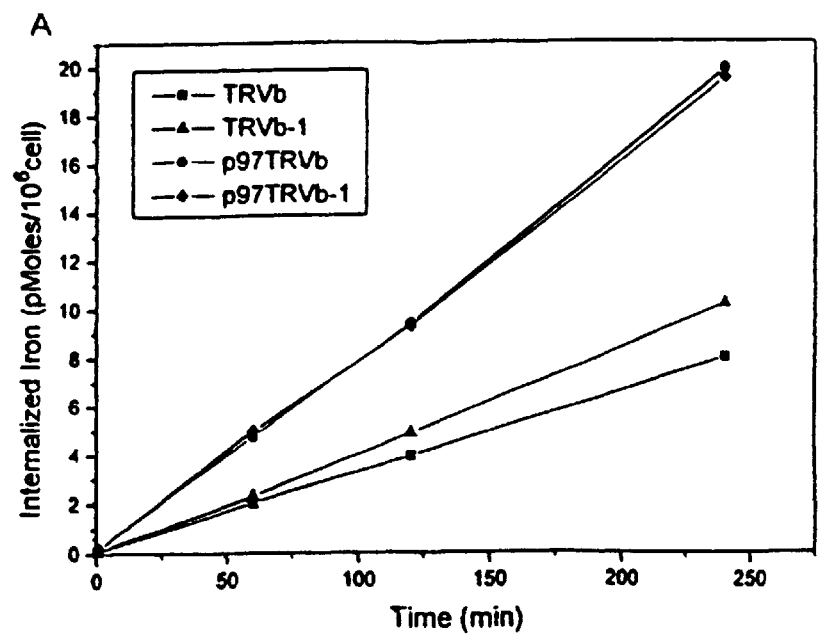
FIG. 37A is a graph showing the internalization of Fe as a function of time for TRVb, p97TRVb, TRVb-1 and p97TRVB-1 cells.
Figure 37B:
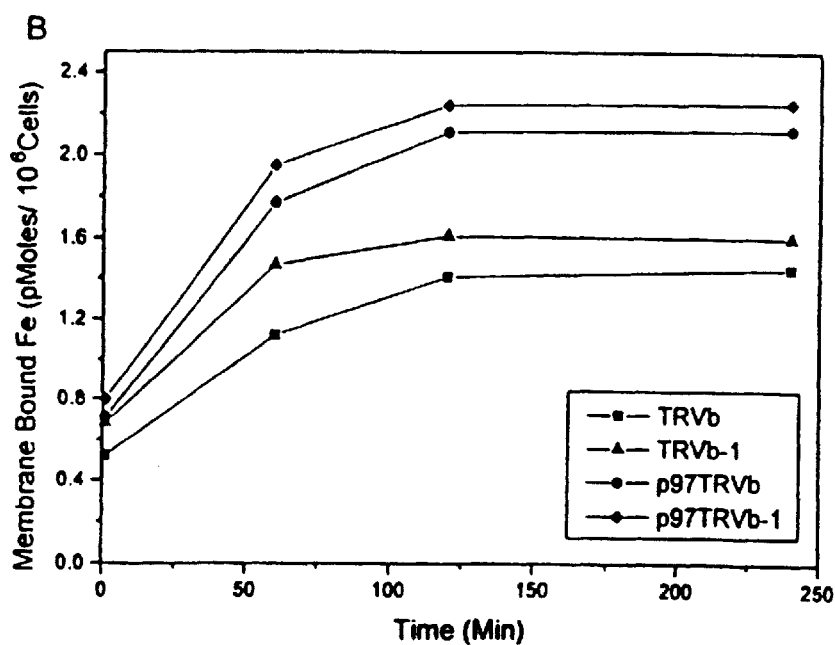
FIG. 37B is a graph showing membrane bound Fe as a function of time for TRVb, p97TRVb, TRVb-1 and p97TRVB-1 cells.

FIGS. 37A and 37B show the Fe uptake from Fe-citrate as a function of time at 37° C. for all four cell lines for incubation times up to 4 h in the presence of Fe-citrate complexes at an Fe concentration of 2.5 $\mu$M. After Fe incubation, the cells were treated with pronase at 4° C. for 30 min to separate the internalized Fe (FIG. 37A) from the membrane bound Fe (FIG. 37B). Results shown are the means of three derminations.

FIG. 37A clearly shows that for cells transfected with p97 (i.e. p97TRVb and p97TRVb-1) the internalized Fe uptake is greater than double that found for cells without p97 (ie. TRVb and TRVb-1). The level of internalized Fe increased linearly with no apparent induction period, which was observed by Olakanmi et al. (Olakanmi, O. et al, J. Immunol., 153, 2691–2703, 1994) who studied the uptake of Fe from low molecular weight chelates by human monocyte-derived macrophages. The internalization was virtually identical for p97TRVb and p97TRVb-1 at 20 pMoles/10$^6$ cell after 4 h, whereas it was 8 and 10 pMoles/10$^6$ cell for TRVb and TRVb-1 respectively. FIG. 37B shows the membrane-bound Fe for all cell lines plateaus off after about 60 min of incubation at a level of 1.6 pMoles/10$^6$ cell for TRVb and TRVb-1 and at 2.2 pMoles/10$^6$ cell for p97TRVb and p97TRVb-1, which is less than one fifth to one tenth the internalized Fe after 4 h. It is important to note that the membrane-bound Fe after 4 h is greater for cells expressing p97 and this is probably due to Fe bound to p97 at the cell surface. All cell lines, therefore, appear to internalize Fe from the Fe-citrate, even the TRVb cells which have neither TR or human p97. Presumably TRVb is internalizing its Fe either by Fe non specifically binding to membrane proteins followed by endocytosis or pinocytosis or by a specific membrane-bound channel or carrier (Egyed, A., Br. J. Haematology, 68, 483–486, 1988; Morgan, E. H. Biochim. Biophys. Acta, 934, 428–439, 1988). It is even possible that this internalization may indicate the presence of a hamster p97.

D. Effect of Temperature on Fe Uptake

Figure 38A:
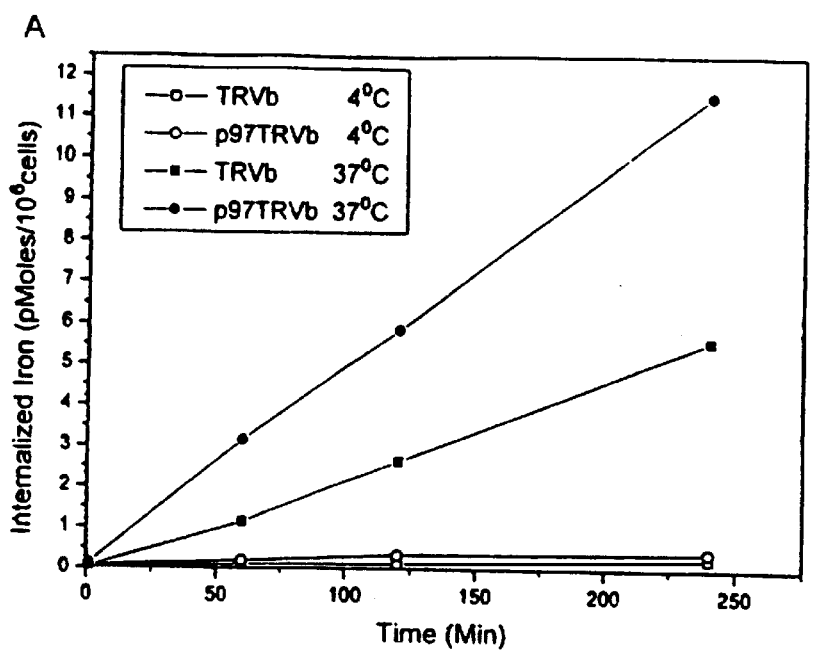
FIG. 38A is a graph showing the internalization of Fe as a function of time at 37 and 4° C. for TRVb and p97TRVb, cells.
Figure 38B:
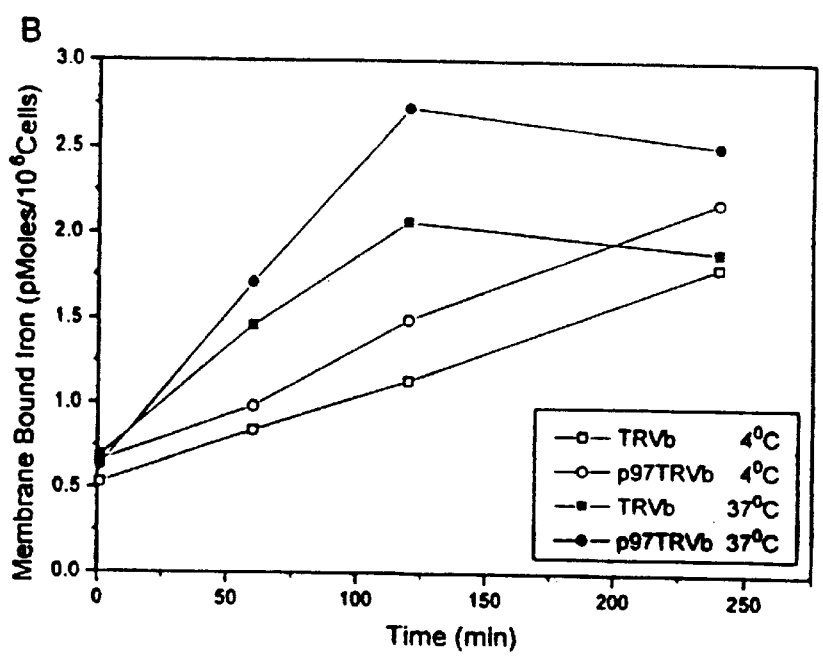
FIG. 38B is a graph showing membrane bound Fe as a function of time at 37 and 4° C. for TRVb and p97TRVb cells.

The uptake of Fe at 4oC was compared with that at 37oC for TRVb and p97TRVb. FIGS. 38A and 38B show Fe uptake as a function of time at 37oC for TRVb, TRVb-1, p97IRVb and p97TRVb-1. Cells were incubated for up to 4 h in the presence of Fe-citrate complexes at an Fe concentration of 2.5 $\mu$M. After Fe incubation, the cells were treated with pronase at 4oC for 30 min to separate the internalized Fe (FIG. 38A) from the membrane-bound Fe (FIG. 38B). Results are means of three determinations.

As seen in FIG. 38A the level of internalized Fe is reduced twenty fold at 4oC. The internalized Fe uptake for p97TRVb is over double that of TRVb at both 37oC and 4oC. The level of membrane-bound Fe appears to be relatively unaffected by temperature (FIG. 38B) although it took longer at 4oC to reach the saturation level. At 4oC the amount of internalized Fe is reduced to one quarter the level of membrane-bound Fe. This strong dependence of temperature on Fe uptake indicates that the internalization process is most likely mediated by an active transport mechanism. Even at 4oC the presence of p97 has increased the level of internalized and membrane-bound Fe. Similar results were obtained for TRVb-1 and p97TRVb-1 (data not shown).

E. Effect of Pronase on Levels of p97 p97 was shown in example 3 to be relatively insensitive to pronase treatment. It was, therefore, possible that the difference between internalized Fe uptake levels could just be due to Fe bound to surface p97 that had not been removed by the pronase treatment. However, from FIG. 37B it is clear that pronase treatment of cells released markedly more Fe from cells transfected with p97 than those not transfected with p97. If it is assumed that p97 is completely pronase insensitive and that there are about 1×106 molecules of p97 per cell surface, then the maximum amount of Fe that could be bound to the surface p97 is about 1.7 pMoles/106 cell assuming that one molecule of p97 binds one atom of Fe (Baker, E. N. et al., FEBS LETTERS, 298, 215–218, 1992). Even if it assumed that two atoms of Fe are able to bind per molecule of p97, this level is still not sufficient to explain the difference of 10 pMoles/$10^6$ cell between the Fe internalized by TRVb and p97TRVb after 4 h (see FIG. 37A). Furthermore, if the p97 is totally resistant to pronase, then the membrane-bound p97 should be the same for both TRVb and p97TRVb. This is clearly not the case as seen in FIG. 37B. The membrane-bound Fe was always between 0.6 and 0.9 pMoles/106 cell greater for p97TRVb than TRVb after 4 h. These levels are less than the amount that could be bound by 1×106 molecules of p97 and indicate that the pronase treatment only partially removes the p97.

Figure 39:
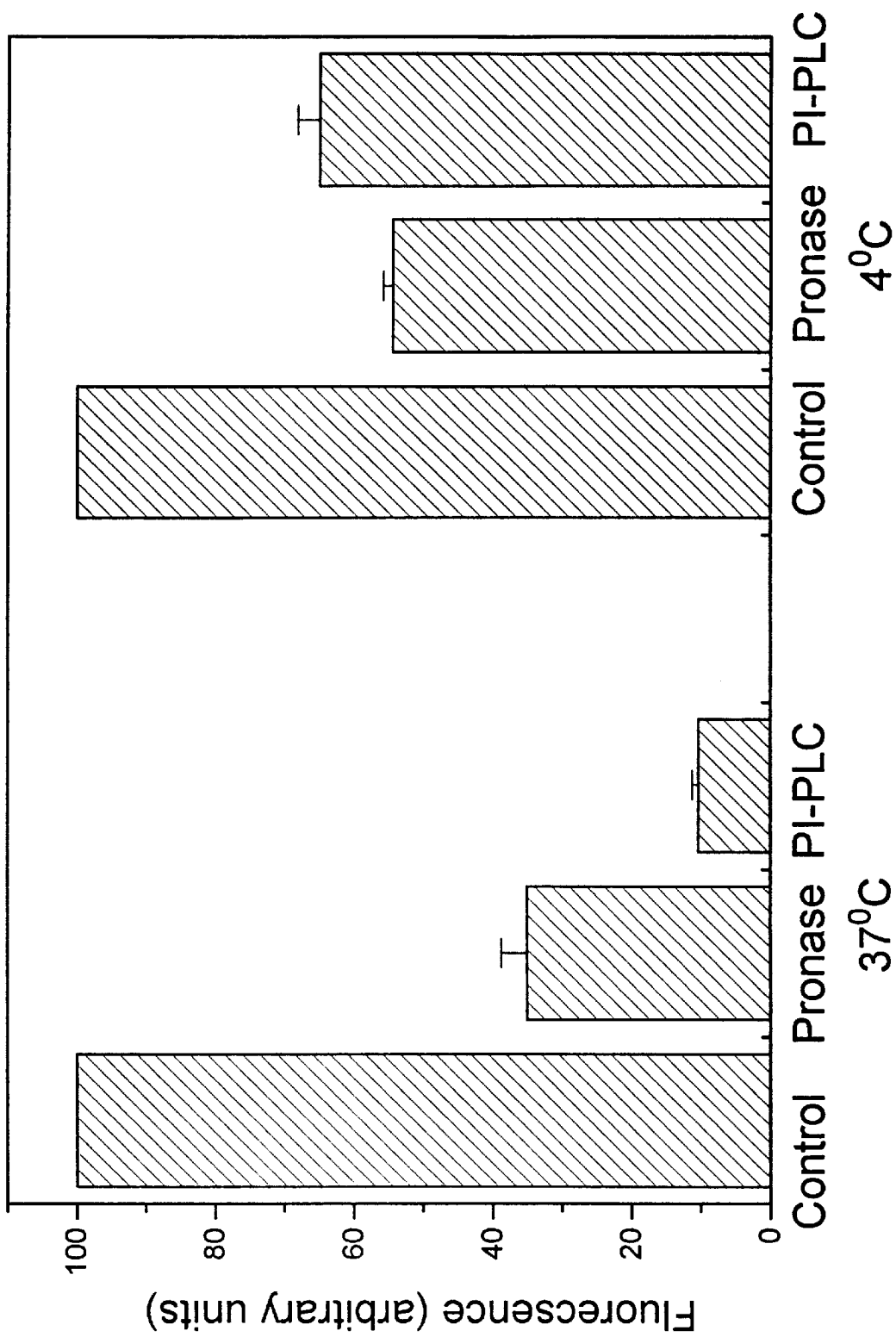
FIG. 39 is a graph showing the effect of PI-PLC and pronase on the removal of surface levels of p97 from TRVb and p97TRVb cells.

Based on the above considerations the effect of pronase on p97 removal was studied. Plates of washed p97TRVb and p97TRVb-1 were incubated with 1.5 mL of: a)BSS, b)BSS plus 300 mU/mL PI-PLC and c)BSS plus 1 mg/mL pronase for 30 min at 37° C. and 4° C. Cells were removed with 1 mM EDTA and assayed for surface levels of p97 using fluorescence concentration analysis. FIG. 39 shows the effect of PI-PLC (300 mU/mL) and pronase (1 mg/mL) on the removal of surface levels of p97 from TRVb and p97TRVb. Cells incubated for 30 min at 37° C. and 4° C. Cell surface levels of p97 were determined using fluorescence concentration analysis. Results are the mean of two experiments. FIG. 39 compares the effect of pronase and PI-PLC on p97 removal from p97TRVb (similar results were obtained for p97TRVb-1) at 4° C. and 37° C. These results clearly show that p97 is partially sensitive to pronase and that about 45% of p97 is removed by the pronase at 4° C. For comparison, the PI-PLC is more effective at 37° C. and is able to remove over 90% of the p97. Therefore, it can be concluded that the difference between the membrane-bound levels of Fe is due to the 45% removal surface p97 with bound Fe. If we assume that there are 1×106 molecules of p97 per cell and that one molecule of p97 binds only one atom of Fe, and the pronase treatment removes only 45% of the p97, then the calculated difference between the membrane-bound levels of Fe for TRVb and p97TRVb is 0.75 pMoles/106 cell, which is within the observed range of 0.6 to 0.9 pMoles/106 cell (FIG. 37B). Furthermore, the amount of Fe bound to pronase resistant p97 is only about 1.0 pMoles/106 cell and accounts for only 10% of the difference in internalized Fe after 4 h.

F. Effect of Fe Concentration on Fe Uptake

Figure 40:
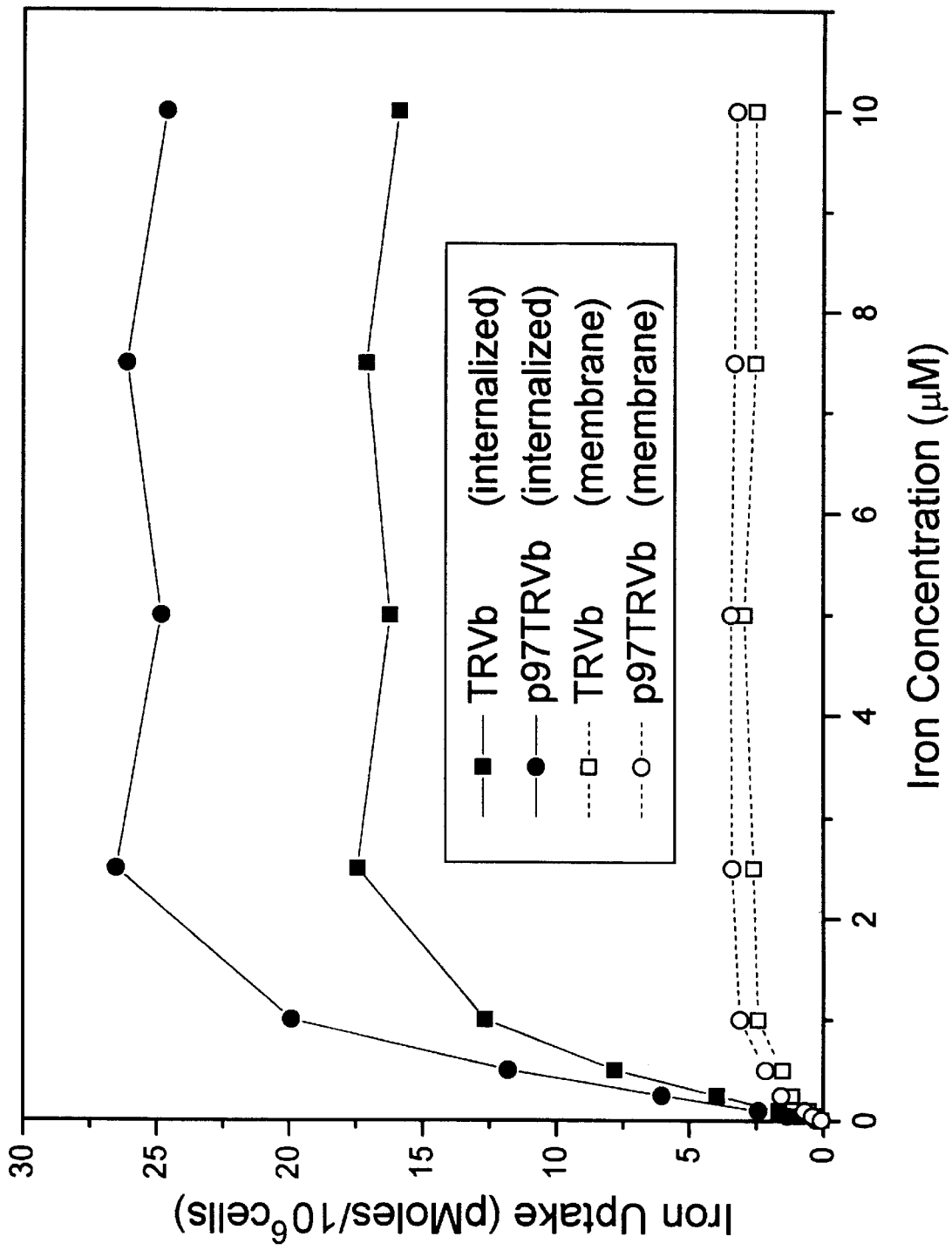
FIG. 40 is a graph showing Fe uptake as a function of medium Fe concentration by TRVb and p97TRVb cells.

To determine if the internalization of Fe is saturatable, the concentration of the Fe in the medium was varied from 0.01 to 10 $\mu$M. Fe uptake was measured after a 4 h incubation period. FIG. 40 shows Fe uptake as a function of medium Fe concentration by TRVb and p97TRVb after 4 h at 37° C. Results are the mean of three determinations. FIG. 40 again shows the difference in Fe uptake between TRVb and p97TRVb. The figure also shows that the process saturates at around 2.5 $\mu$M, which corresponds to a rate of approximately 4.4×104 atoms Fe/cell per min for TRVb and 6.7× 104 atoms Fe/cell per min p97TRVb. Since the internalized Fe uptake from Fe-citrate followed Michaelis-Menten type kinetics (FIG. 40) it was possible to derive Vmax and Km parameters for Fe uptake using the Eadie-Hofstee plot. The Vmax for TRVb was found to be about 0.13 pMoles Fe/106 cell per min (0.79×105 atoms of Fe/cell per min) and about 0.24 pMoles Fe/106 cell per min (1.45×105 atoms of Fe/cell per min) for p97TRVb. The corresponding values for Km were 1.74 and 2.01 $\mu$M. These values compare well with other Tf-independent Fe uptake studies (Sturrock, A. et al., J. Biol. Chem., 265, 3139–3145, 1990; Morgan, E. H. Biochim. Biophys. Acta, 934, 428–439, 1988). By subtracting the Fe uptake for p97TRVb from that of TRVb it was possible to determine the specific Fe uptake due to p97, with a corresponding Vmax of 0.1 pMoles Fe/106 cell per min (0.61×105 atoms of Fe/cell per min) and a Km of 2.58 $\mu$M.

Based on the knowledge that the difference between the membrane-bound Fe levels was due to 45% removal of p97 it was possible to extrapolate the data from FIG. 40 to construct a Scatchard plot. This plot revealed that, at saturation, approximately 1.25×106 atoms of Fe are bound per cell to the surface p97. Since there are approximately 1.0×106 surface molecules of p97/cell then each molecule of p97 is only able to bind one atom of Fe.

G. Effect of PI-PLC on Fe Uptake

To confirm that p97 was playing a role in the Fe uptake, cells were treated with PI-PLC prior to the Fe uptake experiments. p97 was removed from the cell surface prior to the Fe uptake experiments using phosphatidylinositol-phospholipase C (PI-PLC). Cell plates that had been washed once with MEM were preincubated with 300 mU of PI-PLC in MEM for 45 min at 37° C. After incubation the cells were washed twice in MEM for 30 min at 37° C. to ensure complete removal of PI-PLC and bovine Tf. The cells were then incubated in medium containing 59Fe-citrate and treated as before.

Figure 41:
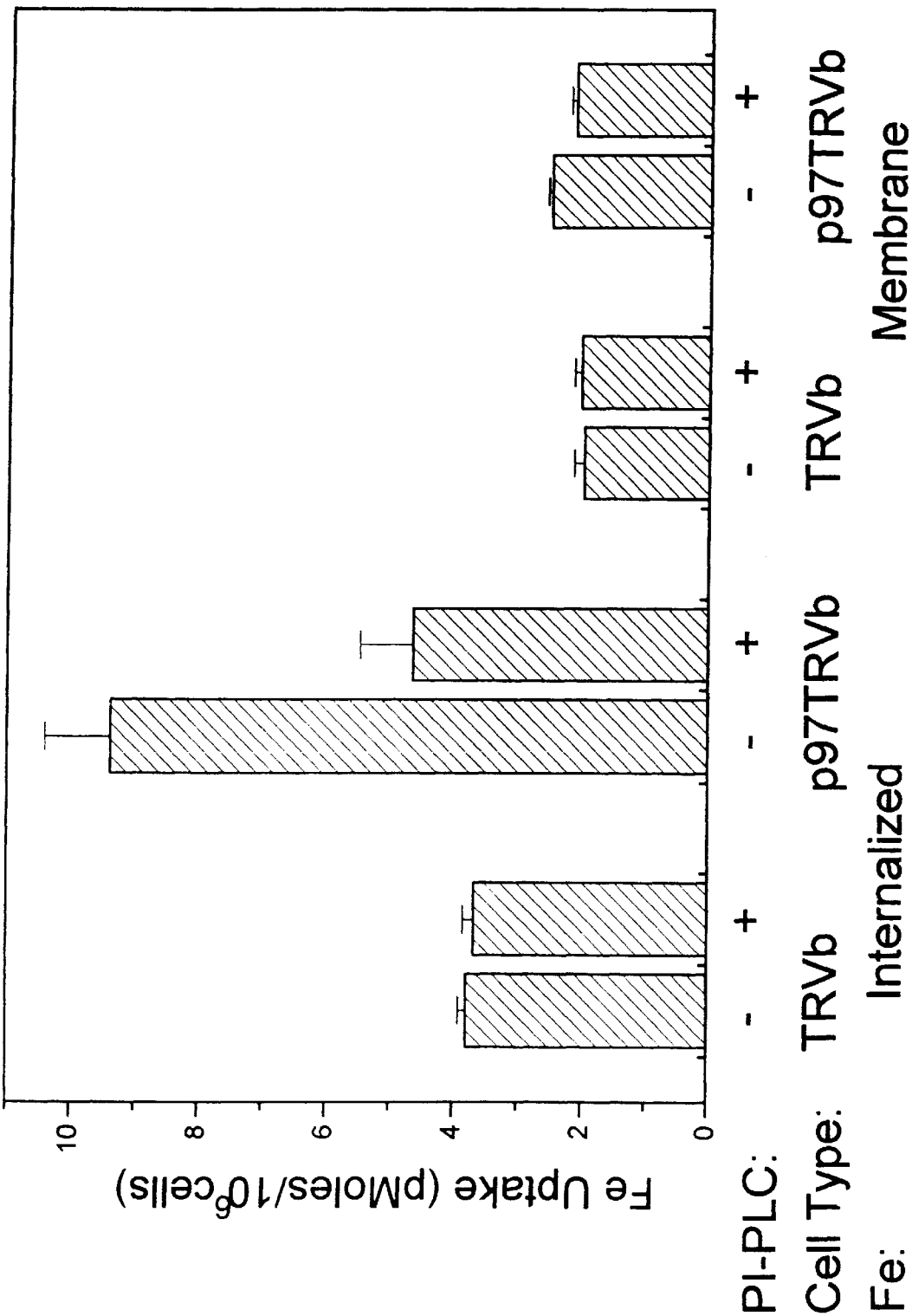
FIG. 41 is a graph showing the effect of pre-treating TRVb and p97TRVb cells with PI-PLC on Fe uptake.

FIG. 41 shows the effect of pretreating TRVb and p97TRVb with PI-PLC (300 mU/mL) for 45 min at 37° C. on Fe uptake. Cells were incubated for 2 h in the presence of Fe-citrate complexes at an Fe concentration of 2.5 $\mu$M. Results are mean of three experiments. FIG. 41 compares the Fe uptake from Fe-citrate after 2 h for cells preincubated with and without PI-PLC. The PI-PLC treatment had little effect on internalized and membrane-bound Fe for the TRVb cell line, which does not express human p97. In contrast, Fe internalized by the p97TRVb cells was reduced by over 50%, and is almost reduced to the level found for TRVb. Futhermore, there is also a slight reduction of the membrane-bound Fe due to removal of the surface p97. Similar results were obtained for TRVb-1 and p97TRVb-1. These results show that removal of surface p97 reduces the amount of internalized Fe uptake from Fe-citrate and again confirms a role of p97 in Fe uptake from low molecular weight Fe chelates.

H. Effect of Monoclonal Antibodies Specific to p97 on Fe Uptake

This experiment was carried out to see if MoAbs specific to p97 could block the binding of Fe or, as observed in the case of Fe uptake by SK-MEL-28 cells (Richardson, D. R. and Baker, E. Biochim. Biophys. Acta, 1093, 20–28, 1991b), actually increase the internalization of Fe. Cell plates were washed to remove bovine Tf, as described previously and then preincubated with the following monoclonal antibodies against p97: 96.5 (Dr. J. Brown, Oncogene, Seattle), L235 (ATCC), 0,961 (The Wistar Institute, Philadelphia). OKT9 (ATCC), which is against the human TR, was used as a control. The cells were incubated for 2 h with the MoAbs at 30 µg/mL in MEM plus NEAA, Hepes and BSA. After the preincubation period, the medium was replaced with medium containing 59Fe-citrate plus the same concentration of MoAb and incubated for 2 h. The cells were then treated as before.

FIG. 42 shows the effect of preincubating TRVb and p97TRVb with MoAbs against p97 (30 µg/mL) for 2 h at 37° C. on Fe uptake. Cells were incubated for 2 h in the presence of Fe-citrate complexes at an Fe concentration of 2.5 µM plus the same concentration of MoAb. Results are mean of three determinations. The MoAb OKT9 was used as a control since it is specific to the human TR. Incubation with the MoAbs specific to p97 had little effect on the internalization of Fe cells lacking human p97 (i.e. TRVb). However, in the case of cells transfected with p97 (i.e. p97TRVb), after a two hour incubation the internalization was increased by 47% for MoAb96.5, 31% for MoAbL235 and 47% for MoAb0,916 (see FIG. 42). OKT9 had little effect on either of the cell lines. The MoAbs also had relatively little effect on membrane-bound Fe. The significant increase in the internalization of Fe by p97TRVb suggests that the binding of the MoAbs and the modulation of p97 results in an increase in the rate of internalization of the MoAb-p97-Fe complex.

I. Fe Uptake from Fe Bound to Tf

To investigate the uptake of Fe from Fe bound to Tf, all four cell lines were incubated with Fe-Tf. Human apo-Tf was prepared and labelled with 59Fe as described previously (Richardson, D. R. and Baker, E. Biochim. Biophys. Acta, 1053, 1–12, 1990), by saturating the apo-Tf with 59Fe using ferric nitriloacetate. After washing the cells to remove bovine Tf the cells were incubated with 59Fe-Tf at an Fe concentration of 2.5 µM in MEM containing NEAA, Hepes and BSA for 2 h at 37° C. The cells were then treated as before.

Figure 43A:
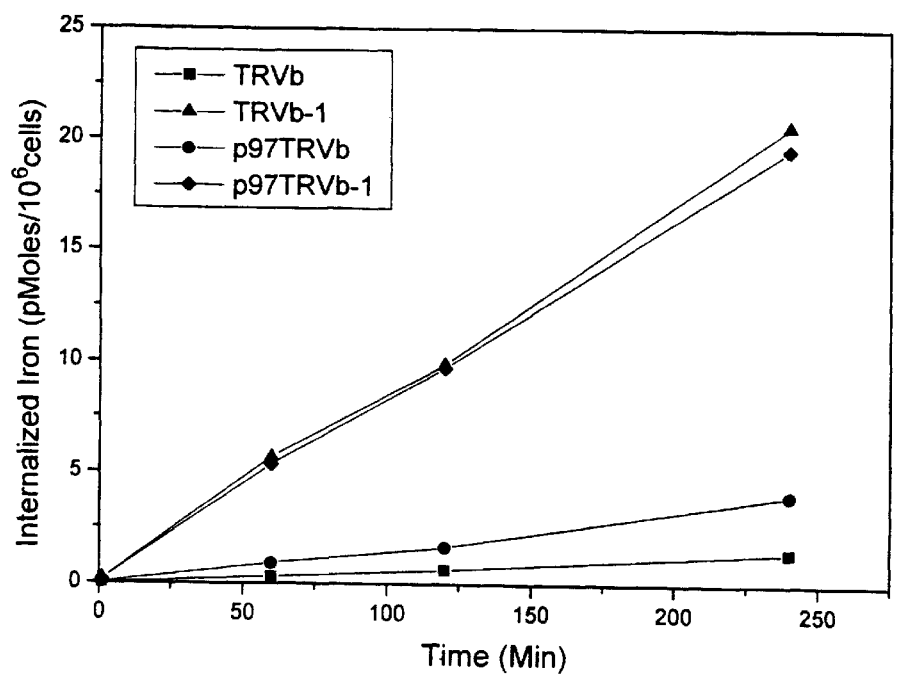
FIG. 43A is a graph showing Fe uptake as a function of time for TRVb, p97TRVb, TRVb-1 and p97TRVB-1 cells.
Figure 43B:
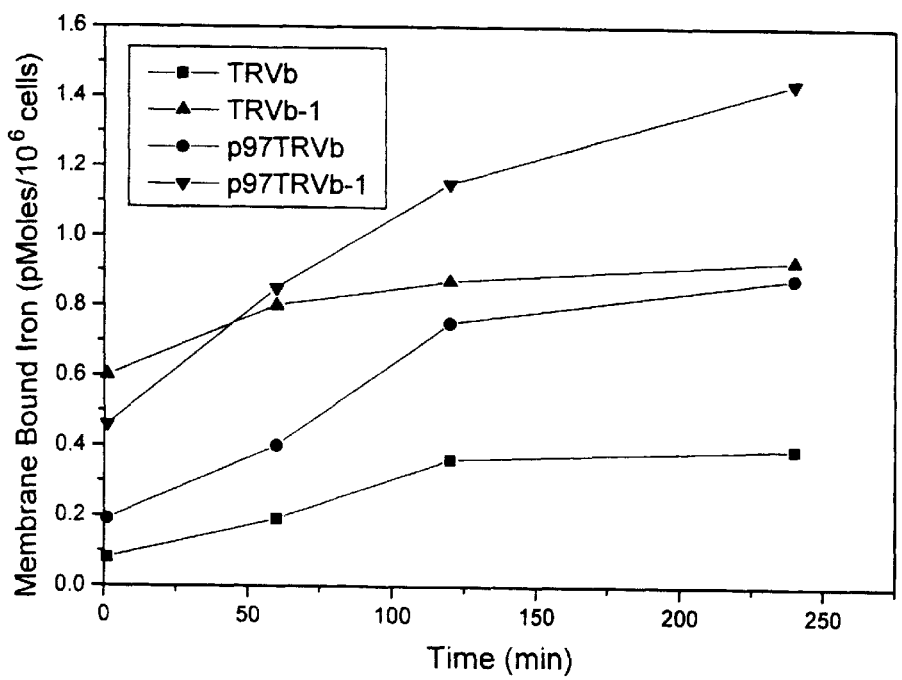
FIG. 43B is a graph showing membrane bound Fe as a function of time for TRVb, p97TRVb, TRVb-1 and p97TRVB-1 cells.

FIGS. 43A and 43B show Fe uptake as a function of time at 37° C. for TRVb, TRVb-1, p97TRVb and p97TRVb-1. Cells were incubated for up to 4 h in the presence of Fe-Tf at an Fe concentration of 2.5 µM. After Fe incubation, the cells were treated with pronase at 4° C. for 30 min to separate the internalized Fe (a) from the membrane-bound Fe (b). Results are means of three determinations.

FIG. 43A shows that uptake of internalized Fe for TRVb-1 and p97TRVb-1 were linear with time up to 4 h and virtually identical with an internalization rate of about 5.0×105 atoms Fe/cell per min, which was similar to studies involving the human melanoma cell line, SK-MEL-28 (Richardson, D. R. and Baker, E. Biochim. Biophys. Acta, 1093, 20–28, 1991b). Uptake for TRVb and p97TRVb, which have no TR, was reduced to less than a tenth and was similar to observations by McGraw et al. (McGraw, T. E. et al. J. Cell Biol., 105, 207–214, 1987) who compared the TRVb and TRVb-1 cell lines. The membrane-bound Fe levels (FIG. 43B) were highest for TRVb-1 and p97TRVb-1 and 0.56 pMoles Fe/106 cell greater than for TRVb and p97TRVb. This difference can be accounted for by the amount of Fe-Tf bound to the 1.5×106 TR/cell (McGraw, T. E. et al. J. Cell Biol., 105, 207–214, 1987). These results show that the human TR is functional in transfected cells (McGraw, T. E. et al. J. Cell Biol., 105, 207–214, 1987) as well as indicating that cells without the TR are still able to internalize a low level of Fe-Tf. It is likely, that in the case of TRVb and p97TRVb, Fe-Tf is binding non specifically to the cell membrane and being internalized by endocytosis or pinocytosis. The internalized Fe for p97TRVb is almost three times that of TRVb (4.1 vs. 1.42 pMoles Fe/106 cell) after 4 h and may indicate that the Fe from the non specifically bound Fe-Tf is transferred to p97 at the surface and is then internalized. There is also a considerable difference in the amount of Fe bound to the membrane (0.88 vs. 0.39 pMoles Fe/106 cell).

Example 17 p97 Levels in the Serum of Alzheimer Patients

A. Assay for the Detection of p97 in Human Blood Serum

An assay for measuring levels of p97 in human blood serum was developed based on a rapid immunofluorescent technique, "Particle concentration fluorescence immunoassay" (PCFIA) introduced in 1984 (Jolley et al. 1984, J. Immunol. Meth., 67, 21–35). This method employs capture antibodies (Ab) bound to sub-micron polystyrene beads. This "activated" solid phase acts as a specific absorbent for the protein of interest. A fluorescent labeled second Ab, also specific for the protein, was then incubated with the solid capture phase to form a complex whose fluorescent signal was proportional to the original protein concentration. The reactions were carried out in specially designed 96 well plates (Catalog 22-400-1; Idexx Laboratories Inc., Wesbrook, Me.). Each well contained a 0.22 µm cellulose acetate membrane that allowed the wells to be drained under vacuum to concentrate the flourescent complex in the base of each well. These plates were then washed and each well read for fluorescence at varying wavelengths using a Pandex Fluorescence Concentration Analyzer (FCA; Idexx).

Activated beads for use in the assay were prepared using the following antibodies to coat carboxy polystyrene particles (0.77 µm, 0.25% v/v; Idexx): the anti-p97 mouse monoclonal Ab, Hyb C (33B6E4; Dr. Shuen-Kuei Liao, McMaster University, Hamilton, ON), or 9B6 (Dr. Wilf Jefferies, Biotechnology Laboratory, UBC, B.C.), or anti-p97 rabbit antisera (Dr. Wilf Jefferies, Biotechnology Laboratory, UBC, B.C.). 1 mL of the particles (vortexed and sonicated for 1 min) were centrifuged and resuspended in 8 mL of 0.1 M MES [2(4-morpholino) ethanesulphonic acid] buffer pH 4.5. To this 5.0 mg of EDC [1-ethyl-3-(3-dimethylaminopropyl) carbodiimide] was added followed by 1 mL of antibody (1 mg/mL). The mixture was vortexed periodically, incubated overnight at room temperature and centrifuged at 6000 rpm for 10 min (Sorval HB4) and the beads were resuspended in 20 mL of phosphate buffered saline (PBS) containing 0.2% sodium azide (NaN3) and 2% w/v bovine serum albumen (BSA). The beads were then centrifuged at 6000 rpm for 10 min and the coated beads were stored in 32 mL of PBS containing 0.2% NaN3 and 2% BSA at 4° C. (~concentration of antibody, 25 µg/mL).

The fluorescently labelled second antibody was prepared using the anti-p97 mouse monoclonal antibody, L235 (ATCC-HB8446 L235 (H-19)) or anti-p97 rabbit antisera (Dr. Wilf Jefferies, Biotechnology Laboratory, UBC, B.C.), fluoresceinated with fluorescein isothiocyanate (FITC) as follows. FITC was added at 1 mg/mL to phosphate buffer pH 9.5 (0.15 M Na2HPO4). In the absence of azide, 0.5 mL of the antibody at 4 mg/mL was added to the FITC solution (0.15 mL of FITC solution at 1 mg/mL) and incubated overnight at room temperature in the dark. The fluoresceinated Ab was ready for use and stored at 4° C.

A p97 standard was prepared from p97 purified from the supernatant of phosphatidylinositol phospholipase C (PI-PLC) treated Chinese hamster ovary (CHO) cells, transfected with human p97), by immunoaffinity chromatography. Approximately $10^9$ transfected CHO cells were treated with 1 mL of PI-PLC (300 mU/mL) in PBS for 1 hr at 37° C. The supernatant was recovered from the cells by centrifugation and filtered through a 0.2 $\mu$m membrane. The supernatant was then applied to a column (1×10) of Ab (HybC) immobilized on Affi-Gel 10 (Bio-Rad, Mississauga, ONT). The column had been previously washed and regenerated in PBS at pH 7.2. Bound p97 was eluted with 0.1 M citric acid, pH 3.0, followed by neutralization with 1 M Tris-HCL, pH 9.0. The purified p97 was concentrated using a 30,000 MW ultrafiltration membrane. Dialysed against PBS and sterile filtered. The concentration of the standard p97 was determined using the p97 extinction coefficient at 280 nm 1%=12.0 cm-1 (Baker et al. 1992) Blood serum samples were prepared as follows. For each patient the following samples were taken: (a)serum sample stored at-20° C. and (b) fresh blood stored at 4° C. Before testing the samples, the fresh blood was centrifuged and the serum recovered. Both types of sample were tested neat and/or diluted in 50% v/v fetal calf serum (FCA) in Pandex buffer (DNEM containing 0.1% NaH3 and 1.0% w/v BSA).

The blood serum p97 assay was carried out in the special 96 well plates (22-401-1; Idexx) and the fluorescence read in the FCA (Idexx) as follows. 60 $\mu$L of the blood serum sample at the appropriate dilution in the 50% FCA solution was added to a well on the 96 well plate. Each sample was tested in duplicate or triplicate. To each plate p97 standards were also added in duplicate (300, 150, 120, 90, 60, 30, 15, 9, 6 ng/mL). These standards were diluted in the 50% FCA solution and used for calibration curve preparation. A sample calibration curve preparation is shown in Table 4 and a calibration curve is shown in FIG. 44. 20 $\mu$L of the anti-p97 coated beads (~25 $\mu$g Ab/mL) was added to each sample and incubated at room temperature for 40 min. The contents of the wells were gently mixed by tapping the sides of the 96 well plate. Following the incubation, 20 $\mu$L of the fluoresceinated second anti-p97 Ab was added (diluted 1/75 in Pandex buffer (~25–40 $\mu$g/mL)) to the sample and beads and incubated for 5–10 min at room temperature. The plates were then placed in the FCA, drained and washed 3–5 times in PBS containing 0.1% NaH3 and 1% w/v BSA. The drained plates were then read with the 485/535 nm filter pair at 25×gain.

Figure 45:
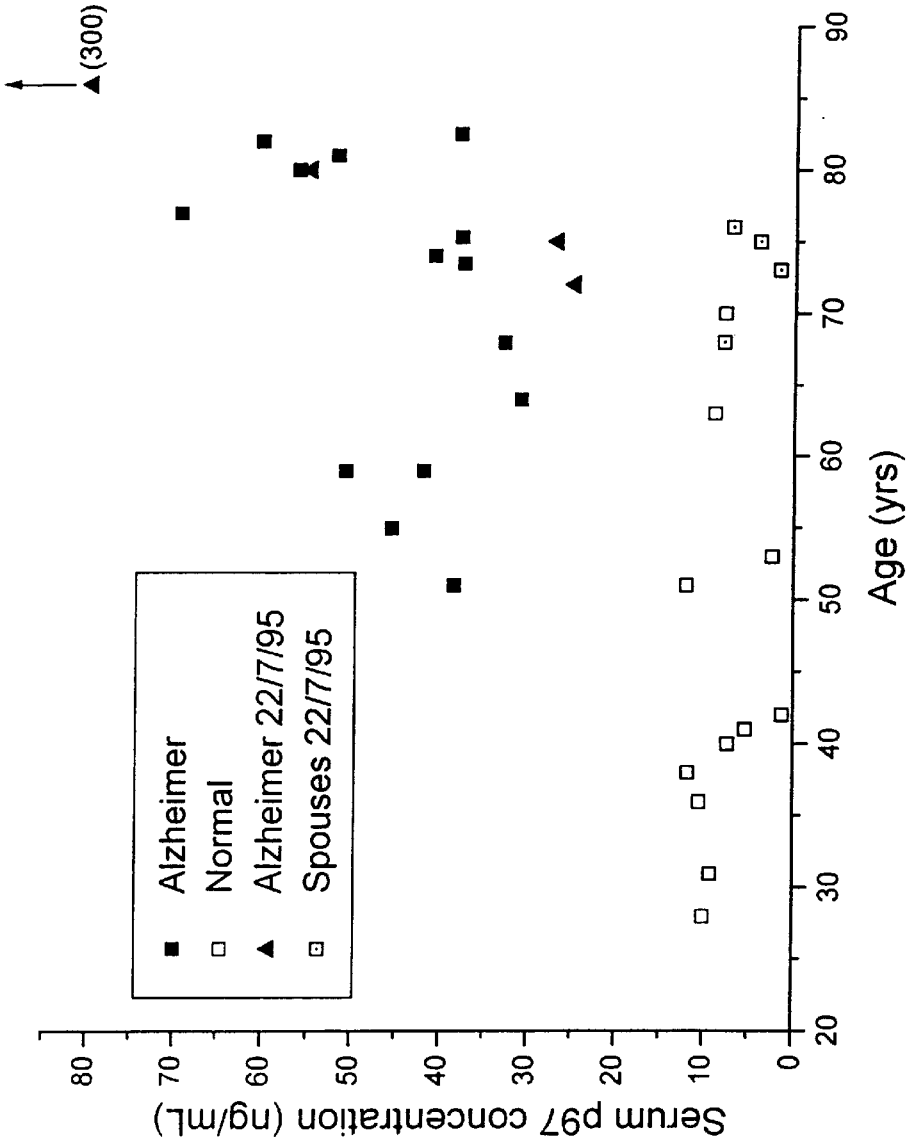
FIG. 45 is a graph showing a comparison between serum p97 levels for Alzheimer's disease patients and control subjects based on age.

Blood serum samples were obtained from Alzheimer (AD) patients, from spouse controls and from unrelated controls. Table 5 shows sample results of p97 blood serum concentrations of p97 in AD patients. Duration of the disease indicates the number of years since diagnosis of the condition. However, it is quite possible that an individual patient had been suffering from the disease for some time prior to diagnosis. Table 6 shows the p97 blood serum concentrations in AD patient and control samples. Levels of p97 in the serum of unrelated controls ranged between 2.4 to 12 ng/ml and levels were found not to increase with age of the subject (FIG. 45). As shown in FIG. 45, levels of p97 in the serum of AD patients was significantly elevated compared to the controls and levels appeared to increase with age of the patient. AD patients had levels of p97 in the serum of at least 20 ng/ml. The maximum level found was 300 ng/ml.

Importantly, serum p97 levels were found to be correlated with duration of disease in AD patients as shown in FIG. 46. Increasingly higher levels of p97 were found in the serum of patients with longer duration of disease.

Figure 47:
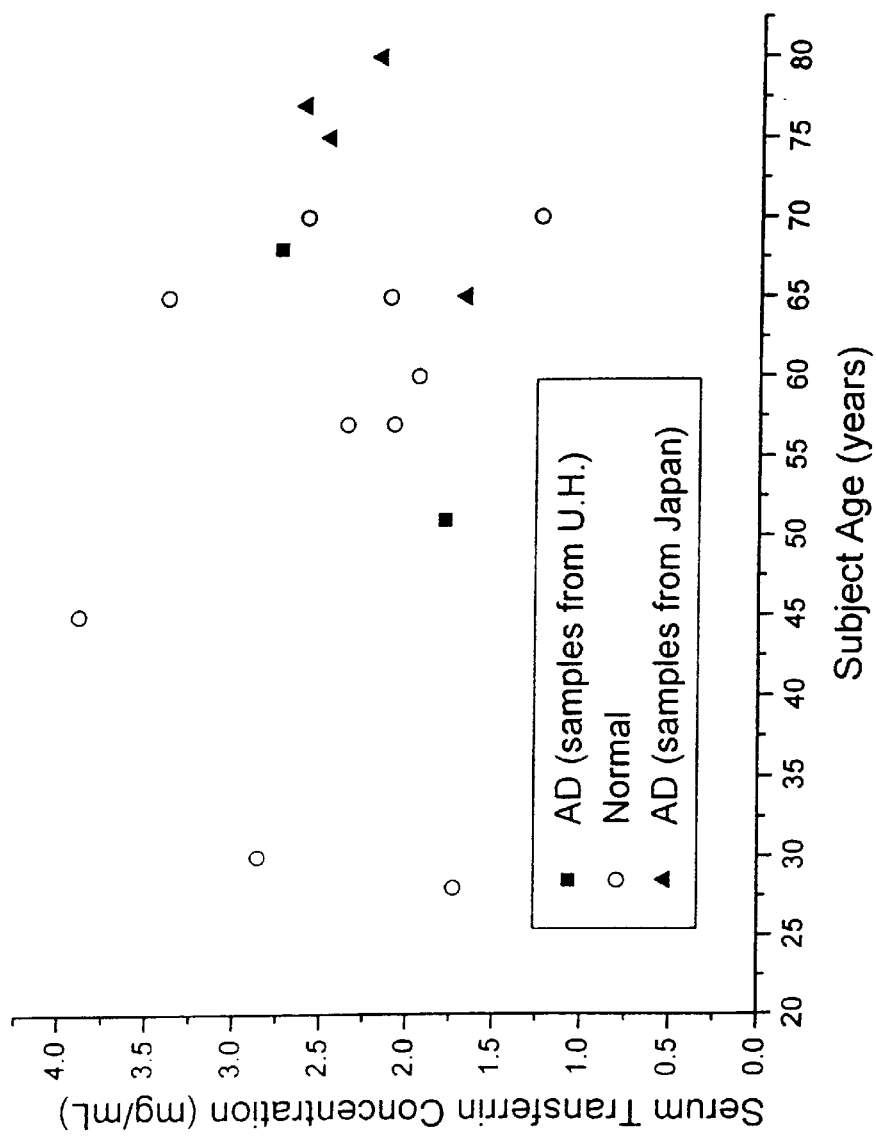
FIG. 47 is a graph showing a comparison between serum transferrin levels for Alzheimer's disease patients and control subjects based on age.

Serum transferrin levels were also measured in samples from AD patients and controls. No apparent difference was found in serum transferrin levels between AD patients and controls and no correlation was found between age of the subject and serum levels of transferrin (FIG. 47).

Transferrin and p97 levels were also measured in CSF and serum samples previously obtained from a group of Japanese AD patients and control subjects. These samples had been frozen for two years and subjected to thawing and refreezing, thus the actual levels of protein may not reflect the absolute levels originally present in the samples. However, the results, shown in Table 7 confirmed the above findings that p97 levels were elevated in the serum of AD patients compared to levels in control subjects. The results also indicated that p97 levels in CSF were elevated in AD patients compared to controls. Transferrin levels in the serum and CSF of the AD patients were not elevated over control levels.

Example 18

P97 Production from Spheroid, Porous and Solid Microcarrier CHO Cell Cultures

A. Spinner Cultures

Adherent CHO cells cotransfected with p97 and G418 resistance as described herein were maintained in spinner culture in Ham's F12 medium (Gibco, Burlington, ON) supplemented with 10% NCS (Gibco) and 2 mM L-glutamine (Gibco) at 37° C. in a 5% $CO_2$ humidified atmosphere. The porous microcarriers, Cultispher-GH and CultispherG(Percell Biolytica, Lund, Sweden), consisted of crosslinked gelatin with hydrated mean diameters of 320 and 200 $\mu$m, respectively. There were approximately $4.2\times10^5$ beads/g dry weight for Cultispher-GH and $8\times10^5$ beads/g dry weight for Cultispher-G. The porous microcarriers were hydrated in $Ca^{2+}$ and $Mg^{2+}$ free PBS (1 g bead dry weight/100 mL) at room temperature for at least 1 h. The PBS was removed and the beads washed and resuspended in fresh PBS prior to sterilization at 121° C. for 30 min. The porous microcarriers were resuspended in Ham's F12 medium (Gibco, Burlington, ON) supplemented with 10% NCS (Gibco), 2mM L-glutamine (Gibco), 100 U/mL penicillin (Gibco), and 100 $\mu$g/mL streptomycin (Gibco) and transferred to 500-mL spinners with 250 mL working volume (Bellco, Vineland, N.J.). The spinner cultures were initiated according following the methods described in Kennard and Piret, (Biotech. Bioeng. 44:45–54, 1994) with 0.6 g dry weight/L porous microcarriers and cell concentrations of between 3.5 and $5\times10^5$ cells/mL (approximately 1000 cells/bead for Cultispher-GH and 500 cells/bead for Cultispher-G).

The solid microcarrier, Cytodex-1, consisted of a cross-linked dextran matrix with a hydrated mean diameter of 180 $\mu$m and approximately $6\times10^6$ microcarriers/g dry weight. The microcarriers were hydrated and sterilized in a similar fashion to that used for the porous microcarriers. The spinner cultures were initiated with 1 g dry weight/L solid microcarriers and $5\times10^4$ cells/mL (approximately 5–10 cells/bead). The low cell-to-bead ratio was used in order to prevent cell and bead clumping and to allow an even coverage of cells over the surface of the microcarriers.

Spheroids of CHO cells were prepared by first growing multilayers of cells in T-flasks. (Kennard and Piret, Biotech. Bioeng. 44:45–54, 1994) After several medium changes the cells began to aggregate and then formed freely suspended spheroids. These spheroids were recovered and transferred to 250-mL working volume spinner flasks. The spheroids were maintained in 10% NCS containing medium and grown to an average 500 μm diameter over 40 days.

After inoculation all spinner cultures were maintained at 37° C. and 5% $CO_2$ humidified atmosphere in Ham's F12 medium supplemented with 10% NCS, 2mM L-glutamine, 100 U/mL penicillin, and 100 μg/mL streptomycin. The spinner cultures were maintained in this medium for 10 days for Cultispher beads, 20 days for Cytodex-1, and 40 days for spheroids before the serum content of the medium was reduced to 2% NCS. The cells were then allowed to adapt for 15 days to the 2% NCS level before performing p97 harvesting experiments. The spinner cultures were operated at 50 rpm without pH or dissolved oxygen control. The glucose and free cell concentrations were regularly monitored in bead-free samples. The medium was replaced with fresh medium when the glucose concentration fell below 0.5 g/L (or after each p97 harvest) by allowing the beads to settle under gravity and decanting the spent medium. Periodically, a sample of approximately 50 beads or spheroids was removed to determine the cell density and bead size. The mean diameter of beads and spheroids was determined using an optical microscope with a measuring scale. Cell density was determined by washing the beads and spheroids with PBS for 5 min and then treating with 0.1% trypsin in a 0.4 mM ethylenediaminetetraacetic acid (EDTA) solution (Gibco) at 37° C. for up to 15 min with gentle vortexing. (Kennard and Piret, Biotech. Bioeng. 44:45–54, 1994) After disaggregation of the cells and dissolution of the Cultispher porous microcarriers, (Kennard and Piret, Biotech. Bioeng. 44:45–54, 1994) the suspension was centrifuged at 250 g for 5 min and the pellet resuspended in fresh serum containing medium. The cells were then counted in a haemocytometer and their viability determined by trypan blue dye exclusion.

Cultispher-GH cultures were used to study the effect of varying medium serum level and harvest cycle time on harvested p97 concentration. Cultispher-GH cultures (1 g dry weight/L) were established in 1-L spinners with a working volume of 450 mL and maintained in 10% NCS containing medium. After 15 days the cultures were split into four parallel 250-mL cultures and harvested every 24, 48, 72, or 96 h. To investigate the effect of reduced serum, four parallel 250-mL cultures were maintained in 10, 2, 0.5, and 0% NCS containing media for 20 days prior to p97 harvesting experiments.

After inoculation all spinner cultures were maintained at 37° C. and 5% $CO_2$ humidified atmosphere in Ham's F12 medium supplemented with 10% NCS, 2mM L-glutamine, 100 U/mL penicillin, and 100 μg/mL streptomycin. The spinner cultures were maintained in this medium for 10 days for Cultispher beads, 20 days for Cytodex-1, and 40 days for spheroids before the serum content of the medium was reduced to 2% NCS. The cells were then allowed to adapt for 15 days to the 2% NCS level before performing p97 harvesting experiments. The spinner cultures were operated at 50 rpm without pH or dissolved oxygen control. The glucose and free cell concentrations were regularly monitored in bead-free samples. The medium was replaced with fresh medium when the glucose concentration fell below 0.5 g/L (or after each p97 harvest) by allowing the beads to settle under gravity and decanting the spent medium. Periodically, a sample of approximately 50 beads or spheroids was removed to determine the cell density and bead size. The mean diameter of beads and spheroids was determined using an optical microscope with a measuring scale. Cell density was determined by washing the beads and spheroids with PBS for 5 min and then treating with 0.1% trypsin in a 0.4 mM ethylenediaminetetraacetic acid (EDTA) solution (Gibco) at 37° C. for up to 15 min with gentle vortexing. After disaggregation of the cells and dissolution of the Cultispher porous microcarriers, the suspension was centrifuged at 250 g for 5 min and the pellet resuspended in fresh serum containing medium. The cells were then counted in a haemocytometer and their viability determined by trypan blue dye exclusion.

Cultispher-GH cultures were used to study the effect of varying medium serum level and harvest cycle time on harvested p97 concentration. Cultispher-GH cultures (1 g dry weight/L) were established in 1-L spinners with a working volume of 450 mL and maintained in 10% NCS containing medium. After 15 days the cultures were split into four parallel 250-mL cultures and harvested every 24, 48, 72, or 96 h. To investigate the effect of reduced serum, four parallel 250-mL cultures were maintained in 10, 2, 0.5, and 0% NCS containing media for 20 days prior to p97 harvesting experiments.

B. PI-PLC Treatment and p97 Harvesting

For harvesting, the beads were first allowed to settle for 5 min under gravity without agitation and the medium decanted. All the beads were then transferred using a 10-mL glass pipette to a 15-mL sterile conical centrifuge tube (Fisher Scientific). The remaining medium was removed and the settled beads were washed twice with 10 mL sterile PBS. For all harvesting experiments, unless otherwise stated, PI-PLC (300 mU/mL) in PBS was added to the washed beads at a ratio of 2 mL of settled beads to 1 mL of enzyme solution and incubated with shaking at 200 rpm in a water bath at 37° C. for 1 h.

After incubation the beads were allowed to settle and the enzyme solution containing harvested p97 recovered for analysis as descrubed below. The enzyme treated beads were washed 3 times with 10 mL of PBS (10 min per wash with intermittent shaking), then resuspended in fresh growth medium and returned to the spinner containing 250 mL fresh growth medium. The beads were then cultured a further 48 h (unless otherwise stated) before the harvesting process was repeated.

Samples of p97 released by PI-PLC were centrifuged at 10,000 g for 10 min, filtered through a 0.2 μm low protein binding membrane (Acrodisc 25, Gelman Sciences, Ann Arbor, Mich.), and stored at −20° C. prior to analysis of p97. The concentration of p97 was determined by a rapid immunofluorescent technique(Jervis and Kilburn, Biotechnol. Prog. 7:28–32, 1991, Kennard et al., Biotechnol. Bioeng. 42(4): 480–486, 1993) using a fluorescence concentration analyzer (IDEXX, Westbrook, Me.). The purity of the samples were evaluated by comparing the p97 concentration with the overall protein concentration based on a total protein assay (Bio-Rad) using albumin as a standard. (Kennard et al., Biotechnol. Bioeng. 42(4): 480–486, 1993) Glucose concentration was monitored using a Beckman glucose analyzer II (Brea, Calif.).

C. Selection of Harvesting Conditions

Figure 48:
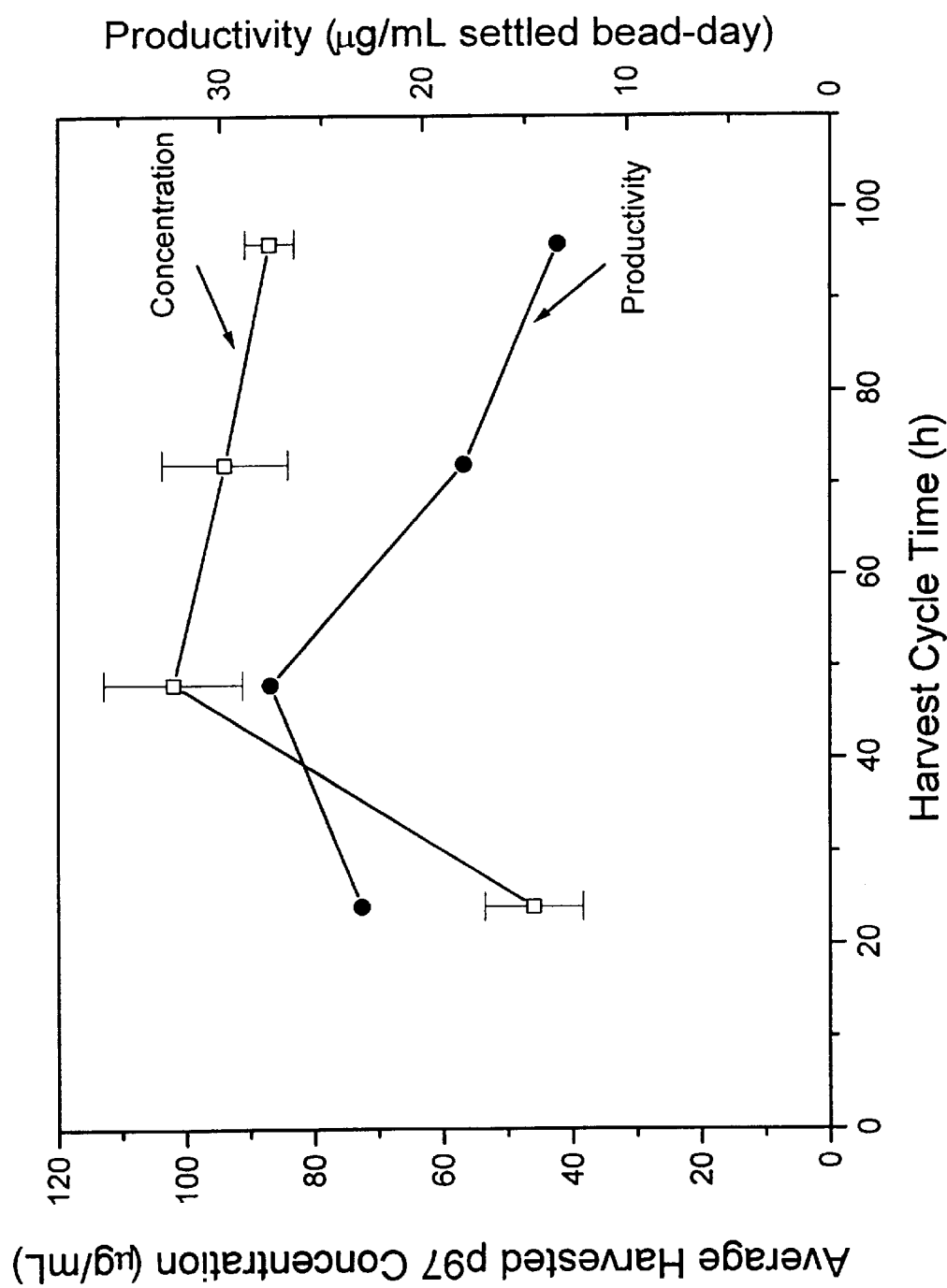
FIG. 48 is a graph showing the effect of harvest cycle time on concentrations and production of p97 harvested from cells cultured on Cultispher-GH.

Parallel, high cell density cultures were established on Cultispher-GH, and after 15 days the p97 was harvested from the cells every 24, 48, 72, or 96 h. The p97 concentration recovered from each harvest cycle was steady over a 13-day period and the highest p97 concentrations and productivity were obtained with the 48-h cycle time as shown in FIG. 48. FIG. 48 shows the effffect of harvest cycle time on concentrations and production of p97 harvested from cells cultured on Cultispher-GH. Results averaged over a 13 day period. Error bars show standard deviation of repeated harvests. The glucose concentration on average decreased from 1.8 g/L to 0.98, 0.56, and 0.1 g/L for the 24-, 48-, and 72-h cycle times, respectively. In the case of the 96-h cycle time, the medium was changed after 72 h since the glucose concentration had fallen below 0.1 g/L. The slight drop in p97 concentrations for the 96-72-h cycle times may therefore have been due to glucose or other nutrient limitations. Nevertheless, viability remained over 95% throughout this time period. The 48-h harvest cycle was selected for all subsequent experiments based on the higher productivity and concentration of p97 (FIG. 48).

Figure 49:
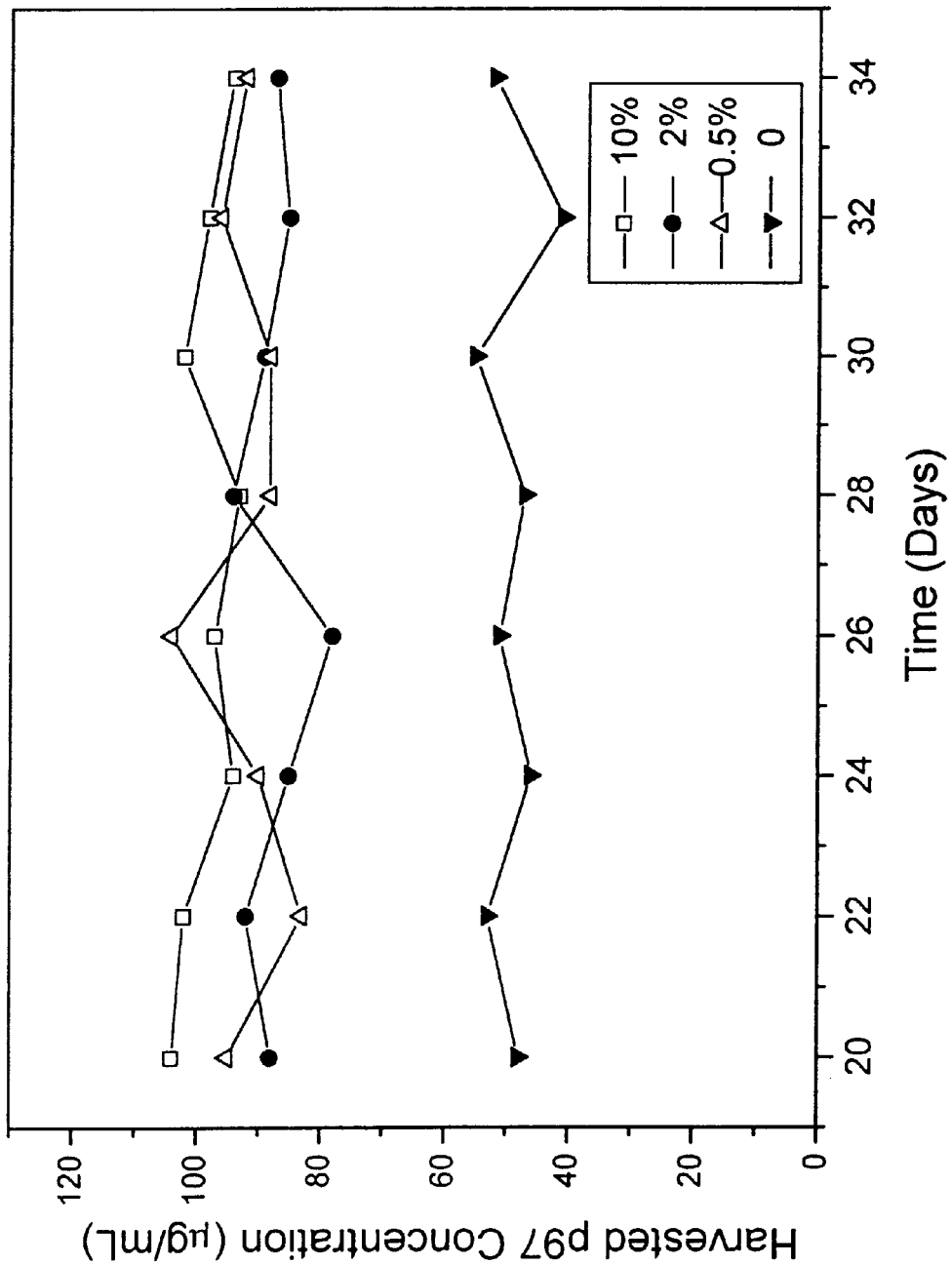
FIG. 49 is a graph showing the effect of culture medium serum content on harvested p97 concentrations from cells cultured on Cultispher-GH and harvested every 48 h.

To study the serum requirements of cells cultured on porous microcarriers, parallel high cell density cultures established on Cultispher-GH and maintained in 10% NCS for 15 days were transferred to media containing 0, 0.5, 2, or 10% NCS. After allowing 20 days for adaptation to the new media, the cells were harvested 8 times at 48-h intervals (FIG. 49). FIG. 49 shows the effect of culture medium serum content on harvested p97 concentrations from cells cultured on Cultispher-GH and harvested every 48 h. The results show that reducing the serum level from 10 to 0.5% had little effect on the concentration of harvested p97. The purity of harvested p97 was increased from 28 to 40% by reducing the medium serum from 10 to 0.5%. Therefore, reducing the medium serum would not only reduce media costs but also improve downstream processing by improving the purity of recovered p97. Since cells maintained in 2% NCS had slightly improved viability and growth compared to 0.5% NCS, all other experiments were carried out on cultures maintained in 2% NCS.

D. Effect of Bead Type on Harvested p97

Figure 50:
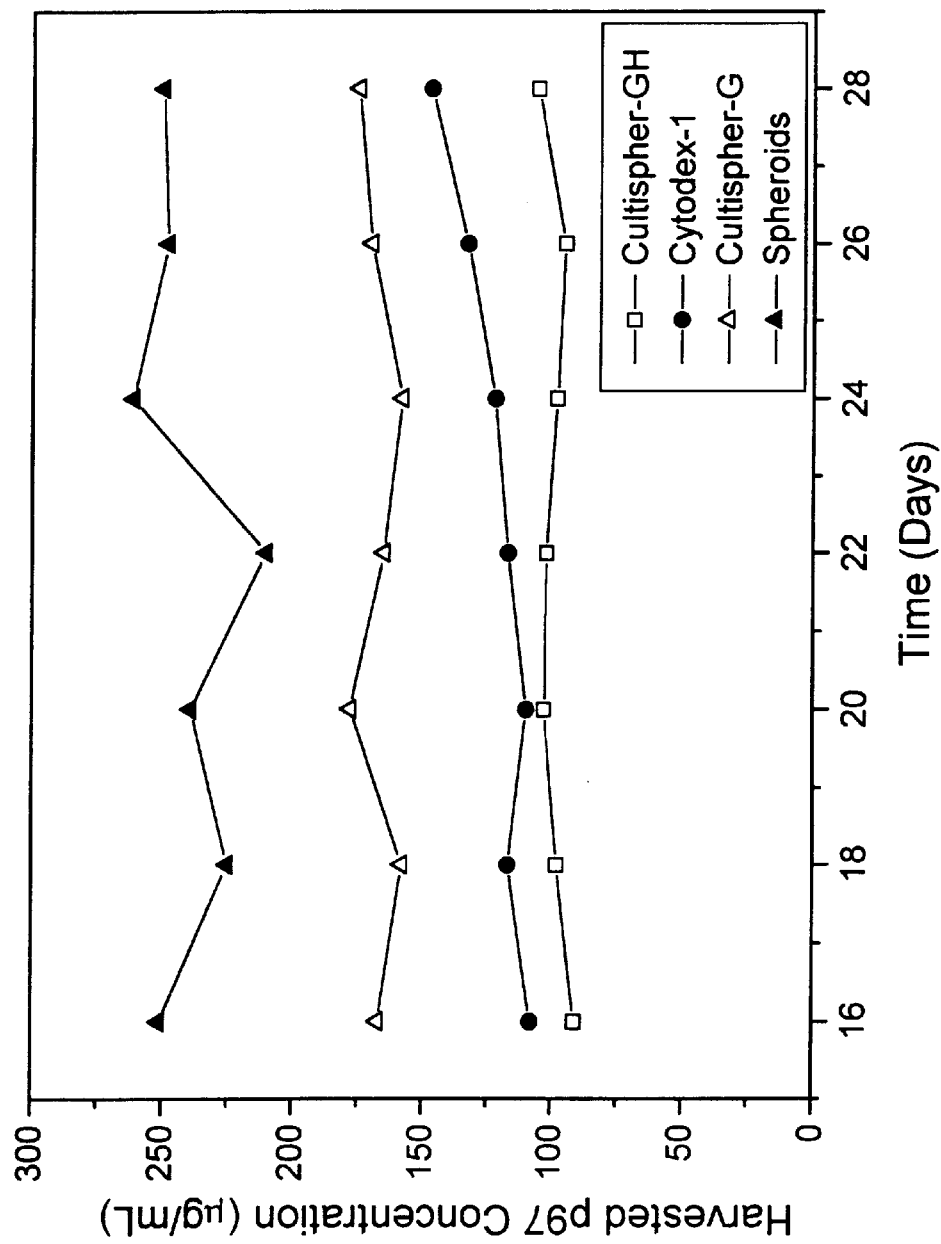
FIG. 50 is a graph showing a comparison of harvested p97 concentrations from Cultispher, Cytodex, and spheroid cultures harvested every 48 h.

FIG. 50 compares the results of harvesting p97 every 48 h over a 12-day period from CHO cells cultured on Cultispher-GH, Cultispher-G, and Cytodex-1 and as spheroids. The harvested p97 concentrations for all cultures remained steady over the 12 days. Compared to Cultispher-GH the harvested p97 concentrations were increased using the smaller Cultispher-G and Cytodex-1 and more than doubled using spheroids. Table 8 compares the results of cell growth and p97 production averaged over the 12-day period. The average bead diameter of Cultispher-G was almost half that of Cultispher-Gh (274 vs. 460 $\mu$m). This reduced transport and oxygen limitations within the beads and resulted in a 20% increase in cell viability and a 67% increase in total cell specific p97 production. The increase in viability, however, did not completely account for the increased p97 production. Harvesting Cytodex-1 cultures, which had similar average bead diameters to Cultispher-G, resulted in average harvested p97 concentrations of 122 $\mu$g/mL. Since the cells do not grow inside the beads, cell densities were reduced from about $3.0\times10^8$ to $1.8\times10^8$ cells/mL settled based volume and the cell viability was 96%. The total cell specific p97 production was increased to $3.2\times10^{-7}$ $\mu$g/cell. Even when the cell specific p97 production was based on viable cells, Cytodex-1 cultures still maintained the highest cell specific p97 production (Table 8). The highest concentration of 241 $\mu$g/mL harvested p97 was recovered from spheroids of similar average bead diameter (482 $\mu$m) to Cultispher-GH. The over two fold increase in concentration was due to the higher cell concentration per milliliter of settled beads ($6.2\times10^8$ vs. $2.8\times10^8$ cells/mL). However, cell viability or total cell specific p97 production was not increased.

These results appear to confirm that mass transfer limitations influenced the growth and protein harvest of cells grown in porous microcarrier culture. Smaller beads with increased specific surface area and reduced diffusional distances allowed increased access of oxygen, growth, and enzyme harvest media to the cells within the interior of the bead, resulting in increased cell viability and improved recovery of p97 from harvested cells. The maximum cell viability and total cell specific p97 production was achieved with Cytodex-1 microcarriers, which contained only two to three layers of cells on their surface. The lower total cell specific p97 production from the larger Cultispher-GH and spheroids appeared to indicate that harvesting was incomplete, even accounting for the large necrotic cores. The results showed that the low total cell specific p97 production of spheroid, Cultispher-GH and Cultispher-G cultures were not due to incomplete harvesting or limited PI-PLC transport into the beads. The low harvest of p97 was due to (i) necrosis within the bead of up to 40% dead cells, (ii) lower p97 expression of resting cells, (iii) dilution effects of up to 40% liquid volume associated with settled beads, and (iv) incomplete recovery of p97 from the extracelluar space within the beads. Considering these factors the viable cell specific p97 production of cells growing on Cultispher-GH was actually over $5.2\times10^{-7}$ $\mu$g/cell. The higher concentration of p97 harvested from Cultispher-G was due to reduced necrosis, greater recovery of p97 from within the beads, and a slight reduction in liquid associated with the settled beads. Cells growing on Cytodex-1 had the highest cell specific p97 production and yield of p97 on medium. This was due to there being no necrotic core or p97 trapped within the solid Cytodex-1 beads and to a lower amount of liquid associated with the settled beads. However, the highest harvested p97 concentrations (241 $\mu$g/mL) were recovered from CHO cells growing as spheroids, which had the highest overall settled bead cell density. Although providing the highest harvested p97 concentration, spheroids had a similar total cell specific p97 production to Cultispher-GH due to similar levels of necoris, bead size, and levels of p97 remaining in the bead after harvesting. Furthermore, it took a considerably longer time to establish a stable spheroid culture (35–45 days) compared to a Cytodex-1 culture (15–20 days).

E. Effects of Incubation Time on Harvested p97

Figure 51:
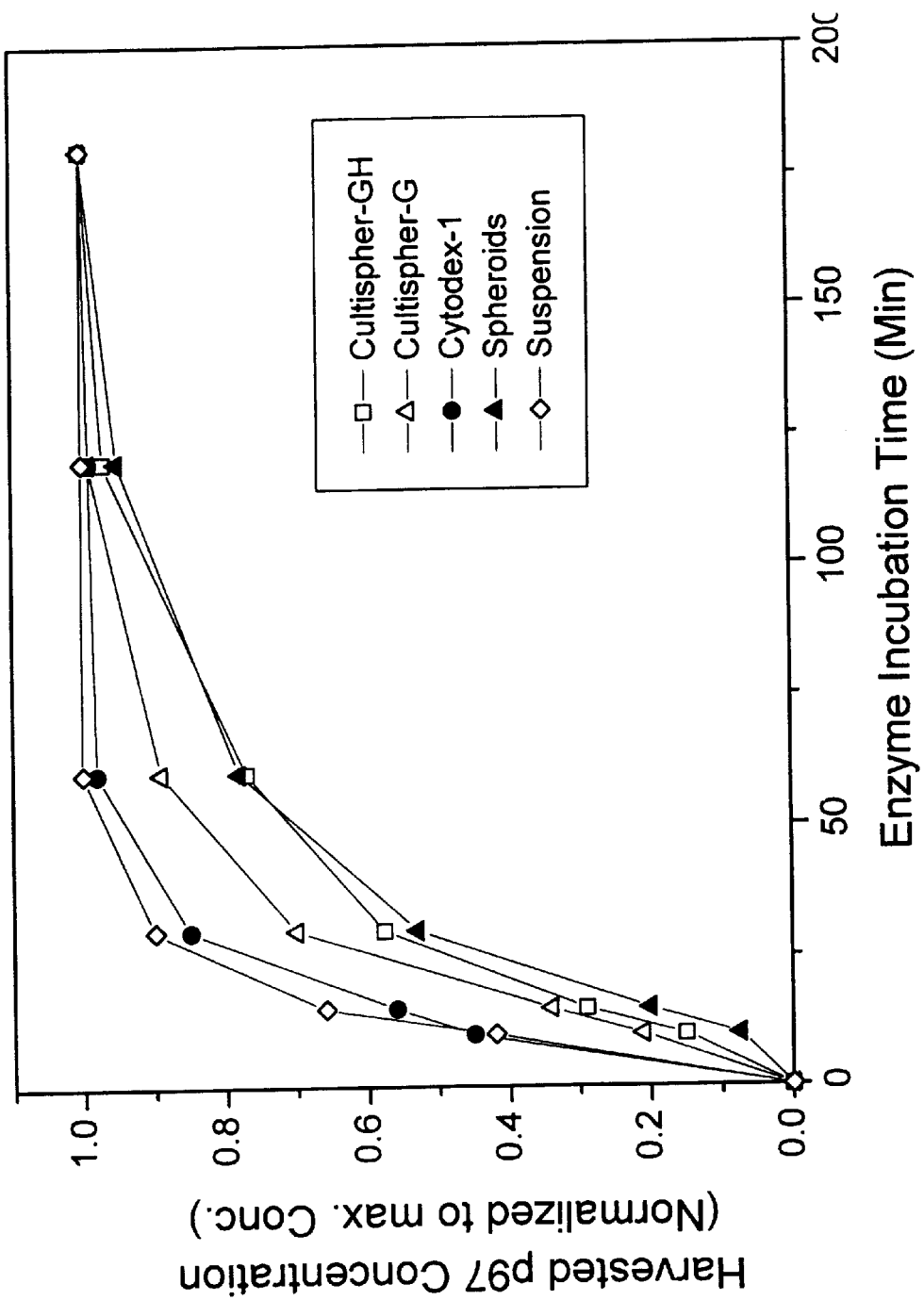
FIG. 51 is a graph showing the effect of enzyme treatment time on harvested p97 from high cell density cultures and compared with harvesting from a suspension CHO cell culture.

FIG. 51 shows harvested p97 concentrations normalized against p97 concentration recovered within 3 h incubation for various bead types and including harvesting from suspension CHO cells. FIG. 51 shows the effect of enzyme treatment time on harvested p97 from high cell density. Concentrations were normalized to the maximum p97 concentration recovered after 3 h incubation. Spheroids and Cultispher-GH had the lowest rate of p97 release, with 90% of p97 released within 100 min. Cytodex-1 release rate were similar to suspension cells (90% release within 35 min) and Cultispher-G release rates were intermediate (90% release within 60 min). The high rate of release from p97 from suspension cells appears to indicate that transport limitations within the Cultispher beads and spheroids resulted in incomplete harvesting or release of p97 after 1 h incubation time. This incomplete harvesting after 1 h could be due to limited access of PI-PLC to the cells and/or time dependent release of p97 from within the beads. At equilibrium, a proportion of harvested p97 remained in the extracelluar space within the porous structure of Cultispher and spheroid beads. This retention of p97 could be minimized by using solid Cytodex-1 beads.

F. Investigation of Incomplete Harvesting from Porous Microcarriers

Figure 52:
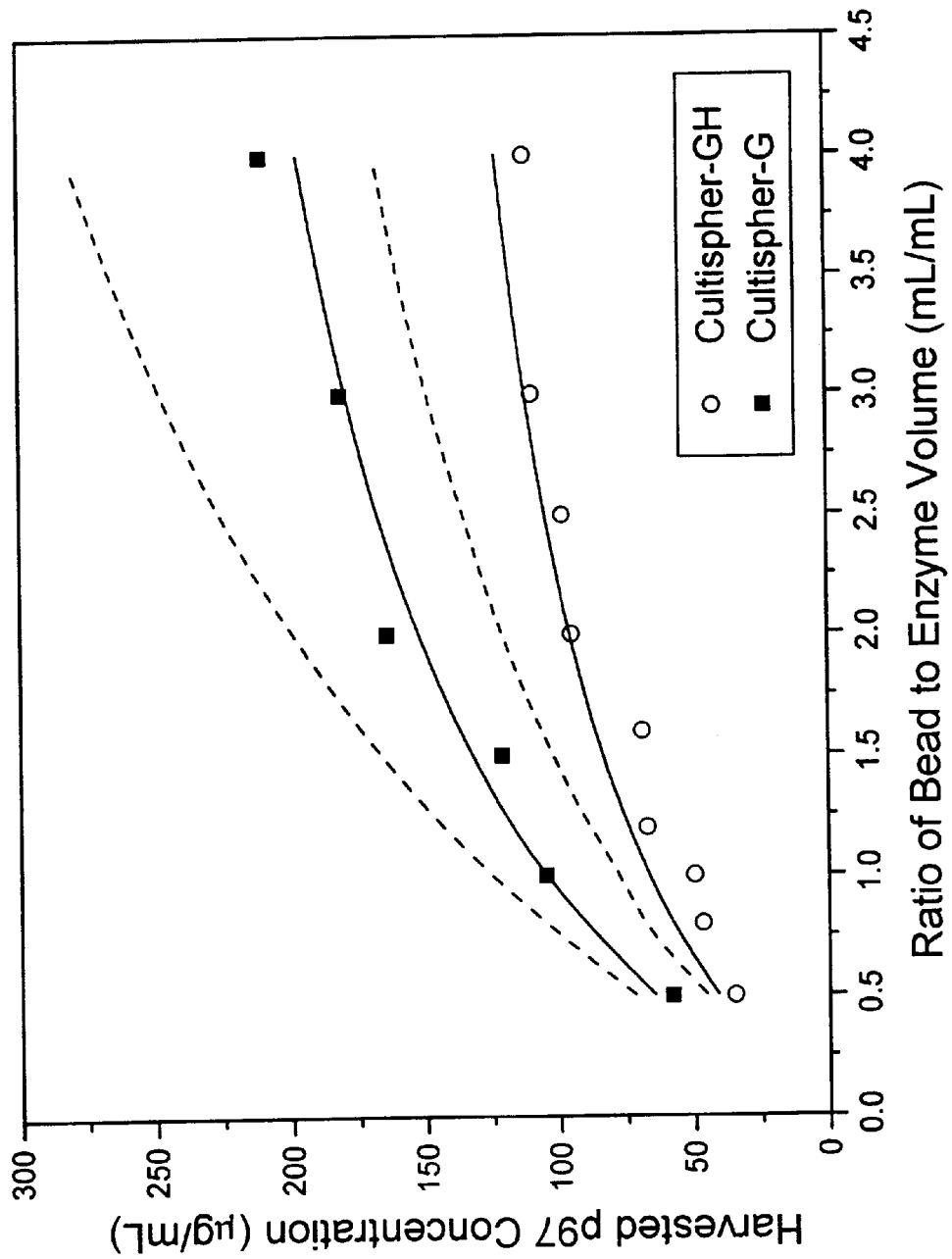
FIG. 52 is graph showing the effect of PI-PLC concentration on harvested p97 concentrations from Cultispher-GH and Cultispher-G cultures.

To determine whether access of PI-PLC to cells within the interior of the bead was limited, 2 mL of beads (Cultispher-GH, Cultispher-G, and Cytodex-1) was harvested and then trypsinized to disperse the cells. The suspended cells were then reharvested for 1 h with 1 mL of 300 mU/mL PI-PLC solution. Trypsinizing the CHO cells did not affect cell associated levels of harvested p97. The p97 released in the second harvest should have been recovered from cells that had not been harvested in the first harvest. Table 9 shows that the second harvest recovered only a small amount of p97 and indicated that the first harvest was nearly complete for all bead types. Thus the low total cell specific p97 production of Cultispher-GH cultures was not due to limited access of PI-PLC and incomplete harvesting of cells. This was further confirmed when the effect of PI-PLC concentration on harvested p97 concentration from Cultispher-GH and Cultispher-G cultures was determined (FIG. 52). The 300 mU/mL of PI-PLC used in the p97 harvesting experiments was shown to be in excess and not limiting since increasing PI-PLC concentrations to over 1000 mU/mL had little effect on harvested p97 concentration.

Untrypsinized 2-mL samples of harvested beads were also subjected to a second 1-h harvest using either 1 mL of 300 mU/mL PI-PLC solution or pure PBS (Table 9). The second harvest recovered a large amount of p97, and there was virtually no difference between using the enzyme solution or pure PBS. This result showed that the p97 recovered in the second harvest was not dependent on the addition of more PI-PLC. The second harvest was probably due to liquid associated with the settled beads and to previously harvested p97 remaining within the bead. Centrifugation Cultispher-GH, Cultispher-G and Cytodex beads at 1000 g for 10 min revealed that settled beads contained at least 40, 35, and 32% volume of liquid per total volume of settled beads, respectively. This associated liquid, mainly from the spaces between the beads, effectively diluted the harvested p97 concentrations. However, simple calculations show that the second harvest was much higher, especially for Cultispher-GH, than could be accounted for by the dilution effects of the liquid associated with the beads. For example, based on the 40% liquid volume between the beads, the predicted second harvest concentration in PBS from Cultispher-GH was approximately 42.5 μg/mL whereas 85.7 μg/mL was recovered. In another experiment, 12–16 μg/mL of p97 was recovered from 2 mL of harvested Cultispher-GH and Cultispher-G beads that had been previously washed for 5 min in 10 mL of PBS. Furthermore, small amounts of p97 could still be recovered from 2 mL of Cultispher-GH beads after three 5-min washes with 10 mL of PBS. This recovered p97 probably came from p97 remaining within the beads after harvesting. It is likely that this p97 was the source of p97 released into the growth medium from beads between harvests (<0.05 μg/mL The lower concentrations of p97 recovered in the second harvest with PBS from Cytodex-1 beads reflected the non-porous structure of the beads and the smaller volume of liquid associated with the settled beads.

G. Effect of Bead-to-Enzyme-Solution Volume Ratio

Figure 53A:
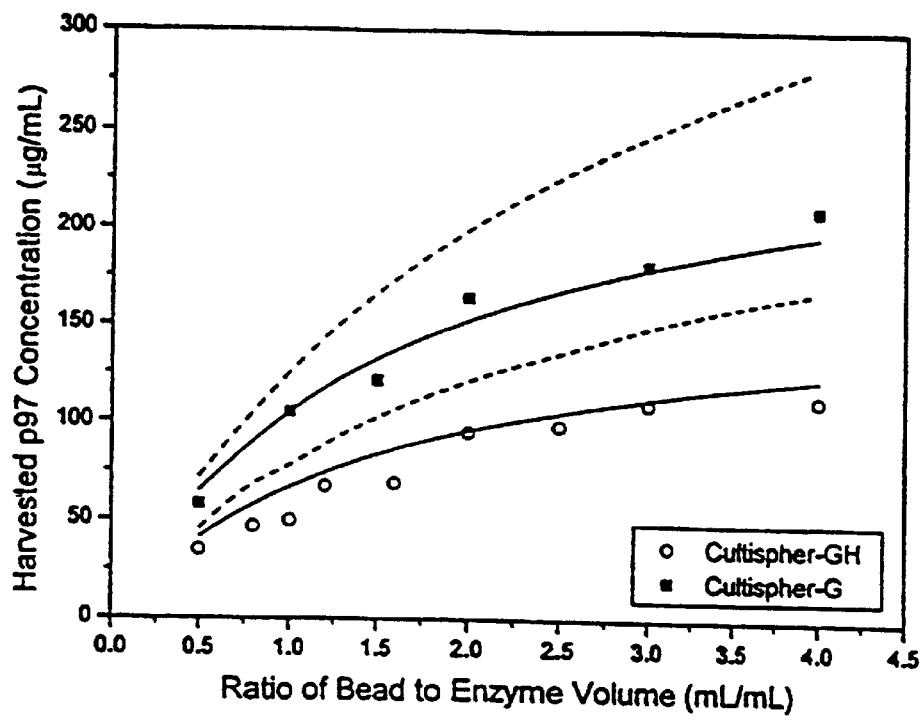
FIG. 53A is a graph showing the effect of the ratio of settled bead-to-enzyme-solution volume ($V_{SB}/V_E$) on harvested p97 from Cultispher-GH and Cultispher-G cultures; harvested p97 concentration (symbols) compared with the predictions of Equation (1) (dashed lines) and Eq. (2) (solid lines).
Figure 53B:
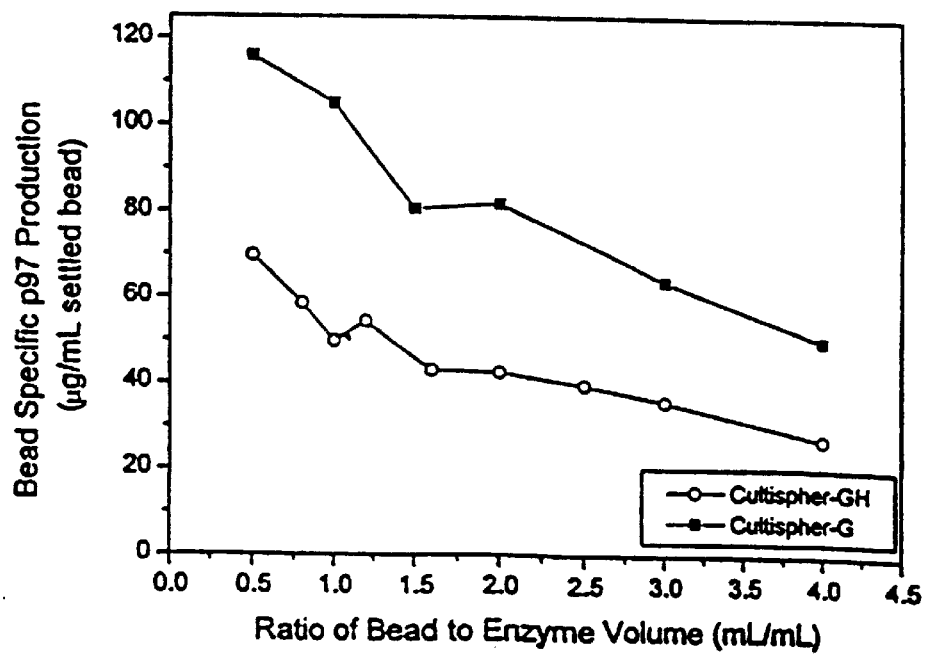
FIG. 53B is a graph showing the effect of the ratio of settled bead-to-enzyme-solution volume ($V_{SB}/V_E$) on harvested p97 from Cultispher-GH and Cultispher-G cultures; bead specific p97 production.

The dilution effect of liquid associated with settled beads was further investigated by varying the ratio of settled bead volume to PI-PLC volume. These experiments were initially motivated by a desire to increase the recovered concentration of p97. FIGS. 53A and 53B show the effect of the ratio of settled bead-to-enzyme-solution volume ($V_{SB}/V_E$) on harvested p97 from Cultispher-GH and Cultispher-G cultures. FIG. 53A shows the harvested p97 concentration (symbols) compared with the predictions of Equation (1) (dashed lines) and Equation (2) (solid lines). FIG. 53B shows the bead specific p97 production.

FIGS. 53A and 53B show that as the settled bead-to-enzyme volume was increased from 0.5 to 4, the harvested p97 concentration steadily increased. The increase was however, not linear and resulted in the bead specific p97 production (FIG. 53B) falling from 69.8 to 25.9 μg/mL of settled beads for Cultispher-GH and from 100 to 50.2 μg/mL of settled beads for Cultispher-G. This drop can be partially accounted for by the dilution effect of the 35–40% volume of liquid associated with settled beads. For example, assume 40% of the settled bead volume is liquid, 2 mL of settled beads in 1 mL of enzyme solution is in fact 1.2 mL of solid beads in 1.8 mL of solution. Since only 1 mL of this solution is recovered by a single harvest, almost 45% of the p97 removed from the cells is not retrieved.

Accounting for this dilution effect, it is then possible to predict the harvested p97 concentration using the following relationship:

$$P = qXv \frac{V_{SB}}{(V_E + \epsilon V_{SB})} \quad (1)$$

where P is harvested p97 concentration (μg/mL), q the viable cell specific p97 production determined from cells in the resting phase ($6.0 \times 10^{-7}$ μg/cell for T-flask cultures, X is the concentration of cells per unit volume of settled beads ($2.8 \times 10^8$ and $6.2 \times 10^8$ cells/mL settled bead for Cultispher-GH and Cultispher-G, respectively), v is the viable cell fraction within the beads (0.65 and 0.88 for Cultispher-GH and Cultispher-G, respectively), $V_{SB}$ is the settled bead volume (mL), $V_E$ is the added enzyme volume (mL), and $\epsilon$ is the liquid fraction of the settled bead volume (0.4 and 0.35 for Cultispher-GH and Cultispher-G, respectively). Although Eq. (1) shows a similar increase in harvested p97 concentration for Cultispher-GH and Cultispher-G (FIG. 53B), it overpredicts the measured concentration. The equation can be improved by including the volume fraction (δ) that accounts for the extracelluar space within the beads between packed cells and in unoccupied pores. Equation (1) then becomes $$P = qXv \frac{V_{SB}}{(V_E + \epsilon V_{SB} + (1-\epsilon)\delta V_{SB})} \quad (2)$$

The volume fraction δ is difficult to measure. However, if we assume a value of 0.4, which is within the range for normal tissue, (Levick, J. R., J. Exp. Physiol. 72:409–438, 1987) then Eq. (2) agrees well with the measured harvested p97 concentrations (FIG. 53B).

Based on this analysis, the concentration of p97 harvested from porous microcarrier cultures will always be diluted by liquid associated with the settled beads and within the beads. Losses could be minimized by decreasing the settled bead-to-enzyme ratios. However, the concentration of the harvested p97 would be reduced. Alternatively the balance of harvested p97 could be recovered with subsequent washes in PBS. Washing 2 mL of harvested Cytodex-1 beads (133.3 μg/mL recovered in 1 mL of PI-PLC solution) twice with 1 mL of PBS for 10 min recovered 56.3 μg/mL for the first wash and 20.1 μg/mL for the second wash. Thus a further 57% of p97 could be recovered by two PBS washes, in effect increasing the total cell specific p97 production from approximately $3.7 \times 10^{-7}$ to $5.8 \times 10^{-7}$ μg/cell.

Increasing the harvested p97 concentration by increasing the ratio of settled bead-to-enzyme solution volume resulted in increased losses of p97 in the liquid associated with the settled beads. It was possible to reduce this loss of p97 by either reducing the bead-to-enzyme solution volume ratio and/or carrying out a second harvest in PBS immediately after the PI-PLC harvest. For example, the beads could first be harvested in PI-PLC for 45 min followed by a 10 min wash in PBS. Two-stage cyclic harvesting of cells cultivated on the small Cultispher-G or Cytodex-1 beads would therefore minimize p97 loss and maximize cell specific protein production.

Example 19
p97 Binding to the Transferrin Receptor

Transferrin and p97 binding to TRVb and TRVb-1 CHO cells was investigated as follows. As described previously, TRVb cells have no human transferrin receptor and TRVb-1 cells have been transformed with the human transferrin receptor.

The following antibodies were used: Ab against human transferrin labelled with FITC; Ab's L235 and HybC against p97 labelled with FITC; and Ab OKT-9 against transferrin receptor not labelled.

Cells were prepared by blocking pandex cellular assay plates with 5% FCS for 2 h. TRVb and TRVb-1 cells, cultured in T-flasks, were resuspended in pandex buffer—DMEM plus 0.1% azide and 1% FCS. Cells were counted, diluted to $1.25 \times 10^6$ cells/mL and split into two sets and one set was acid washed in 5 mL DMEM, 10% FCS+2.6 mL glycine buffer+182 µL NaCl, 1.5 M, pH 4 for 10 min at room temperature. The acid washed cells were resuspended in pandex buffer at $1.25 \times 10^6$ cells/mL. 3×1 mL of each TRVb, TRVb-1, TRVb acid washed and TRVb-1 acid washed cells were placed in 5 mL tubes. The cells were spun and resuspended at $1.25 \times 10^6$ cells/mL in: a) 30 µg/mL transferrin in pandex buffer b) 30 µg/mL p97 in pandex buffer or c) 30 µg/mL transferrin plus 30 µg/mL p97 in pandex buffer and incubated for 45 min at 4° C.

Transferrin and p97 were assayed as follows(Plates 906, 911 and 919). 40 µL of variously treated cells, as described above, were added to each well on blocked pandex plates (approximately 50,000 cells/well). The wells were drained and washed once in PBS containing 1% FCS and 0.1% azide. 40 µL of 1/75 dilution of the anti-transferrin FITC antibody or the anti-p97 FITC antibody (L235 or HybC) was added and cells were incubated for 10 min at room temperature. The cells were drained and washed 3–4× with PBS containing 1% FCS and 0.1% azide and the fluorescence read.

The transferrin receptor was assayed as follows (Plates 911 and 919). 40 µL of variously treated cells, as described above, were added to each well on blocked pandex plates (approximately 50,000 cells/well). 40 µL of 1/75 dilution of the anti-transferrin antibody (OKT9) was added and the cells were incubated for 45 minues at 4° C. The wells were drained and washed once in PBS containing 1% FCS and 0.1% azide. 40 µL of 1/75 dilution of GAM FITC was incubated for 10 min at room temperature. Following draining and washing 3–4× with PBS containing 1% FCS and 0.1% azide the fluorescence was read.

Transferrin and p97 were assayed on plate 922 as above except to Ab's FITC which were previously incubated with GAM FITC in an attempt to increase the signal. Transferrin and p97 were assayed on plate 925 as assays for transferrin receptor i.e. Abs against transferrin and p97 were not labelled with FITC.

Results for plates 906, 911, 919, 922 and 925 are shown in Tables 10, 11, 12, 13 and 14 respectively. Background fluorescence was high for all fluorescinated Abs. Little difference was found between acid washed or non acid washed cells.

Binding of transferrin to cells was detected with Ab against transferrin. The fluorescence of TRVb-1 was always higher than TRVb although some minor non specific binding of transferrin to TRVb was found. The fluoresence apeared to be reduced when p97 was added. For p97 alone there was no difference between TRVb and TRVb1, both showed no or low increase in fluorescence.

Binding of p97 to cells was detected with two Abs against p97. The fluorescence of TRVb-1 was always higher than TRVb although some non specific binding of p97 to TRVb was noted. The fluorescence was reduced when Tf was added. With only transferrin no difference was found between TRVb and TRVb-1, both had no or low increase in fluorescence. Similar results were obtained with L235 and HybC Ab against p97 although the signal for L235 was lower.

The presence of transferrin receptor was detected with Ab OKT-9. The fluorescence of TRVb-1 was always higher than TRVb. However, the fluorescence was low indicating few receptors Adding GAM FITC in order to increase the signal had little effect only a slight increase 15–40%. Possibly the binding of GAM FITC to fluorescinated Abs is weak. Adding GAM FITC to non fluorescinated Abs gave a very poor signal.

The results, which were also repeated using FACS analysis, confirmed that the L235 and HybC antibodies were specific for p97 and that the labelled anti human transferrin and OKT-9 antibodies were specific for transferrin. TRVb-1 cells incubated with p97 bound p97, whereas TRVb cells, lacking in the transferrin receptor, were found not to bind p97. When TRVb-1 cells were incubated with p97 and transferrin, p97 appeared to compete for binding with transferrin, providing further evidence that p97 is in fact binding to the transferrin receptor.

Figure 54:
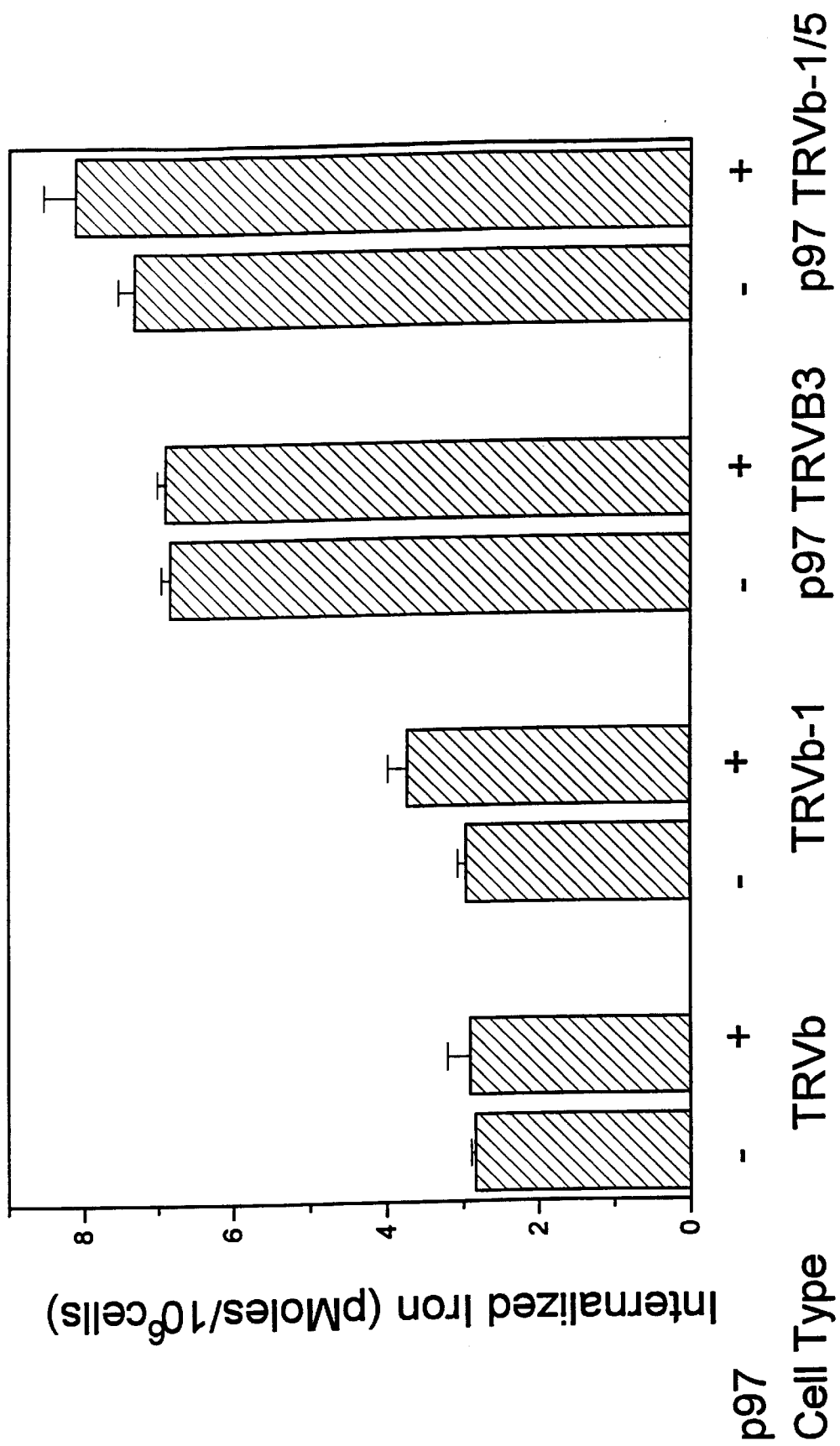
FIG. 54 is a graph showing the effect of the addition of p97 on the internalization of iron.

For further confirmation of the binding of p97 to the transferrin receptor, TRVb, TRVB-1, p97TRb and p97TRVB-1 cells were pre-incubated with p97 and p97 was added with $Fe^{59}$. The results are shown in FIG. 54. Cells with the transferrin receptor were found to have increased iron uptake.

Example 20
P97 Antibody Binding to Mouse Brain Capillaries

The localization of soluble p97 antibodies injected into mice was investigated as follows. Mice were injected in the tail vein with a solution of purified rabbit antiserum for soluble human p97 (0.5 ml of 4 mg/ml). The mice were sacrificed and tissue from the brain, heart, lung, kidney, liver, spleen and skin was fixed in 4% paraformaldehyde in 0.1 M phosphate buffer pH 7.4 and stored in 15% sucrose in 0.01 M phosphate buffered saline at −80° C. 15–30 micron sections were prepared and incubated with an anti-rabbit antibody-peroxidase conjugate. The peroxidase label was visualised with the purple reaction product of diaminobenzidine and nickel ammonium sulphate. Control samples from mice which had not been injected, or which had been injected with normal rabbit serum were similarly prepared.

Mice injected in the tail vein with p97 antibodies showed clear staining on the brain capillary walls and in patches of brain tissue. The concentration of staining in the brain capillaries, capillary walls and within brain tissue indicated that the p97 antibodies had been transported across the blood brain barrier and provided further confirmation of the role of p97 in transport across the blood brain barrier. The localization of staining in the brain endothelium was similar to the localization of p97 determined by α p97 staining described in Example 10 herein. Some stained cells were also noted in the blood vessels of control mice.

From the foregoing, it will be appreciated that, although specific embodiments of the invention have been described herein for purposes of illustration, various modifications may be made without deviating from the spirit and scope of the invention. Accordingly, the invention is not limited except as by the appended.

TABLE 1

FACS RESULTS

| SAMPLE | FLUORESCENCE - converted linear value |
|---|---|
| SK.MEL.28 − NFA | 0.00 |
| SK.MEL.28 − + anti-p97 | 127.92 |
| SK.MEL.28 − + PI-PLC + anti-p97 | 4.52 |
| uninfected Sf9 − NFA | 0.00 |
| uninfected Sf9 − + anti-p97 | 0.70 |
| uninfected Sf9 − + PI-PLC + anti-p97 | 0.96 |
| AcMNPC (WT) − NFA | 0.00 |
| AcMNPC (WT) − + anti-p97 | −0.06 |
| AcMNPC (WT) − + PI-PLC + anti-p97 | −0.06 |
| p97 B-1-1 − NFA | 0.00 |
| p97 B-1-1 − + anti-p97 | 111.66 |
| p97 B-1-1 − + PI-PLC + anti-p97 | 5.74 |
| p97 B-2-1 − NFA | 0.00 |
| p97 B-2-1 − + anti-p97 | 97.38 |
| p97 B-2-1 − + PI-PLC + anti-p97 | 6.85 |

TABLE 2

| Antigen | Cells | Treatment | Fluorescene Intensity (% of Control) |
|---|---|---|---|
| p97 | SK-MEL 28 | PI-PLC | 10.8 ± 2.6 |
| P97 | SK-MEL 28 | Pronase | 82.6 ± 17.7 |
| TR | SK-MEL 28 | PI-PLC | 120.5 ± 16.2 |

TABLE 2-continued

| Antigen | Cells | Treatment | Fluorescene Intensity (% of Control) |
|---|---|---|---|
| TR | SK-MEL 28 | Pronase | 15.9 ± 10.8 |
| Thy-1 | EL-4 | PI-PLC | 32.5 ± 6.4 |
| Thy-1 | EL-4 | Pronase | 136.4 ± 20.2 |
| TR | EL-4 | PI-PLC | 93.1 ± 9.4 |
| TR | EL-4 | Pronase | 1.9 ± 1.0 |
| p97 | p97aWTBc3 | PI-PLC | 6.8 ± 4.0 |
| p97 | p97aWTBc7 | PI-PLC | 7.5 ± 5.1 |

TABLE 3

| Method | Cell Density ($10^6$/mL) | p97 (µg/mL) | Total Protein (µg/mL) | P97 as % of Total Protein |
|---|---|---|---|---|
| Release into serum media - adherent | 2.0 | 1.2 | 5400 | 0.02 |
| Release into serum-free medium-suspension | 6.0 | 3.0 | 380 | 0.8 |
| Cyclic harvest of suspension cells | 100 | 30 | 100 | 30 |

TABLE 4

Test on Alzheimer serum-Patients ans Spouses 3 × wash DATE 07-24-1995 PLATE NO. 231

Fluorescence readings

|   | 1 | 2 | 3 | 4 | 5 | 6 | 7 | 8 | 9 | 10 | 11 | 12 |
|---|---|---|---|---|---|---|---|---|---|---|---|---|
| A | 15296 | 15934 | 522 | 554 | 0 | 450 | 486 | 550 | 15426 | 15356 | 18694 | 0 |
| B | 7250 | 7550 | 488 | 410 | 0 | 660 | 598 | 678 | 734 | 678 | 680 | 0 |
| C | 6388 | 5366 | 130 | 274 | 0 | 280 | 0 | 282 | 1064 | 1338 | 1182 | 0 |
| D | 3870 | 3740 | 16 | 32 | 0 | 2084 | 2264 | 1904 | 180 | 378 | 294 | 0 |
| E | 3550 | 2764 | 0 | 0 | 0 | 640 | 600 | 438 | 2832 | 3090 | 2886 | 0 |
| F | 1690 | 1589 | 1214 | 1304 | 1210 | 0 | 0 | 0 | 20 | 167 | 198 | 0 |
| G | 782 | 714 | 318 | 326 | 200 | 894 | 726 | 746 | 0 | 0 | 0 | 0 |
| H | 656 | 689 | 13604 | 13476 | 13792 | 578 | 526 | 754 | 0 | 0 | 0 | 0 |

Plate mask (S-standards, U-unknowns)

|   | 1 | 2 | 3 | 4 | 5 | 6 | 7 | 8 | 9 | 10 | 11 | 12 |
|---|---|---|---|---|---|---|---|---|---|---|---|---|
| A |  |  | s6 | s6 |  | ud1 | ud1 | ud1 | uc2 | uc2 | uc2 |  |
| B |  |  | s7 | s7 |  | ue1 | ue1 | ue1 | ud2 | ud2 | ud2 |  |
| C |  |  | s8 | s8 |  | uf1 | uf1 | uf1 | ue2 | ue2 | ue2 |  |
| D | s1 | s1 | s9 | s9 |  | ug1 | ug1 | ug1 | uf2 | uf2 | uf2 |  |
| E | s2 | s2 |  |  |  | uh1 | uh1 | uh1 | ug2 | ug2 | ug2 |  |
| F | s3 | s3 | ua1 | ua1 | ua1 |  |  |  | uh2 | uh2 | uh2 |  |
| G | s4 | s4 | ub1 | ub1 | ub1 | ua2 | ua2 | ua2 |  |  |  |  |
| H | s5 | s5 | uc1 | uc1 | uc1 | ub2 | ub2 | ub2 |  |  |  |  |

Calculation of the calibration curve

| REGRESSION DATA | | | | | WEIGHT MODEL | | off | |
|---|---|---|---|---|---|---|---|---|
| CONC | CODE | FLUOR | STD | % CV | REGRESSION RESULTS SUMMARY | | | |
| 90 | s1 | 3805 | 65 | 1.7083 | PWR | 1 | COUNT | 9 |
| 60 | s2 | 3157 | 393 | 12.449 | SLOPE | 45.835 | Xw | 5.09436 |
| 30 | s3 | 1639.5 | 50.5 | 3.0802 | INTER | 59.6656 | Yw | 293.165 |

TABLE 4-continued

Test on Alzheimer serum-Patients ans Spouses 3 × wash DATE 07-24-1995 PLATE NO. 231

| 15 | s4 | 748 | 34 | 4.5455 | Sxow | 1.72061 | Yo | 293.165 |
|---|---|---|---|---|---|---|---|---|
| 12 | s5 | 672.5 | 16.5 | 2.4535 | Syxw | 74.8169 | E_Xo | 5.09436 |
| 9 | s6 | 538 | 16 | 2.974 | R_SQR | 0.9929 | E_Cl | 3.66489 |
| 6 | s7 | 449 | 39 | 8.686 | | | | |
| 3 | s8 | 202 | 72 | 35.644 | | | | |
| 0 | s9 | 24 | 8 | 33.333 | | | | |

Determination of the concentration of p97 in the samples

| OVL | AVRG | STDEV | % CV | DLFT | CONC | 90% Cl | STD | % CV | RNG |
|---|---|---|---|---|---|---|---|---|---|
| ua1 | 1242.7 | 43.4 | 3.4925 | 1 | 25.81 | 4.3469 | 2.0408 | 7.9071 | OK |
| ua2 | 788.67 | 74.928 | 9.5006 | 1 | 15.905 | 3.8626 | 1.8134 | 11.402 | OK |
| ub1 | 281.33 | 57.604 | 20.475 | 1 | 4.8362 | 3.665 | 1.7207 | 35.579 | OK |
| ub2 | 619.33 | 97.561 | 15.753 | 1 | 12.21 | 3.7518 | 1.7614 | 14.425 | OK |
| uc1 | 13624 | 129.78 | 0.9526 | 1 | 295.94 | 33.024 | 15.504 | 5.239 | BAD |
| uc2 | 16492 | 1557.3 | 9.4428 | 1 | 358.51 | 40.049 | 18.602 | 5.2445 | BAD |
| ud1 | 495.33 | 41.355 | 8.3489 | 1 | 9.5051 | 3.6985 | 1.7364 | 18.268 | OK |
| ud2 | 697.33 | 25.94 | 3.7199 | 1 | 13.912 | 3.7976 | 1.7829 | 12.815 | OK |
| ue1 | 645.33 | 34.267 | 5.31 | 1 | 12.778 | 3.7661 | 1.7681 | 13.837 | OK |
| ue2 | 1194 | 111.37 | 9.3272 | 1 | 24.748 | 4.2837 | 2.0111 | 8.1264 | OK |
| uf1 | 187.33 | 132.47 | 70.712 | 1 | 2.7854 | 3.6741 | 1.7249 | 61.929 | OK |
| uf2 | 284 | 81.142 | 28.571 | 1 | 4.8944 | 3.665 | 1.7206 | 35.155 | OK |
| ug1 | 2084 | 146.97 | 7.0523 | 1 | 44.166 | 5.7333 | 2.6917 | 6.0945 | OK |
| ug2 | 2938 | 111.1 | 3.7842 | 1 | 62.754 | 7.4677 | 3.506 | 5.5868 | OK |
| uh1 | 559.33 | 87.336 | 15.614 | 1 | 10.901 | 3.723 | 1.7479 | 16.034 | OK |
| uh2 | 128.33 | 77.642 | 60.5 | 1 | 1.4982 | 3.6873 | 1.7311 | 115.55 | OK |

TABLE 5

Blood serum tests for p97 concentration from Ad patients and normal controls AD Subjects:

| Subject | M/F | Date | Age (yr) | Duration (yr) | p97 conc (ng/mL) |
|---|---|---|---|---|---|
| 1 | F | 4/11/94 | 51 | 2 | 42.7 |
| 1 | F | 7/11/94 | 51 | 2 | 40.66 |
| 1 | F | 10/11/94 | 51 | 2 | 38.5 |
| 2 | F | 10/11/94 | 68 | 2 | 41.25 |
| 3 | F | 30/11/94 | 75 | 5 | 38.7 |
| 2 | F | 30/11/94 | 68 | 2 | 34.7 |
| 4 | F | 30/11/94 | 82 | 11 | 60.4 |
| 5 | F | 30/11/94 | 82.5 | 4.5 | 38.2 |
| 6 | M | 30/11/94 | 64 | 1.5 | 31 |
| 7 | F | 30/11/94 | 73.5 | 5.5 | 37.7 |
| 8 | F | 30/11/94 | 81 | 7.0 | 52 |
| 5 | F | 15/4/94 | 82 | 4 | 87.1 |
| 6 | M | 20/4/94 | 63.5 | 1 | 47.2 |
| 9 | M | 27/4/94 | 74 | 3 | 41 |
| 10 | M | 18/3/94 | 59 | 9 | 50.8 |
| 11 | M | 8/6/94 | 77 | 7 | 69.6 |
| 8 | F | 15/7/94 | 80.5 | 6.5 | 56.4 |
| 12 | F | 29/7/94 | 55 | 4 | 45.6 |
| 13 | M | 4/5/94 | 59 | 5 | 40.6 |
| 13 | M | 21/9/94 | 59.5 | 5.5 | 42 |

TABLE 6

Samples tested 21 and 24/7/95 - patients and spouse controls

| | | | Age | Duration | P97 Concentration (ng/mL) | |
|---|---|---|---|---|---|---|
| Subject | M/F | Date | (yr) | (yr) | Blood | Serum |
| 1 | M | 21/7 | 75 | 2 | 28 | 24 |
| 1-spouse | F | 21/7 | 75 | — | 3 | 2 |
| 2 | M | 21/7 | 86 | 1 | 321 | 145 |
| 2-spouse | F | 21/7 | 76 | — | 3 | 4 |
| 3 | F | 21/7 | 72 | 4 | 25 | 22 |
| 3-spouse | M | 21/7 | 73 | — | 1 | 1 |
| 4 | M | 21/7 | 80 | 9 | 43 | 50 |
| 4-spouse | F | 21/7 | 68 | — | 7 | 3 |
| 1 | M | 24/7 | 75 | 2 | 26 | 20 |
| 1-spouse | F | 24/7 | 75 | — | 3 | 9 |
| 2 | M | 24/7 | 86 | 1 | 365 | 374 |
| 2-spouse | F | 24/7 | 76 | — | 9.5 | 12 |
| 3 | F | 24/7 | 72 | 4 | 28.3 | 27 |
| 3-spouse | M | 24/7 | 73 | — | 2 | 3 |
| 4 | M | 24/7 | 80 | 9 | 52.3 | 76 |
| 4-spouse | F | 24/7 | 68 | — | 9.4 | 12 |

Unrelated Control Subjects

| Subject | Age (yr) | p97 Concentration (ng/mL) |
|---|---|---|
| 1 | 31 | 9.2 |
| 2 | 28 | 10 |
| 3 | 36 | 10.5 |
| 4 | 38 | 11.8 |
| 5 | 40 | 7.3 |
| 6 | 41 | 5.3 |
| 7 | 42 | 1.2 |
| 8 | 51 | 12 |
| 9 | 53 | 2.4 |
| 10 | 63 | 8.9 |
| 11 | 70 | 7.8 |

TABLE 7

Cerebral Spinal Fluid (CSF) and Blood Serum Samples from Japanese subjects Tested for Transferrin (Tf) and p97

CSF

| Alzheimer Subject | Tf conc. ($\mu$g/mL) | p97 Conc. (ng/mL) |
|---|---|---|
| 1 | 13.63 | — |
| 2 | 23.34 | — |
| 3 | 28.21 | 14.2 |

TABLE 7-continued

Cerebral Spinal Fluid (CSF) and Blood Serum Samples from Japanese subjects Tested for Transferrin (Tf) and p97

| | | |
|---|---|---|
| 27 | 15.8 | — |
| 30 | 25.6 | 40.4 |
| 38 | 21.3 | 20.5 |
| 67 | 16.9 | 18.6 |
| 79 | 18 | 18.5 |
| Control | | |
| 4 | 18.0 | 11 |
| 5 | 12.4 | 11 |
| 6 | 9.9 | — |
| 7 | 12.2 | 10 |
| 8 | 23.4 | 0.5 |
| 9 | 13.9 | 9.9 |

SERUM

| Alzheimer Subject | Tf Conc. (mg/mL) | p97 Conc. (ng/mL) |
|---|---|---|
| 1 | 2.19 | 8.8 |
| 3 | 2.62 | 8.2 |
| 27 | 1.68 | — |
| 30 | 2.48 | 14.0 |
| Control | | |
| 4 | 3.4 | 0.1 |
| 5 | 2.06 | 0.8 |
| 6 | 1.25 | 2.0 |
| 7 | 2.12 | 2.1 |
| 10 | 1.95 | 5.6 |

TABLE 8

Comparison of p97 harvesting from Cultispher, Cytodex, and spheroid cultures.

| Bead type | Bead Size ($\mu$m) | Harvested p97 ($\mu$g/mL) | Total cells/mL settled bead ($10^8$) | Cell viability (%) | Cell specific p97 recovered per total cells ($10^{-7}$ $\mu$g/cell) | Cell specific p97 recovered per viable cells ($10^{-7}$ $\mu$g/cell) |
|---|---|---|---|---|---|---|
| Cultispher-GH | 460 ± 40 | 99 ± 5.2 | 2.8 ± 0.2 | 65 | 1.77 ± 0.22 | 2.72 ± 0.34 |
| Cultispher-G | 274 ± 28 | 167 ± 6.8 | 3.2 ± 0.2 | 88 | 2.60 ± 0.27 | 2.97 ± 0.31 |
| Cytodex-1 | 228 ± 18 | 122 ± 2.7 | 1.8 ± 0.1 | 96 | 3.39 ± 0.26 | 3.53 ± 0.27 |
| Spheroid | 482 ± 220 | 241 ± 34 | 6.2 ± 0.5 | 68 | 1.94 ± 0.43 | 2.85 ± 0.61 |

Note: Beads harvested every 48 h and results averaged over a 12-day period.

TABLE 9

Effect of carrying out a second p97 harvest on PI-PLC treated Cultispher-GH, Cultispher-G, and Cytodex-1 cultures.

| Second harvest method | Bead type | First p97 harvest ($\mu$g/mL) | Second p97 harvest ($\mu$g/mL) |
|---|---|---|---|
| Harvested beads trypsinized and incubated in PI-PLC | Cultispher-GH | 94.3 | 3.9 |
| | Cultispher-G | 171 | 9.6 |
| | Cytodex-1 | 134 | 1.6 |
| Repeat incubation of harvested beads in PI-PLC | Cultispher-GH | 98.2 | 85.7 |
| | Cultispher-G | 148 | 69.4 |
| | Cytodex-1 | 128 | 48.3 |
| Incubation of harvested beads in PBS | Cultispher-GH | 95.6 | 80.4 |
| | Cultispher-G | 139 | 69.7 |
| | Cytodex-1 | 136 | 52.2 |

TABLE 10

Test of transferrin (Tf) and P97 binding to TRVb and TRVb-1 cells 25/3
Plate 906 Gain 100 4× Wash

| | Ab-Tf | Less control (TRVb) | Ab-p97 | Less Control (TRVb) |
|---|---|---|---|---|
| Untreated Cells | | | | |
| TRVb | 31501 | | 25710 | |
| ThVb-1 | 32704 | | 22410 | |
| ThVb + Tf | 36758 | 5257 | 25912 | 202 |
| TRVb-1 + Tf | 40144 | 8643 | 23534 | 0 |
| TRVb + p97 | 26268 | 0 | 25724 | 14 |
| TRVb-1 + p97 | 32298 | 797 | 28948 | 3238 |
| TRVb + Tf + p97 | 35468 | 3967 | 18105 | 0 |
| TRVb-1 + Tf + p97 | 37600 | 6099 | 20618 | 0 |
| Acid washed cells | | | | |
| TRVb | 33229 | | 24670 | |
| TRVb-1 | 30431 | | 21561 | |
| ThVb + Tf | 39500 | 6271 | 20723 | 0 |
| TRVb-1 + Tf | 44458 | 11229 | 22721 | 0 |
| TRVb + p97 | 33868 | 639 | 26492 | 1822 |
| TRVb-1 + p97 | 33980 | 751 | 32085 | 7451 |
| TRVb + Tf + p97 | 38404 | 5175 | 26547 | 1787 |
| TRVb-1 + Tf + p97 | 40664 | 7435 | 28144 | 3474 |
| TRVb no Ab | 1304 | TRVb acid washed no Ab | | 1404 |
| TRVb-1 no Ab | 789 | TRVb-1 acid washed no Ab | | 1009 |
| Ab-Tf only | 31625 | | | |
| Ab-p97 only | 12306 | | | |

TABLE 11

Test of transferrin (Tf) and P97 binding to TRVb and TRVb-1 cells 25/3
Plate 911 Gain 25 3× Wash

| | Ab-Tf | Less control (TRVb) | Ab-p9 | Less Control (TRVb) |
|---|---|---|---|---|
| Untreated Cells | | | | |
| TRVb | 10985 | | 8500 | |
| TRVb-1 | 19310 | | 8254 | |
| TRVb + Tf | 15834 | 4849 | 7016 | 0 |
| TRVb-1 + Tf | 23178 | 12193 | 7718 | 0 |
| TRVb + p97 | 13560 | 2575 | 6828 | 0 |
| TRVb-1 + p97 | 14560 | 3575 | 10648 | 2148 |
| TRVb + Tf + p97 | 16546 | 5471 | 8586 | 86 |
| TRVb-1 + Tf + p97 | 22592 | 11607 | 10054 | 1554 |

TABLE 11-continued

Test of transferrin (Tf) and P97 binding to TRVb and TRVb-1 cells 25/3
Plate 911 Gain 25 3× Wash

|  | Ab-Tf | Less control (TRVb) | Ab-p97 | Less Control (TRVb) |
|---|---|---|---|---|
| Acid washed cells | | | | |
| TRVb | 13450 | | 8698 | |
| TRVb-1 | 16270 | | 9639 | |
| TRVb + Tf | 18328 | 4888 | 7548 | 0 |
| TRVb-1 + Tf | 26534 | 13084 | 7518 | 0 |
| TRVb + p97 | 13758 | 308 | 8490 | 0 |
| TRVb-1 + p97 | 15058 | 1608 | 12560 | 3862 |
| TRVb + Tf + p97 | 16878 | 3428 | 9550 | 852 |
| TRVb-1 + Tf + p97 | 18718 | 5268 | 9928 | 1230 |

TABLE 11-continued

Test of transferrin (Tf) and P97 binding to TRVb and TRVb-1 cells 25/3
Plate 911 Gain 25 3× Wash

| TRVb no Ab | 664 | TRVb acid washed no Ab | 459 |
|---|---|---|---|
| TRVb-1 no Ab | 510 | TRVb-1 acid washed no Ab | 567 |
| Ab-Tf only | 9810 | | |
| Ab-p97 only | 4102 | | |

|  | no Ab | Ab-OKT-9 | Less control |
|---|---|---|---|
| Ab against Transferrin receptor (OKT-9) | | | |
| TRVb | 1508 | 2193 | 685 |
| TRVb-1 | 2097 | 4755 | 3247 |
| TRVb acid washed | 1658 | 2588 | 930 |
| TRVb-1 acid washed | 2076 | 7135 | 5059 |

TABLE 12

Test of transferrin (Tf) and p97 binding to TRVb and TRVb-1 cells 30/3
Plate 919   Gain 100   4 × Wash

Untreated cells

|  | Ab-Tf | Less control (TRVb) | Ab - p9 Hybc | Less Control (TRVb) | L235 | Less Control (TRVb) |
|---|---|---|---|---|---|---|
| TRVb | 34655 | | 9878 | | 5580 | |
| TRVb-1 | 27034 | | 10080 | | 5000 | |
| TRVb + Tf | 39502 | 4847 | 9130 | 0 | 4475 | 0 |
| TRVb-1 + Tf | 54844 | 20189 | 8988 | 0 | 5331 | 0 |
| TRVb + p97 | 32603 | 0 | 10546 | 668 | 6212 | 632 |
| TRVb-1 + p97 | 34644 | 0 | 11510 | 1632 | 6540 | 960 |
| TRVb + Tf + p97 | 36625 | 1970 | 8218 | 0 | 5368 | 0 |
| TRVb-1 + Tf + p97 | 51410 | 16755 | 10130 | 252 | 5159 | 0 |

Acid washed cells

|  | Ab-Tf | Less control (TRVb) | Ab - p97 HybC | Less Control (TRVb) | L235 | Less Control (TRVb) |
|---|---|---|---|---|---|---|
| TRVb | 32284 | | 8266 | | 4200 | |
| TRVb-1 | 32853 | | 9278 | | 3526 | |
| TRVb + Tf | 40342 | 8058 | 8574 | 308 | 3690 | 0 |
| TRVb-1 + Tf | 57774 | 25490 | 9686 | 1420 | 5322 | 1122 |
| TRVb + p97 | 29074 | 0 | 8770 | 504 | 4786 | 586 |
| TRVb-1 + p97 | 29589 | 0 | 12216 | 3950 | 6768 | 2568 |
| TRVb + Tf + p97 | 36065 | 3781 | 9276 | 1010 | 4345 | 145 |
| TRVb-1 + Tf + p97 | 45255 | 12971 | 10866 | 2600 | 5924 | 1724 |

| TRVb no Ab | 207 | TRVb acid washed no Ab | 0 |
|---|---|---|---|
| TRVb-1 no Ab | 262 | TRVb-1 acid washed no Ab | 0 |
| Ab-Tf only | 18726 | | |
| Ab-p97 (HybC) only | 5495 | | |
| Ab-p97 (L235) only | 3661 | | |

Ab against Transferrin receptor (OKT-9)

|  | No first Ab | Ab-TR + GAM FITC | Less control |
|---|---|---|---|
| TRVb | 2122 | 5301 | 3179 |
| TRVb-1 | 2048 | 13586 | 11538 |
| TRVb acid washed | 2340 | 7166 | 4826 |
| TRVb-1 acid washed | 2037 | 12472 | 10435 |

TABLE 13

Test of transferrin (Tf) and p97 binding to TRVb and TRVb-1 cells 30/3
Ab-Tf and Ab-p97 FITC initially incubated with GAM FITC
Plate 922   Galn 100   4 × Wash

Untreated cells

|  | Ab-Tf | Less control (TRVb) | Ab - p9 Hybc | Less Control (TRVb) | L235 | Less Control (TRVb) |
|---|---|---|---|---|---|---|
| TRVb | 40540 |  | 15442 |  | 9842 |  |
| TRVb-1 | 32309 |  | 15336 |  | 7140 |  |
| TRVb + Tf | 41334 | 794 | 14286 | 0 | 7568 | 0 |
| TRVb-1 + Tf | 56182 | 15642 | 14396 | 0 | 7443 | 0 |
| TRVb + p97 | 33240 | 0 | 18638 | 3196 | 10432 | 590 |
| TRVb-1 + p97 | 37414 | 0 | 21246 | 5804 | 12968 | 3126 |
| TRVb + Tf + p97 | 36260 | 0 | 15407 | 0 | 8154 | 0 |
| TRVb-1 + Tf + p97 | 51079 | 10539 | 16787 | 1345 | 8896 | 0 |

Acid washed cells

|  | Ab-Tf | Less control (TRVb) | Ab - p97 HybC | Less Control (TRVb) | L235 | Less Control (TRVb) |
|---|---|---|---|---|---|---|
| TRVb | 31356 |  | 13898 |  | 6115 |  |
| TRVb-1 | 27721 |  | 14286 |  | 7935 |  |
| TRVb + Tf | 36272 | 4916 | 12250 | 0 | 4696 | 0 |
| TRVb-1 + Tf | 64802 | 33446 | 16868 | 2582 | 6222 | 107 |
| TRVb + p97 | 28887 | 0 | 15166 | 880 | 7322 | 1207 |
| TRVb-1 + p97 | 31725 | 369 | 16556 | 2280 | 11646 | 5531 |
| TRVb + Tf + p97 | 35019 | 3663 | 13948 | 0 | 7064 | 949 |
| TRVb-1 + Tf + p97 | 42881 | 11525 | 16006 | 1720 | 8182 | 2067 |

| TRVb no Ab | 450 | TRVb acid washed no Ab | 459 |
|---|---|---|---|
| TRVb-1 no Ab | 360 | TRVb-1 acid washed no Ab | 201 |
| Ab-Tf only | 20945 |  |  |
| Ab-p97 (HybC) only | 8973 |  |  |
| Ab-p97 (L235) only | 4780 |  |  |
| GAM FITC | 2122 |  |  |

TABLE 14

Test of transferrin (Tf) and p97 binding to TRVb and TRVb-1 cells 30/3
Ab-Tf and Ab-p97 first followed by GAM FITC
Plate 925   Galn 100   4 × Wash

Untreated cells

|  | Ab-Tf | Less control (TRVb) | Ab - p9 Hybc | Less Control (TRVb) | L235 | Less Control (TRVb) |
|---|---|---|---|---|---|---|
| TRVb | 1570 |  | 1865 |  | 2278 |  |
| TRVb-1 | 626 |  | 2158 |  | 2772 |  |
| TRVb + Tf | 2038 | 468 | 1013 | 0 | 3132 | 854 |
| TRVb-1 + Tf | 1747 | 177 | 2024 | 159 | 2515 | 237 |
| TRVb + p97 | 1554 | 0 | 2115 | 250 | 1955 | 0 |
| TRVb-1 + p97 | 1595 | 25 | 2455 | 590 | 3250 | 972 |
| TRVb + Tf + p97 | 1867 | 297 | 1966 | 101 | 1966 | 0 |
| TRVb-1 + Tf + p97 | 1552 | 0 | 2322 | 457 | 3792 | 1514 |

Acid washed cells

|  | Ab-Tf | Less control (TRVb) | Ab - p97 HybC | Less Control (TRVb) | L235 | Less Control (TRVb) |
|---|---|---|---|---|---|---|
| TRVb | 924 |  | 1142 |  | 2201 |  |
| TRVb-1 | 910 |  | 1140 |  | 3132 |  |
| TRVb + Tf | 2138 | 1214 | 1963 | 821 | 2590 | 634 |
| TRVb-1 + Tf | 2662 | 1738 | 2192 | 1050 | 2714 | 758 |
| TRVb + p97 | 1086 | 25 | 2194 | 1052 | 2005 | 49 |
| TRVb-1 + p97 | 1324 | 162 | 3900 | 2758 | 2100 | 144 |
| TRVb + Tf + p97 | 1654 | 730 | 2212 | 1070 | 3286 | 1330 |
| TRVb-1 + Tf + p97 | 2015 | 1091 | 2938 | 1796 | 3928 | 1972 |

| TRVb no Ab | 200 | TRVb acid washed no Ab | 230 |
|---|---|---|---|
| TRVb-1 no Ab | 198 | TRVb-1 acid washed no Ab | 256 |
| Ab-Tf only | 1008 |  |  |

TABLE 14-continued

Test of transferrin (Tf) and p97 binding to TRVb and TRVb-1 cells 30/3
Ab-Tf and Ab-p97 first followed by GAM FITC
Plate 925   Galn 100   4 × Wash

| | |
|---|---|
| Ab-p97 (HybC) only | 986 |
| Ab-p97 (L235) only | 450 |
| GAM FITC | 2122 |

We claim:

1. A method for delivering an agent across the blood brain barrier comprising administering a composition which comprises soluble melanotransferrin conjugated to the agent.

2. A method according to claim 1 wherein the agent is a therapeutic agent.

3. A method according to claim 2 wherein the therapeutic agent is selected from the group consisting of an iron sequestering compound, an anti-inflammatory drug, a growth factor and a lymphokine.

4. A method according to claim 3 wherein the growth is nerve growth factor or a neurotrophic factor.

5. A method according to claim 3 wherein the lymphokine is gamma interferon, tumor necrosis factor, an interleukin, GM-CSF, CSF-1 and G-CSF.

6. A method according to claim 2 for use in the treatment of a brain tumor.

7. A method according to claim 1 wherein the (a) soluble melanotransferrin conjugated to the agent is a melanotransferrin fusion protein containing soluble melanotransferrin fused to the agent.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
    (A) LENGTH: 2368 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 61..117

(ix) FEATURE:
    (A) NAME/KEY: CDS
    (B) LOCATION: 118..2274

(xi) SEQUENCE DESCRIPTION: SEQ ID NO:1:

```
GCGGACTTCC TCGGACCCGG ACCCAGCCCC AGCCCGGCCC CAGCCAGCCC CGACGGCGCC         60

ATG CGG GGT CCG AGC GGG GCT CTG TGG CTG CTC CTG GCT CTG CGC ACC         108
Met Arg Gly Pro Ser Gly Ala Leu Trp Leu Leu Leu Ala Leu Arg Thr
 1               5                  10                  15

GTG CTC GGA GGC ATG GAG GTG CGG TGG TGC GCC ACC TCG GAC CCA GAG         156
Val Leu Gly Gly Met Glu Val Arg Trp Cys Ala Thr Ser Asp Pro Glu
             1               5                  10

CAG CAC AAG TGC GGC AAC ATG AGC GAG GCC TTC CGG GAA GCG GGC ATC         204
Gln His Lys Cys Gly Asn Met Ser Glu Ala Phe Arg Glu Ala Gly Ile
         15                  20                  25

CAG CCC TCC CTC CTC TGC GTC CGG GGC ACC TCC GCC GAC CAC TGC GTC         252
Gln Pro Ser Leu Leu Cys Val Arg Gly Thr Ser Ala Asp His Cys Val
 30                  35                  40                  45

CAG CTC ATC GCG GCC CAG GAG GCT GAC GCC ATC ACT CTG GAT GGA GGA         300
Gln Leu Ile Ala Ala Gln Glu Ala Asp Ala Ile Thr Leu Asp Gly Gly
                 50                  55                  60

GCC ATC TAT GAG GCG GGA AAG GAG CAC GGC CTG AAG CCG GTG GTG GGC         348
Ala Ile Tyr Glu Ala Gly Lys Glu His Gly Leu Lys Pro Val Val Gly
         65                  70                  75

GAA GTG TAC GAT CAA GAG GTC GGT ACC TCC TAT TAC GCC GTG GCT GTG         396
Glu Val Tyr Asp Gln Glu Val Gly Thr Ser Tyr Tyr Ala Val Ala Val
     80                  85                  90

GTC AGG AGG AGC TCC CAT GTG ACC ATT GAC ACC CTG AAA GGC GTG AAG         444
Val Arg Arg Ser Ser His Val Thr Ile Asp Thr Leu Lys Gly Val Lys
 95                 100                 105

TCC TGC CAC ACG GGC ATC AAT CGC ACA GTG GGC TGG AAC GTG CCC GTG         492
Ser Cys His Thr Gly Ile Asn Arg Thr Val Gly Trp Asn Val Pro Val
```

-continued

```
          110                 115                 120                 125
GGC TAC CTG GTG GAG AGC GGC CGC CTC TCG GTG ATG GGC TGC GAT GTA         540
Gly Tyr Leu Val Glu Ser Gly Arg Leu Ser Val Met Gly Cys Asp Val
                    130                 135                 140

CTC AAA GCT GTC AGC GAC TAT TTT GGG GGC AGC TGC GTC CCG GGG GCA         588
Leu Lys Ala Val Ser Asp Tyr Phe Gly Gly Ser Cys Val Pro Gly Ala
                145                 150                 155

GGA GAG ACC AGT TAC TCT GAG TCC CTC TGT CGC CTC TGC AGG GGT GAC         636
Gly Glu Thr Ser Tyr Ser Glu Ser Leu Cys Arg Leu Cys Arg Gly Asp
            160                 165                 170

AGC TCT GGG GAA GGG GTG TGT GAC AAG AGC CCC CTG GAG AGA TAC TAC         684
Ser Ser Gly Glu Gly Val Cys Asp Lys Ser Pro Leu Glu Arg Tyr Tyr
        175                 180                 185

GAC TAC AGC GGG GCC TTC CGG TGC CTG GCG GAA GGG GCA GGG GAC GTG         732
Asp Tyr Ser Gly Ala Phe Arg Cys Leu Ala Glu Gly Ala Gly Asp Val
190                 195                 200                 205

GCT TTT GTG AAG CAC AGC ACG GTA CTG GAG AAC ACG GAT GGG AAG ACG         780
Ala Phe Val Lys His Ser Thr Val Leu Glu Asn Thr Asp Gly Lys Thr
                210                 215                 220

CTT CCC TCC TGG GGC CAG GCC CTG CTG TCA CAG GAC TTC GAG CTG CTG         828
Leu Pro Ser Trp Gly Gln Ala Leu Leu Ser Gln Asp Phe Glu Leu Leu
            225                 230                 235

TGC CGG GAT GGT AGC CGG GCC GAT GTC ACC GAG TGG AGG CAG TGC CAT         876
Cys Arg Asp Gly Ser Arg Ala Asp Val Thr Glu Trp Arg Gln Cys His
        240                 245                 250

CTG GCC CGG GTG CCT GCT CAC GCC GTG GTG GTC CGG GCC GAC ACA GAT         924
Leu Ala Arg Val Pro Ala His Ala Val Val Val Arg Ala Asp Thr Asp
255                 260                 265

GGG GGC CTC ATC TTC CGG CTG CTC AAC GAA GGC CAG CGT CTG TTC AGC         972
Gly Gly Leu Ile Phe Arg Leu Leu Asn Glu Gly Gln Arg Leu Phe Ser
270                 275                 280                 285

CAC GAG GGC AGC AGC TTC CAG ATG TTC AGC TCT GAG GCC TAT GGC CAG        1020
His Glu Gly Ser Ser Phe Gln Met Phe Ser Ser Glu Ala Tyr Gly Gln
                290                 295                 300

AAG GAT CTA CTC TTC AAA GAC TCT ACC TCG GAG CTT GTG CCC ATC GCC        1068
Lys Asp Leu Leu Phe Lys Asp Ser Thr Ser Glu Leu Val Pro Ile Ala
            305                 310                 315

ACA CAG ACC TAT GAG GCG TGG CTG GGC CAT GAG TAC CTG CAC GCC ATG        1116
Thr Gln Thr Tyr Glu Ala Trp Leu Gly His Glu Tyr Leu His Ala Met
        320                 325                 330

AAG GGT CTG CTC TGT GAC CCC AAC CGG CTG CCC CCC TAC CTG CGC TGG        1164
Lys Gly Leu Leu Cys Asp Pro Asn Arg Leu Pro Pro Tyr Leu Arg Trp
    335                 340                 345

TGT GTG CTC TCC ACT CCC GAG ATC CAG AAG TGT GGA GAC ATG GCC GTG        1212
Cys Val Leu Ser Thr Pro Glu Ile Gln Lys Cys Gly Asp Met Ala Val
350                 355                 360                 365

GCC TTC CGC CGG CAG CGC CTC AAG CCA GAG ATC CAG TGC GTG TCA GCC        1260
Ala Phe Arg Arg Gln Arg Leu Lys Pro Glu Ile Gln Cys Val Ser Ala
                370                 375                 380

AAG TCC CCC CAA CAC TGC ATG GAG CGG ATC CAG GCT GAG CAG GTC GAC        1308
Lys Ser Pro Gln His Cys Met Glu Arg Ile Gln Ala Glu Gln Val Asp
            385                 390                 395

GCT GTG ACC CTA AGT GGC GAG GAC ATT TAC ACG GCG GGG AAG AAG TAC        1356
Ala Val Thr Leu Ser Gly Glu Asp Ile Tyr Thr Ala Gly Lys Lys Tyr
        400                 405                 410

GGC CTG GTT CCC GCA GCC GGC GAG CAC TAT GCC CCG GAA GAC AGC AGC        1404
Gly Leu Val Pro Ala Ala Gly Glu His Tyr Ala Pro Glu Asp Ser Ser
    415                 420                 425

AAC TCG TAC TAC GTG GTG GCC GTG GTG AGA CGG GAC AGC TCC CAC GCC        1452
```

```
Asn Ser Tyr Tyr Val Val Ala Val Val Arg Arg Asp Ser Ser His Ala
430                 435                 440                 445

TTC ACC TTG GAT GAG CTT CGG GGC AAG CGC TCC TGC CAC GCC GGT TTC      1500
Phe Thr Leu Asp Glu Leu Arg Gly Lys Arg Ser Cys His Ala Gly Phe
                    450                 455                 460

GGC AGC CCT GCA GGC TGG GAT GTC CCC GTG GGT GCC CTT ATT CAG AGA      1548
Gly Ser Pro Ala Gly Trp Asp Val Pro Val Gly Ala Leu Ile Gln Arg
                465                 470                 475

GGC TTC ATC CGG CCC AAG GAC TGT GAC GTC CTC ACA GCA GTG AGC GAG      1596
Gly Phe Ile Arg Pro Lys Asp Cys Asp Val Leu Thr Ala Val Ser Glu
            480                 485                 490

TTC TTC AAT GCC AGC TGC GTG CCC GTG AAC AAC CCC AAG AAC TAC CCC      1644
Phe Phe Asn Ala Ser Cys Val Pro Val Asn Asn Pro Lys Asn Tyr Pro
        495                 500                 505

TCC TCG CTG TGT GCA CTG TGC GTG GGG GAC GAG CAG GGC CGC AAC AAG      1692
Ser Ser Leu Cys Ala Leu Cys Val Gly Asp Glu Gln Gly Arg Asn Lys
510                 515                 520                 525

TGT GTG GGC AAC AGC CAG GAG CGG TAT TAC GGC TAC CGC GGC GCC TTC      1740
Cys Val Gly Asn Ser Gln Glu Arg Tyr Tyr Gly Tyr Arg Gly Ala Phe
                530                 535                 540

AGG TGC CTG GTG GAG AAT GCG GGT GAC GTT GCC TTC GTC AGG CAC ACA      1788
Arg Cys Leu Val Glu Asn Ala Gly Asp Val Ala Phe Val Arg His Thr
                545                 550                 555

ACC GTC TTT GAC AAC ACA AAC GGC CAC AAT TCC GAG CCC TGG GCT GCT      1836
Thr Val Phe Asp Asn Thr Asn Gly His Asn Ser Glu Pro Trp Ala Ala
            560                 565                 570

GAG CTC AGG TCA GAG GAC TAT GAA CTG CTG TGC CCC AAC GGG GCC CGA      1884
Glu Leu Arg Ser Glu Asp Tyr Glu Leu Leu Cys Pro Asn Gly Ala Arg
        575                 580                 585

GCC GAG GTG TCC CAG TTT GCA GCC TGC AAC CTG GCA CAG ATA CCA CCC      1932
Ala Glu Val Ser Gln Phe Ala Ala Cys Asn Leu Ala Gln Ile Pro Pro
590                 595                 600                 605

CAC GCC GTG ATG GTC CGG CCC GAC ACC AAC ATC TTC ACC GTG TAT GGA      1980
His Ala Val Met Val Arg Pro Asp Thr Asn Ile Phe Thr Val Tyr Gly
                610                 615                 620

CTG CTG GAC AAG GCC CAG GAC CTG TTT GGA GAC GAC CAC AAT AAG AAC      2028
Leu Leu Asp Lys Ala Gln Asp Leu Phe Gly Asp Asp His Asn Lys Asn
                625                 630                 635

GGG TTC AAA ATG TTC GAC TCC TCC AAC TAT CAT GGC CAA GAC CTG CTT      2076
Gly Phe Lys Met Phe Asp Ser Ser Asn Tyr His Gly Gln Asp Leu Leu
            640                 645                 650

TTC AAG GAT GCC ACC GTC CGG GCG GTG CCT GTC GGA GAG AAA ACC ACC      2124
Phe Lys Asp Ala Thr Val Arg Ala Val Pro Val Gly Glu Lys Thr Thr
        655                 660                 665

TAC CGC GGC TGG CTG GGG CTG GAC TAC GTG GCG GCG CTG GAA GGG ATG      2172
Tyr Arg Gly Trp Leu Gly Leu Asp Tyr Val Ala Ala Leu Glu Gly Met
670                 675                 680                 685

TCG TCT CAG CAG TGC TCG GGC GCA GCG GCC CCG GCG CCC GGG GCG CCC      2220
Ser Ser Gln Gln Cys Ser Gly Ala Ala Ala Pro Ala Pro Gly Ala Pro
                690                 695                 700

CTG CTC CCG CTG CTG CTG CCC GCC CTC GCC GCC CGC CTG CTC CCG CCC      2268
Leu Leu Pro Leu Leu Leu Pro Ala Leu Ala Ala Arg Leu Leu Pro Pro
                705                 710                 715

GCC CTC TGAGCCCGGC CGCCCCGCCC CAGAGCTCCG ATGCCCGCCC GGGGAGTTTC       2324
Ala Leu

CGCGGCGGCC TCTCGCGCTG CGGAATCCAG AAGGAAGCTC GCGA                     2368
```

(2) INFORMATION FOR SEQ ID NO:2:

(i) SEQUENCE CHARACTERISTICS:
    (A) LENGTH: 19 amino acids
    (B) TYPE: amino acid
    (D) TOPOLOGY: linear (ii) MOLECULE TYPE: protein (xi) SEQUENCE DESCRIPTION: SEQ ID NO:2:

```
Met Arg Gly Pro Ser Gly Ala Leu Trp Leu Leu Leu Ala Leu Arg Thr
 1               5                  10                  15

Val Leu Gly
```

(2) INFORMATION FOR SEQ ID NO:3:

(i) SEQUENCE CHARACTERISTICS:
        (A) LENGTH: 719 amino acids
        (B) TYPE: amino acid
        (D) TOPOLOGY: linear (ii) MOLECULE TYPE: protein (xi) SEQUENCE DESCRIPTION: SEQ ID NO:3:

```
Gly Met Glu Val Arg Trp Cys Ala Thr Ser Asp Pro Glu Gln His Lys
 1               5                  10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285
```

```
Ser Ser Phe Gln Met Phe Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
                340                 345                 350

Ser Thr Pro Glu Ile Gln Lys Cys Gly Asp Met Ala Val Ala Phe Arg
                355                 360                 365

Arg Gln Arg Leu Lys Pro Glu Ile Gln Cys Val Ser Ala Lys Ser Pro
370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Lys Tyr Gly Leu Val
                405                 410                 415

Pro Ala Ala Gly Glu His Tyr Ala Pro Glu Asp Ser Ser Asn Ser Tyr
                420                 425                 430

Tyr Val Val Ala Val Val Arg Arg Asp Ser Ser His Ala Phe Thr Leu
            435                 440                 445

Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
                500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                565                 570                 575

Ser Glu Asp Tyr Glu Leu Leu Cys Pro Asn Gly Ala Arg Ala Glu Val
                580                 585                 590

Ser Gln Phe Ala Ala Cys Asn Leu Ala Gln Ile Pro Pro His Ala Val
            595                 600                 605

Met Val Arg Pro Asp Thr Asn Ile Phe Thr Val Tyr Gly Leu Leu Asp
    610                 615                 620

Lys Ala Gln Asp Leu Phe Gly Asp Asp His Asn Lys Asn Gly Phe Lys
625                 630                 635                 640

Met Phe Asp Ser Ser Asn Tyr His Gly Gln Asp Leu Leu Phe Lys Asp
                645                 650                 655

Ala Thr Val Arg Ala Val Pro Val Gly Glu Lys Thr Thr Tyr Arg Gly
                660                 665                 670

Trp Leu Gly Leu Asp Tyr Val Ala Ala Leu Glu Gly Met Ser Ser Gln
            675                 680                 685

Gln Cys Ser Gly Ala Ala Ala Pro Ala Pro Gly Ala Pro Leu Leu Pro
    690                 695                 700
```

```
Leu Leu Leu Pro Ala Leu Ala Ala Arg Leu Leu Pro Pro Ala Leu
705                 710                 715
```

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:4:

GCGGACTTCC TCGG                          14

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:5:

TCGCGAGCTT CCT                           13

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:6:

CTCAGAGGGC CGCTGCGCCC                     20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:7:

CCAGCGCAGC TAGCGGGGCA G                   21

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued (ii) MOLECULE TYPE: cDNA (iii) HYPOTHETICAL: NO (xi) SEQUENCE DESCRIPTION: SEQ ID NO:8:

ACACCAGCGC AGCTCGAGGG GCAGCCG                                        27

(2) INFORMATION FOR SEQ ID NO:9:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

CGCGTACGTA TGATCACCCG AGCACTGCTG AGACGAC                             37

(2) INFORMATION FOR SEQ ID NO:10:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:10:

GCGCTACGTA CTCGAGGCCC CAGCCAGCCC CGACGGCGCC                          40

(2) INFORMATION FOR SEQ ID NO:11:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:11:

CGCGTACGTA TGATCATCAG CCCGAGCACT GCTGAGACGA C                        41